United States Patent
Manuguerra et al.

(10) Patent No.: US 10,352,930 B2
(45) Date of Patent: *Jul. 16, 2019

(54) MULTIPLEX IMMUNO SCREENING ASSAY

(71) Applicant: INSTITUT PASTEUR, Paris (FR)

(72) Inventors: Jean-Claude Manuguerra, Paris (FR); Jessica Vanhomwegen, Paris (FR); Philippe Despres, La Garenne-Colombes (FR); Sylvie Paulous, Sarcelles (FR)

(73) Assignee: INSTITUT PASTEUR, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/654,272

(22) Filed: Jul. 19, 2017

(65) Prior Publication Data

US 2018/0038852 A1 Feb. 8, 2018

Related U.S. Application Data

(62) Division of application No. 15/480,451, filed on Apr. 6, 2017, now Pat. No. 10,197,562, which is a division
(Continued)

(30) Foreign Application Priority Data

Dec. 9, 2011 (WO) .................. PCT/EP11/072387

(51) Int. Cl.
*G01N 33/53* (2006.01)
*C12Q 1/70* (2006.01)
(Continued)

(52) U.S. Cl.
CPC .. *G01N 33/54306* (2013.01); *G01N 33/54313* (2013.01); *G01N 33/54353* (2013.01);
(Continued)

(58) Field of Classification Search
None
See application file for complete search history.

(56) References Cited

U.S. PATENT DOCUMENTS 4,358,388 A 11/1982 Daniel et al.
4,654,267 A 3/1987 Ugelstad et al.
(Continued)

FOREIGN PATENT DOCUMENTS

EP 1204869 B1 5/2002
WO 84/01153 A1 3/1984
(Continued)

OTHER PUBLICATIONS

Andresen et al., Deciphering the Antibodyome—Peptide Arrays for Serum Antibody Biomarker Diagnostics, Antibody Biomarker Diagnostics, Current Proteomics, Bentham Science, Publishers, GB, vol. 6, No. 1, Apr. 1, 2009 (Apr. 1, 2009), pp. 1-12.
(Continued)

*Primary Examiner* — M Franco G Salvoza
(74) *Attorney, Agent, or Firm* — Arrigo, Lee, Guttman & Mouta-Bellum LLP

(57) ABSTRACT

The present invention provides an immunoassay leading to the rapid and simultaneous detection of antibodies to a wide range of infectious pathogens in biological fluids of infected patients. This immunoassay involves the covalent and oriented coupling of fusion proteins comprising an AGT enzyme and a viral antigen on an identifiable solid support (e.g. fluorescent microspheres). The thus obtained antigen-coupled microspheres show enhanced capture of specific antibodies as compared to antigen-coupled microspheres produced by standard amine coupling procedures.

13 Claims, 12 Drawing Sheets
Specification includes a Sequence Listing.

Related U.S. Application Data of application No. 13/883,339, filed on May 3, 2013, now Pat. No. 9,638,692, which is a division of application No. PCT/EP2012/074986, filed on Dec. 10, 2012.

(60) Provisional application No. 61/642,924, filed on May 4, 2012.

(51) Int. Cl.

| | | |
|---|---|---|
| *G01N 33/543* | (2006.01) | |
| *G01N 33/569* | (2006.01) | |
| *G01N 33/564* | (2006.01) | |
| *G01N 33/68* | (2006.01) | |

(52) U.S. Cl.
CPC ..... *G01N 33/564* (2013.01); *G01N 33/56983* (2013.01); *G01N 33/6845* (2013.01); *G01N 2333/18* (2013.01); *G01N 2333/185* (2013.01); *G01N 2469/20* (2013.01); *Y02A 50/51* (2018.01); *Y02A 50/53* (2018.01); *Y02A 50/56* (2018.01); *Y02A 50/58* (2018.01); *Y02A 50/60* (2018.01)

(56) References Cited

U.S. PATENT DOCUMENTS

| | | | |
|---|---|---|---|
| 4,774,265 | A | 9/1988 | Ugelstad et al. |
| 5,320,944 | A | 6/1994 | Okada et al. |
| 5,356,713 | A | 10/1994 | Charmot et al. |
| 5,459,127 | A | 10/1995 | Felgner et al. |
| 5,736,330 | A | 4/1998 | Fulton |
| 5,817,514 | A | 10/1998 | Li et al. |
| 5,879,926 | A | 3/1999 | Lemoine et al. |
| 5,981,180 | A | 11/1999 | Chandler et al. |
| 6,057,107 | A | 5/2000 | Fulton |
| 6,268,222 | B1 | 7/2001 | Chandler et al. |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,682,907 | B1 | 1/2004 | Charneau et al. |
| 7,939,284 | B2 | 5/2011 | Johnsson et al. |
| 9,109,219 | B2 | 8/2015 | Despres et al. |
| 9,546,380 | B2 | 1/2017 | Manuguerra et al. |
| 9,638,692 | B2 | 5/2017 | Manuguerra et al. |
| 2004/0115130 | A1 | 6/2004 | Johnsson et al. |
| 2004/0197769 | A1* | 10/2004 | Wong ............... C12Q 1/04 435/5 |
| 2006/0166268 | A1 | 7/2006 | Grus et al. |
| 2006/0292651 | A1 | 12/2006 | Juillerat et al. |
| 2010/0009872 | A1 | 1/2010 | Eid et al. |
| 2015/0099656 | A1 | 4/2015 | Manuguerra et al. |
| 2017/0088843 | A1 | 3/2017 | Despres et al. |
| 2017/0276672 | A1 | 9/2017 | Manuguerra et al. |
| 2017/0336412 | A1 | 11/2017 | Manuguerra et al. |

FOREIGN PATENT DOCUMENTS

| | | |
|---|---|---|
| WO | 87/02670 A1 | 5/1987 |
| WO | 95/02059 A1 | 1/1995 |
| WO | 95/18863 A1 | 7/1995 |
| WO | 95/21931 A1 | 8/1995 |
| WO | 96/17823 A1 | 7/1996 |
| WO | 96/25508 A1 | 8/1996 |
| WO | 99/055892 A1 | 11/1999 |
| WO | 01/27300 A1 | 4/2001 |
| WO | 02/083937 A2 | 10/2002 |
| WO | 2004/031404 A1 | 4/2004 |
| WO | 2004/031405 A1 | 4/2004 |
| WO | 2005/085470 A1 | 9/2005 |
| WO | 2010/107433 A1 | 9/2010 |
| WO | 2012/076715 A1 | 6/2012 |

OTHER PUBLICATIONS

Avrameas S., Natural autoantibodies: from 'horror autotoxicus' to 'gnothi seauton', Immunol. Today, May 1991;12(5):154-9.

Bond et al., The *Drosophila melanogaster* Actin 5C Gene Uses Two Transcription Initiation Sites and Three Polyadenylation Sites to Express Multiple mRNA Species, Mol Cell. Biol. 6:2080 (1986).

Brecht et al, SNAP-tag(TM): Self-Labeling Protein tag for medium throughput and HTS assay formats, Poster P7016 Booth 345, Sep. 19, 2006 (Sep. 19, 2006), SBS 12th Annual Conference and Exhibition, Advancing Drug Discovery: From Better Hits to Better Candidates Sep. 17-21, 2006—Seattle, WA, USA.

Brinster et al., Regulation of metallothionein-thymidine kinase fusion plasmids injected into mouse eggs, Nature, 296:39-42, 1982.

Damoiseaux et al., Synthesis and Applications of Chemical Probes for Human O6-Alkylguanine-DNA Alkyltransferase, Chembiochem. 4:285-287, 2001.

Daniels D.S. et al., Active and alkylated human AGT structures: a novel zinc site, inhibitor and extrahelical base binding, EMBO J. 19: 1719-1730, 2000.

Engin et al., Benzylguanine Thiol Self-Assembled Monolayers for the Immobilization of SNAP-tag Proteins on Microcontact-Printed Surface Structures, LANGMUIR, vol. 26, No. 9, May 4, 2010 (May 4, 2010), pp. 6097-6101.

Felgner et al., Lipofection: A highly efficient, lipid-mediated DNA-transfection procedure, Proc. Natl. Acad. Sci. U.S.A., 84:7413-7417, 1987.

Hellwig et al., Plant cell cultures for the production of recombinant proteins, Nat. Biotechnol.2004; 22(11)1415-22.

Juillerat et al., Directed Evolution of O6-Alkylguanine-DNA Alkyltransferase for Efficient Labeling of Fusion Proteins with Small Molecules In Vivo, Chemistry ET Biology, vol. 10, 313-317, 2003.

Kim et al., Competitive ELISA for the detection of Antibodies to Rift Valley Fever Virus in Goats and Cattle, The Journal of Veterinary Medical Science, 2011.

Kindermann M. et al., Covalent and Selective Immobilization of Fusion Proteins, Journal of The American Chemical Society, vol. 125, No. 26, Jul. 2, 2003 (Jul. 2, 2003), pp. 7810-7811.

Kolpe et al., Display of enterovirus 71 VP1 on baculovirus as a type II transmembrane protein elicits protective B and T cell responses in immunized mice, Virus Research 2012; 168:64-72.

Kufer, et al., Covalent immobilization of recombinant fusion proteins with hAGT for single molecule force spectroscopy, European Biophysics Journal, vol. 35, No. 1, Dec. 1, 2005 (Dec. 1, 2005), pp. 72-78.

Lastowski-Perry et al., Nucleotide Sequence and Expressionof a *Drosophila metallothionein*, J.Biol. Chem. 260:1527 (1985).

Lim et al., The nuclear targeting and nuclear retention properties of a human DNA repair protein 06-methylguanine-DNA methyltransferase are both required for its nuclear localization: the possible implications, EMBO J. 15: 4050-4060, 1996.

Machy et al., Gene transfer from targeted liposomes to specific lymphoid cells by electroporation, Proc. Natl. Acad. Sci. U.S.A., 85:8027-8031, 1988.

Miller and Rosman, Improved Retroviral Vectors for Gene Transfer and Expression, Biotechniques, 7:980-990, 1992.

Neuman De Vegvar et al., Microarray profiling of antiviral antibodies for the development of diagnostics, vaccines, and therapeutics, Clinical Immunology, vol. 111, No. 2, May 1, 2004 (May 1, 2004), pp. 196-201.

Pan et al., Fusion of Two Malaria Vaccine Candidate Antigens Enhances Product Yield, Immunogenicity, and Antibody-Mediated Inhibition of Parasite Growth In Vitro, The Journal of Immunology, 2004, 172:6167-6174.

Robinson et al., Autoantigen microarrays for multiplex characterization of autoantibody responses, Nature Medicine, vol. 8, No. 3, Mar. 1, 2002 (Mar. 1, 2002), pp. 295-301.

Sivakolundu et al., Serological diagnosis of leptospiral uveitis by HbpA IgG ELISA, Journal of Medical Microbiology, 61:1681-1687, 2012.

(56) References Cited

OTHER PUBLICATIONS

Wibley J.E.A. et al., Crystal structure of the human O6-alkylguanine-DNA alkyltransferase, Nucleic Acids Research, 2000, vol. 28, No. 2, 393-401.
Williams et al., Introduction of foreign genes into tissues of living mice by DNA-coated microprojectiles, Proc. Natl. Acad. Sci. U.S.A., 88:2726-2730, 1991.
Wilson et al., Hepatocyte-directed Gene Transfer in Vivo Leads to Transient Improvement of Hypercholesterolemia in Low Density Lipoprotein Receptor-deficient Rabbits, The Journal of Biological Chemistry, vol. 267, No. 2, Issue of Jan. 15, pp. 963-967,1992.
Wong et al., Detection of Human Anti-Flavivirus Antibodies with a West Nile Virus Recombinant Antigen Microsphere Immunoassay, Journal of Clinical Microbiology 42, No. 1 (Jan. 2004): 65-72.
Wu and Wu, Receptor-mediated Gene Delivery and Expression in Viuo, J. Biol. Chem., 263:14621-14624, 1988.
Xu-Welliver et al., Role of Codon 160 in the Sensitivity of Human O6-Alkylguanine-DNA Alkyltransferase to O6-Benzylguanine, Biochemical Pharmacology 58: 1279-85, 1999.
Zimmerman et al., Multivariate statistical comparison of autoantibody-repertoires (Western blots) by discriminant analysis, Electrophoresis Jun. 1995;16(6):941-7.
Margison and Santibanez-Koref, O6-alkylguanine-DNA alkyltransferase: role in carcinogenesis and chemotherapy, BioEssays vol. 24, pp. 255-266, 2002.
Juillerat et al., Engineering substrate specificity of O6-alkylguanine-DNA alkyltransferase for specific protein labeling in living cells, ChemBioChem 2005, vol. 6, pp. 1263-1269.
Mullapudi et al., DNA repair protein O6-alkylguanine-DNA alkyltransferase is phosphorylated by two distinct and novel protein kinases in human brain tumour cells, Journal of Biochem., 2000, vol. 351, pp. 393-402.

\* cited by examiner

< SNAP+SBV.N (50-kDa)

MW

MULTIPLEX IMMUNO SCREENING ASSAY

BACKGROUND OF THE INVENTION

Infectious diseases and viral hemorrhagic fevers (VHFs) pose a significant public health problem, due to the severity of the diseases, high lethality, inter-human contagiousness of certain agents, and lack of effective treatment for most of them.

Some of them are caused by highly infectious RNA viruses from several families including the Flaviviridae (dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses) the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg). Transmission usually occurs by contact with infected animal reservoirs or arthropod vectors. Although the majority of those viruses have a higher occurrence in the tropics and subtropics, the geographic expansion of their natural reservoirs and vectors, and the increase in international travel have made the emergence of these agents in non-endemic areas highly probable. Control of epidemics crucially depends on the rapid detection and accurate identification of the agent, in order to define and implement timely and appropriate action. In this context, it is essential to produce and validate tools for early detection of outbreaks, precise identification of the etiologic agent, and improved disease surveillance.

In this respect, detection of antibodies in body fluids constitutes a major part of the diagnosis of virally induced diseases, autoimmune diseases and the detection of cancer. As a matter of fact, certain antibodies can serve as markers in diagnosis and can lead to prognosis and treatment, as their presence are known to correlate with the outbreak of a pathogen. This is particularly the case for the antibodies targeting viral antigens exclusively.

Current methods for detecting the presence of antibodies include diverse techniques such as immunofluorescence microscopy, chemiluminescence assay, Western blotting, Radio Immuno-Precipitation assay (RIP) and ELISA. For example, the team of Kim H-J. et al. recently developed a competitive ELISA for the detection of antibodies to Rift Valley Fever virus in goat and cattle (*The Journal of Veterinary Medical Science* 2011). However, such techniques require measurement of each antibody separately, a d thus are not useful for parallel, rapid, and high throughput analysis of multiple antibodies in a single sample of biological fluid. The parallel detection of several antibodies simultaneously may be particularly useful by minimizing the matrix effects that exist between individual assays, such as in ELISAs, because the calibrators and the antibodies are analyzed under the same conditions; it therefore will generate comparable results for the measurement of multiple antibodies present within the same sample.

Complicating the straightforward identification of pathogenically relevant antibodies, however, is that normal sera contain large amounts of natural antibodies which manifest themselves in complex staining patterns (Avrameas S. *Immunol. Today* 1991). The presence of these natural antibodies can complicate the differentiation of disease-associated antibodies from the complex background of "autoimmune noise", i.e. naturally occurring autoantibodies. That's why most of previous studies evaluated one or a few specific disease-related antibodies and have screened only a limited number of purified homologous or heterologous proteins as antigens by means of ELISA or RIA. A diagnosis based on these antibodies was impossible to establish. On the other hand, Western blotting has evolved as the most important tool to detect antibodies because it permits simultaneous screening for a wide spectrum of different antigens. A recent new technique, capable of analyzing these complex staining patterns of Western blots simultaneously, is based on digital image analysis. This technique has been successfully used in studies of myasthenia gravis, Graves' disease and experimental uveitis (Zimmerman C W, *Electrophoresis* 1995). The antibodies may also be detected and measured on a protein chip array using surface-enhanced laser desorption/ionization (SELDI) or matrix assisted laser desorption/ionization mass spectrometry techniques, preferably SELDI mass spectrometry technique (US 2006/166268). Yet, these techniques use large cumbersome equipment that is complex and expensive to maintain, and requires high amount of the biological samples to achieve the detection of antibodies being in a low amount.

In view of the foregoing, there exists a need for addressable systems and methods, which can provide additional improvements in high throughput, cost-effectiveness, and accuracy for molecular diagnosis of antibody-generating diseases. The present invention satisfies these and other needs.

FIGURE LEGENDS

FIG. 1 represents the oriented coupling of chimeric AGT-antigen proteins to substrate-coated microspheres. First step of coupling consists of coupling the AGT substrate BG-PEG-NH2 to the activated microspheres by amine coupling. The second step consists of contacting the substrate-coated microspheres with fusion proteins containing AGT (for example the SNAP mutant), said enzyme being intended to covalently attach to its BG-PEG-NH2 substrate, that is, to the microspheres.

FIG. 2 shows the coupling efficiency of chimeric SNAP-viral antigens proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-ZIKA), as followed by anti-SNAP antibody.

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through a standard amine coupling procedure, e.g. Bio-Plex Amine Coupling Kit, BIORAD.

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex fomat with other chimeric SNAP-viral Ags proteins (SNAP-DV2.EDIII, SNAP.DV3.EDIII, SNAP.DV4.EDIII, SNAP-WNV, SNAP-YF, SNAP-JE, SNAP-TBE) coupled to microspheres.

(A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA) coupled to microspheres.

Figure 7A:
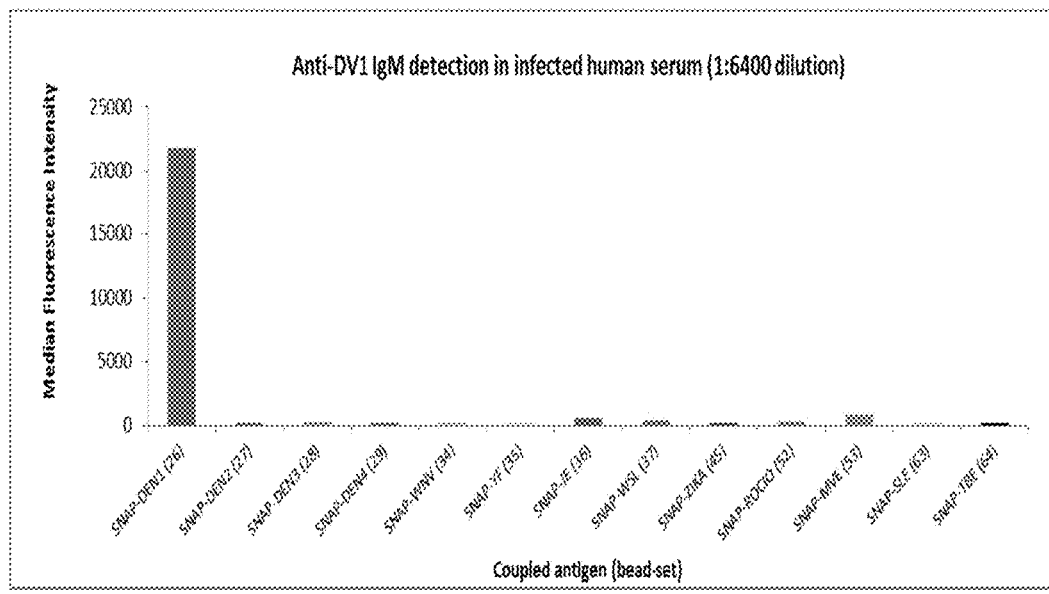
Figure 7B:
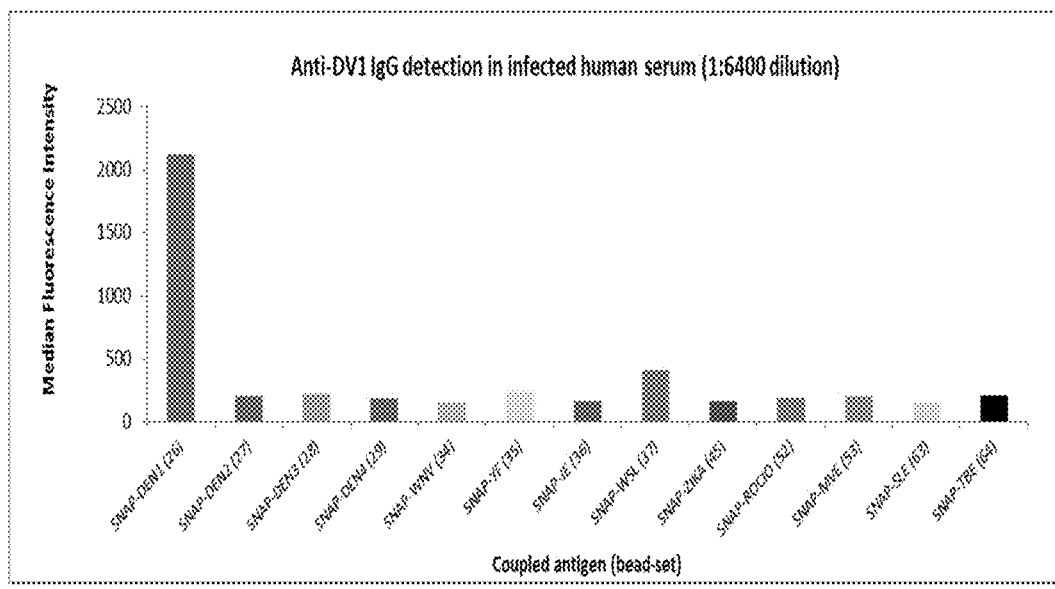

FIGS. 7A-7B show the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA, SNAP-TBE) coupled to microspheres.

Figure 8:
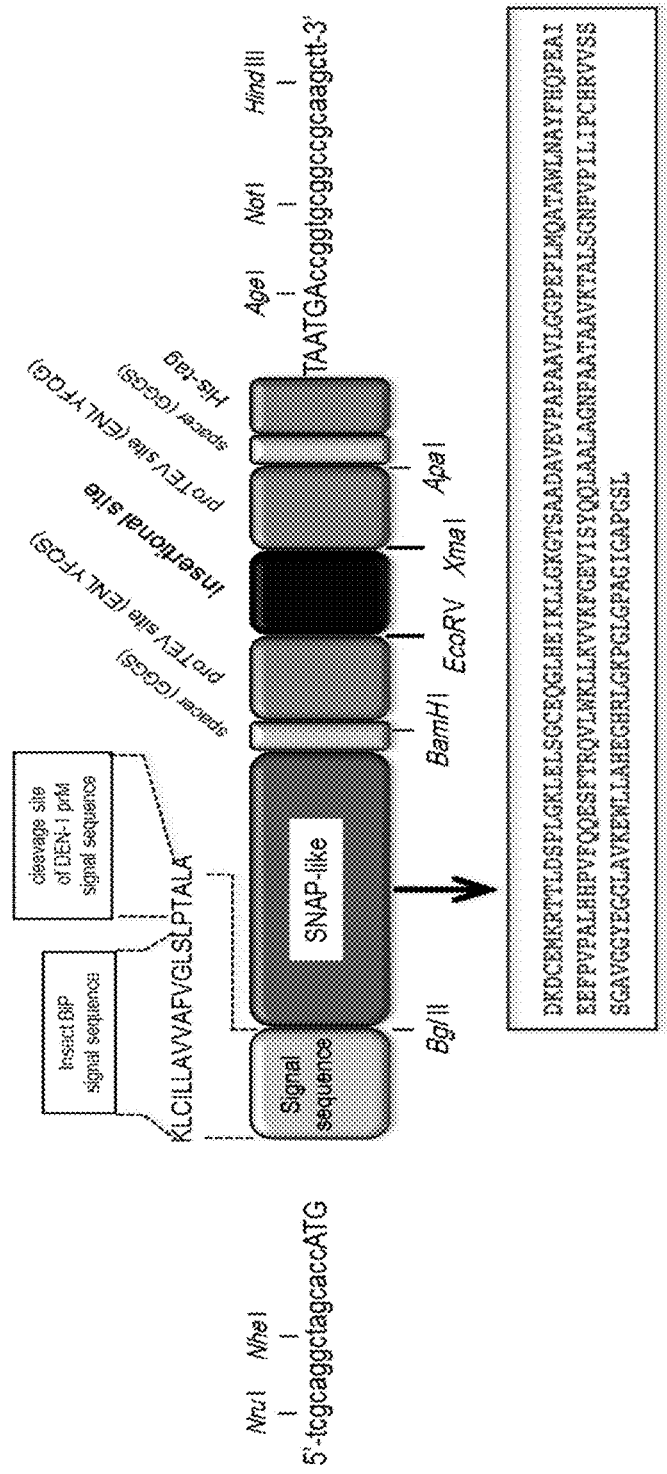

FIG. 8 discloses the structure of the pDeSNAPuniv cassette showing nucleotide sequences (nucl. 2-20 and 774-798 of SEQ ID NO:34), amino acid sequence of signal sequence (aa 2-22 of SEQ ID NO 24), SNAP-like amino acid sequence (aa 33-192 of SEQ ID NO:1), and amino acid sequence of proTev site (SEQ ID NO:32).

Figure 9:
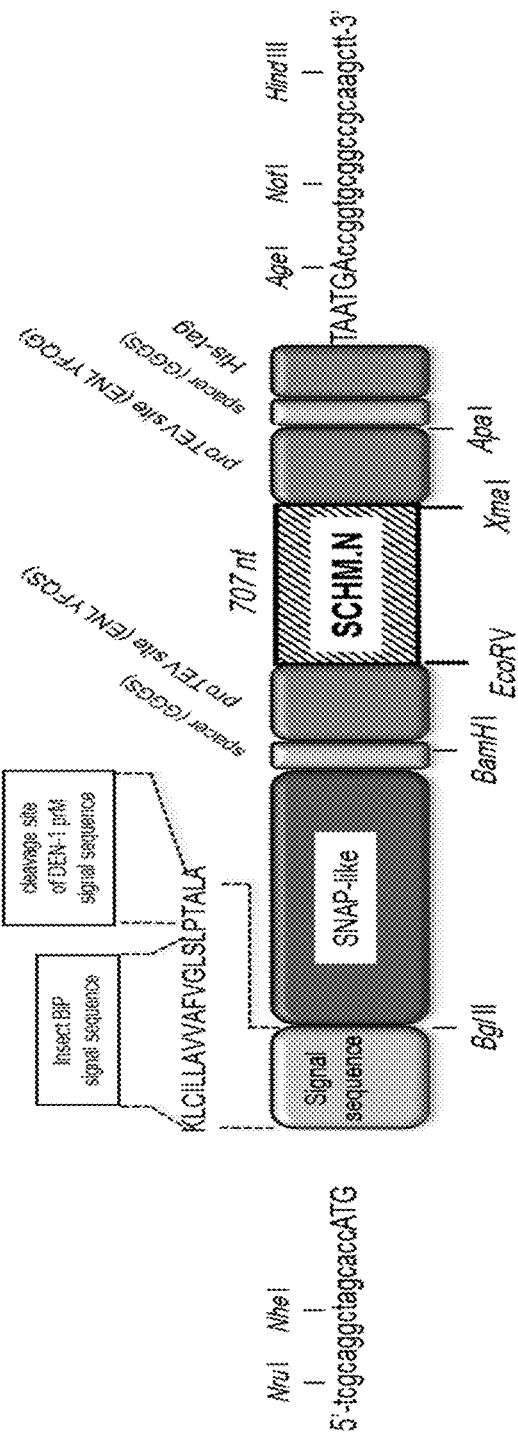

FIG. 9 discloses the structure of the pDeSNAPuniv/SBV.N cassette showing nucleotide sequences (nucl. 2-20 and 774-798 of SEQ ID NO:34), amino acid sequence of signal sequence (aa 2-22 of SEQ ID NO 24), and amino acid sequence of proTev site (SEQ ID NO:32).

Figure 10A:
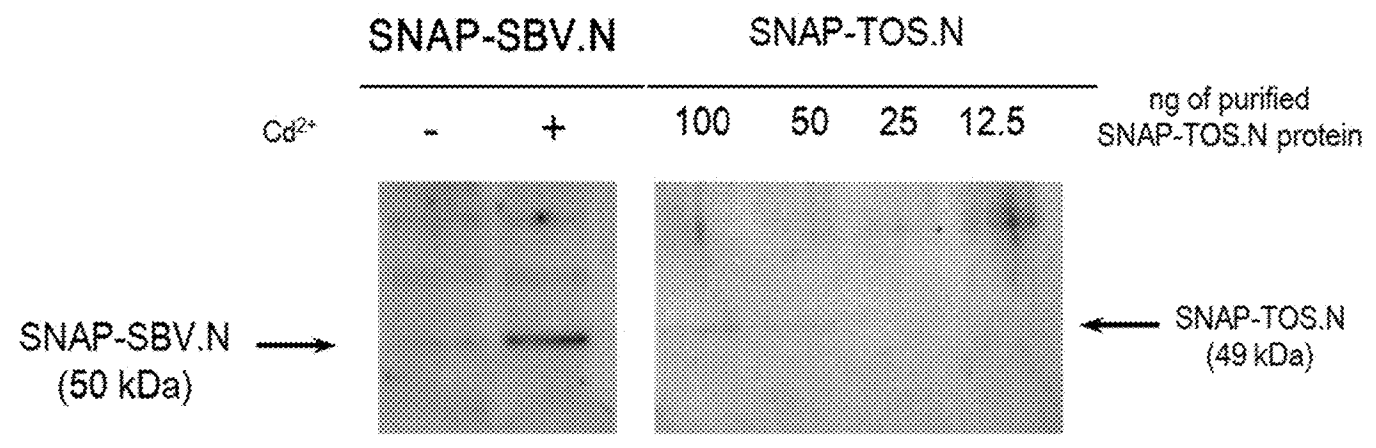
Figure 10B:
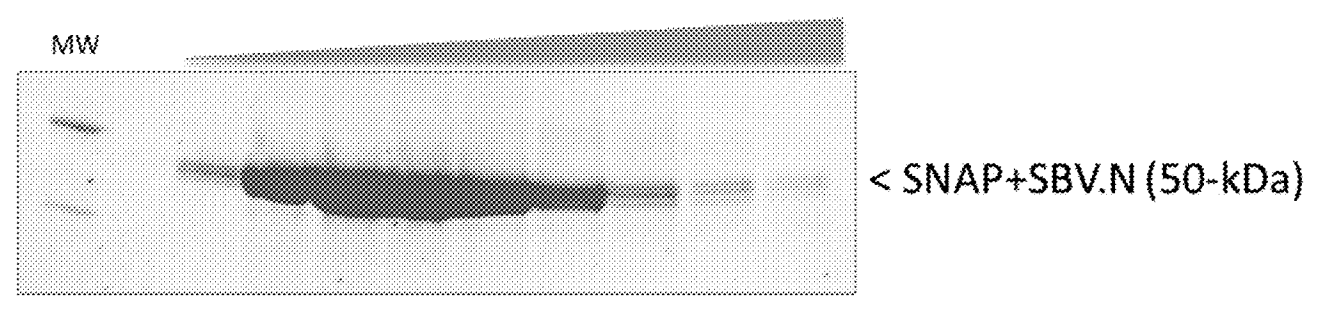

FIG. 10A shows an immunoblot assay performed on the supernatants of S2/SNAP-SBV.N cells induced for 10 days with $Cd^{2+}$ (+) or non induced (−). The secreted chimeric protein SNAP-SBV.N (theorical MWV 50 kDa) was detected using an anti-$His_{tag}$ antibody, in comparison to define amounts of highly purified chimeric protein SNAP-TOS.N (theorical MW 49 kDa). FIG. 10B shows an immunoblot performed on fractions of size-exclusion chromatography column (Coomassie blue staining of PAGE-SDS) corresponding to the final purification step of secreted SNAP+SBV.N protein from induced S2/SNAP+SBV.N cells for 10 days.

Figure 11:
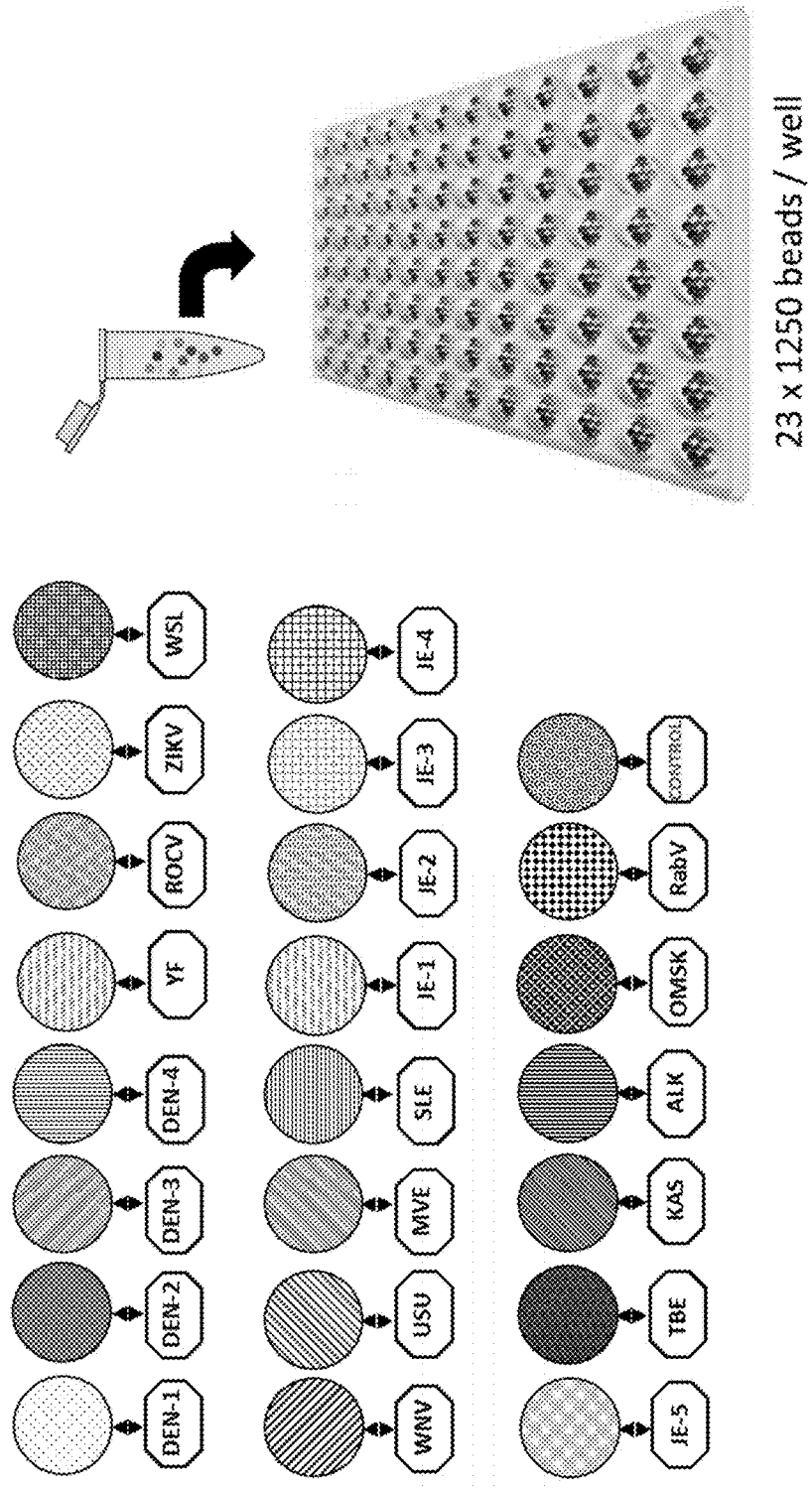

FIG. 11 shows an example of a device containing the antigen-coated microspheres of the invention.

DETAILED DESCRIPTION OF THE INVENTION

The 6-alkylguanine-DNA-alkyltransferase enzyme (AGT, also known as ATase or MGMT, and hereafter referred to as "AGT") is numbered EC 2.1.1.63 in the IUBMB enzyme nomenclature. It is a 6-alkylguanine-DNA-alkyltransferase DNA repair enzyme of 207 amino acid residues whose function in the cells is to repair alkylated DNA. More precisely, AGT acts on $O^6$-methylated guanine in DNA by irreversibly transferring the methyl group in an $S_N2$ reaction to a reactive cysteine residue (Cys 145). Recently, a number of O6-benzylguanine derivatives have been shown to irreversibly react with said enzyme by transferring their benzyl group to the active site cysteine of the AGT enzyme (cf. Damoiseaux et al., ChemBiochem., 2001, WO 2004/031404 and WO 2005/085470).

The present inventors have developed and validated immunoassays leading to rapid and simultaneous detection of several antibodies generated by a wide range of diseases, in particular arboviral diseases and VHFs, in biological fluids.

To achieve both optimal sensitivity and specificity for the detection of low amount of antibodies, an oriented antigen coupling procedure has been developed. This oriented antigen coupling procedure is based on the covalent interaction between the AGT enzymes and their substrates, the O6-benzylguanine derivatives, which irreversibly react with AGT enzymes by transferring their benzyl group to the active site cysteine of the enzyme. Accordingly, a number of target antigens can be fused to an AGT enzyme moiety, resulting in different chimeric fusion proteins (hereafter referred to as [AGT-Antigen] fusion proteins), that can be used as capture reagents for the antibodies present in a biological sample. The present inventors have shown that this antibody capture is enhanced when these fusion proteins are bound to solid supports thanks to the specific AGT-substrate interaction. Coating the said solid supports with AGT-substrate is thus an essential step of the immunoassay of the invention.

Figure 1:
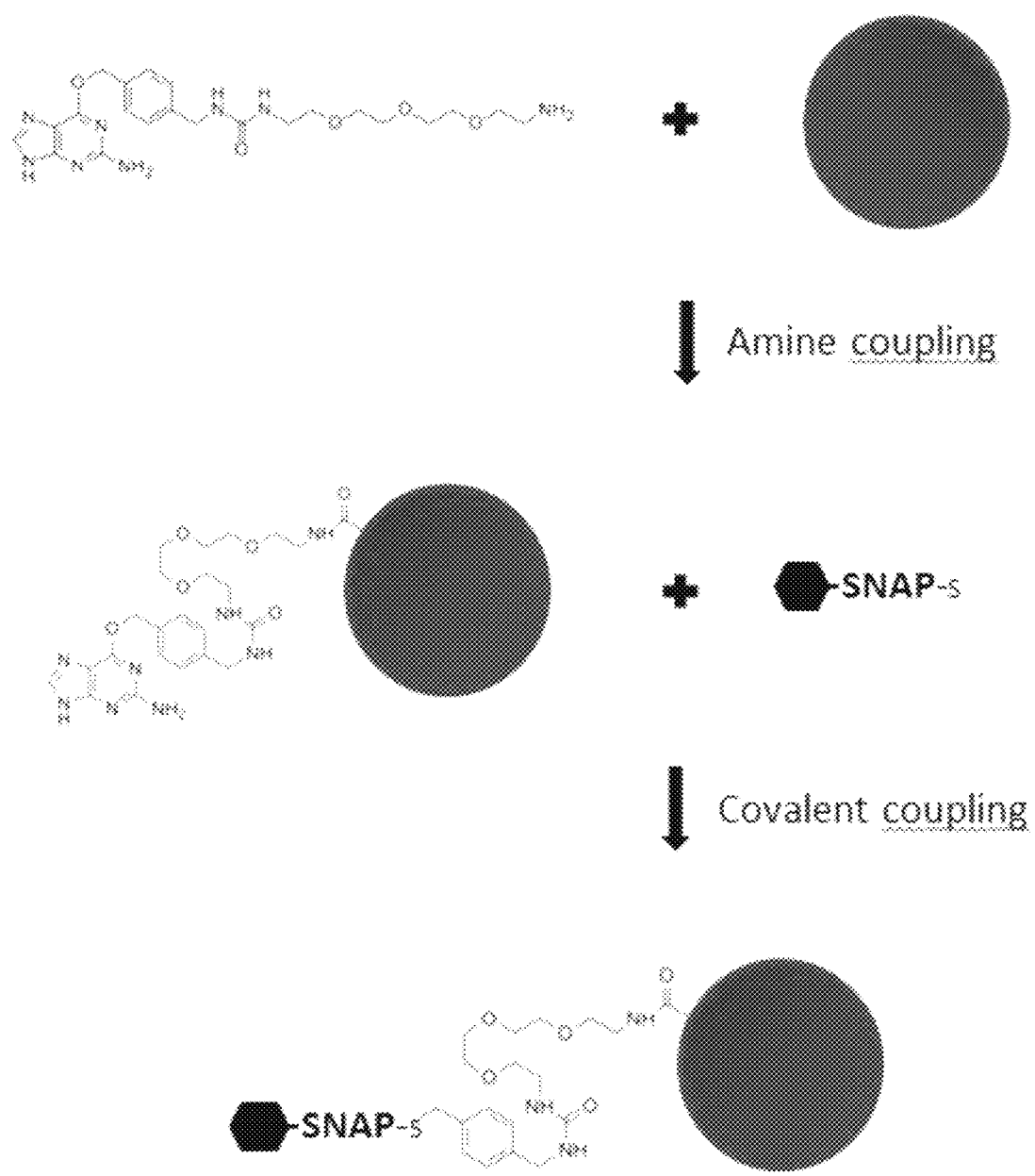

More precisely, in the context of the invention, the method for coupling antigens to solid supports comprises the two following steps: i) the coating of solid surfaces with an AGT substrate (e.g. BG-PEG-amino), and ii) the covalent immobilization of chimeric [AGT-Antigen] fusion proteins using the AGT substrate as an anchor (see FIG. 1). Before being coated with said AGT substrate, the solid surfaces are advantageously functionalized, preferably by using an optimized two-step carbodiimide process (Kufer S K, Eur. Biophys. J. 2005), so that the AGT substrate is covalently attached to the solid surfaces. Once these steps have been performed, the solid surfaces carry AGT substrates that are irreversibly linked to the chimeric [AGT-antigen]fusion proteins. Due to the high specificity of this reaction, the fusion protein is exclusively coupled via the cysteine-containing domain of the AGT enzyme, thus leaving the antigen accessible for its interactions with antibodies.

This coupling procedure is very advantageous as it allows the binding of the antigen in an oriented manner on the solid supports. Also, this antigen coupling procedure advantageously enables to obtain a multimeric antigen organization on a solid surface, so as to enhance immunoglobulin G, and potentially immunoglobulin M, capture efficiency. Consequently, the antigen-coupled microspheres developed in the experimental part of the application have shown enhanced capture of specific antibodies as compared to antigen-coupled microspheres produced by standard non-oriented amine coupling procedures (see the experimental part below and FIG. 3). Finally, this antigen coupling procedure enables to obtain a high coupling efficiency and a long-term stability of the antigen-conjugated microspheres (>6 months at 4° C.).

Importantly, the solid supports used in the immunoassays of the invention should be intrinsically identifiable, so that it is possible to determine precisely which antigen is carried by which solid support. The antigen-coupled and identifiable solid supports are then used as capture reagents for specific human immunoglobulins and are therefore contacted with the biological sample of the patient.

The final step of the method of the invention involves the detection of the solid supports which are effectively bound to immunoglobulins. The identification of immunoglobulin-coated solid support(s) enables to diagnose which pathogen was infecting the patient (as each solid support matches with a defined pathogenic antigen). This final detection step is performed by any usual means, for example by using labeled detection antibodies and by identifying the nature of the solid support.

Advantageously, the method of the invention involves only the detection of the presence of antibodies in diseased patients, but knowledge about the identity of those antibodies is not required.

As shown in the experimental part of the application, the inventors have used the antigen-coupling procedure of the invention to generate a number of different antigen-coated fluorescent microspheres. Presently, 16 distinct sets of microspheres have been coupled with 16 purified chimeric [AGT-Antigen] fusion proteins, allowing titration of 16 serum antibodies specific to different proteins of the dengue serotypes 1 to 4, West Nile, yellow fever, Japanese encephalitis, tick-borne encephalitis, Saint-Louis encephalitis, Murray Valley encephalitis, Wesselsbron, Zika, Rocio, Usutu, Rift Valley fever, and chikungunya virus. These 16 distinct sets of microspheres have been mixed in a single sample without affecting the sensitivity and specificity of the detection (see FIG. 5). The production of this system is highly time- and cost-effective, as only a very small amount of recombinant antigen (<50 µg) is required to produce one set of antigen-coupled microspheres (~$1.25 \times 10^6$ microspheres), such set being sufficient to perform 500 individual assays.

In a first aspect, the present invention relates to a method for detecting at least two target antibodies in a biological sample comprising:
(a) contacting a first solid support comprising an AGT substrate covalently coupled to a first fusion protein comprising an AGT polypeptide having a O6-alkylguanine-DNA alkyltransferase activity and a first epitope that is recognized by a first target antibody with the biological sample;
(b) contacting a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody with the biological sample; and
(c) detecting the presence or absence of the two target antibodies.

More precisely, the present invention relates to an in vitro assay method for detecting at least two different target antibodies present in a biological sample from a subject, said method comprising the steps of:
(a) providing a first fusion protein comprising:
  a polypeptide comprising a first epitope that is recognized by a first target antibody and
  a AGT polypeptide having a O6-alkylguanine-DNA alkyltransferase activity,
(b) contacting said first fusion protein with a first solid support, said support being covalently coupled with a substrate of said AGT polypeptide,
(c) obtaining a first solid support covalently coupled with a first epitope that is recognized by the first target antibody,
(d) providing a second fusion protein comprising:
  a polypeptide comprising a second epitope, said second epitope being recognized by a second target antibody but not by said first target antibody, and
  a AGT polypeptide having a O6-alkylguanine-DNA alkyltransferase activity,
(e) contacting said second fusion protein with a second solid support, said support being covalently coupled with a substrate of said AGT polypeptide,
(f) obtaining a second solid support covalently coupled with a second epitope that is recognized by the second target antibody, but not by said first target antibody, wherein said first and second solid supports can be specifically identified from each other,
(g) contacting said biological sample with the first and second solid supports obtained in steps (c) and (f),
(h) detecting the presence of said at least two target antibodies.

As used hereafter, the terms "an antibody", "a fusion protein", "an epitope", "an antigen", "an AGT polypeptide", "a solid support" and the like have obviously to be understood as usual in the art, that is, in a broad manner. In particular, they encompass not only particular single molecules but a number of said molecules. For example, the term "solid support" encompasses a subset of numerous identical solid supports, the term "microparticle" encompasses a subset of numerous identical microparticles, and the term "fusion protein" encompasses a number of identical single protein molecules. In the context of the present invention, it is noteworthy that a solid support carries a number of identical fusion proteins, said fusion proteins containing, apart from the AGT polypeptide, identical antigen, and therefore identical epitopes, so that the antibodies which will be detected on the solid support can be unambiguously identified.

As used herein, the term "fusion protein" means a polypeptide containing a protein or a polypeptide created through the artificial joining of two or more polypeptides. In the immunoassays of the invention, said fusion proteins contain a AGT polypeptide and an antigen, containing at least one epitope. Fusion proteins can be obtained through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either. If the two entities are proteins, a linker (or "spacer") peptides can be added, which makes it more likely that the proteins fold independently and behave as expected. In particular, the fusion proteins of the invention can be obtained by providing vectors comprising AGT encoding sequences in frame with an epitope or antigen encoding sequences, either attached to the N-terminal or to the C-terminal side of the AGT DNA sequence. These vectors may be introduced in prokaryotic hosts, including eubacteria such as $E.\ coli$ bacteria, or eukaryotic hosts, e.g., yeast, insect cells or mammalian cells and the recombinant fusion proteins may be produced under appropriate conditions. Typical constructions are presented in the experimental part of this application.

The term "antibody" as used herein is intended to include monoclonal antibodies, polyclonal antibodies, and chimeric antibodies. Preferably, the antibodies which are to be detected by the immunoassays of the invention are polyclonal antibodies, which are present in biological samples of diseased patients, and have therefore been generated from different B cell sources. As such, they recognize different epitopes exhibited by a pathogenic antigen (on the other hand, monoclonal antibodies are derived from a single cell line and recognize the same epitope).

An antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VII and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

Antibody can be of different isotypes (namely IgA, IgD, IgE, IgG or IgM). Both IgG and IgM type antibodies can be detected by the present method. Of note, these isotypes are composed of two identical heavy chains and two identical light chains that are joined by disulfide bonds. Importantly, IgM antibodies form polymers where multiple immunoglobulins are covalently linked together with disulfide bonds, mostly as a pentamer but also as a hexamer, so that they have a molecular mass of approximately 900 kDa (in their pentamer form). Because each monomer has two antigen binding sites, a pentameric IgM has 10 binding sites. Typically, however, IgM antibodies cannot bind 10 antigens at the same time because the large size of most antigens hinders binding to nearby sites. Due to its polymeric nature, IgM possesses high avidity.

Antibody fragments can also be detected thanks to the present method. This term is intended to include Fab, Fab', F(ab)2, scFv, dsFv, ds-scFv, dimers, minibodies, diabodies, and multimers thereof and bispecific antibody fragments.

Monoclonal antibodies can be used in the present immunoassays; for example for detecting the immunoglobulins that are bound to the solid supports. As used herein, "monoclonal antibody" defines an antibody arising from a homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

The term "antigen" herein means any substance that causes the immune system to produce antibodies against the said substance. An "immunogenic" antigen is a specific type of antigen which is able to stimulate an adaptive immune response if injected on its own. At the molecular level, an antigen is thus characterized by its ability to be "bound" to the antigen-binding site of an antibody.

In the context of the present invention, an antibody is said to "bind" a define antigen (or epitope) or to "recognize" said antigen (or epitope) if said antibody has an affinity constant $K_a$ (which is the inverted dissociation constant, i.e. $1/K_d$) higher than $10^5$ $M^{-1}$, preferably higher than $10^6$ $M^{-1}$, more preferably higher than $10^7$ $M^{-1}$ for said antigen (or epitope). This affinity can be measured for example by equilibrium dialysis or by fluorescence quenching, both technologies being routinely used in the art.

In the context of the invention, antigens or epitopes include: proteins, lipoproteins, polysaccharides, and glycoproteins. Said proteins include viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, linear peptides, oligopeptides etc. Said antigens can also be tumor associated antigens such as carcinoembryonic antigen (CEA), CA 15-3, CA 125, CA 19-9, prostate specific antigen (PSA), TAA complexes, SSX2 or NERCMSL. Said antigens can also be haptens, and other moieties comprising low molecular weight molecules, such as saccharides, oligosaccharides, polysaccharides, peptides, mucins, toxins, and allergens (pollen, egg white). Infectious toxins are well known in the art. One can cite, as examples, the botulinum neurotoxins, the *Clostridium perfringens* epsilon toxin, ricin, saxitoxin, shigatoxin, tetrodotoxin, staphylococcal enterotoxins, etc. Mucins are also well known in the art. MUC5AC, MUC5B and MUC2 are examples thereof. In particular, they can be naturally-occurring polysaccharides such as Group B steptococcal and pneumococcal capsular polysaccharides (including type III), *Pseudomonas aeruginosa* mucoexopolysaccharide, and capsular polysaccharides (including fisher type I), and *Haemophilus influenzae* polysaccharides.

In another preferred embodiment, said antigen or epitope is expressed by a virus which is selected in the group consisting of: the influenza virus, the hepatitis A virus, the Hepatitis B virus, the Hepatitis C virus, the Hepatitis E virus, the Hepatitis G virus, the HIV virus, the yellow fever virus, the dengue virus, the Japanese encephalitis virus, the tick-borne encephalitis virus, the Usutu or West Nile viruses, the Rift Valley fever or Toscana viruses, the chikungunya virus, the respiratory synticial virus, the Rocio virus, the morbillivirus, the Murray encephalitis virus, the Wesselbron virus, the Zika virus, the lymphocytic choreomeningitis virus, the Ebola virus, the Marburg virus, the Crimean-Congo hemorrhagic fever virus, the Lassa virus, the Junin virus, the Machupo virus, the Sabia virus, the Guanarito virus, the mumps virus, the rabies virus, the rubella virus, the varicella zoster virus, the *herpes simplex* types 1 and 2, more generally an alphavirus, an adenovirus, an echovirus, a rotavirus, a flavivirus, a rhinovirus, an orthobunyavirus, a poliovirus, a human parvovirus, an enterovirus, a coronavirus, a human papillomavirus, the human cytomegalovirus, the Epstein-Barr virus, the *parainfluenzae* viruses from types 1, 2 and 3, or any identified virus.

In another preferred embodiment, said antigen or epitope is expressed by a virus belonging to a family which is selected from the group consisting of: the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg).

In another preferred embodiment, said antigen or epitope is expressed by a parasitic protozoa (such as those from the *Leishmania* genus, or *Toxoplasma Gondii, Entamoeba histolytica, Plasmodium falciparum, Pneumocystis carinii*, or

*Giardia lambia*), worms (such as nematodes, cestodes, or trematodes), or arthropods (such as crustaceans, insects, arachnids).

In another preferred embodiment, said antigen or epitope is expressed by an infectious bacterium, for example of the genera *Salmonella, Shigella, Streptococcus, Staphylococcus, Mycoplasma, Diphteriae, Leptospirosa, Rickettsia* or *Escherichia*. In a further preferred embodiment, the said bacterium belongs to one of the species selected from *H. influenzae, S. pneumoniae, Klebsiella pneumoniae, S. aureus, Bacillus anthracis, Listeria monocytogenes, Bordetella pertussis, Clostridium tetani, S. epidermidis, N. meningiditis, Pseudomonas aeruginosa, Chlamydia trachomatis, Mycobacterium tuberculosis, Coxiella burnetii, Leptospirosa interrogans* and *E. coli*.

In another preferred embodiment, said antigen or epitope is expressed by a fungus or yeast (e.g. from the species *Candida, Aspergillus, Cryptococcus, Histaplasma, Pneumocystis,* or Stachybotrys).

Antigens usually present several surface features that can act as points of interaction for specific antibodies. Any such distinct molecular feature constitutes an epitope. As used herein, the term "epitope" therefore designates a particular molecular surface feature of an antigen, for example a fragment of an antigen, which is capable of being bound by at least one antibody. On a molecular level, an epitope therefore corresponds to a particular molecular surface feature of an antigen (for example a fragment of an antigen) which is recognized and bound by a specific antibody. In the context of the present invention, the "fusion proteins" contain at least one epitope that is recognized by a target antibody. Preferably, said fusion proteins contain whole antigens, comprising several epitopes. These epitopes can be linear or conformational epitopes. As used herein, a linear (or sequential) epitope is an epitope that is recognized by antibodies by its linear sequence of amino acids, or primary structure. In contrast, a conformational epitope is recognized by its specific three-dimensional shape. Preferably, the fusion proteins of the invention contain conformational epitopes, as most polyclonal antibodies recognize same.

It is important however that such antigens do not present cross-reactive epitopes, i.e. epitopes that are recognized by non-specific antibodies that will bind thereto. If it was the case, the specificity of the method of the invention would be decreased.

In a more preferred embodiment, said epitope is present on a viral protein which is selected in the group consisting of: the EDIII protein of the dengue virus 1 encoded by SEQ ID NO:3, the EDIII protein of the dengue virus 2 encoded by SEQ ID NO:4, the EDIII protein of the dengue virus 3 encoded by SEQ ID NO:5, the EDIII protein of the dengue virus 4 encoded by SEQ ID NO:6, the EDIII protein of the West Nile virus encoded by SEQ ID NO:7, the EDIII protein of the yellow fever virus encoded by SEQ ID NO:8, the EDIII protein of the Japanese encephalitis virus encoded by SEQ ID NO:9, the EDIII protein of the Zika virus encoded by SEQ ID NO:10, the EDII protein of the Wesselbron virus encoded by SEQ ID NO:11, the EDIII protein of the Rocio virus encoded by SEQ ID NO:12, the EDIII protein of the Murray encephalitis virus encoded by SEQ ID NO:13, the EDIII protein of the Saint-Louis encephalitis virus encoded by SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, and the EDII protein of the Rabensburg virus encoded by SEQ ID NO:58 and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

In a preferred embodiment, the first and second epitopes (or antigens) that are fused with the hAGT enzyme in the fusion proteins used in the method of the invention belong to the same taxonomic level, i.e. they belong to the same family (e.g. the Flaviviridae family, the Bunyaviridae family, the Arenaviridae family or the Filoviridae family) or genus or species, but which have different serotypes. In other words, the said first and second epitopes can be expressed by closely related viruses, e.g. belong to the same family, genus or species but having different serotypes such as the dengue virus 1, 2, 3, or 4.

Alternatively, in another preferred embodiment, said first and second epitopes (or antigens) belong to unrelated biological families or genus or specie.

Importantly, the immunoassays of the invention rely on the detection of a large number of antibodies, which are known or unknown. By "large number", it is herein understood at least 5, more preferably at least 15, more preferably at least 50 and even more preferably at least 100 antibodies. Therefore, in a preferred embodiment, the assay method of the invention is used to detect at least 5, more preferably at least 15, and preferably at least 50 and even more preferably at least 100 target antibodies in a biological sample from a subject. It is of no relevance for the method of the invention whether the particular antibodies are properly characterized, since the procedure relies only on the detection of the presence of said antibodies, and not on their nature.

In a preferred embodiment of the invention, the said first and second fusion proteins that are coupled with the said first and second solid supports are selected in the group consisting of:

SEQ ID NO:21 (corresponding to the fusion protein [SNAP-DEN1.EDIII])

SEQ ID NO:42 (corresponding to the fusion protein [SNAP-SBV.N])

SEQ TD NO:49 (corresponding to the fusion protein [SNAP-EV71.VP1])

SEQ ID NO:51 (corresponding to the fusion protein [SNAP-JE.sE])

SEQ ID NO:53 (corresponding to the fusion protein [SNAP-JE-1.EDIII])

SEQ ID NO:60 (corresponding to the fusion protein [SNAP-JE-2.EDIII])

SEQ ID NO:62 (corresponding to the fusion protein [SNAP-JE-4.EDIII])

SEQ ID NO:64 (corresponding to the fusion protein [SNAP-JE-5.EDIII])

SEQ ID NO:66 (corresponding to the fusion protein [SNAP-RabV.EDIII])

SEQ ID NO:68 (corresponding to the fusion protein [SNAP-flavivirus.EDIII])

SEQ ID NO:70 (corresponding to the fusion protein [SNAP-RR.sE2])

SEQ ID NO:72 (corresponding to the fusion protein [SNAP-MAY.sE2])

SEQ ID NO:74 (corresponding to the fusion protein [SNAP-WEE.sE2])

SEQ ID NO:76 (corresponding to the fusion protein [SNAP-EEE.sE2])

SEQ ID NO:78 (corresponding to the fusion protein [SNAP-VEE.sE2])
SEQ ID NO:80 (corresponding to the fusion protein [SNAP-AKA.N])
SEQ ID NO:82 (corresponding to the fusion protein [SNAP-AIN.N])
SEQ ID NO:84 (corresponding to the fusion protein [SNAP-SHA.N])
SEQ ID NO:86 (corresponding to the fusion protein [SNAP-huCOV.N])
SEQ ID NO:88 (corresponding to the fusion protein [SNAP-huCOV.S])
SEQ ID NO:90 (corresponding to the fusion protein [SNAP-HCV.C])
SEQ ID NO:92 (corresponding to the fusion protein [SNAP-MSP+AMA])
SEQ ID NO:94 (corresponding to the fusion protein [SNAP-HbpA1])
SEQ ID NO:96 (corresponding to the fusion protein [SNAP-MUB40])
SEQ ID NO:98 (corresponding to the fusion protein [SNAP-moCLEC5A])
SEQ ID NO:100 (corresponding to the fusion protein [SNAP-huCLEC5A])
SEQ ID NO: 102 (corresponding to the fusion protein [SNAP-cxVAGO])
SEQ ID NO:104 (corresponding to the fusion protein [SNAP-aaVAGO])
SEQ ID NO:109 (corresponding to the fusion protein [SNAP-CCHF.N])
SEQ ID NO:111 (corresponding to the fusion protein [SNAP-EBO.N])
SEQ ID NO:113 (corresponding to the fusion protein [SNAP-MAR.N])
SEQ ID NO:115 (corresponding to the fusion protein [SNAP-LAS.N])
SEQ ID NO:117 (corresponding to the fusion protein [SNAP-JUN.N])
SEQ ID NO:119 (corresponding to the fusion protein [SNAP-MAC.N])
SEQ ID NO:121 (corresponding to the fusion protein [SNAP-GUA.N])
SEQ ID NO:123 (corresponding to the fusion protein [SNAP-SAB.N])
SEQ ID NO:125 (corresponding to the fusion protein [SNAP-OMSK.EDIII])
SEQ ID NO:127 (corresponding to the fusion protein [SNAP-KYA.EDIII])
SEQ ID NO:129 (corresponding to the fusion protein [SNAP-ALK.EDIII])
SEQ ID NO:131 (corresponding to the fusion protein [SNAP-LAS.ectoGP1])
SEQ ID NO:133 (corresponding to the fusion protein [SNAP-JUN.ectoGP1])
SEQ ID NO:135 (corresponding to the fusion protein [SNAP-MAC.ectoGP1])
SEQ ID NO:137 (corresponding to the fusion protein [SNAP-GUA.ectoGP1])
SEQ ID NO:139 (corresponding to the fusion protein [SNAP-SAB.ectoGP1])
SEQ ID NO:141 (corresponding to the fusion protein [SNAP-LAS.ectoGP2])
SEQ ID NO:143 (corresponding to the fusion protein [SNAP-JUN.ectoGP2])
SEQ ID NO:145 (corresponding to the fusion protein [SNAP-MAC.ectoGP2])
SEQ ID NO:147 (corresponding to the fusion protein [SNAP-GUA.ectoGP2])
SEQ ID NO:149 (corresponding to the fusion protein [SNAP-SAB.ectoGP2]), and
SEQ ID NO:151 (corresponding to the fusion protein [SNAP-HEV.C]).

Consequently, the in vitro method of the invention enables to detect target disease(s) that is (are) viral, bacterial, yeast or fungi-mediated infection. Preferably said viral infection is caused by a Papillomavirus or RNA viruses from the families of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg). Preferably, said bacterial infection is caused by *Leptospirosa Interrogans*. Preferably, said infection is caused by *Plasmodium falciparum*.

As used herein, the term "biological sample" refers to any samples which have been obtained from a patient and which might contain antibodies. Preferably, said biological sample is a biological fluid, for example an unfiltered biological fluid such as urine, cerebrospinal fluid, pleural fluid, synovial fluid, peritoneal fluid, amniotic fluid, gastric fluid, blood, serum, plasma, lymph fluid, interstitial fluid, saliva, physiological secretions, tears, mucus, sweat, milk, semen, seminal fluid, vaginal secretions, fluid from ulcers and other surface eruptions, blisters, and abscesses. It also refers to an extract of tissues including biopsies of normal, malignant, and suspect tissues or any other constituents of the body which may contain antibodies. The said biological sample can be pre-treated prior to use, such as preparing plasma from blood, diluting viscous fluids, or the like; methods of treatment can involve filtration, distillation, concentration, inactivation of interfering compounds, and the addition of reagents. In a preferred embodiment, said biological sample is chosen from whole blood, serum, plasma, urine, seminal fluid, cerebrospinal fluid and saliva.

Any polypeptide having $O^6$-alkylguanine-DNA alkyltransferase activity can be used in the method of the present invention. For the purpose of the invention, these polypeptides will be referred to as "AGT polypeptides".

AGT irreversibly transfers the alkyl group from its substrate, $O^6$-alkylguanine-DNA, to one of its cysteine residues. A substrate analogue that rapidly reacts with AGT is $O^6$-benzyl-guanine, the second order rate constant being approximately $10^3$ sec$^{-1}$ M$^{-1}$.

In the context of the invention, a polypeptide is said to have "$O^6$-alkylguanine-DNA alkyltransferase activity" (or "AGT activity") if it is capable of irreversibly transferring an alkyl group from a $O^6$-alkylguanine-containing molecule to one of its own cysteine residues. The "$O^6$-alkylguanine-DNA alkyltransferase activity" of the said polypeptide can be demonstrated by, for example, contacting known labeled $O^6$-benzyl-guanine derivatives and monitoring the transfer of said label on to the tested polypeptide. If the assay is performed in cellulo or in cell extracts, the reaction of the endogenous AGT of the host cells should be controlled, so that endogenous AGT does not interfere with the said polypeptide. Therefore, known AGT-deficient cell lines are preferably used. Assays for identifying AGT activity are now well described. Several $O^6$-benzyl-guanine derivatives are commercially available ($O^6$-benzyl-guanine is distributed for example by Santa Cruz biotechnology, and fluorescently-labeled O⁶-benzyl-guanine derivatives can be obtained from New England Biolabs NEB). Some of these assays are disclosed in WO 2005/085470 and in WO 2004/031405.

In the context of the invention, the "catalytic domain" of the AGT polypeptide corresponds to the active site of said enzyme, or, in other words, to the part of the enzyme at which the transfer of the alkyl group from its substrate, O⁶-alkylguanine-DNA, to a reactive cysteine residue, occurs. In the structure of hAGT bound with O⁶-benzylguanine in its active site, four amino acids are in proximity of either the benzyl ring (Pro140, Ser159, Gly160), or could make contact with the N9 of the nucleobase (Asn157). Mutations at position Pro140 and Gly160 have previously been shown to affect the reaction of hAGT with O⁶-benzyl-guanine (Xu-Welliver et al., Biochemical Pharmacology 1999): a proline at position 140 is believed to be essential for its interaction with the benzyl ring, and the mutation Gly160Trp has been shown to increase the reactivity of hAGT towards O⁶-benzylguanine.

In a preferred embodiment, the AGT polypeptide having O⁶-alkylguanine-DNA alkyltransferase activity is the human AGT polypeptide (referenced as NP_002403.2) of sequence SEQ ID NO: 1, the mouse AGT identified as NP_032624.1 (SEQ ID NO: 18), the rat MGMT identified as NP_036993.1 (SEQ ID NO: 19) or a homologous sequence thereof, said homologous sequence having O⁶-alkylguanine-DNA alkyltransferase activity.

As used herein, the term "homologous" refers to sequences that have sequence similarity. The term "sequence similarity", in all its grammatical forms, refers to the degree of identity or correspondence between nucleic acid or amino acid sequences. In the context of the invention, two amino acid sequences are "homologous" when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of the amino acids are similar. Preferably the similar or homologous polypeptide sequences are identified by using the algorithm of Needleman and Wunsch.

Preferably, the homologous sequence to the AGT enzyme shares at least 64% amino acid sequence identity, preferably at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity with SEQ ID NO: 1. In a preferred embodiment, an homologous sequence of SEQ ID NO: 1 is at least 64%, preferably 70%, and more preferably 80% identical to SEQ ID NO: 1.

In a preferred embodiment, the said homologous polypeptide is a fragment or a mutant of the hAGT polypeptide of SEQ ID NO: 1, said fragment or mutant having a O⁶-alkylguanine-DNA alkyltransferase activity.

Said fragments can have a size of at least 50, preferably 100, and more preferably 150 amino acids, and contain at least the "catalytic domain" of the AGT polypeptide as defined above, which is responsible of the O⁶-alkylguanine-DNA alkyltransferase activity of the AGT enzyme. These fragments can be obtained using common techniques which are known by the skilled person.

Different mutant enzymes derived from native AGT have been described so far (Lim A. et al, 1996; Daniels D. S. et al, 2000; Juillerat A. et al, 2003, WO 2005/085470, WO 2004/031405). In particular, a mutant protein of 20 kDa containing the mutations Cys62Ala, Lys125Ala, Ala127Thr, Arg128Ala, Gly131Lys, Gly132Thr, Met134Leu, Arg135Ser, Cys150Ser, Asn157Gly, Ser159Glu truncated at amino acid 182 has been obtained (the so-called "AGT26" mutant in WO 2005/085470, also called "SNAP 26" in WO 2006/114409). This particular mutant "SNAP26" has been shown to have enhanced labelling activity.

In the context of the present invention, the sequence of a more preferred AGT polypeptide contains the mutations described in WO 2005/085470, which positions can be easily transposed in view of SEQ ID NO: 1, the starting methionine residue of SNAP26 corresponding to the methionine residue in position 32 of SEQ ID NO: 1 (31 amino acids should therefore be added to the positions disclosed in WO 2005/085470 so as to obtain the corresponding ones in SEQ ID NO: 1).

In a preferred embodiment, the AGT homologous sequence useful in the invention corresponds to the native AGT sequence of SEQ ID NO: 1, in which between 1 and 30, preferably between 6 and 25, and in particular 14, 15, 16, 17, 18, 19, 20, 21, 22, or 23 amino acids are substituted by other amino acids, and/or 1 to 40, preferably 1 to 20, in particular 10 to 20 amino acids, more preferably 15 amino acids at the C-terminus are deleted.

In a more preferred embodiment, the AGT homologous sequence contains the following mutations as compared with SEQ ID NO: 1:
(A) Lys31 replaced by Arg, or Met32 replaced by Ser, or Cys93 replaced by Ala, or Lys156 replaced by Ala, or Ala158 replaced by Thr, or Arg159 replaced by Ala, or Gly162 replaced by Lys, or Gly163 replaced by Thr, or Met165 replaced by Leu, or Arg166 replaced by Ser, or Cys181 replaced by Ser, or Asn188 replaced by Gly, or Ser190 replaced by Glu, or Gly214 replaced by Pro, or Ser215 replaced by Ala, or Ser216 replaced by Gly, or Gly217 replaced by Ile, or Leu218 replaced by Gly, or Gly220 replaced by Pro, or Ala221 replaced by Gly, or Trp222 replaced by Ser, or (B) Lys31-Met32 replaced by Arg-Ser, or Ala158-Arg159 replaced by Thr-Ala, or Gly162-Gly163 replaced by Lys-Thr, or Met165-Arg166 replaced by Leu-Ser, or Gly162-Gly163/Met165-Arg166 replaced by Lys-Thr/Leu-Ser, or Asn188/Ser190 replaced by Gly/Glu, or Gly214-Ser215-Ser216-Gly217-Leu218 replaced by Pro-Ala-Gly-Ile-Gly, or Gly220-Ala221-Trp222 replaced by Pro-Gly-Ser, preferably in combination with any other amino acid replacements cited in (A), or (C) Truncation after Leu223 (amino acids 224-238 are deleted), preferably in combination with any other amino acid replacement cited in (A) or (B).

Preferred AGT homologous sequences are those being truncated after Leu223.

Preferred AGT homologous sequences are those wherein two out of the modifications (B) are present, and optionally truncation after Leu223.

Preferred AGT homologous sequences are those wherein three out of the modifications (B) are present, and optionally truncation after Leu223.

Preferred AGT homologous sequences are those wherein four out of the modifications (B) are present, and optionally truncation after Leu223.

Preferred AGT homologous sequences are those wherein five out of the modifications (B) are present, and optionally truncation after Leu223.

Preferred AGT homologous sequences are those wherein six out of the modifications (B) are present, and optionally truncation after Leu223.

Other preferred AGT homologous sequences are those containing a combination of 2, 3, 4, 5, 6, 7, 8, 9, 10, 11, 12, 13, 14, 15, 16, 17, 18, 19, or 20 mutations chosen among the modifications disclosed in (A), and optionally truncated after Leu223.

In a far more preferred embodiment, the AGT polypeptide of the invention is the SNAP mutant of SEQ ID NO: 2, which is homologous to the hAGT enzyme and contains the mutations Lys31Arg, Met32Ser, Cys93Ala, Lys156Ala, Ala158Thr, Arg159Ala, Gly162Lys, Gly163Thr, Met165Leu, Arg166Ser, Cys181Ser, Asn188Gly, Ser190Glu, Gly214Pro, Ser215Ala, Ser216Gly, Gly217Ile, Leu218Gly, Gly220Pro, Ala221Gly, Trp222Ser and truncation after Leu223 as compared with SEQ ID NO: 1. The SNAP mutant of SEQ ID NO: 2 shares 77% homology with the amino acid sequence of the human 6-methylguanine-DNA-methyltransferase (NP_002403.2, SEQ ID NO: 1), and 70% homology with the amino acid sequence of the mouse 6-methylguanine-DNA-methyltransferase (NP_032624.1, SEQ ID NO: 18).

In an even more preferred embodiment, the AGT enzyme is the SNAP mutant protein of SEQ ID NO: 2 or a homologous thereof, having $O^6$-alkylguanine-DNA alkyltransferase activity. Preferably, said homologous sequence to the SNAP mutant protein is at least identical at more than 80%, preferably 81%, more preferably 82%, more preferably 83%, more preferably 84%, more preferably 85%, preferably 86%, more preferably 87%, more preferably 88%, more preferably 89%, more preferably 90%, more preferably 91%, more preferably 92%, more preferably 93%, more preferably 94%, more preferably 95%, more preferably 96% to the and even more preferably 97% to the SNAP mutant protein of sequence SEQ ID NO: 2, and has $O^6$-alkylguanine-DNA alkyltransferase activity as defined above.

Said homologous polypeptides having $O^6$-alkylguanine-DNA alkyltransferase activity can be produced using protein engineering techniques known to the skilled person and/or using molecular evolution to generate and select new $O^6$-alkylguanine-DNA alkyltransferase. Such techniques are e.g. targeted mutagenesis, phage display methods, saturation mutagenesis, error prone PCR to introduce variations anywhere in the sequence, DNA shuffling used after saturation mutagenesis and/or error prone PCR, or family shuffling using genes from several species.

In the most preferred embodiment, the AGT polypeptide used in the method of the invention is the SNAP mutant of SEQ ID NO: 2.

The AGT enzyme irreversibly transfers the alkyl group from its substrate, $O^6$-alkylguanine-DNA, to one of its cysteine residues. However, substitutions of $O^6$-benzylguanine at the C4 of the benzyl ring do not significantly affect the reactivity of AGT against $O^6$-benzylguanine derivatives. This property has been used to transfer a label attached to the C4 of the benzyl ring to AGT (see WO 2004/031404 and WO 2005/085470).

A number of $O^6$-benzylguanine derivatives have been shown to react with the AGT enzyme by transferring their benzyl group to the active site cysteine of the AGT enzyme (cf. Damoiseaux et al., *ChemBiochem.*, 2001, WO 2004/031404 and WO 2005/085470).

In a preferred embodiment, the AGT substrates used in the method of the invention are $O^6$ benzyl guanine derivatives having the formula I:

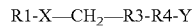

wherein:
R1 is a group recognized by said AGT polypeptide as a substrate, such as a heteroaromatic group containing 1 to 5 nitrogen atoms, and preferably a purine radical of the formula:

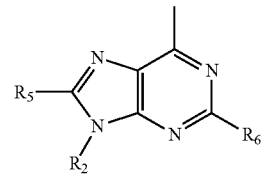

wherein R5 is hydrogen, halogen, e. g. chloro or bromo, trifluoromethyl, or hydroxy; R6 is hydrogen, hydroxy or unsubstituted or substituted amino; and R2 is hydrogen, an alkyl of 1 to 10 carbon atoms, or a saccharide moiety;

X is an oxygen or sulfur atom; preferably an oxygen atom;

R3 is an aromatic or a heteroaromatic group, or an optionally substituted unsaturated alkyl, cycloalkyl or heterocyclyl group with the double bond connected to $CH_2$; preferably a phenyl, e.g. a phenyl substituted by R4 in para or meta position, R4 is a linker moiety, Y is a reactive group, preferably an amino group.

In a preferred embodiment, said linker moiety R, is a flexible linker. Linker units are chosen in the context of the envisioned application, i.e. in the transfer of the substrate to a fusion protein comprising AGT. The linker does not interfere with the reaction with AGT nor with the target antibody.

For example, it can be a straight or branched chain alkylene group with 1 to 20 carbon atoms, preferably 5 to 15 carbon atoms, wherein:
(a) one or more carbon atoms are replaced by oxygen, in particular wherein every third carbon atom is replaced by oxygen, e.g. a polyethyleneoxy group with 1 to 5 ethyleneoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH=CH— or —C≡C—;
(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;
(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

In a preferred embodiment, R4 is a polyethyleneoxy group with 1 to 8 ethyleneoxy units, further comprising one to four nitrogen atoms carrying a hydrogen atom, which adjacent carbon atoms are substituted by oxo, representing an amide function —NH—CO—.

In a more preferred embodiment, R4 is —CH$_2$—NH—CO—NH—[C2H$_4$—O]$_n$—, wherein n is comprised between 1 to 8, preferably 2 to 6, and is most preferably 3.

In a preferred embodiment, said reactive group is a functional group that facilitates the attachment and bonding of the substrate on the solid support. Such functional groups are well-known in the art. They include amine, activated esters, acrylamides, acyl azides, acyl halides, acyl nitriles, aldehydes, ketones, alkyl halides, anhydrides, aryl halides, aziridines, boronates, activated carnoxylic acids, carbodiimides, diazoalkanes, epoxides, haloacetamides, haloplatinate, halotriazines, imido esters, isocyanates, isothiocyanates, maleimides, phosphoramidites, solyl halides, sulfonate esters and sulfonyl halides. It is preferably the amine group —NH$_2$.

On the opposite side, the solid support should be functionalized by complementary groups corresponding to such reactive groups. The complementary groups corresponding to each of these reactive groups are well-known in the art. They are given for example on the table I of WO 2010/107433.

In a preferred embodiment, the AGT substrate used in the method of the invention is:

In another preferred embodiment, the AGT substrate used in the method of the invention is the fluorescent linker designated "SNAP-Cell® 505", having the following formula:

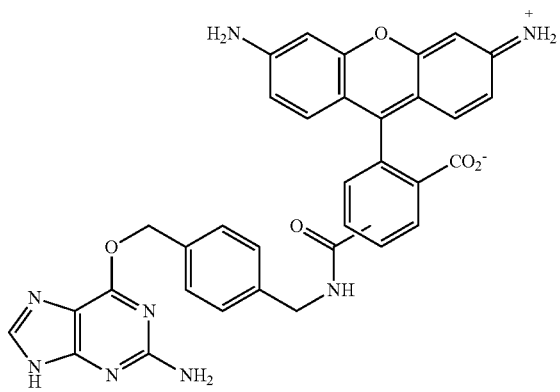

This benzylguanine derivative possesses one benzyl purine group (guanine) for the specific interaction with the SNAP domain, as well as one free amine group for the covalent coupling to the microsphere surface. It is commercialized by New England BioLaps and has been successfully coupled to the surface of the microparticles of the invention.

Substrates of the invention are generally prepared by standard methods known in the art. Particular methods are explained e.g. in patent application WO 2005/085470.

The methods of the invention require that the AGT substrates be covalently coupled to the solid supports. In the context of the present invention, an AGT substrate is "covalently coupled" to a solid support if it is permanently attached to the said solid support, and will not desorb or leach over time. According to the invention, an AGT substrate is permanently attached to the said solid support if it stays attached for a long period of storage, e.g., typically, at least 6 months of storage. A number of coupling proceedings have been described so far. Any of these coupling proceedings can be used in the immunoassay of the invention, provided that the AGT substrate becomes permanently attached to the solid support.

In the immunoassay of the invention, the covalent coupling is preferably performed by contacting the AGT substrates (with contain a reactive group Y, as mentioned above) with solid supports which have been previously functionalized with a complementary group such as those disclosed in table I of WO 2010/107433, the disclosure of which is incorporated herein by reference.

Thus, in a preferred embodiment, the methods of the invention use solid supports that have been functionalized with a group which is complementary to the reactive group of the AGT substrate, before being contacted with the AGT substrate.

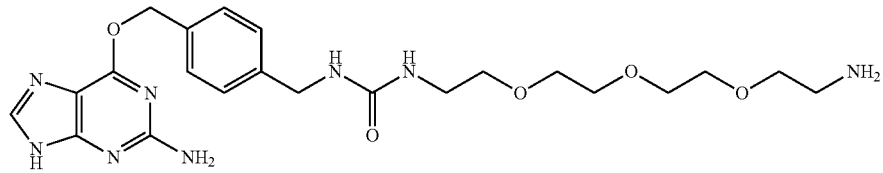 [SMILES: NCCOCCOCCOCCNC(=O)NCc1ccc(COc2nc(N)nc3[nH]cnc23)cc1]

A preferred and conventional procedure for covalently coupling an AGT substrate to the surface of solid supports is based on the carbodiimide reaction and uses water-soluble carbodiimide.

According to this procedure, solid supports have surface carboxyl groups available for attachment of the reactive amine- or sulfhydryl-containing AGT substrate. Thus, in this preferred embodiment, the methods of the invention use solid supports that have been functionalized with surface carboxyl groups prior to be contacted with the AGT substrate.

In this case, the first step of the method of the invention is to activate the carboxyl groups coating the solid supports. This activation is usually performed by adding a so-called "activation buffer", for example a 50 mg/mL EDAC solution or a 50 mg/mL S-NHS solution. These solutions are commercially available. Activation of the solid supports is typically performed by incubating said supports with the activation buffer at room temperature for a few minutes (e.g. 5 minutes to 30 minutes), according to the manufacturer's instructions.

Importantly, covalent coupling of the AGT substrate to the solid support has to be performed under particular conditions, so as to preserve the AGT substrate solubility and the integrity of the bead (internal fluorochrome). The inventors have observed that the AGT substrates should be suspended in a "covalent coupling" buffer containing between 0 and 20% of dimethylsulfoxide (DMSO). In particular, the inventors have observed that concentrations of DMSO above 20% may affect the detection step of the methods of the invention. Preferably, said buffer is a PBS buffer containing between 0 and 20% of DMSO, more preferably between 10% and 20% of DMSO.

Advantageously, the unspecific sites on the solid supports that have not been covalently attached to the AGT substrate can be further blocked by any conventional means, for example, by using a blocking buffer containing 1% of bovine serum albumin (BSA) or any saturating protein (e.g. casein).

Once the solid supports of the invention have been covalently coupled with the AGT substrate (preferably through a carbodiimide covalent linkage), the solid supports are then contacted by the fusion proteins of the invention, so as to couple the epitopes that are specifically recognized by the target antibodies to said supports.

Again, this coupling step has to be performed under particular conditions. As a matter of fact, the catalytic site of the AGT enzyme and the conformational structure of the antigens/epitopes which are carried by the fusion proteins have to be conserved during the coupling proceedings. The inventors identified that the fusion protein should be suspended in a dithiothreitol (DTT)-containing buffer, preferably a PBS/DTT buffer, for the coupling to be efficient. Advantageously, the said coupling buffer contains tween 20; indeed, it has been observed by the present inventors that addition of tween 20 to the coupling medium helps avoiding bead aggregation. Preferably, the coupling buffer contains 0.02% tween 20. More preferably, the covalent coupling buffer of the invention is a PBS buffer of pH 7,4, containing 0,02% tween 20, and 1 mM DTT.

Other coupling conditions are usual ones. Preferably, the covalent coupling of the AGT substrate and the coupling of the fusion protein to the solid supports are performed at room temperature. If the solid supports are fluorescently labeled, said proceedings are more preferably performed in darkness.

In a second aspect, the present invention is thus drawn to a method for covalently coupling a AGT polypeptide having $O^6$-alkylguanine-DNA alkyltransferase activity, on a functionalized solid support, comprising the following steps:
a) activating the said functionalized solid support,
b) adding a substrate of said AGT polypeptide, said substrate being suspended in a buffer containing between 0 and 20% of DMSO, in appropriate conditions so that the substrate is covalently attached to said support,
c) contacting the said AGT polypeptide with the substrate-coated support of step b) in a PBS/DTT buffer,
wherein unbound molecules are washed out after steps b) and c).

Washings can be performed by using any kind of appropriate washing buffers. Such buffers are routinely used by the person of skills in the art and need not be further detailed here. Preferably, a PBS buffer is used.

As used herein, "appropriate conditions" are usual ones. Preferably, the covalent coupling of the AGT substrate is performed at room temperature and, if the solid supports are fluorescently labeled, in darkness.

The functionalization of the solid support can be performed by any conventional means (as those reminded above). The activation of said functionalized solid support is performed accordingly. In a preferred embodiment, the said solid supports are functionalized with surface carboxyl groups and further activated with a classical activation buffer, for example a 50 mg/mL EDAC solution or a 50 mg/mL S-NHS solution.

In a preferred embodiment, DTT is at a concentration of 1 mM in the PBS/DTT buffer.

The present invention is also drawn to a solid support which has been obtained by the said method, and to the use of said solid support in the immunoassay of the invention.

Said solid supports can then be stored in conventional storage buffers, for example containing 0.5 g/L sodium azide, 0.1% BSA, 0.02% tween 20, and/or 1 mM DTT.

All these coupling steps are preferably performed in vitro, in buffers which are devoid of living cells, so that there is no need to take into account the reaction with endogenous AGT enzymes, and the reaction of the (exogenous) AGT fusion protein is therefore highly specific.

The solid supports that can be used in the methods of the invention can be of any kind, e.g. test tubes, microtiter wells, sheets, beads, chips, and/or microparticles, provided that they can be specifically identified from each other. Such identification is possible for example when they are separately located in space (e.g. the wells in a microtiter plate, or different locations on a chip) or when they are differently labeled. A "solid support" has therefore to be understood in a broad meaning, that is, by designating either discrete small parts of a whole solid supports (in case of a plate or a biochip) or a large number of identical microparticles that share common detectable characteristics (hereafter referred to as microparticles "subset").

In a preferred embodiment, the solid supports used in this invention can be specifically identified by their specific location, size, diameter, weight, granulometry, and/or labeling. Such labeling is for example a fluorochrome, a fluorophore, a chromophore, a radioisotope, a mass tag, or any kind of detectable tag which is known in the art.

The solid supports used in the invention can be made of any material, for example in polystyrene, cellulose, nitrocellulose, glass, ceramic, resin, rubber, plastic, silica, silicone, metal, and/or polymer. Polymeric materials include brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, or combinations thereof, that are acceptable as well. Most of these supports are commercially available. For example, beads from synthetic polymers such as polystyrene, polyacrylamide, polyacrylate, or latex are commercially available from numerous sources such as Bio-Rad Laboratories (Richmond, Calif.) and LKB Produkter (Stockholm, Sweden). Beads formed from natural macromolecules and particles such as agarose, cross-linked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia.

When polymeric supports were used, carboxyl groups can be added to the surface of the solid support by incorporating monomers containing such groups into the polymers (for example, acrylic acid, methacrylic acid, itaconic acid, and the like). Alternatively, they can be added to the support by further chemical reaction of a polymer having other precursor reactive groups which can be converted to carboxyl groups (for example, by hydrolysis of anhydrides, such as maleic anhydride, or by oxidation of surface methylol or aldehyde end groups), as already described.

In a preferred embodiment, the solid supports used in the invention are microparticles. Said microparticles have preferably a diameter of less than one millimeter, preferably a diameter ranging from about 0.1 to about 1,000 micrometers (µm). Even though the microparticles can be of any size, the preferred size is 1-100 µm, more preferably 2-50 µm, more preferably 3-25 µm, and even more preferably about 6-12 µm. Microparticles are made of any regularly shaped material. The preferred shape is spherical; however, particles of any other shape can be employed since this parameter is immaterial to the nature of the invention. The shape of the particle can serve as an additional distinction parameter, which is discriminated by flow cytometry, e.g., by a high-resolution slit-scanning method.

As used hereinafter the terms "microparticles", "microspheres", or "microbeads" are used interchangeably and bear equivalent meanings as they refer to small particles with overall diameter that falls essentially in the micrometer range. The terms "nanospheres", "nanoparticles", or "nanobeads" refer to smaller particles with overall size that falls essentially in the nanometer range. As used hereinafter the general term particles, spheres, or "beads" refers both to microparticles and nanoparticles, which can effectively serve as solid supports in the methods of the invention.

In the context of the present invention, a "subset" of microparticles corresponds to numerous identical microparticles having the same characteristics and that have been coated with the same epitope. Importantly, each subset of microparticles should be distinguishable from other subsets of the population by at least one characteristic (e.g. location, size, diameter, weight, granulometry, and/or labeling).

In a preferred embodiment, the different subsets of microparticles can be distinguished as they are differently labeled (e.g. with a fluorochrome, a fluorophore, a chromophore, a radioisotope, a mass tag, or any kind of detectable tag which is known in the art).

In a more preferred embodiment, the different subsets of microparticles can be distinguished as they are differently fluorescently labeled, as proposed in U.S. Pat. Nos. 5,736,330, 5,981,180, 6,057,107, 6,268,222, 6,449,562, 6,514,295, U.S. Pat. Nos. 6,524,793 and 6,528,165. More precisely, these different subsets can be dyed with different fluorescent dyes, and/or different concentrations of one or more fluorescent dyes. As such, the different subsets can have different fluorescent signatures (e.g. different fluorescent wavelength(s), different fluorescent intensities, etc.) that can be measured and used by a measurement system to determine the subset that individual microparticles belong to (i.e., to classify the microparticles according to the subset).

In a preferred embodiment, the microparticles used in the invention are internally labeled with fluorescent dyes, as proposed in EP 1 204 869.

These microparticles may also incorporate magnet or magnetically responsive metal oxides selected from the group consisting of superparamagnetic, paramagnetic, and ferromagnetic metal oxide. Magnetic beads are for example commercially available from sources such as Dynal Inc. (Great Neck, N.Y.) or can be prepared using known in the art methods as disclosed for example in U.S. Pat. Nos. 4,358,388; 4,654,267; 4,774,265; 5,320,944; and 5,356,713. In a preferred embodiment, the solid supports used in the invention are therefore magnetic.

In a more preferred embodiment, the solid supports used in the invention are microparticles internally labeled with fluorescent dyes with magnetite encapsulated in a functional polymer outer coat containing surface carboxyl groups for covalent coupling of ligands, such as those marketed by Luminex Corp under the trade name MagPlex.

It is also possible to use MicroPlex microspheres (sold by Luminex) that are carboxylated polystyrene micro-particles that have been color coded into spectrally distinct regions. These regions can be quickly distinguished by an xMAP Instrument allowing for the interrogation of up to 100 different analytes simultaneously from one single sample volume.

It is also possible to use SeroMAP microspheres (sold by Luminex) which are a special formulation of MicroPlex microspheres which have been optimized to reduce non-specific binding in serology assays.

The last step of the method of the invention consists in detecting the presence of the antibodies that are bound to the epitopes and therefore to the detectable solid support. By analyzing to which subset of microparticles antibodies are bound, it can be easily inferred which antibodies were present in the biological sample, and therefore by which pathogen the tested subject was infected.

Any known technology can be used to detect the presence of the antibodies that are bound to the solid supports. For example, labeled secondary antibodies recognizing specifically the constant part of the subject immunoglobulins can be used, as shown in the experimental part below. It is important to note that the labeling of the detecting-antibodies should be different from the one of the solid support, so as to distinguish between the solid supports that are coupled to antibodies, and those that are not.

Alternatively, immunoglobulins present in sera from infected animals or humans can be directly conjugated to R-phycoerythrin (R-PE), using a one-step antibody labeling protocol (Lightning-Link™ R-Phycoerythrin Conjugation Kit—Innova Biosciences). The hands-on time for the entire procedure is usually 20-30 seconds, and allows the labeling of small quantities of immunoglobulins with 100% recovery. This procedure eliminates the need for secondary reagents, such as conjugated anti-species antibodies and streptavidin-R-phycoerythrin, in multiplex-immunoassay experiments.

When microparticles internally labeled with fluorescent dyes are used, the fluorescent detection instrument should be equipped with a first laser for detecting the type of microsphere, and a second laser to ensure the quantification of captured IgM or IgG by exciting the fluorophore which is conjugated to the specific detection antibody.

With its extensive multiplexing capabilities and lower limit of detection, this approach offers substantial cost and sample savings over traditional ELISA measurements. Moreover, the selected sets of microspheres are adaptable to an affordable, compact, and robust fluorescent detection system such as the MagPix (Luminex Corporation).

In this embodiment, the method of the invention makes it possible to simultaneously analyze up to 100 types of coupled microspheres per well by using a flow analysis tool, and affords greatly enhanced sensitivity that is expected to be on the order of several orders of magnitude larger than that of currently used systems and methods.

Interestingly, the method of the invention enables to perform high throughput serological screening to diagnose multiple infections in an individual, either a human or an animal.

In a third aspect, the present invention provides a kit which is suitable for use in the detection of antibodies according to the method of the invention.

This kit comprises at least two solid supports as defined above, more precisely:
   a first solid support as obtained in step (c) of the method of the invention, said support being covalently coupled with a first epitope that is recognized by a first target antibody, and
   a second solid support as obtained in step (f) of the method of the invention, said support being covalently coupled with a second epitope that is recognized by a second target antibody, and not by said first target antibody,
wherein the at least two solid supports can be specifically identified from each other and enable to detect two different target antibodies.

In other terms, the present invention relates to a kit for the detection of at least two target antibodies in a biological sample comprising.
   (a) a first solid support comprising an AGT substrate covalently coupled to a first fusion protein comprising an AGT polypeptide having a O6-alkylguanine-DNA alkyltransferase activity and a first epitope that is recognized by a first target antibody; and
   b) a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody.

In a preferred embodiment, said first and/or second epitope is present on a viral protein chosen in the group consisting of: the EDIII protein of the dengue virus 1 of SEQ ID NO:3, the EDIII protein of the dengue virus 2 of SEQ ID NO:4, the EDIII protein of the dengue virus 3 of SEQ ID NO:5, the EDIII protein of the dengue virus 4 of SEQ ID NO:6, the EDIII protein of the West Nile virus of SEQ ID NO:7, the EDIII protein of the Yellow Fever virus of SEQ ID NO:8, the EDIII protein of the Japanese encephalitis virus of SEQ ID NO:9, the EDIII protein of the Zika virus of SEQ ID NO:10, the EDIII protein of the Wesselbron virus of SEQ ID NO:11, the EDIII protein of the Rocio virus of SEQ ID NO:12, the EDIII protein of the Murray encephalitis virus of SEQ ID NO:13, and the EDIII protein of the Saint-Louis encephalitis virus of SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, the EDIII protein of the Rabensburg virus encoded by SEQ ID NO:58, and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

Preferably, this kit also contains the means to detect the at least two target antibodies which are bound to the solid supports. Said means are more preferably secondary antibodies recognizing the constant part of the target antibodies. Said secondary antibodies can be labeled, provided that the labeling is not the same as the ones that are present on the solid support. However, it is possible to use the same labeling for all the secondary antibodies that are used for detecting the antibodies bound to solid support(s), since the information concerning the infectious pathogen(s) are given only by the identification of the solid support which is bound to the antibodies.

The kit of the invention may contain other ingredients that are accepted as standard reagents such as a wash buffer, necessary plasticware, and the like.

In a preferred embodiment, the kit of the invention comprises at least 10, preferably at least 50, more preferably at least 100 differently coupled-solid supports, said solid supports being for example subsets of microparticles as defined above.

In a more preferred embodiment, the said solid supports are microspheres, for example those which are internally labeled with a fluorescent dye with magnetite encapsulated in a functional polymer outer coat containing surface carboxyl groups.

In another preferred embodiment, in the kit of the invention, the said solid supports are mixed together in at least one single compartment.

Advantageously, the kit of the invention contains conventional support(s), e.g., microtiter plates, containing the different antigen-coated microparticles subsets defined above. In a preferred embodiment, the said microparticles subsets are mixed together in at least one single compartment (e.g. a well or a tube). Such a device is disclosed on FIG. 11.

The kit of the invention may also contain recipients (e.g., tubes) containing the said subsets of antigen-coated microparticles.

The present invention also targets the use of the kit of the invention for detecting at least two, preferably at least 10, more preferably at least 50 and even more preferably at least 100 target antibodies in a biological sample from a subject.

In a preferred embodiment, the kit of the invention is used for detecting at least two, preferably at least 10, and more preferably at least 20 target antibodies that are generated upon infection by endemic viruses or parasites of the same geographic region. For example, the kit of the invention could contain microparticles that are coated with antigens of viruses or parasites that are specific of Africa regions, such as the Dengue virus type 1, type 2, type 3, type 4, the Yellow fever virus, the West-Nile virus, the Usutu virus, the Zika virus, the Wesselsbron virus, the Shamonda virus, the Rift Valley fever virus, the Chikungunya virus, the Crimean-Congo hemorrhagic fever virus, the Ebola virus, the Marburg virus, the Lassa virus, the Hepatitis C virus, the Hepatitis E virus, the Enterovirus 71, *Plasmodium falciparum*, or *Leptospira interrogans*.

Table 1 below discloses examples of antigen-coupled microspheres combinations which can be included in the kit of the invention depending on the geographic region it is intended for (Asia, Europa, America, Oceania, or Africa).

The kit of the invention may alternatively contain antigen-coupled microspheres that enable the diagnosis of viruses or parasites inducing specific symptoms (flu-like, encephalitis, or hemorrhagic fever) or infecting specific animals, so that it can be adapted to each patient/animal.

Table 1 below discloses examples of antigen-coupled microspheres combinations which can be included in the kit of the invention depending on the symptoms of the patient or of the animal.

Finally, kits containing antigen combinations that are proposed by national sanitary agencies are obviously also encompassed in the present invention.

In particular, the kit of the invention comprises at least two solid supports coated with at least two fusion proteins that are selected in the group consisting of: SEQ ID NO:21, SEQ ID NO:42, SEQ ID NO:49, SEQ ID NO:51, SEQ ID NO:53, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:109, SEQ ID NO:111, SEQ ID NO:113, SEQ TD NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149 and SEQ ID NO:151.

In a preferred embodiment, the kit of the invention contains a combination of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen or at least twenty solid supports coated with said fusion proteins.

In a more preferred embodiment, the kit of the invention contains a combination of at least five solid supports (e.g., microsphere subsets) that are coated with at least five different fusion proteins containing antigens as recommended by the Food and Drug Administration, namely, antigens from the HBV, HCV, HIV1, HIV2 and West Nile viruses.

TABLE 1

| Advantageous combinations of antigen-coupled microspheres to be included in the kit of the invention | | | | | | | | | | | | | |
|---|---|---|---|---|---|---|---|---|---|---|---|---|---|
| | | | | Microsphere panels | | | | | | | | | |
| | | | | Geographical | | | | | Syndromic | | | Veterinary | |
| Agent | | Antigen-coupled microspheres | | | | | | | | | | | |
| Genus | Species | Abbreviation | Description | Africa | Asia | Europe | Americas | Oceania | Flu-like | Encephalitis | Hemorrhagic fever | Bovine disease | Equine disease |
| *Flavivirus* | *Dengue virus* type 1 | SNAP+DEN1.EDIII | Domain III of envelope E protein | x | x | x | x | x | x | | x | | |
| | *Dengue virus* type 2 | SNAP+DEN2.EDIII | Domain III of envelope E protein | x | x | x | x | x | x | | x | | |
| | *Dengue virus* type 3 | SNAP+DEN3.EDIII | Domain III of envelope E protein | x | x | x | x | x | x | | x | | |
| | *Dengue virus* type 4 | SNAP+DEN4.EDIII | Domain III of envelope E protein | x | x | x | x | x | x | | x | | |
| | *Yellow fever virus* | SNAP+YF.EDIII | Domain III of envelope E protein | x | | | x | | x | | x | | |
| | *West-Nile virus* | SNAP+WNV.EDIII | Domain III of envelope E protein | x | x | x | x | x | x | x | | | x |
| | | WNV.prM-sE+SNAP | secreted soluble form of envelope E protein | x | x | x | x | x | x | x | | | x |
| | *Usutu virus* | SNAP+USU.EDIII | Domain III of envelope E protein | x | | x | | | | x | | | x |
| | *Japanese encephalitis virus* genotype 3 | JE.prM-sE+SNAP | secreted soluble form of envelope E protein | | x | | | x | x | x | | | |
| | *Japanese encephalitis virus* genotype 1 | SNAP+JE-1.EDIII | Domain III of envelope E protein | | x | | | x | x | x | | | |
| | *Japanese encephalitis virus* genotype 2 | SNAP+JE-2.EDIII | Domain III of envelope E protein | | x | | | x | x | x | | | |
| | *Japanese encephalitis virus* genotype 3 | SNAP+JE-2.EDIII | Domain III of envelope E protein | | x | | | x | x | x | | | |
| | *Japanese encephalitis virus* genotype 4 | SNAP+JE-4.EDIII | Domain III of envelope E protein | | x | | | x | x | x | | | |
| | *Japanese encephalitis virus* genotype 5 | SNAP+JE-5.EDIII | Domain III of envelope E protein | | x | | | x | x | x | | | |
| | *Murray Valley encephalitis virus* | SNAP+MVE.EDIII | Domain III of envelope E protein | | x | | | x | x | x | | | |
| | *Saint-Louis encephalitis virus* | SNAP+SLE.EDIII | Domain III of envelope E protein | | | | x | | x | x | | | x |
| | *Zika virus* | SNAP+ZIKV.EDIII | Domain III of envelope E protein | x | x | | | x | x | | | | |
| | *Wesselsbron virus* | SNAP+WSL.EDIII | Domain III of envelope E protein | x | | | | | x | | | x | |
| | *Rocio virus* | SNAP+ROCV.EDIII | Domain III of envelope E protein | | | | x | | x | | | | |
| | *Rabensburg virus* | SNAP+RabV.EDIII | Domain III of envelope E protein | | | x | | | | | | | |
| | *Insectivore flavivirus* (coll. La Timone) | SNAP+Insectflavi.EDIII | Domain III of envelope E protein | | | x | | | | | | | |
| | *Tickborne encephalitis virus* | SNAP+TBE.EDIII | Domain III of envelope E protein | | | x | | | | | | x | x |
| | *Omsk Hemorrhagic Fever virus* | SNAP+OMSK.EDIII | Domain III of envelope E protein | | x | | | | | | x | | |
| | *Kyasanur Forest Disease virus* | SNAP+KAS.EDIII | Domain III of envelope E protein | | x | | | | | | x | | |
| | *Akhumra virus* | SNAP+ALK.EDIII | Domain III of envelope E protein | | x | | | | | | x | | |
| *Orthobunyavirus* | *Schmallenberg virus* | SNAP+AKA.N | Nucleoprotein N | | | x | | | | | | x | |
| | *Akabane virus* | SNAP+AKA.N | Nucleoprotein N | | | x | | x | | | | x | |
| | *Aino virus* | SNAP+AIN.N | Nucleoprotein N | | | x | | x | | | | x | |
| | *Shamonda virus* | SNAP+SHA.N | Nucleoprotein N | x | | x | | | | | | x | |
| *Bunyavirus* | *Rift Valley fever virus* | SNAP+RVF.N | Nucleoprotein N | x | | x | | | x | | x | x | |

TABLE 1-continued

Advantageous combinations of antigen-coupled microspheres to be included in the kit of the invention

| Agent | | Antigen-coupled microspheres | | Microsphere panels | | | | | | | | | |
|---|---|---|---|---|---|---|---|---|---|---|---|---|---|
| | | | | Geographical | | | | | Syndromic | | | Veterinary | |
| Genus | Species | Abbreviation | Description | Africa | Asia | Europe | Americas | Oceania | Flu-like | Encephalitis | Hemorrhagic fever | Bovine disease | Equine disease |
| *Alphavirus* | *Chikungunya virus* | CHIK.sE2+SNAP | secreted soluble form of envelope E2 protein | x | x | x | x | x | x | | | | |
| | *Ross River virus* | RR.sE2+SNAP | secreted soluble form of envelope E2 protein | | | | | x | x | | | | x |
| | *Mayaro virus* | MAY.sE2+SNAP | secreted soluble form of envelope E2 protein | | | | x | | x | | | | |
| | *Eastern equine encephalitis virus* | EEE.sE2+SNAP | secreted soluble form of envelope E2 protein | | | | x | | x | | | | x |
| | *Western equine encephalitis virus* | WEE.sE2+SNAP | secreted soluble form of envelope E2 protein | | | | x | | x | | | | x |
| | *Venezuelan equine encephalitis* | VEE.sE2+SNAP | secreted soluble form of envelope E2 protein | | | | x | | x | | | | x |
| *Nairovirus* | *Crimean-Congo hemorrhagic fever virus* | SNAP+CCHF.N | Nucleoprotein N | x | x | x | | | | | x | x | |
| *Ebolavirus* | *Ebola virus* (Zaire) | SNAP+EBO.N | Nucleoprotein N | x | | | | | | | x | | |
| *Marburgvirus* | *Marburg virus* | SNAP+MAR.N | Nucleoprotein N | x | | | | | | | x | | |
| *Arenavirus* | *Lassa virus* | LAS.ectoGP1+SNAP | Ectodomain of Glycoprotein 1 | x | | | | | | | x | | |
| | | LAS.ectoGP2+SNAP | Ectodomain of Glycoprotein 2 | x | | | | | | | x | | |
| | | SNAP+LAS.N | Nucleoprotein N | x | | | | | | | x | | |
| | *Junin virus* | JUN.ectoGP1+SNAP | Ectodomain of Glycoprotein 1 | | | | x | | | | x | | |
| | | JUN.ectoGP2+SNAP | Ectodomain of Glycoprotein 2 | | | | x | | | | x | | |
| | | SNAP+JUN.N | Nucleoprotein N | | | | x | | | | x | | |
| | *Machupo virus* | MAC.ectoGP1+SNAP | Ectodomain of Glycoprotein 1 | | | | x | | | | x | | |
| | | MAC.ectoGP2+SNAP | Ectodomain of Glycoprotein 2 | | | | x | | | | x | | |
| | | SNAP+MAC.N | Nucleoprotein N | | | | x | | | | x | | |
| | *Sabia virus* | SAB.ectoGP1+SNAP | Ectodomain of Glycoprotein 1 | | | | x | | | | x | | |
| | | SABectoGP2+SNAP | Ectodomain of Glycoprotein 2 | | | | x | | | | x | | |
| | | SNAP+SAB.N | Nucleoprotein N | | | | x | | | | x | | |
| | *Guanarito virus* | GUA.ectoGP1+SNAP | Ectodomain of Glycoprotein 1 | | | | x | | | | x | | |
| | | GUA.ectoGP2+SNAP | Ectodomain of Glycoprotein 2 | | | | x | | | | x | | |
| | | SNAP+GUA.N | Nucleoprotein N | | | | x | | | | x | | |
| *Betacoronavirus* | *Human betacoronavirus* (2cEMC/2012) | SNAP+huCOV.N | Nucleoprotein N | | x | | | | | | | | |
| | | huCOV.S+SNAP | Soluble form of spike S protein | | x | | | | | | | | |
| *Hepacivirus* | *Hepatitis C virus* genotype 1b (strain TCHM-R2/03) | SNAP+HCV.C | Caspid protein C | x | x | x | x | x | | | | | |
| *Hepevirus* | *Hepatitis E virus* | SNAP+HEV.C | Caspid protein C | x | x | x | x | x | | | | | |
| *Enterovirus* | *Enterovirus* 71 (strain JL-AFP-EV71-07-03) | SNAP+EV71.VP1 | Caspid protein VP1 | x | x | x | x | x | | x | | | |
| *Plasmodium* | *Plasmodium falciparum* | SNAP+MSP-1(19) + AMA-1 (III) | Proteins MSP-1(19) + AMA-1(III) in tandem | x | x | x | x | x | x | x | | | |
| *Leptospira* | *Leptospira interrogans serovar* Lai str. 56601 | SNAP+HbpA | The 55 kDa-form of protein HbpA | x | x | x | x | x | x | | x | x | |

In another aspect, the present invention relates to a method for manufacturing the kit of the invention as defined above, said method comprising the steps of:
  (a) providing a least a first fusion protein comprising:
    a polypeptide comprising a first epitope that is recognized by a first target antibody and
    a AGT polypeptide having a O6-alkylguanine-DNA alkyltransferase activity,
  (b) contacting said first fusion protein with a first solid support, said support being covalently coupled with a substrate of said AGT polypeptide,
  (c) obtaining a first solid support covalently coupled with a first epitope that is recognized by the first target antibody,
  (d) providing at least a second fusion protein comprising:
    a polypeptide comprising a second epitope, said second epitope being recognized by a second target antibody but not by said first target antibody, and
    a AGT polypeptide having a O6-alkylguanine-DNA alkyltransferase activity,
  (e) contacting said second fusion protein with a second solid support, said support being covalently coupled with a substrate of said AGT polypeptide,
  (f) obtaining a second solid support covalently coupled with a second epitope that is recognized by the second target antibody, but not by said first target antibody,
  wherein said at least first and at least second solid supports can be specifically identified from each other,
  the kit of the invention comprising at least said first and second supports.

In another aspect, the present invention relates to a multiplex immuno screening assay comprising at least 2, 25, 50, 96 solid supports as defined above and wherein each of said solid supports emits a different and distinguishable wave length after excitation.

In another aspect, the present invention relates to a multiplex immuno screening assay method comprising:
  a) contacting one or several biological sample(s) with at least 2, 25, 50, 96 solid supports as defined above and wherein each of the solid supports emits a different and distinguishable wave length after excitation, and
  b) detecting the presence or absence of target antibodies.

In a preferred embodiment, said target antibodies are specific to antigen from viruses to be detected in blood bank according to WHO or FDA guidelines, such as for example viruses selected from HBV, HCV, HIV1, HIV2, and WNV.

In another preferred embodiment, said target antibodies are specific to oncogenic HPV strains such as HPV 16, 18, 31, 33, 35, 39, 45, 51, 52, 56, 58, 59, 66 and 68.

In another preferred embodiment, each of said target antibodies are labeled with a detectable label.

In another aspect, the present invention relates to an apparatus for carrying out the method for manufacturing the kit of the invention as defined above, comprising a technical device for detecting the light sources emitted from the solid supports and the light source emitted from the target antibodies or labeled antibodies binding to the target antibodies, and a calculating or computer device for identifying which solid supports are bound with target antibodies, thereby indicating the presence or absence of antigens, bacteria, virus, or parasites in the analyzed sample.

In another aspect, the present invention relates to an in vitro method for diagnosing at least one target disease in a subject, said target disease being known to induce the synthesis of at least one target antibody in said subject, comprising performing the immunoassay of the invention, wherein said subject is diagnosed to be suffering from said at least one target disease if the amount of said at least one target antibody is higher than a control value.

This diagnosing method preferably enables to diagnose two, preferably three, and more preferably four target diseases in a subject in need thereof. This number is however not limiting: it is indeed possible to diagnose until 100 target diseases in so far as it is possible to detect until 100 different antibodies with the detecting method of the invention.

In a preferred embodiment, said at least one target disease is a viral, a bacterial, a yeast or a fungi-mediated infection, preferably a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum*.

In a preferred embodiment, said in vitro method is used to diagnose at least 5, more preferably at least 15, more preferably at least 50, and even more preferably at least 100 viral and/or bacterial and/or parasite infections in said subject.

In a preferred embodiment, the control value used in said method represents the amount of said target antibody in a sample from a subject which is not suffering from said target disease, preferably, a healthy subject.

The methods of the invention can be used to diagnose infections in animals.

In particular, they can be used for the diagnosis of animal diseases, as well as a DIVA (Differentiating Infected from Vaccinated Animals) approach to differentiate naturally infected animals from vaccinated animals. The use of a DIVA strategy complementing novel vaccines would allow the implementation of vaccination as targeted control strategy alongside conventional strategies (test, slaughter and meat inspection). Moreover, increased test specificity would have a major economic benefit by reducing the numbers of false-positive animals that may be slaughtered needlessly. Lastly, improved sensitivity, particularly when novel diagnostic assays are used, would have a further benefit in reducing the economic burden of disease control even in the absence of vaccination In a preferred embodiment, the methods of the invention are applied to human individuals.

The present invention finally relates to the use of the kit of the invention for diagnosing at least two target diseases in a subject, wherein said target disease is a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum*.

A new emerging arbovirus has been recently sequenced and affects cattle in Germany, Benelux and France. This virus is called Schmallenberg virus (SBV), and is related to the Akabane virus belonging to the Simbu serogroup of the Orthobunyavirus genus of the Bunyaviridae family. The viral genome of the Schmallenberg virus comprises three single-stranded RNA segments known as S, L and M. The S segment encodes the N nucleoprotein and the NSs non-structural protein. The N nucleoprotein shares antigenic determinants with different Bunyaviruses. The three RNA viral sequences of the BH80/11-4 strain of the Schmallenberg virus are available under the numbers IIE649913.1, HE649914.1, and HE649912.1.

The present inventors observed that the fusion as a chimeric protein of the 6-alkylguanine-DNA-alkyltransferase enzyme (AGT) with the SBV N protein greatly improves the production of recombinant N protein, in particular in invertebrate cells such as S2 cells.

The present inventors propose here for the first time to use the AGT enzyme (EC 2.1.1.63), a mutant thereof, a catalytic domain thereof or sub-fragments thereof, for enhancing the production of the N nucleoprotein from SBV in host cells, in particular in non-vertebrate cells. The enhancing effect is observed when the host cells express a fusion polypeptide comprising at least i) a secretion signal peptide which is functional in said host cells, ii) the AGT enzyme, mutant, catalytic domain or sub-fragments thereof, and iii) the N nucleoprotein of SBV. For the enhancing effect to occur, the AGT enzyme has to be physically linked, directly or indirectly (spacers and other amino acids might be introduced), to the protein of interest. Without being bound by theory, it is contemplated that the AGT enzyme acts as a chaperone protein, for example by facilitating the secretion from the host cell and stabilising the synthesised fusion polypeptide in the supernatant of the host cells, or for preventing it to be metabolised during and after its synthesis and secretion from the host cells. In addition, it has been observed that AGT has a 3D globular structure comprising α helix (Wibley J. E. A. et al, 2000), which is compatible with a scaffolding role of AGT.

In the context of the present invention, "host" cells are any cells which can be used for producing recombinant proteins, such as "non-vertebrate" (or invertebrate) cells, vertebrate cells, plant cells, yeast cells, or prokaryote cells. They are preferably non-vertebrate and vertebrate cells.

Non-vertebrate (also known as invertebrate) comprises different phyla, the most famous being the Insect, Arachnida, Crustacea, Mollusca, Annelida, Cirripedia, Radiata, Coelenterata and Infusoria. They are now classified into over 30 phyla, from simple organisms such as sea sponges and flatworms to complex animals such as arthropods and molluscs. In the context of the invention, non-vertebrate cells are preferably insect cells, such as *Drosophila* or Mosquito cells, more preferably *Drosophila* S2 cells.

Examples of cells derived from vertebrate organisms that are useful as host cell lines include non-human embryonic stem cells or derivative thereof, for example avian EBX cells; monkey kidney CVI line transformed by SV40 sequences (COS-7, ATCC CRL 1651); a human embryonic kidney line (293); baby hamster kidney cells (BHK, ATCC CCL 10); Chinese hamster ovary cells (CHO); mouse sertoli cells [TM4]; monkey kidney cells (CVI, ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells [HTC, M1.5]; YB2/O (ATCC no CRL1662); NIH3T3; HEK and TRI cells. In the context of the invention, vertebrate cells are preferably EBX, CIIO, YB2/O, COS, HEK, NIH3T3 cells or derivatives thereof.

Plant cells which can be used in the context of the invention are the tobacco cultivars Bright Yellow 2 (BY2) and *Nicotiana tabaccum* 1 (NT-1).

Yeast cells which can be used in the context of the invention are: *Saccharomyces cerevisiae, Schizosaccharomyces pombe*, and *Hansenula polymorpha*, as well as methylotropic yeasts like *Pichia pastoris* and *Pichia methanolica*.

Prokaryote cells which can be used in the context of the invention are typically *E. coli* bacteria or *Bacillus subtilis* bacteria.

In another aspect, the present invention is thus drawn to a vector for expressing the N nucleoprotein from SBV in an host cell (SBV.N), comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the N nucleoprotein of SBV of SEQ ID NO: 16.

The N nucleoprotein from SBV will be referred to hereafter as the "heterologous protein", the "protein of interest", "chimeric protein", or the "recombinant protein".

The term "vector" herein means the vehicle by which a DNA or RNA sequence of a foreign gene can be introduced into a host cell so as to transform it and promote expression of the introduced sequence. As understood herein, a vector is a nucleic acid molecule, such as, for example, plasmids, phages, and viruses. They are discussed in greater detail below. Any type of plasmid, cosmid, YAC or viral vector may be used to prepare a recombinant nucleic acid construct which can be introduced to a host cell where expression of the protein of interest is desired. When expression of the protein of interest in a particular type of host cell is desired, viral vectors that selectively infect the desired cell type or tissue type can be used. Also important in the context of the invention are vectors for use in gene therapy (i.e. which are capable of delivering the nucleic acid molecule to a host organism).

For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques*, 7:980-990, 1992).

Viral vectors that are actually preferred in the present invention are those that are well suited for use in vertebrate and non-vertebrate cells.

For non-vertebrate cells, preferred vectors are the arboviruses, the West Nile virus being particularly preferred, which are arthropod vectors. Other vectors that are known to efficiently be expressed in non-vertebrate cells are the baculoviruses.

For vertebrate cells, lentiviral, AAV, baculoviral and adenoviral vectors are preferred. The vectors suited for expression in mammalian host cells can also be of non-viral (e.g. plasmid DNA) origin. Suitable plasmid vectors include, without limitation, pREP4, pCEP4 (Invitrogen), pCI (Promega), pCDM8 and pMT2PC, pVAX and pgWiz.

For prokaryotic cells, plasmid, bacteriophage and cosmid vectors are preferred. Suitable vectors for use in prokaryotic systems include without limitation pBR322 (Gibco BRL), pUC (Gibco BRL), pBluescript (Stratagene), p Poly, pTrc; pET 11d; pIN; and pGEX vectors.

For plant cells, plasmid expression vectors such as Ti plasmids, and virus expression vectors such as Cauliflower mosaic virus (CaMV) and tobacco mosaic virus TMV are preferred.

Expression of recombinant proteins in yeast cells can be performed using three types of vectors: integration vectors (YIp), episomal plasmids (YEp), and centromeric plasmids (YCp): Suitable vectors for expression in yeast (e.g. *S. cerevisiae*) include, but are not limited to pYepSec1, pMFa, pJRY88, pYES2 (Invitrogen Corporation, San Diego, Calif.) and pTEF-MF (Dualsystems Biotech Product code: P03303).

Vectors which can be used for gene therapy are well-known in the art. They are for example lentivirus, retrovirus, adenovirus, poxvirus, herpes virus, measles virus, foamy virus or adeno-associated virus (AAV). Viral vectors can be replication-competent, or can be genetically disabled so as to be replication-defective or replication-impaired. Preferred gene therapy vector are the DNA Flap vectors as described in WO 99/055892, U.S. Pat. No. 6,682,507 and WO 01/27300.

A sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

The vector of the invention contains a nucleotide sequence encoding a 6-alkylguanine-DNA-alkyltransferase enzyme (AGT), a mutant, a fragment or a catalytic domain thereof. These polypeptides have been defined above. Preferably, said AGT mutant is the SNAP enzyme of SEQ ID NO: 2, and is encoded for example by SEQ ID NO:15 or SEQ ID NO: 31, the latter having a G/C content of 51%.

Preferably, the nucleotide expression vector of the invention further comprises cloning sites enabling the in-frame insertion of a heterologous DNA sequence encoding the protein of interest.

As meant in the present invention, the term "secretion signal peptide" designates a short (3-60 amino acids long) peptide chain that directs the transport of the N nucleoprotein outside the host cells.

Examples of secretion signals appropriate for the present invention include, but are not limited to, the signal peptide sequences of the mating factor (MF) alpha (U.S. Pat. No. 5,879,926); invertase (WO 84/01153); PHO5 (DK 3614/83); YAP3 (yeast aspartic protease 3; WO 95/02059); and BAR1 (WO 87/02670).

In the context of the invention, this secretion signal peptide is preferably functional either in non-vertebrate cells or in vertebrate cells, or both.

Examples of secretion signal peptides which are functional in insect cells are: the insect ssBiP (SEQ ID NO: 37, for example encoded by the DNA sequence SEQ ID NO: 22), the BiP-like peptide signal of SEQ ID NO: 24 (for example encoded by the DNA sequence SEQ ID NO: 23), the BiP-like peptide signal of SEQ ID NO:153 (for example encoded by the DNA sequence SEQ ID NO:152) and any peptide signal present in an arbovirus, for example the envelop E protein of the West-Nile virus (SEQ ID NO: 38).

Interestingly, the above-mentioned BiP-like peptide signal of SEQ ID NO:24 is functional in both non-vertebrate and vertebrate cells. This BiP-like signal corresponds to the BiP peptide signal of SEQ ID NO: 37 in which the last Glycine amino acid has been replaced by the amino acid sequence Pro Thr Ala Leu Ala (SEQ ID NO: 39) which corresponds to the cleavage site of the E protein of the Dengue virus. Accordingly, the BiP-like signal will be advantageously cleaved once the protein will be translated and secreted in the supernatant of the host cells.

A variety of secretion signals is also available for expression in yeast host cells, e.g. in *S. cerevisiae*. These include the prepro-alpha factor, HSp150, PHO1, SUC2, KILM1 (killer toxin type 1),and GGP1.

A cloning site is a sequence which facilitates cloning of a gene encoding a protein of interest into the expression system. It contains restriction sites, or restriction recognition sites, i.e. locations on a DNA molecule containing specific sequences of nucleotides, which are recognized by restriction enzymes (see for example in the figures). These are generally palindromic sequences (because restriction enzymes usually bind as homodimers), and a particular restriction enzyme may cut the sequence between two nucleotides within its recognition site, or somewhere nearby. The cloning sites are well known for the man skilled in the art.

In a preferred embodiment of the invention, the DNA sequence encoding said AGT enzyme is located in 5' or in 3' of the DNA sequence encoding said heterologous protein of interest, preferably in 5'. Therefore, the AGT enzyme is directly or indirectly linked to the heterologous protein/polypeptide of interest, and preferably located at the N-terminal end of the heterologous protein/polypeptide of interest. The DNA sequence encoding the fusion polypeptide comprising said peptide signal, said AGT enzyme, mutant or catalytic domain, and said recombinant protein of interest, can be operatively associated with an inducible promoter which is functional in the same host cells as the peptide signal is.

More preferably, in the vector of the invention, said open reading frame is operatively associated with an inducible promoter which is functional in the same host cell as the peptide signal is.

A coding sequence is "operatively associated with" an expression control sequence (i.e. transcriptional and translational control sequences) in a cell, when RNA polymerase transcribes the coding sequence into RNA, which is then trans-RNA spliced (if it contains introns) and, if the sequence encodes a protein, is translated into that protein.

A "promoter" is a sequence of nucleotides from which transcription may be initiated of DNA operably linked downstream (i.e. in the 3' direction on the sense strand of double-stranded DNA). Within the promoter sequence will be found a transcription initiation site (conveniently found, for example, by mapping with nuclease S1), as well as protein binding domains (consensus sequences) responsible for the binding of RNA polymerase.

Promoters which may be used to control gene expression in the context of the present invention are for example the one that are functional in non-vertebrate cells or in vertebrate cells. For example, for non-vertebrate cells, the regulatory sequences of the metallothionein gene can be used (Brinster et al., *Nature*, 296:39-42, 1982).

Preferably, the inducible promoter which is present in the vector of the invention has a promoter activity in an insect cell, and more preferably in a *Drosophila* cell. It is for example the *Drosophila metallothionein* promoter pMT (Lastowski-Perry et al, *J. Biol. Chem.* 260:1527 (1985)), which directs high level transcription of the gene in the presence of metals, e.g. $CuSO_4$. Alternatively, the *Drosophila* actin 5C gene promoter, which is a constitutive promoter and does not require addition of a metal, can be used (B. J. Bond et al, *Mol. Cell. Biol.* 6:2080 (1986)). Examples of other known *Drosophila* promoters include, e.g. the inducible heatshock (Hsp70) and COPTA LTR promoters. The SV40 early promoter gives lower level of expression than the *Drosophila* metallothionein promoter.

Preferably, the inducible promoter which is present in the vector of the invention has a promoter activity in a *Drosophila melanogaster* cell, preferably in *Drosophila* S2 cells. It is for example the metallothionein promoter which is thoroughly described in Lastowski-Perry et al, *J. Biol. Chem.* 260: 1527 (1985).

Promoters suitable for constitutive expression in mammalian cells include the cytomegalovirus (CMV) immediate early promoter, the adenovirus major late promoter, the phosphoglycero kinase (PGK) promoter, and the thymidine kinase (TK) promoter of *herpes simplex* virus (HSV)-1. Inducible eukaryotic promoters regulated by exogenously supplied compounds, include without limitation, the zinc-inducible metallothionein (MT) promoter, the dexamethasone (Dex)-inducible mouse mammary tumor virus (MMTV) promoter, the T17 polymerase promoter system (WO 98/10088), the ecdysone insect promoter, the tetracycline-repressible promoter, the tetracycline-inducible promoter, the RU486-inducible promoter and the rapamycin-inducible promoter.

Preferably, the promoter which is present in the vector of the invention has a promoter activity in a mammal cell, preferably in HeLa cells. It is for example the SV 40 promoter.

A range of yeast promoters is available for protein expression in yeast host cells. Some like ADH2, SUC2 are inducible and others like GAPDH are constitutive in expression. Other promoters suitable for expression in yeast include the TEF, PGK, MF alpha, CYC-1, GAL-1, GAL4A, GAL10, PHO5, glyceraldehyde-3-phosphate dehydrogenase (GAP or GAPDH), and alcohol dehydrogenase (ADH) promoters.

For use in plant cells, the most commonly used promoter is the cauliflower mosaic virus (CaMV) 35S promoter or its enhanced version, but a number of alternative promoter can be used, such as the hybrid (ocs)3mas promoter or the ubiquitin promoter from maize and *Arabidospsis thaliana*. In contrast to these constitutive promoters, the rice α-amylase RAmy3D promoter is induced by sugar deprivation (Hellwig S et al., *Nat. Biotechnol.* 2004; 22(11):1415-22).

Promoters suitable for expression in *E. coli* host cell include, but are not limited to, the bacteriophage lamba pL promoter, the lac, TRP and IPTG-inducible pTAC promoters.

It is preferred that the secretion signal peptide and the inducible promoter are functional in the same host cell.

More preferably, the secretion signal peptide and the inducible promoter are functional in both *Drosophila* S2 cells and vertebrate cells.

The term "inducible" as applied to a promoter is well understood by those skilled in the art.

In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Once an appropriate vector has been constructed and transfected into the selected host cell, preferably a *Drosophila* cell line, the expression of a heterologous protein is induced by the addition of an appropriate inducing agent for the inducible promoter. For example cadmium or copper are inducing agents for the Hsp70 promoter. For constitutive promoters, such as the actin 5C promoter, no inducing agent is required for expression.

In another embodiment of the invention, the nucleotide expression vector encodes at least one peptide cleavage site, which is preferably located between the AGT enzyme or its catalytic domain and the recombinant protein of interest.

A peptide cleavage site (also called "peptide cleavage site") is an amino acid sequence which is recognized by at least one protease enzyme (for example serine protease, cysteine protease, among others). An example of a peptide cleavage site is the enterokinase cleavage site of SEQ ID NO: 40 (AspAspAspAspLys/Asp). The enterokinase is a serine protease enzyme (EC 3.4.21.9) which is known to convert inactive trypsinogen into active trypsin by cleavage at the C-terminal end of the sequence: Val--(Asp)$_4$--Lys--Ile--Val~(trypsinogen)→Val--(Asp)$_4$--Lys (hexapeptide)+Ile--Val~(trypsin). Enterokinase cleaves after lysine if the Lys is preceded by four Asp and not followed by a proline residue.

Another useful peptide cleavage site is the cleavage site of the so-called "TEV protease", having the amino acid sequence SEQ ID NO: 32 (pro-TEV1) or SEQ ID NO: 33 (pro-TEV2) (Glu Asn Leu Tyr Phe Gin Ser or Gly respectively). Such cleavage sites can be encoded for example by SEQ ID NO:29 and 30. TEV protease is the common name for the 27 kDa catalytic domain of the nuclear inclusion protein encoded by the tobacco etch virus. It is commercially available (Invitrogen).

The cleavage site from the membrane precursor prM from Dengue virus serotype 1 (SEQ ID NO: 39) may also be used in the vector of the invention.

In another embodiment, the nucleotide expression vector of the invention further encodes a label, preferably located at the C-terminal end of the recombinant protein in the fusion polypeptide of the invention (comprising the peptide signal, the AGT protein or homologous thereof, and the recombinant protein). In the context of the invention, a "label" is dedicated to facilitate the recovery of the polypeptide from the crude lysate of the host cell, and is preferably selected from the group comprising: fluorescent proteins, poly-histidine (poly-his) or poly-histidine-glycine (poly-his-gly) tags; flu HA tags; c-myc tag Herpes simplex virus glycoprotein D (gD) tags, Flag-peptides, alpha-tubulin epitopes, or T7 gene 10 protein peptide tags. However, any other label might be used. In a preferred embodiment of the invention, the vectors comprise the DNA of SEQ ID NO: 28 encoding a hexa-histidine tag which has the SEQ ID NO: 27.

In another embodiment, the nucleotide expression vector of the invention further encodes spacer sequence(s), located preferably between the AGT enzyme (or its catalytic domain) and the recombinant protein of interest and/or between the recombinant protein of interest and the label. In the context of the invention, a spacer sequence is an amino acid sequence comprising at least three amino acids, dedicated to spatially separate two linked polypeptides (these polypeptides being then indirectly linked). Such spacer can be for example the amino acid sequence Glycine-Glycine-Glycine-Serine (GGGS, SEQ ID NO: 25) and the DNA spacer sequence encoding it can be SEQ ID NO: 26. In the context of this invention, this DNA sequence is hereafter designated as "DNA spacer sequence" and is located between the DNA encoding AGT or its catalytic domain, and the recombinant DNA sequence, preferably upstream from the DNA sequence encoding the peptide cleavage site.

As used herein, the term "pDeSNAPUniv" designates a DNA cassette encoding, in a single open reading frame, from 5' to 3':
a) a secretion signal peptide,
b) an AGT protein of SEQ ID NO:1, a mutant, a fragment or a catalytic domain thereof, in particular the SNAP mutant of SEQ ID NO:2,
c) at least one peptide cleavage site,
d) at least one label, and
e) at least one spacer sequence.

This pDeSNAPUniv DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

More preferably, the pDeSNAPUniv DNA cassette comprises, from 5' to 3', the sequence SEQ ID NO:23 encoding the BiP-like secretion signal, the SEQ ID NO:15 or 31 encoding the SNAP mutant, the spacer sequence of SEQ ID NO:26, the peptide cleavage site pro-TEV of SEQ ID NO:29, the peptide cleavage site pro-TEV of SEQ ID NO:30, the spacer sequence of SEQ ID NO:26 and the sequence SEQ ID NO:28 encoding the His-tag label (see FIG. 8, showing the structure of the pDeSNAPUniv cassette). Such a pDeSNAPUniv DNA cassette is for example SEQ ID NO:34.

This "pDeSNAPUniv" cassette is held as "universal" since it can be inserted in any kind of vectors dedicated to transfect host cells in order to produce heterologous proteins, namely vertebrate vectors (such as pcDNA3 or pCI-neo vectors) as well as non-vertebrate vectors (such as pMT/BiP/V5-HisA which is useful in the DES system from Invitrogen). Examples of plasmid comprising said universal sequence is SEQ ID NO:43 (pMT/BiP/V5-HisA from Invitrogen comprising the pDeSNAP Univ cassette), SEQ ID NO:44 (pUC57 from Invitrogen comprising the pDeSNAP Univ cassette) or SEQ ID NO:45 (pcDNA3 from Invitrogen comprising the pDeSNAP Univ cassette).

Another example of plasmid comprising said universal sequence is SEQ ID NO:105 which is a pUC57 plasmid comprising, from 5' to 3', the constitutive promoter of *Orgyia pseudotsugata* multicapsid nucleoprotein virus-immediate-early 2 promoter (OpIE2SP) the BiPlike signal peptide of SEQ ID NO:152, the SNAP-like sequence of SEQ ID NO:31, the spacer sequence of SEQ ID NO:26, the pro-TEV1 sequence SEQ ID NO:29, and the C-term peptide tag of SEQ ID NO:106.

Once the heterologous sequence of a protein of interest such as SBV.N is cloned herein, such a vector can be advantageously transfected in either vertebrate or non-vertebrate host cells, so as to produce the protein of interest in high amounts.

In a preferred embodiment, the vector of the invention comprises a so-called "pDeSNAP Univ/SBV.N cassette" i.e., a pDeSNAPUniv DNA cassette in which the sequence of the N nucleoprotein of SBV has been inserted, said pDeSNAP Univ/SBV.N cassette comprising a nucleotide sequence encoding, in a single open reading frame, from 5' to 3':
a) a secretion signal peptide,
b) an AGT protein of SEQ ID NO:1, a mutant, a fragment or a catalytic domain thereof, in particular the SNAP mutant of SEQ ID NO:2,
c) at least one peptide cleavage site,
d) the N nucleoprotein of SBV of SEQ ID NO: 16,
e) at least one label, and
f) at least one spacer sequence.

This pDeSNAP Univ/SBV.N DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, the N nucleoprotein of SBV of SEQ ID NO:16, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

More preferably, the pDeSNAP Univ/SBV.N DNA cassette comprises, from 5' to 3', the sequence SEQ ID NO:23 encoding the BiP-like secretion signal or the SEQ ID NO:22 encoding the ssBiP secretion signal, the SEQ ID NO:15 or 31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label.

Even more preferably, the pDeSNAP Univ/SBV.N DNA cassette comprises, from 5' to 3', the sequence SEQ ID NO:22 encoding the ssBiP secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:35.

Alternatively, the pDeSNAP Univ/SBV.N DNA cassette can comprise, from 5' to 3', the sequence SEQ ID NO:23 encoding the BiP-like secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:36 (whose structure is shown on FIG. 9).

Thus, in a preferred embodiment, the vector of the invention comprises the pDeSNAP Univ/SBV.N cassette having the nucleotide sequence SEQ ID NO: 35 or the nucleotide sequence SEQ ID NO:36.

More precisely, the pDeSNAP Univ/SBV.N cassette nucleotide sequence of SEQ ID NO:35 comprises:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the SBV.N DNA sequence SEQ ID NO: 17 (which corresponds to the natural SBV.N sequence, in which the internal EcoRV site has been deleted and two EcoRV and XmaI sites have been added at the extremities),
a DNA sequence SEQ ID NO: 30 encoding a pro-TEV2 cleavage site of sequence ENLYFQG (SEQ ID NO: 33), a DNA sequence SEQ ID NO: 28 encoding a HisTag sequence.

And the pDeSNAP Univ/SBV.N cassette nucleotide sequence SEQ ID NO:36 comprises (see also FIG. 9):
- an insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

Interestingly, the pDeSNAP Univ/SBV.N cassette nucleotide sequence of SEQ ID NO:36 cassette also comprises in addition an NheI site upstream of the ATG, a BglII site between the BiP-like sequence and the SNAP-like sequence, and an AgeI site and a HindIII site which are both located downstream of the stop codon.

Vectors of the invention are for example SEQ ID NO:43 (which is the pMT/BiP/V5-HisA plasmid from Invitrogen comprising the pDeSNAP Univ cassette) in which the SBV.N DNA sequence SEQ ID NO: 17 has been inserted, SEQ TD NO:44 (which is the pUC57 plasmid from Invitrogen comprising the pDeSNAP Univ cassette) in which the SBV.N DNA sequence SEQ ID NO: 17 has been inserted or SEQ ID NO:45 (which is the pcDNA3 plasmid from Invitrogen comprising the pDeSNAP Univ cassette) in which the SBV.N DNA sequence SEQ ID NO: 17 has been inserted.

Vectors of the invention are also provided in the S2 cells which have been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another aspect, the present invention targets a recombinant cell which is stably transfected by a vector of the invention, preferably a vector comprising the nucleotide sequence SEQ ID NO: 35 or SEQ ID NO: 36.

Preferably, in this aspect of the invention, said recombinant cell is a non-vertebrate cell, preferably an insect cell, and more preferably a S2 cell.

Non-vertebrate cells can be any cells from the Insect, Arachnida, Crustacea, Mollusca, Annelida, Cirripedia, Radiata, Coelenterata and Infusoria. In the context of the invention, non-vertebrate cells are preferably insect cells, such as Drosophila or Mosquito cells. They are more preferably a Drosophila S2 cells. In this case, the expression vector of the invention comprises for example SEQ ID NO: 35.

Drosophila S2 cells have been widely described. They are especially suited to high-yield production of protein, because they can be maintained in suspension cultures at room temperature (24±1° C.). Culture medium is $M_3$ supplemented with between 5 and 10% (v/v) heat-inactivated fetal bovine serum (FBS). In the preferred embodiment of the invention, the culture medium contains 5% FBS. After induction, the cells are cultured in serum-free media. In this media, the S2 cells can be grown in suspension cultures, for example in 250 mL to 2000 mL spinner flasks, with stirring at 50-60 rpm. Cells densities are typically maintained between $10^6$ and $10^7$ cells per mL.

In a preferred embodiment, the recombinant cell of the invention is the S2 cell which has been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another preferred embodiment, said recombinant cell is a vertebrate cell.

Preferably, said vertebrate recombinant cell is a mammal cell, a preferably CHO, YB2/O, COS, HEK, NIH3T3, HeLa cell or derivatives thereof. More preferably, in this case, the expression vector of the invention comprises SEQ ID NO: 36.

In another aspect of the present invention, the said recombinant cell is used to amplify and purify the expression vectors of the invention, preferably those comprising SEQ ID NO: 35 or 36.

In this aim, the nucleotide expression vectors of the invention may also comprise a gene encoding a selection marker, and/or a terminator sequence. Selection markers genes that can be included in the construct are typically those that confer selectable phenotypes such as resistance to antibiotics (e.g. blasticidin, ampicillin, kanamycin, hygromycin, puromycin, chloramphenicol).

Methods for producing expression vectors are well-known in the art.

In another aspect, the recombinant cell of the invention is used so as to produce the N nucleoprotein of the Schmallenberg virus in high amounts.

Thus, in a particular embodiment, the present invention is also drawn to a method for the production of the N nucleoprotein of the Schmallenberg virus, the method comprising the steps of:
- (a) obtaining the vector of the invention, said vector comprising for example the DNA sequence SEQ ID NO:35 or SEQ ID NO:36,
- (b) transfecting an host cell (preferably an insect cell or a mammal cell) with the polynucleotide obtained under step (a);
- (c) allowing for the expression of said polynucleotide obtained under step (b) to produce the N nucleoprotein of the Schmallenberg virus;
- (d) optionally, cleaving the AGT polypeptide,
- (e) recovering the N nucleoprotein of the Schmallenberg virus,
- (f) optionally, purifying the N nucleoprotein of the Schmallenberg virus.

For performing the different steps of the method of the present invention, there may be employed conventional molecular biology, microbiology and recombinant DNA techniques within the skills of the person of the art. Such techniques are fully explained in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

The term "transfection" means the introduction of a foreign nucleic acid into a eukaryotic host cell so that the host cell will express the introduced gene or sequence to produce the N nucleoprotein of Schmallenberg virus. A host cell that receives and expresses introduced DNA or RNA has been "transfected" and is a "transfectant" or a "clone". The DNA or RNA introduced to a host cell can come from any source, including cells of the same genus or species as the host cell or cells of a different genus or species.

In the context of the invention, the transfection of the host cells with the polynucleotides can be performed by a classical method in the art, for example by transfection, infection, or electroporation. In another embodiment, the vector of the invention can be introduced in vivo by lipofection (as naked DNA), or with other transfection facilitating agents (peptides, polymers, etc.). Synthetic cationic lipids can be used to prepare liposomes for in vivo transfection of a gene encoding a marker (Felgner et al., *Proc. Natl. Acad. Sci. U.S.A.*, 84:7413-7417, 1987). Useful lipid compounds and compositions for transfer of nucleic acids are described in WO 95/18863 and WO 96/17823, and in U.S. Pat. No. 5,459,127. Lipids may be chemically coupled to other molecules for the purpose of targeting (see, Mackey et al., *Proc. Natl. Acad. Sci. U.S.A.*, 85:8027-8031, 1988). Targeted peptides, such as hormones or neurotransmitters, and proteins such as antibodies, or non-peptide molecules could be coupled to liposomes chemically. Other molecules are also useful for facilitating transfection of a nucleic acid in vivo, such as a cationic oligopeptides (see WO 95/21931), peptides derived from DNA binding proteins (see WO 96/25508), or a cationic polymer (see WO 95/21931). It is also possible to introduce the vector in vivo as a naked DNA plasmid. Naked DNA vectors for gene therapy can be introduced into the desired host cells by methods known in the art, such as electroporation, microinjection, cell fusion, DEAE dextran, calcium phosphate precipitation, use of a gene gun, or use of a DNA vector transporter (see, Wu et al., *J. Biol. Chem.*, 267:963-967, 1992; Wu and Wu, *J. Biol. Chem.*, 263:14621-14624, 1988; Williams et al., *Proc. Natl. Acad. Sci. U.S.A.*, 88:2726-2730, 1991).

The term "allowing for the expression" of a polynucleotide herein means that the stimulus of the regulatory sequences that are present in the vector (e.g. the stimulus activating the inducible promoter), and all the required components are present in a sufficient amount for the translation of the polynucleotide to occur.

If need be, the AGT/SNAP polypeptide can be cleaved off the produced fusion protein by adding a protease having a defined cleavage site to the supernatant of or into the recombinant cells. For example, when a vector comprising the pDeSNAP Univ cassette of SEQ ID NO: 35 or 36 is used, the cleavage of the pro-TEV cleavage site ENLKYFQ/G(S) is obtained by adding the TEV protease to the supernatant of the recombinant cells. Alternatively, the AGT/SNAP polypeptide can be maintained so as to enhance the life-span of the N nucleoprotein from SBV.

Moreover, the skilled artisan will appreciate that an expressed or secreted protein or polypeptide can be detected in the culture medium used to maintain or grow the present host cells. The culture medium can be separated from the host cells by known procedures, such as centrifugation or filtration. The protein or polypeptide can then be detected in the cell-free culture medium by taking advantage of known properties characteristic of the protein or polypeptide. Such properties can include the distinct immunological, enzymatic or physical properties of the protein or polypeptide. For example, if a protein or polypeptide has a unique enzyme activity an assay for that activity can be performed on the culture medium used by the host cells. Moreover, when antibodies reactive against a given protein or polypeptide are available, such antibodies can be used to detect the protein or polypeptide in any known immunological assay (for example as in Harlowe, et al., 1988, Antibodies: A Laboratory Manual, Cold Spring Harbor Laboratory Press).

Recovery of the nucleoprotein N from SBV is mediated by the means well-known in the art, including, but not limited to, preparative disc-gel electrophoresis, isoelectric focusing, HPLC, reversed-phase HPLC, gel filtration, ion exchange and partition chromatography, precipitation and salting-out chromatography, extraction, and countercurrent distribution, and the like. As it is preferable to produce the protein of interest in the recombinant system of the invention linked with a label, said label will facilitate the recovery of the polypeptide from the crude lysate of the host cell by chromatography on an appropriate solid-phase matrix. Alternatively, antibodies produced against the protein or against peptides derived therefrom can be used as recovery reagents.

The present Inventors discovered that the fusion proteins generated with the method of the invention generally do not need to be further purified. However, a further step (g) of purification may be performed, if required.

A purified material may contain less than about 50%, preferably less than about 75%, and most preferably less than about 90%, of the cellular components with which it was originally associated. The term "substantially pure" indicates the highest degree of purity which can be achieved using conventional purification techniques known in the art.

In an embodiment of the invention, the methods of the invention enable to obtain at least 40 mg/L, preferably at least 50 mg/L, more preferably at least 60 mg/L of the substantially pure N nucleoprotein of the Schmallenberg virus in the recovered cell culture supernatant.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein of Schmallenberg virus of SEQ ID NO: 16.

In this fusion polypeptide, said AGT enzyme is preferably the protein of SEQ ID NO: 2, or a homologue thereof (said homologous being as defined above).

This fusion polypeptide preferably further comprises a label, as defined above. This label is preferably a polyhistidine label, and is preferably located at the C terminal end of the N nucleoprotein of the Schmallenberg virus.

The fusion polypeptide of the invention is for example the amino acid sequence of SEQ ID NO: 41 (corresponding to the BiPlike/SNAP/SBV.N/Histag fusion protein) or SEQ ID NO: 46 (corresponding to the ssBiP/SNAP/SBV.N/Histag fusion protein) or SEQ ID NO:42 (corresponding to the SNAP/SBV.N fusion protein).

Finally, the chimeric protein SNAP-SBV. N may be useful as a diagnostic agent for the detection of the viral infection by the Schmallenberg virus, or for the detection of antibodies specific of the said virus in biological fluids, such as blood, serum, saliva, and the like.

Thus, in another aspect, the present invention is also drawn to the use of the fusion protein [SNAP-SBV. N] obtained by any method of the invention for identifying the presence of said pathogenic or non-pathogenic microorganisms in a biological sample, for example thanks to the immunoassay of the present invention.

In other aspects, the present invention also relates to vectors expressing fusion proteins of particular interest, said fusion proteins comprising a 6-alkylguanine-DNA-alkyltransferase enzyme (AGT), a mutant, a fragment or a catalytic domain thereof, that is fused in frame with interesting antigens, such as viral or bacterial antigens, microbial peptides and/or polypeptides of interest. These vectors are detailed below.

Echovirus Antigen

In another aspect, the present invention relates to a vector for expressing an echovirus antigen, for example the VP1 protein of the enterovirus 71 (Picornaviridae), in a host cell. In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VP1 protein of the enterovirus 71 (EV71, see for example Kolpe A. B. et al, *Virus Research* 2012).

In a preferred embodiment, this vector comprises a so-called "pDeSNAP Univ/EV71.VP1 cassette" i.e., a pDeSNAPUniv DNA cassette as defined above, in which the sequence SEQ ID NO:47 encoding the VP1 protein from the EV71 virus strain JL-AFP-EV71-07-03 (Genebank#JQ715713) has been inserted.

In a preferred embodiment, this vector comprises the pDeSNAP Univ/EV71.VP1 cassette having the nucleotide sequence SEQ ID NO: 48 comprising:
 an insect BiP sequence of SEQ ID NO: 22,
 the SNAP-like sequence of SEQ ID NO: 31,
 a first DNA sequence SEQ ID NO: 26 encoding the spacer sequence GGGS (SEQ ID NO: 25),
 a DNA sequence SEQ ID NO: 29 encoding a pro-TEV1 cleavage site of sequence ENLYFQS (SEQ ID NO: 32),
 the DNA sequence SEQ ID NO:47 encoding the VP1 protein from the EV71 virus strain JL-AFP-EV71-07-03 (Genebank#JQ715713),
 a DNA sequence SEQ ID NO: 30 encoding a pro-TEV2 cleavage site of sequence ENLYFQG (SEQ ID NO: 33),
 a second DNA sequence SEQ ID NO: 26 encoding the spacer sequence GGGS (SEQ ID NO: 25),
 a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VP1 protein from the EV71 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 49 (corresponding to the SNAP-like/proTEV1/EV71.VP1/proTEV2/Histag fusion protein).

Thus, in another aspect, the present invention is also drawn to the use of this fusion protein [SNAP-EV71.VP1] for identifying the presence of the enterovirus 71 in a biological sample, for example thanks to the immunoassay of the present invention.

Flavivirus Antigens

In another aspect, the present invention relates to vectors for expressing particular Flavivirus antigens in a host cell.

In a preferred embodiment, said Flavivirus antigen is the soluble E protein (sE) from the Japanese Encephalitis virus (JEV.sE). More particularly, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE protein from the Japanese Encephalitis virus.

In a preferred embodiment, this vector comprises a so-called "pDeSNAP Univ/JEV.sE cassette" i.e., a pDeSNAPUniv DNA cassette as defined above, in which the sequences of gene encoding the soluble E protein (sE) from the Japanese Encephalitis virus (JEV) have been inserted.

In a preferred embodiment, this vector comprises the pDeSNAP Univ/JEV.sE cassette having the nucleotide sequence SEQ ID NO: 50 comprising, from 5' to 3':
 an insect BiP sequence of SEQ ID NO: 22,
 the DNA sequence encoding the prM/M sequence from JEV strain SA-14 (Genbank#M55506),
 the DNA sequence encoding the E[1-395] sequence from JEV strain SA-14 (Genbank#M55506),
 a DNA sequence SEQ ID NO: 26 encoding the spacer sequence GGGS (SEQ ID NO: 25),
 the SNAP-like sequence of SEQ ID NO: 31,
 a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble E protein (sE) from the Japanese Encephalitis virus (JEV.sE). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 51 (corresponding to the JEV.sE/SNAP-like/Histag fusion protein).

Thus, in another aspect, the present invention is also drawn to the use of this fusion protein [SNAP-JEV.sE] for identifying the presence of the Japanese Encephalitis virus (JEV) in a biological sample, for example thanks to the immunoassay of the present invention.

In a preferred embodiment, said Flavivirus antigen is the domain III of the envelope E protein (EDIII protein) from the Japanese encephalitis virus of genotype 1 (JE-1.EDIII), of genotype 2 (JE-3.EDIII), of genotype 4 (E-4.EDIII), or of genotype 5 QE-5.EDIII).

In another aspect, the present invention therefore relates to a vector for expressing the domain III of the envelope E protein (EDIII protein) from the Japanese encephalitis virus of genotype I (JE-I.EDIII), of genotype 2 QE-2.EDIII), of genotype 4 (JE-4.EDIII), or of genotype 5 (JE-5.EDIII) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the EDIII protein from the Japanese encephalitis virus of genotype 1 (JE-I.EDIII), of genotype 2 (JE-2.EDIII), of genotype 4 (JE-4.EDIII), or of genotype 5 (JE-5.EDIII).

In a preferred embodiment, this vector comprises a so-called "pDeSNAP Univ/JE-I.EDIII cassette" i.e., a pDeSNAPUniv DNA cassette as defined above, in which the sequence of gene encoding the domain III of the envelope E protein (EDIII protein) from the Japanese encephalitis virus of genotype 1 (JE-1.EDIII) has been inserted.

In a preferred embodiment, this vector comprises the pDeSNAP Univ/JE-1.EDIII cassette having the nucleotide sequence SEQ ID NO: 52 comprising:

an insect BiP-like sequence of SEQ ID NO: 23,
the SNAP-like sequence of SEQ ID NO: 31,
the DNA sequence SEQ ID NO:54 encoding the domain III of the envelope E protein (EDIII protein) from the Japanese encephalitis virus of genotype 1 (Genebank#AY377577),
a DNA sequence SEQ ID NO: 28 encoding a HisTag sequence.

In a preferred embodiment, this vector comprises a so-called "pDeSNAP Univ/JE-2.EDIII cassette" i.e., a pDeSNAPUniv DNA cassette as defined above, in which the sequence of the domain III of the envelope E protein (EDIII protein) from the Japanese encephalitis virus of genotype 2 (JE-2.EDIII) has been inserted.

In a preferred embodiment, this vector comprises the pDeSNAP Univ/JE-2.EDIII cassette having the nucleotide sequence SEQ ID NO: 59 comprising
an insect BiP-like sequence of SEQ ID NO: 23,
the SNAP-like sequence of SEQ ID NO: 31,
the DNA sequence SEQ ID NO:55 encoding the domain III of the envelope E protein (EDIII protein) from the Japanese encephalitis virus of genotype 2 (Genebank#L-43566),
a DNA sequence SEQ ID NO: 28 encoding a HisTag sequence.

In a preferred embodiment, this vector comprises a so-called "pDeSNAP Univ/JE-4.EDIII cassette" i.e., a pDeSNAPUniv DNA cassette as defined above, in which the sequence of the domain III of the envelope E protein (EDIII protein) from the Japanese encephalitis virus of genotype 4 (JE-4.EDIII) has been inserted.

In a preferred embodiment, this vector comprises the pDeSNAP Univ/JE-4.EDIII cassette having the nucleotide sequence SEQ ID NO: 61 comprising:
an insect BiP-like sequence of SEQ ID NO: 23,
the SNAP-like sequence of SEQ ID NO: 31,
the DNA sequence SEQ ID NO:56 encoding the domain III of the envelope E protein (EDIII protein) from the Japanese encephalitis virus of genotype 4 (Genebank# U70408),
a DNA sequence SEQ ID NO: 28 encoding a HisTag sequence.

In a preferred embodiment, this vector comprises a so-called "pDeSNAP Univ/JE-5.EDIII cassette" i.e., a pDeSNAPUniv DNA cassette as defined above, in which the sequence of the gene encoding the domain III of the envelope E protein (EDIII protein) from the Japanese encephalitis virus of genotype 5 (JE-5.EDIII) has been inserted.

In a preferred embodiment, this vector comprises the pDeSNAP Univ/JE-5.EDIII cassette having the nucleotide sequence SEQ ID NO: 63 comprising:
an insect BiP-like sequence of SEQ ID NO: 23,
the SNAP-like sequence of SEQ ID NO: 31,
the DNA sequence SEQ ID NO:57 encoding the domain III of the envelope E protein (EDIII protein) from the Japanese encephalitis virus of genotype 5 (Genebank#JN587258),
a DNA sequence SEQ ID NO: 28 encoding a HisTag sequence.

In another aspect, the present invention relates to recombinant cells which are stably transfected by said vectors.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the JE-1, JE-2, JE-4, or JE-5 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 53 (corresponding to the SNAP-like/JE-1.EDIII/Histag fusion protein), SEQ ID NO: 60 (corresponding to the SNAP-like/JE-2.EDIII/Histag fusion protein) SEQ ID NO: 62 (corresponding to the SNAP-like/JE-4.EDIII/Histag fusion protein) or SEQ ID NO: 64 (corresponding to the SNAP-like/JE-5.EDIII/Histag fusion protein).

Thus, in another aspect, the present invention is also drawn to the use of any of these fusion proteins [SNAP-JE-1.EDIII], [SNAP-JE-2.EDIII], [SNAP-JE-4.EDIII] or [SNAP-JE-5.EDIII] for identifying the presence of the Japanese encephalitis virus of genotype 1, 2, 4 or 5 respectively in a biological sample, for example thanks to the immunoassay of the present invention.

In another aspect, the present invention is drawn to a vector for expressing the domain III of the envelope E protein (EDIII protein) from the Rabensburg virus (RabV) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the envelope E protein (EDIII protein) from the Rabensburg virus (RabV).

In a preferred embodiment, this vector comprises a so-called "pDeSNAP Univ/RabV.EDIII cassette" i.e., a pDeSNAPUniv DNA cassette as defined above, in which the sequence of the EDIII protein from the Rabensburg virus has been inserted.

In a preferred embodiment, this vector comprises the pDeSNAP Univ/RabV.EDIII cassette having the nucleotide sequence SEQ ID NO: 65 comprising
an insect BiP-like sequence of SEQ ID NO: 23,
the SNAP-like sequence of SEQ ID NO: 31,
the DNA sequence SEQ ID NO:58 encoding the domain III of the envelope E protein (EDIII protein) from the Rabensburg virus (Genebank#AY65264),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Rabensburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 66 (corresponding to the SNAP-like/RabV.EDIII/Histag fusion protein).

Thus, in another aspect, the present invention is also drawn to the use of this fusion protein [SNAP-RabV.EDIII] for identifying the presence of the Rabensburg virus in a biological sample, for example thanks to the immunoassay of the present invention.

Alphavirus Antigens

In another aspect, the present invention is relates to vectors for expressing particular alphavirus antigens, for example the soluble E2 protein from the Ross River virus (RR.sE2) or from the Mayaro virus (MAY.sE2), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Ross River virus.

In a preferred embodiment, this vector comprises a so-called "pDeSNAP Univ/RR.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/RR.sE2 cassette having the nucleotide sequence SEQ ID NO: 69 comprising.
- an insect BiP sequence of SEQ ID NO: 22,
- the DNA sequence encoding the sE2 protein of the Ross River virus strain QML1 (Genbank#GQ433354),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Ross River virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 70 (corresponding to the RR.sE2/SNAP-like/Histag fusion protein).

Thus, in another aspect, the present invention is also drawn to the use of this fusion protein [SNAP-RR.sE2] for identifying the presence of the Ross River virus in a biological sample, for example thanks to the immunoassay of the present invention.

The present invention is also drawn to a vector for expressing the soluble E2 protein from the Mayaro virus (MAY.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Mayaro virus.

In a preferred embodiment, this vector comprises a so-called "pDeSNAP Univ/MAY.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/MAY.sE2 cassette having the nucleotide sequence SEQ ID NO: 71 comprising:
- an insect BiP sequence of SEQ ID NO: 22,
- the DNA sequence encoding the corrected sE2 protein (E2-S203C) of the Mayaro virus strain IQD2668 (Genbank#DQ487429.1),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Mayaro virus (MAY.sE2). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 72 (corresponding to the MAY.sE2/SNAP-like/Histag fusion protein).

Thus, in another aspect, the present invention is also drawn to the use of this fusion protein [SNAP-MAY.sE2] for identifying the presence of the Mayaro virus in a biological sample, for example thanks to the immunoassay of the present invention.

Equine Encephalitis Virus Antigens

In another aspect, the present invention relates to vectors for expressing particular Equine Encephalitis virus antigens, for example the soluble E2 protein from the Western Equine Encephalitis virus (WEE.sE2), the Eastern Equine Encephalitis virus (EEE.sE2) or the Venezuelan Equine Encephalitis virus (VEE.sE2) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Western Equine Encephalitis virus.

In a preferred embodiment, this vector comprises a so-called "pDeSNAP Univ/WEE.sE2 cassette" i.e., a pDeSNAPUniv DNA cassette as defined above, in which the sequence of the sE2 gene from the Western Equine Encephalitis virus has been inserted.

In a preferred embodiment, this vector comprises the pDeSNAP Univ/WEE.sE2 cassette having the nucleotide sequence SEQ ID NO: 73 comprising.
- an insect BiP sequence of SEQ ID NO: 22,
- the DNA sequence encoding the sE2 protein from Western Equine Encephalitis virus strain (Genbank#NC00390808),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the WEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 74 (corresponding to the WEE.sE2/SNAP-like/Histag fusion protein).

Thus, in another aspect, the present invention is also drawn to the use of this fusion protein [SNAP-WEE.sE2] for identifying the presence of the Western Equine Encephalitis virus in a biological sample, for example thanks to the immunoassay of the present invention.

In another embodiment, the present invention is also drawn to a vector for expressing the soluble E2 protein from the Eastern Equine Encephalitis virus (EEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Eastern Equine Encephalitis virus.

In a preferred embodiment, this vector comprises a so-called "pDeSNAP Univ/EEE.sE2 cassette" i.e., a pDeSNAPUniv DNA cassette as defined above, in which the sequence of the sE2 gene from the Eastern Equine Encephalitis virus has been inserted.

In a preferred embodiment, this vector comprises the pDeSNAP Univ/EEE.sE2 cassette having the nucleotide sequence SEQ ID NO: 75 comprising:
- an insect BiP sequence of SEQ ID NO: 22,
- the DNA sequence encoding the sE2 protein from Eastern Equine Encephalitis virus strain (Genbank#EF151502),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the EEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 76 (corresponding to the EEE.sE2/SNAP-like/Histag fusion protein).

Thus, in another aspect, the present invention is also drawn to the use of this fusion protein [SNAP-EEE.sE2] for identifying the presence of the Eastern Equine Encephalitis virus in a biological sample, for example thanks to the immunoassay of the present invention.

In another embodiment, the present invention is also drawn to a vector for expressing the soluble E2 protein from the Venezuelan Equine Encephalitis virus (VEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Venezuelan Equine Encephalitis virus.

In a preferred embodiment, this vector comprises a so-called "pDeSNAP Univ/VEE.sE2 cassette" i.e., a pDeSNAPUniv DNA cassette as defined above, in which the sequence of the sE2 gene from the Venezuelan Equine Encephalitis virus has been inserted.

In a preferred embodiment, this vector comprises the pDeSNAP Univ/VEE.sE2 cassette having the nucleotide sequence SEQ ID NO: 77 comprising.
- an insect BiP sequence of SEQ ID NO: 22,
- the DNA sequence encoding the sE2 protein from Venezuelan Equine Encephalitis virus strain (Genbank#AY973944),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the VEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 78 (corresponding to the VEE.sE2/SNAP-like/Histag fusion protein).

Thus, in another aspect, the present invention is also drawn to the use of this fusion protein [SNAP-VEE.sE2] for identifying the presence of the Venezuelan Equine Encephalitis virus in a biological sample, for example thanks to the immunoassay of the present invention.

Orthobunyavirus Antigens

In another aspect, the present invention relates to vectors for expressing particular orthobunyavirus antigens, for example the Nucleoprotein N from the Akabane virus (AKA.N), from the Aino virus (AIN.N) or from the Shamonda virus (SHA.N), in a host cell.

In particular, the present invention relates to a vector comprising the nucleotide sequence encoding a) a secretion signal peptide which is functional in said host cells, and h) a 6-alkylguanine-DNA-alkyltransferase enzyme (AGT), a mutant, a fragment or a catalytic domain thereof, and c) the Nucleoprotein N from the Akabane virus.

In a preferred embodiment, this vector comprises a so-called "pDeSNAP Univ/AKA.N cassette" i.e., a pDeSNAPUniv DNA cassette as defined above, in which the sequence of the gene encoding the Nucleoprotein N from the Akabane virus has been inserted.

In a preferred embodiment, this vector comprises the pDeSNAP Univ/AKA.N cassette having the nucleotide sequence SEQ ID NO: 79 comprising.
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Akabane virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Akabane virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 80 (corresponding to the SNAP-like/proTEV1/AKA.N/pro-TEV2/Histag fusion protein).

Thus, in another aspect, the present invention is also drawn to the use of this fusion protein [SNAP-AKA.N] for identifying the presence of the Akabane virus in a biological sample, for example thanks to the immunoassay of the present invention.

In another embodiment, the present invention is drawn to a vector for expressing the Nucleoprotein N from the Aino virus (AIN.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Aino virus.

In a preferred embodiment, this vector comprises a so-called "pDeSNAP Univ/AIN.N cassette" i.e., a pDeSNAPUniv DNA cassette as defined above, in which the sequence of the gene encoding the Nucleoprotein N from the Aino virus has been inserted.

In a preferred embodiment, this vector comprises the pDeSNAP Univ/AIN.N cassette having the nucleotide sequence SEQ ID NO: 81 comprising:
- an insect BiP sequence of SEQ ID NO: 22,
- the SNAP-like sequence of SEQ TD NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Aino virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Aino virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 82 (corresponding to the SNAP-like/proTEV1/AIN.N/pro-TEV2/Histag fusion protein).

Thus, in another aspect, the present invention is also drawn to the use of this fusion protein [SNAP-AIN.N] for identifying the presence of the Aino virus in a biological sample, for example thanks to the immunoassay of the present invention.

In another embodiment, the present invention is drawn to a vector for expressing the Nucleoprotein N from the Shamonda virus (SHA.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Shamonda virus.

In a preferred embodiment, this vector comprises a so-called "pDeSNAP Univ/SHA.N cassette" i.e., a pDeSNAPUniv DNA cassette as defined above, in which the sequence of the gene encoding the Nucleoprotein N from the Shamonda virus has been inserted.

In a preferred embodiment, this vector comprises the pDeSNAP Univ/SHA.N cassette having the nucleotide sequence SEQ ID NO: 83 comprising.

an insect BiP sequence of SEQ ID NO: 22, the SNAP-like sequence of SEQ ID NO: 31, a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32), the DNA sequence encoding the natural N nucleoprotein of the Shamonda virus, a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Shamonda virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 84 (corresponding to the SNAP-like/proTEV1/SHA.N/pro-TEV2/Histag fusion protein).

Thus, in another aspect, the present invention is also drawn to the use of this fusion protein [SNAP-SHA.N] for identifying the presence of the Shamonda virus in a biological sample, for example thanks to the immunoassay of the present invention.

Betacoronavirus Antigens

In another aspect, the present invention relates to vectors for expressing particular betacoronavirus antigens, for example the Nucleoprotein N from human betacoronavirus (huCOV.N) or the protein S of the human betacoronavirus (huCOV.S), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from human betacoronavirus.

In a preferred embodiment, this vector comprises a so-called "pDeSNAP Univ/huCOV.N cassette" i.e., a pDeSNAPUniv DNA cassette as defined above, in which the sequence of the gene encoding the Nucleoprotein N from human betacoronavirus has been inserted.

In a preferred embodiment, this vector comprises the pDeSNAP Univ/huCOV.N cassette having the nucleotide sequence SEQ ID NO: 85 comprising:

an insect BiP sequence of SEQ ID NO: 22, the SNAP-like sequence of SEQ ID NO: 31, a DNA sequence SEQ ID NO: 29 encoding a pro-TEV1 cleavage site of sequence ENLYFQS (SEQ ID NO: 32), the DNA sequence encoding the gene N from human betacoronavirus 2cEMC/2012 (Genbank#JX869059), a DNA sequence SEQ ID NO: 30 encoding a pro-TEV2 cleavage site of sequence ENLYFQG (SEQ ID NO: 33), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 86 (corresponding to the SNAP-like/proTEV1/huCOV.N/proTEV2/Histag fusion protein).

Thus, in another aspect, the present invention is also drawn to the use of this fusion protein [SNAP-huCOV.N] for identifying the presence of the human betacoronavirus in a biological sample, for example thanks to the immunoassay of the present invention.

In another embodiment, the present invention is drawn to a vector for expressing the soluble form of the spike S protein from human betacoronavirus (huCOV.S) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble form of the spike S protein from human betacoronavirus.

In a preferred embodiment, this vector comprises a so-called "pDeSNAP Univ/huCOV.S cassette" i.e., a pDeSNAPUniv DNA cassette as defined above, in which the sequence of the gene S from human betacoronavirus has been inserted.

In a preferred embodiment, this vector comprises the pDeSNAP Univ/huCOV.S cassette having the nucleotide sequence SEQ ID NO: 87 comprising:
an insect BiP sequence of SEQ ID NO: 22,
the DNA sequence encoding the gene S from human betacoronavirus 2cEMC/2012 (Genbank#JX869059),
a DNA sequence SEQ ID NO: 26 encoding the spacer sequence GGGS (SEQ ID NO: 25),
the SNAP-like sequence of SEQ ID NO: 31,
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble form of the spike S protein from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 88 (corresponding to the huCOV.S/SNAP-like/Histag fusion protein).

Thus, in another aspect, the present invention is also drawn to the use of this fusion protein [SNAP-huCOV.S] for identifying the presence of the human betacoronavirus in a biological sample, for example thanks to the immunoassay of the present invention.

Hepacivrus Antigen

In another aspect, the present invention relates to vectors for expressing particular hepacivirus antigens, for example the protein C from Hepatitis C virus (HCV.C) or from Hepatitis E virus (HEV.C), in a host cell.

In one embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis C virus.

In a preferred embodiment, this vector comprises a so-called "pDeSNAP Univ/HCV.C cassette" i.e., a pDeSNAPUniv DNA cassette as defined above, in which the sequence of the gene of the protein C from Hepatitis C virus has been inserted.

In a preferred embodiment, this vector comprises the pDcSNAP Univ/HCV.C cassette having the nucleotide sequence SEQ ID NO: 89 comprising:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the C protein from hepatitis C virus genotype 1b (strain TCHM-R2/03),
a DNA sequence SEQ ID NO: 30 encoding a pro-TEV2 cleavage site of sequence ENLYFQG (SEQ ID NO: 33),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis C virus (HCV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 90 (corresponding to the SNAP-like/proTEV1/HCV.C/proTEV2/Histag fusion protein).

Thus, in another aspect, the present invention is also drawn to the use of this fusion protein [SNAP-HCV.C] for identifying the presence of the Hepatitis C virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis E virus (HEV.C).

In a preferred embodiment, this vector comprises a so-called "pDcSNAP Univ/HEV.C cassette" i.e., a pDeSNAPUniv DNA cassette as defined above, in which the sequence of the gene of the protein C from Hepatitis E virus has been inserted.

In a preferred embodiment, this vector comprises the pDeSNAP Univ/HEV.C cassette having the nucleotide sequence SEQ ID NO: 150 comprising:
an insect BiP-like sequence of SEQ ID NO: 23,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the C protein from hepatitis E virus (Genbank#AB29196),
a DNA sequence SEQ ID NO: 30 encoding a pro-TEV2 cleavage site of sequence ENLYFQG (SEQ ID NO: 33),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis E virus (HEV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 151 (corresponding to the SNAP-like/proTEV1/HEV.C/proTEV2/Histag fusion protein).

Thus, in another aspect, the present invention is also drawn to the use of this fusion protein [SNAP-HEV.C] for identifying the presence of the Hepatitis E virus in a biological sample, for example thanks to the immunoassay of the present invention.

Malaria Antigens In another aspect, the present invention is drawn to a vector for expressing particular Malaria antigens, for example, the MSP-1 and the AMA-1 proteins from *Plasmodium falciparum* (MSP-1+AMA-1) (see Pan W. et al, *The Journal of Immunology*, 2004), in an host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MSP-1 and the AMA-1 proteins from the parasite *Plasmodium falciparum*.

In a preferred embodiment, this vector comprises a so-called "pDeSNAP Univ/MSP-1+AMA-cassette" i.e., a pDeSNAPUniv DNA cassette as defined above, in which the sequence encoding the MSP-1 and the AMA-1 proteins from the parasite *Plasmodium falciparum* has been inserted.

In a preferred embodiment, this vector comprises the pDeSNAP Univ/MSP-1+AMA-1cassette having the nucleotide sequence SEQ ID NO: 91 comprising:
an insect BiP sequence of SEQ TD NO: 22,
the SNAP-like sequence of SEQ ID NO: 31,
a first DNA sequence SEQ ID NO: 26 encoding the spacer sequence GGGS (SEQ ID NO: 25),
the DNA sequence encoding the MSP-1 (19) sequence (50% G+C) from *Plasmodium falciparum*,
a DNA sequence SEQ ID NO: 30 encoding a pro-TEV2 cleavage site of sequence ENLYFQG (SEQ ID NO: 33),
the DNA sequence encoding the AMA-1 (III) sequence (50% G+C) from *Plasmodium falciparum*,
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MSP-1+AMA-1 protein from *Plasmodium falciparum*. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 92 (corresponding to the SNAP-like/MSP-1/proTEV2/AMA-1/Histag fusion protein).

Thus, in another aspect, the present invention is also drawn to the use of this fusion protein [SNAP-MSP-1+AMA-1] for identifying the presence of the parasite *Plasmodium falciparum* in a biological sample, for example thanks to the immunoassay of the present invention.

Leptospirosis Antigens

In another aspect, the present invention is drawn to a vector for expressing a particular leptospirosis antigen, such as the HbpA protein of *Leptospira* bacteria (see Sivakolundu S. et al, *Journal of Medical Microbiology*, 2012), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the HbpA protein from *Leptospira interrogans* bacteria.

In a preferred embodiment, this vector comprises a so-called "pDeSNAP Univ/HbpA cassette" i.e., a pDeSNAPUniv DNA cassette as defined above, in which the sequence encoding the HbpA protein from *Leptospira* bacteria has been inserted.

In a preferred embodiment, this vector comprises the pDeSNAP Univ/HbpA cassette having the nucleotide sequence SEQ ID NO: 93 comprising:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the modified short form of HbpA (TonB-dependent outer membrane receptor or LB191) from *Leptospira interrogans* serovar Lai str.56601 (Genbank#AA51750.1),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25),
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the HbpA protein from *Leptospira interrogans* bacteria. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 94 (corresponding to the SNAP-like/proTEV1/HbpA/proTEV2/Histag fusion protein).

Thus, in another aspect, the present invention is also drawn to the use of this fusion protein [SNAP-HbpA] for identifying the presence of the *Leptospira* bacteria in a biological sample, for example thanks to the immunoassay of the present invention.

Microbial Peptides

In another aspect, the present invention is drawn to a vector for expressing a microbial peptide, for example the microbial peptide MUB-40, in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MUB-40 peptide.

In a preferred embodiment, this vector comprises a so-called "pDeSNAP Univ/MUB40 cassette" i.e., a pDeSNAPUniv DNA cassette as defined above, in which the sequence encoding the MUB40 peptide has been inserted.

In a preferred embodiment, this vector comprises the pDeSNAP Univ/MUB40 cassette having the nucleotide sequence SEQ ID NO: 95 comprising
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32),
the DNA sequence encoding the MUB-40 peptide,
a DNA sequence SEQ ID NO: 30 encoding a pro-TEV2 cleavage site of sequence ENLYFQG (SEQ ID NO: 33), and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MUB 40 peptide. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 96 (corresponding to the SNAP-like/proTEV1/MUB40/proTEV2/Histag fusion protein).

Thus, in another aspect, the present invention is also drawn to the use of this fusion protein [SNAP-MUB40] for identifying the presence of a ligand in a biological sample, for example thanks to the immunoassay of the present invention.

Lectins Involved in Flavivirus Pathogenesis

In another aspect, the present invention is drawn to vectors for expressing particular lectins involved in Flavivirus pathogenesis, for example the mouse or the human soluble form of C-type like lectin (CLEC5A), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the mouse CLEC5A (mo-CLEC5A) or the human CLEC5A (hu-CLEC5A).

In a preferred embodiment, this vector comprises a so-called "pDeSNAP Univ/mo-CLEC5A cassette" i.e., a pDeSNAPUniv DNA cassette as defined above, in which the sequence encoding the mouse soluble form of C-type like lectin has been inserted.

In a preferred embodiment, this vector comprises the pDeSNAP Univ/mo-CLEC5A cassette having the nucleotide sequence SEQ ID NO: 97 comprising.
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ 11D NO: 32),
the DNA sequence encoding the mouse soluble form of C-type like lectin (CLEC5A),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25), and
a DNA sequence SEQ ID NO: 28 encoding a HisTag sequence.

In another aspect, the present invention relates to a recombinant cell which is stably transfected by said vector.

In another preferred embodiment, this vector comprises a so-called "pDeSNAP Univ/hu-CLEC5A cassette" i.e., a pDeSNAPUniv DNA cassette as defined above, in which the sequence encoding the human soluble form of C-type like lectin has been inserted.

In a preferred embodiment, this vector comprises the pDeSNAP Univ/hu-CLEC5A cassette having the nucleotide sequence SEQ ID NO: 99 comprising:
an insect BiP sequence of SEQ ID NO: 22,
the SNAP-like sequence of SEQ ID NO: 31,
a first DNA sequence SEQ ID NO: 26 encoding the spacer sequence GGGS (SEQ ID NO: 25),
a DNA sequence SEQ ID NO: 29 encoding a pro-TEV1 cleavage site of sequence ENLYFQS (SEQ ID NO: 32),
the DNA sequence encoding the human soluble form of C-type like lectin (CLEC5A),
a DNA sequence SEQ ID NO: 30 encoding a pro-TEV2 cleavage site of sequence ENLYFQG (SEQ ID NO: 33),
a second DNA sequence SEQ ID NO: 26 encoding the spacer sequence GGGS (SEQ ID NO: 25), and
a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the mouse or the human soluble form of C-type like lectin (CLEC5A). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 98 (corresponding to the SNAP-like/proTEV1/mo-CLEC5A/proTEV2/Histag fusion protein) or the amino acid sequence of SEQ ID NO: 100 (corresponding to the SNAP-like/proTEV1/hu-CLEC5A/proTEV2/Histag fusion protein).

Thus, in another aspect, the present invention is also drawn to the use of this fusion protein [SNAP-mo-CLEC5A] or [SNAP-hu-CLEC5A] for detection of presence of flaviviruses in a biological sample, for example thanks to the immunoassay of the present invention.

Anti-Flaviviral Mosquito Proteins

In another aspect, the present invention is drawn to vectors for expressing particular antiviral mosquito proteins, for example the VAGO protein from the *Culex* species (cxVAGO) or from the *Aedes* species (aaVAGO) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Aedes albopictus* mosquito.

In a preferred embodiment, this vector comprises a so-called "pDeSNAP Univ/aaVAGO cassette" i.e., a pDeSNAPUniv DNA cassette as defined above, in which the sequence encoding the VAGO protein from the *Aedes albopictus* mosquito has been inserted.

In a preferred embodiment, this vector comprises the pDeSNAP Univ/aaVAGO cassette having the nucleotide sequence SEQ ID NO: 103 comprising:
an insect BiP-like sequence of SEQ ID NO: 152,
the SNAP-like sequence of SEQ ID NO: 31,
a DNA sequence SEQ ID NO: 26 encoding the spacer sequence GGGS (SEQ ID NO: 25),
the DNA sequence encoding the VAGO protein from the *Aedes albopictus* mosquito, and a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Aedes albopictus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 104 (corresponding to the SNAP-like/aaVAGO/Histag fusion protein).

Thus, in another aspect, the present invention is also drawn to the use of this fusion protein [SNAP-aaVAGO] for identifying the presence of a ligand in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Culex quinquefasciatus* mosquito.

In a preferred embodiment, this vector comprises a so-called "pDeSNAP Univ/cxVAGO cassette" i.e., a pDeSNAPUniv DNA cassette as defined above, in which the sequence encoding the VAGO protein from the *Culex quinquefasciatus* mosquito has been inserted.

In a preferred embodiment, this vector comprises the pDeSNAP Univ/cxVAGO cassette having the nucleotide sequence SEQ ID NO: 101 comprising:
- an insect BiP-like sequence of SEQ ID NO: 152,
- the SNAP-like sequence of SEQ ID NO: 31,
- a DNA sequence SEQ ID NO: 26 encoding the spacer sequence GGGS (SEQ ID NO: 25),
- the DNA sequence encoding the VAGO protein from the *Culex quinquefasciatus* mosquito, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Culex quinquefasciatus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 102 (corresponding to the SNAP-like/cxVAGO/Histag fusion protein).

Thus, in another aspect, the present invention is also drawn to the use of this fusion protein [SNAP-cxVAGO] for identifying the presence of a ligand in a biological sample, for example thanks to the immunoassay of the present invention.

Viral Hemorragic Fever Antigens

In another aspect, the present invention is drawn to vectors for expressing particular viral hemorrhagic fever antigens such as:
- the Nucleoprotein N from the Crimean-Congo virus (CCHF.N), from the Ebola virus (EBO.N), from the Marburg virus (MAR.N), from the Lassa virus (LAS.N), from the Junin virus (JUN.N), from the Machupo virus (MAC.N), from the Sabia virus (SAB.N), or from the Guanarito virus (GUA.N),
- the Ectodomain of GP1 from the Lassa virus (LAS.ectoGP1), from the Junin virus (UN.ectoGP1), from the Machupo virus (MAC.ectoGP1), from the Sabia virus (SAB.ectoGP1), or from the Guanarito virus (GUA.ectoGP1),
- the Ectodomain of GP2 from the Lassa virus (LAS.ectoGP2), from the Junin virus (JUN.ectoGP2), from the Machupo virus (MAC.ectoGP2), from the Sabia virus (SAB.ectoGP2), or from the Guanarito virus (GUA.ectoGP2),
- the domain III of the envelope E protein from the Omsk virus (OMSK.EDIII), from the Kasyanur virus (KAS.EDIII), or from the Alkhurma virus (ALK.EDIII).

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Crimean-Congo virus (CCHF.N).

In a preferred embodiment, this vector comprises a so-called "pDeSNAP Univ/CCHF.N cassette" i.e., a pDeSNAPUniv DNA cassette as defined above, in which the sequence encoding the Nucleoprotein N from the Crimean-Congo virus has been inserted.

In a preferred embodiment, this vector comprises the pDeSNAP Univ/CCHF.N cassette having the nucleotide sequence SEQ ID NO: 108 comprising:
- an insect BiP sequence of SEQ ID NO: 22,
- the SNAP-like sequence of SEQ TD NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Crimean-Congo virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Crimean-Congo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 109 (corresponding to the SNAP-like/proTEV1/CCHEN/proTEV2/Histag fusion protein).

Thus, in another aspect, the present invention is also drawn to the use of this fusion protein [SNAP-CCHF.N] for identifying the presence of the Crimean-Congo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Ebola virus (EBO.N).

In a preferred embodiment, this vector comprises a so-called "pDeSNAP Univ/EBO.N cassette" i.e., a pDeSNAPUniv DNA cassette as defined above, in which the sequence encoding the Nucleoprotein N from the Ebola virus has been inserted.

In a preferred embodiment, this vector comprises the pDeSNAP Univ/EBO.N cassette having the nucleotide sequence SEQ ID NO: 110 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Ebola virus (Genbank#NC_002549),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Ebola virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 111 (corresponding to the SNAP-like/proTEV1/EBO.N/proTEV2/Histag fusion protein).

Thus, in another aspect, the present invention is also drawn to the use of this fusion protein [SNAP-EBO.N] for identifying the presence of the Ebola virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Marburg virus (MAR.N).

In a preferred embodiment, this vector comprises a so-called "pDeSNAP Univ/MAR.N cassette" i.e., a pDeSNAPUniv DNA cassette as defined above, in which the sequence encoding the Nucleoprotein N from the Marburg virus has been inserted.

In a preferred embodiment, this vector comprises the pDeSNAP Univ/MAR.N cassette having the nucleotide sequence SEQ ID NO: 112 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Marburg virus (Genbank#NC_001608),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Marburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 113 (corresponding to the SNAP-like/proTEV1/MAR.N/proTEV2/Histag fusion protein).

Thus, in another aspect, the present invention is also drawn to the use of this fusion protein [SNAP-MAR.N] for identifying the presence of the Marburg virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Lassa virus (LAS.N).

In a preferred embodiment, this vector comprises a so-called "pDeSNAP Univ/LAS.N cassette" i.e., a pDeSNAPUniv DNA cassette as defined above, in which the sequence encoding the Nucleoprotein N from the Lassa virus has been inserted.

In a preferred embodiment, this vector comprises the pDeSNAP Univ/LAS.N cassette having the nucleotide sequence SEQ ID NO: 114 comprising.
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Lassa virus (Genbank#NC_004296),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 115 (corresponding to the SNAP-like/proTEV1/LAS.N/proTEV2/Histag fusion protein).

Thus, in another aspect, the present invention is also drawn to the use of this fusion protein [SNAP-LAS.N] for identifying the presence of the Lassa virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Junin virus (JUN.N).

In a preferred embodiment, this vector comprises a so-called "pDeSNAP Univ/JUN.N cassette" i.e., a pDeSNAPUniv DNA cassette as defined above, in which the sequence encoding the Nucleoprotein N from the Junin virus has been inserted.

In a preferred embodiment, this vector comprises the pDeSNAP Univ/JUN.N cassette having the nucleotide sequence SEQ ID NO: 116 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Junin virus (Genbank#NC_005081),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 117 (corresponding to the SNAP-like/proTEV1/JUN.N/proTEV2/Histag fusion protein).

Thus, in another aspect, the present invention is also drawn to the use of this fusion protein [SNAP-JUN.N] for identifying the presence of the Junin virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AG), a mutant, a fragment or a catalytic domain thereof, and c) the Nucleoprotein N from the Machupo virus (MAC.N).

In a preferred embodiment, this vector comprises a so-called "pDeSNAP Univ/MAC.N cassette" i.e., a pDeSNAPUniv DNA cassette as defined above, in which the sequence encoding the Nucleoprotein N from the Machupo virus has been inserted.

In a preferred embodiment, this vector comprises the pDeSNAP Univ/MAC.N cassette having the nucleotide sequence SEQ ID NO: 118 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Machupo virus (Genbank#NC_005078),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 119 (corresponding to the SNAP-like/proTEV1/MAC.N/proTEV2/Histag fusion protein).

Thus, in another aspect, the present invention is also drawn to the use of this fusion protein [SNAP-MAC.N] for identifying the presence of the Machupo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Guanarito virus (GUA.N).

In a preferred embodiment, this vector comprises a so-called "pDeSNAP Univ/GUA.N cassette" i.e., a pDeSNAPUniv DNA cassette as defined above, in which the sequence encoding the Nucleoprotein N from the Guanarito virus has been inserted.

In a preferred embodiment, this vector comprises the pDeSNAP Univ/GUA.N cassette having the nucleotide sequence SEQ ID NO: 120 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Guanarito virus (Genbank#NC_005077),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNAalkyltransferase enzyme (AGT) (EC 2.1.1.63), a mutant or a catalytic domain thereof and b) the Nucleoprotein N from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 121 (corresponding to the SNAP-like/proTEV1/GUA.N/proTEV2/Histag fusion protein).

Thus, in another aspect, the present invention is also drawn to the use of this fusion protein [SNAP-GUA.N] for identifying the presence of the Guanarito virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Sabia virus (SAB.N).

In a preferred embodiment, this vector comprises a so-called "pDeSNAP Univ/SAB.N cassette" i.e., a pDeSNAPUniv DNA cassette as defined above, in which the sequence encoding the Nucleoprotein N from the Sabia virus has been inserted.

In a preferred embodiment, this vector comprises the pDeSNAP Univ/SAB.N cassette having the nucleotide sequence SEQ ID NO: 122 comprising:
  an insect BiP sequence of SEQ ID NO: 22,
  the SNAP-like sequence of SEQ ID NO: 31,
  a first DNA sequence SEQ ID NO: 26 encoding the spacer sequence GGGS (SEQ ID NO: 25),
  a DNA sequence SEQ ID NO: 29 encoding a pro-TEV1 cleavage site of sequence ENLYFQS (SEQ ID NO: 32),
  the DNA sequence encoding the Nucleoprotein N from the Sabia virus (Genbank#NC_006317),
  a DNA sequence SEQ ID NO: 30 encoding a pro-TEV2 cleavage site of sequence ENLYFQG (SEQ ID NO: 33),
  a second DNA sequence SEQ ID NO: 26 encoding the spacer sequence GGGS (SEQ ID NO: 25),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 123 (corresponding to the SNAP-like/proTEV1/SAB.N/proTEV2/Histag fusion protein).

Thus, in another aspect, the present invention is also drawn to the use of this fusion protein [SNAP-SAB.N] for identifying the presence of the Sabia virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Omsk virus (OMSK.EDIII).

In a preferred embodiment, this vector comprises a so-called "pDeSNAP Univ/OMSK.EDIII cassette" i.e., a pDeSNAPUniv DNA cassette as defined above, in which the sequence encoding the EDIII protein from the Omsk virus has been inserted.

In a preferred embodiment, this vector comprises the pDcSNAP Univ/OMSK.EDIII cassette having the nucleotide sequence SEQ ID NO: 124 comprising:
  an insect BiP-like sequence of SEQ ID NO: 152,
  the SNAP-like sequence of SEQ ID NO: 31,
  the DNA sequence encoding the EDIII protein of the Omsk virus (Genbank#NC_005062),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Omsk virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 125 (corresponding to the SNAP-like/OMSK.EDIII/Histag fusion protein).

Thus, in another aspect, the present invention is also drawn to the use of this fusion protein [SNAP-OMSK.EDIII] for identifying the presence of the Omsk virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Kyasanur Forest Disease virus (KYA.EDIII).

In a preferred embodiment, this vector comprises a so-called "pDeSNAP Univ/KYA.EDIII cassette" i.e., a pDeSNAPUniv DNA cassette as defined above, in which the sequence encoding the EDIII protein from the Kyasanur Forest Disease virus has been inserted.

In a preferred embodiment, this vector comprises the pDeSNAP Univ/KYA.EDIII cassette having the nucleotide sequence SEQ ID NO: 126 comprising:
  an insect BiP-like sequence of SEQ ID NO: 152,
  the SNAP-like sequence of SEQ ID NO: 31,
  the DNA sequence encoding the EDIII protein of the Kyasanur Forest Disease virus (Genbank#JF416958),
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Kyasanur Forest Disease virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 127 (corresponding to the SNAP-like/KYA.EDIII/Histag fusion protein).

Thus, in another aspect, the present invention is also drawn to the use of this fusion protein [SNAP-KYA.EDIII] for identifying the presence of the Kyasanur Forest Disease virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain 111 of the Envelop protein E from the Alkhurma virus (ALK.EDIII).

In a preferred embodiment, this vector comprises a so-called "pDeSNAP Univ/ALK.EDIII cassette" i.e., a pDeSNAPUniv DNA cassette as defined above, in which the sequence encoding the EDIII protein from the Alkhurma virus has been inserted.

In a preferred embodiment, this vector comprises the pDcSNAP Univ/ALK.EDIII cassette having the nucleotide sequence SEQ ID NO: 128 comprising:
    an insect BiP-like sequence of SEQ ID NO: 152,
    the SNAP-like sequence of SEQ ID NO: 31,
    the DNA sequence encoding the EDIII protein of the Alkhurma virus (Genbank#NC_004355),
    a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Alkhurma virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 129 (corresponding to the SNAP-like /ALK.EDIII/Histag fusion protein).

Thus, in another aspect, the present invention is also drawn to the use of this fusion protein [SNAP-ALK.EDIII] for identifying the presence of the Alkhurma virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Lassa virus (LAS.ectoGP1).

In a preferred embodiment, this vector comprises a so-called "pDeSNAP Univ/LAS.ectoGP1 cassette" i.e., a pDeSNAPUniv DNA cassette as defined above, in which the sequence encoding the Glycoprotein GP1 ectodomain from the Lassa virus has been inserted.

In a preferred embodiment, this vector comprises the pDeSNAP Univ/LAS.ectoGP1 cassette having the nucleotide sequence SEQ ID NO: 130 comprising.
    an insect BiP sequence of SEQ ID NO: 22,
    the DNA sequence encoding the Glycoprotein GP1 ectodomain from the Lassa virus (Genbank#NC_004296),
    the SNAP-like sequence of SEQ ID NO: 31, and
    a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 131 (corresponding to the SNAP-like/LAS.ectoGP1/Histag fusion protein).

Thus, in another aspect, the present invention is also drawn to the use of this fusion protein [SNAP-LAS.ectoGP1] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Junin virus (JUN.ectoGP1).

In a preferred embodiment, this vector comprises a so-called "pDeSNAP Univ/JUN.ectoGP1 cassette" i.e., a pDeSNAPUniv DNA cassette as defined above, in which the sequence encoding the Glycoprotein GP1 ectodomain from the Junin virus has been inserted.

In a preferred embodiment, this vector comprises the pDeSNAP Univ/JUN.ectoGP1 cassette having the nucleotide sequence SEQ ID NO: 132 comprising:
    an insect BiP sequence of SEQ ID NO: 22,
    the DNA sequence encoding the Glycoprotein GP1 ectodomain from the Junin virus (Genbank#NC_005081),
    the SNAP-like sequence of SEQ ID NO: 31, and
    a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 133 (corresponding to the SNAP-like/JUN.ectoGP1/Histag fusion protein).

Thus, in another aspect, the present invention is also drawn to the use of this fusion protein [SNAP-JUN.ectoGP1] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Machupo virus (MAC.ectoGP1).

In a preferred embodiment, this vector comprises a so-called "pDeSNAP Univ/MAC.ectoGP1 cassette" i.e., a pDeSNAPUniv DNA cassette as defined above, in which the sequence encoding the Glycoprotein GP1 ectodomain from the Machupo virus has been inserted.

In a preferred embodiment, this vector comprises the pDeSNAP Univ/MAC.ectoGP1 cassette having the nucleotide sequence SEQ ID NO: 134 comprising:
- an insect BiP sequence of SEQ ID NO: 22,
- the DNA sequence encoding the Glycoprotein GP1 ectodomain from the Machupo virus (Genbank#NC_005078),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 135 (corresponding to the SNAP-like/MAC.ectoGP1/Histag fusion protein).

Thus, in another aspect, the present invention is also drawn to the use of this fusion protein [SNAP-MAC.ectoGP1] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Guanarito virus (GUA.ectoGP1).

In a preferred embodiment, this vector comprises a so-called "pDeSNAP Univ/GUA.ectoGP1 cassette" i.e., a pDeSNAPUniv DNA cassette as defined above, in which the sequence encoding the Glycoprotein GP1 ectodomain from the Guanarito virus has been inserted.

In a preferred embodiment, this vector comprises the pDeSNAP Univ/GUA.ectoGP1 cassette having the nucleotide sequence SEQ ID NO: 136 comprising:
- an insect BiP sequence of SEQ ID NO: 22,
- the DNA sequence encoding the Glycoprotein GP1 ectodomain from the Guanarito virus (Genbank#NC_005077),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 137 (corresponding to the SNAP-like/GUA.ectoGP1/Histag fusion protein).

Thus, in another aspect, the present invention is also drawn to the use of this fusion protein [SNAP-GUA.ectoGP1] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Sabia virus (SAB.ectoGP1).

In a preferred embodiment, this vector comprises a so-called "pDeSNAP Univ/SAB.ectoGP1 cassette" i.e., a pDeSNAPUniv DNA cassette as defined above, in which the sequence encoding the Glycoprotein GP1 ectodomain from the Sabia virus has been inserted.

In a preferred embodiment, this vector comprises the pDeSNAP Univ/SAB.ectoGP1 cassette having the nucleotide sequence SEQ ID NO: 138 comprising:
- an insect BiP sequence of SEQ ID NO: 22,
- the DNA sequence encoding the Glycoprotein GP1 ectodomain from the Guanarito virus (Genbank#NC_006317),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 139 (corresponding to the SNAP-like/SAB.ectoGP1/Histag fusion protein).

Thus, in another aspect, the present invention is also drawn to the use of this fusion protein [SNAP-SAB.ectoGP1] for identifying the presence of the Sabia virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Lassa virus (LAS.ectoGP2).

In a preferred embodiment, this vector comprises a so-called "pDeSNAP Univ/LAS.ectoGP2 cassette" i.e., a pDeSNAPUniv DNA cassette as defined above, in which the sequence encoding the Glycoprotein GP2 ectodomain from the Lassa virus has been inserted.

In a preferred embodiment, this vector comprises the pDeSNAP Univ/LAS.ectoGP2 cassette having the nucleotide sequence SEQ ID NO: 140 comprising:
- an insect BiP sequence of SEQ ID NO: 22,
- the DNA sequence encoding the Glycoprotein GP2 ectodomain from the Lassa virus (Genbank#NC_004296),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 141 (corresponding to the SNAP-like/LAS.ectoGP2/Histag fusion protein).

Thus, in another aspect, the present invention is also drawn to the use of this fusion protein [SNAP-LAS.ectoGP2] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Junin virus (JUN.ectoGP2).

In a preferred embodiment, this vector comprises a so-called "pDeSNAP Univ/JUN.ectoGP2 cassette" i.e., a pDeSNAPUniv DNA cassette as defined above, in which the sequence encoding the Glycoprotein GP2 ectodomain from the Junin virus has been inserted.

In a preferred embodiment, this vector comprises the pDeSNAP Univ/JUN.ectoGP2 cassette having the nucleotide sequence SEQ ID NO: 142 comprising:
  an insect BiP sequence of SEQ ID NO: 22,
  the DNA sequence encoding the Glycoprotein GP2 ectodomain from the Junin virus (Genbank#NC_005081),
  the SNAP-like sequence of SEQ ID NO: 31, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 143 (corresponding to the SNAP-like/JUN.ectoGP2/Histag fusion protein).

Thus, in another aspect, the present invention is also drawn to the use of this fusion protein [SNAP-JUN.ectoGP2] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Machupo virus (MAC.ectoGP2).

In a preferred embodiment, this vector comprises a so-called "pDeSNAP Univ/MAC.ectoGP2 cassette" i.e., a pDeSNAPUniv DNA cassette as defined above, in which the sequence encoding the Glycoprotein GP2 ectodomain from the Machupo virus has been inserted.

In a preferred embodiment, this vector comprises the pDeSNAP Univ/MAC.ectoGP2 cassette having the nucleotide sequence SEQ ID NO: 144 comprising:
  an insect BiP sequence of SEQ ID NO: 22,
  the DNA sequence encoding the Glycoprotein GP2 ectodomain from the Machupo virus (Genbank#NC_005078),
  the SNAP-like sequence of SEQ ID NO: 31, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 145 (corresponding to the SNAP-like/MAC.ectoGP2/Histag fusion protein).

Thus, in another aspect, the present invention is also drawn to the use of this fusion protein [SNAP-MAC.ectoGP2] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Guanarito virus (GUA.ectoGP2).

In a preferred embodiment, this vector comprises a so-called "pDeSNAP Univ/GUA.ectoGP2 cassette" i.e., a pDeSNAPUniv DNA cassette as defined above, in which the sequence encoding the Glycoprotein GP2 ectodomain from the Guanarito virus has been inserted.

In a preferred embodiment, this vector comprises the pDeSNAP Univ/GUA.ectoGP2 cassette having the nucleotide sequence SEQ ID NO: 146 comprising:
  an insect BiP sequence of SEQ ID NO: 22,
  the DNA sequence encoding the Glycoprotein GP2 ectodomain from the Guanarito virus (Genbank#NC_005077),
  the SNAP-like sequence of SEQ ID NO: 31, and
  a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 147 (corresponding to the SNAP-like/GUA.ectoGP2/Histag fusion protein).

Thus, in another aspect, the present invention is also drawn to the use of this fusion protein [SNAP-GUA.ectoGP2] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Sabia virus (SAB.ectoGP2).

In a preferred embodiment, this vector comprises a so-called "pDeSNAP Univ/SAB.ectoGP2 cassette" i.e., a pDeSNAPUniv DNA cassette as defined above, in which the sequence encoding the Glycoprotein GP2 ectodomain from the Sabia virus has been inserted.

In a preferred embodiment, this vector comprises the pDeSNAP Univ/MAC.ectoGP2 cassette having the nucleotide sequence SEQ ID NO: 148 comprising:
- an insect BiP sequence of SEQ ID NO: 22,
- the DNA sequence encoding the Glycoprotein GP2 ectodomain from the Sabia virus (Genbank#NC_006317),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 149 (corresponding to the SNAP-like/SAB.ectoGP2/Histag fusion protein).

efficiency and demonstrated long-term antigen stability (up to six month). This application is not limited to viral antigens as any peptide or polypeptide can be used for bead coating and subsequent antibody capture.

I. Material and Methods

1. The following buffers and solutions are used:
   a) PBS buffer: 100 mL of 10×PBS, pH 7.4 in 1 L H2O sterile
   b) SNAP coupling buffer (PBS-DTI): 100 mL of 10×PBS, pH 7.4, 0.5 mL 10% tween 20, 1 mL of 1.0 M DTT, in 1 L H$_2$O sterile
   c) blocking/assay buffer (PBS-B): PBS, 1% BSA, pH 7.4 in 1 L H$_2$O sterile
   d) storage buffer (PBS-TBN): 100 mL of 10×PBS, 1 g of BSA, 2 mL of 10% tween 20, 500 mg of sodium azide, 1 mL of 1.0 M DTT, in 1 L H$_2$O sterile
   e) Substrate solution (4 mg/mL): 2 mg of BG-PEG-NH$_2$, DMSO 500 µL.
   f) Activation solution (EDAC/SNHS): 50 mg/mL of EDAC solution or 50 mg/mL of SNSHS in distilled water 2. The following materials were used:
   2.1. MagPlex Luminex microspheres: MC 100XX-ID (where XX is the fluorescence region), XX can be e.g. 26, 27, 28, 29, 34, 35, 36, 37, 45, 52, 53, 63, 64, as mentioned on FIG. 7B
   2.2. hAGT substrate: PEG-BG-NH$_2$ (NED S9150S)

Thus, in another aspect, the present invention is also drawn to the use of this fusion protein [SNAP-SAB.ectoGP2] for identifying the presence of the Sabia virus in a biological sample, for example thanks to the immunoassay of the present invention.

Examples

In the context of the invention, a multiplex bead-based immunoassay was developed for rapid and simultaneous detection of antibodies to arboviruses in biological fluids.

The system is based on the xMAP technology (Luminex corporation) and uses a mixture of antigen-coated microspheres as capture reagents for specific human immunoglobulins. Distinct sets of microspheres (Magplex, Luminex corporation) were coupled with purified AGT fusion proteins, namely the SNAP-tagged viral recombinant proteins: sSNAP-DV1.EDIII, sSNAP-DV2.EDIII, sSNAP-DV3.EDIII, sSNAP-DV4.EDIII, sSNAP-WN.EDIII, sSNAP-JE.EDIII, sSNAP-USU.EDIII, sSNAP-TBE.EDIII, sSNAP-YF.EDIII, sSNAP-MVE.EDIII, sSNAP-Rocio.EDIII, sSNAP-WSLEDIII, sSNAP-ZIKA.EDIII, SNAP-DV1ectoM, sSNAP-N.RVF, sSNAP-N.TOS, and CHIK.sE2-SNAP. Recombinant antigens were covalently coupled to the carboxyl microsphere surface using a substrate of the AGT protein as linker (BG-PEG-NH2, New England Biolabs), thereby enhancing antibody capture efficiency as compared to standard amine coupling procedures. Technical validation using anti-SNAP-tag antibodies and specific mouse monoclonal antibodies confirmed coupling 2.3. Fusion proteins SNAP-viral EDIII:

The generation of a fusion protein comprising AGT and viral EDIII moieties is well-known to the skilled person. Every known synthesis process can be used for this purpose, provided that the AGT enzyme remains active in the fusion protein.

In the present case, the AGT mutant SNAP of SEQ ID NO: 2 has been used and SNAP-viral EDIII fusion proteins have been generated.

The *Drosophila* S2 inducible expression system (DES, Invitrogen), has been chosen for the mass production of individual EDIII from flaviviruses in non-vertebrate cells and the plasmid pMT/BiP/V5-HisA from Invitrogen has been used.

This plasmid contains:
The metallothionein promoter pMT,
An insect ssBiP sequence of SEQ ID NO: 22,
Bgl II and Age I restriction sites,
the DNA of SEQ ID NO: 28 encoding a His$_6$tag located downstream of the AgeI restriction site, and
the DNA spacer sequence of SEQ ID NO: 26 located between the AgeI restriction site and the DNA encoding a His$_6$tag.

The synthetic genes coding for the full-length domain III of the E proteins from flaviviruses WN, USU, JE, TBE, DEN-1 to DEN-4, YF, Rocio, MVE, Zika, SLE, and WSL are listed in SEQ ID NO: 3 to SEQ ID NO: 14. The ED III amino acid sequences were fused in frame to the C-terminus of the SNAP protein, with both moieties being separated by a linker GGGS (SEQ ID NO: 25). The DNA sequences encoding SNAP-EDIII were inserted in the plasmid pMT/BiP/V5-Histag (Invitrogen) to generate the plasmids pMT/BiP/SNAP/EDIII/Histag.

The resulting plasmids pMT/BiP/SNAP-EDIII-Histag, which can drive the expression of secreted SNAP-EDIII-$His_6$ fusion proteins, were co-transfected with selection marker pCo-Blast into S2 cells to generate the stable S2/sS-NAP-ED III-Histag cell line showing resistance to blasticidine.

Stable S2 cell lines grown in spinner (1000 ml) were stimulated 10 days with heavy metal cadmium ($Cd^2$) and proteins from extracellular medium were concentrated and purified.

Accumulation of secreted SNAP-tagged EDIII protein was observed in the supernatants of stable S2/sSNAP-EDIII-Histag cells after 10 days of induction with heavy metal cadmium.

The proteins SNAP-DEN1.EDIII of SEQ ID NO: 21, SNAP-DEN2.EDIII of SEQ ID NO:X, SNAP-DEN3.EDIII of SEQ ID NO:X, SNAP-DEN4.EDIII of SEQ ID NO:X, SNAP-WN.EDIII of SEQ ID NO:X, SNAP-JE.EDIII of SEQ ID NO:X, SNAP-YF.EDIII of SEQ ID NO:X, SNAP-MVE.EDIII of SEQ ID NO:X, SNAP-Rocio.EDIII of SEQ ID NO:X, SNAP-WSLEDIII of SEQ ID NO:X, SNAP-ZIKA.EDIII of SEQ ID NO:X, SNAP-SLE.EDIII of SEQ ID NO:X have been produced accordingly.

3. Preparation of the Antigen-Coupled Beads

The production of antigen-coupled beads comprised two steps: functionalization of microsphere surfaces with an $O^6$-benzylguanine derivative (BG-PEG-amino), and covalent immobilization of the chimeric SNAP-viral Ags proteins using the BG-PEG-amino as an anchor (FIG. 1). The carboxyl microsphere surfaces were covalently coated with BG-PEG-amino substrate using an optimized two-step carbodiimide process (Wong et al *Journal of Clinical Microbiology* 42(1): 65-72, 2004). Subsequently, coupled BG-PEG-amino compounds were irreversibly linked to the chimeric SNAP-viral Ags proteins by transfer of the benzyl group to the active site cysteine of the SNAP protein. Due to the high specificity of this reaction, the fusion protein is exclusively coupled via the SNAP domain, leaving the viral antigen accessible for interactions with antibodies.

3.1. First, the commercial beads were activated as per the manufacturer instructions (by using the EDAC and SNHS activation solutions), and washed in a PBS buffer. All the steps were performed in darkness so as to prevent the fluorescent quenching of the beads, according to the manufacturer instructions.

About $1.25 \times 10^6$ beads were used for each coupling process.

3.2. The AGT substrate PEG-BG-$NH_2$ in the DMSO solution was then added for 6 hours at room temperature or overnight at 4° C. on the activated beads, and subsequently washed with PBS buffer.

3.3. The unbound carboxylic sites were then blocked with the blocking buffer for 30 minutes at room temperature, and the beads subsequently washed with the SNAP coupling buffer.

3.4. SNAP-EDIII proteins resuspended in the SNAP coupling buffer (1 mg/mL) were incubated with the thus obtained beads for two hours at room temperature, and then washed once with the SNAP coupling buffer, and three times with the storage buffer (PBS-TBN).

4. Microsphere Fluorescence Immunoassays

The bead sets, conjugated with different SNAP-viral Ags, were mixed by vortex to ensure total bead dispersal. After adjusting the bead density to 100 beads/µL, 25 µl of each of the bead sets (containing 2500 microspheres) were transferred to a 96-well microtiter plate (Bio-Plex Pro flat bottom plate, BioRad) in separate wells for singleplex assays, or mixed in the same wells for multiplex assays. The microspheres were washed 3 times with 100 µL washing buffer (BioPlex Wash buffer, BioRad) using a microplate wash station for magnetic beads (BioPlex Pro Wash Station, BioRad). The samples (antibodies or sera) were diluted in assay buffer (PBS-BSA) and 50 µL of the resulting solutions were added to the test wells containing the conjugated beads. After incubation in darkness on a plate shaker for 30 min, the plate was washed as previously. Subsequently, a fluorochrome-labeled secondary antibody was diluted in assay buffer (PBS-BSA) at 2 µg/mL, and 50 µL of the resulting solutions were added to the test wells containing the conjugated beads. After incubation in darkness on a plate shaker for 30 min, the plate was washed as previously. Finally, streptavidin-phycoerythrin (SAPE, Invitrogen Molecular Probes) was diluted in assay buffer (PBS-BSA) at 2 µg/ml, and 50 µL of the resulting solution was added to the microplate wells. The plate was incubated in darkness on a plate shaker for 10 min and washed as previously, before resuspending the contents of the wells in 125 µl of assay buffer. The median fluorescence intensity (MFI) of the detection antibody bound to the individual microspheres was evaluated from flow analysis of 50 microspheres per well using a dual-laser flow analyzer (BioPlex 200 instrument, BioRad). The fluorescent detection instrument is equipped with a first laser for detecting the type of bead, and a second to ensure the quantification of captured IgM or IgG by exciting the fluorophore (red-phycoerythrin) conjugated to the specific detection antibody.

4.1 Confirmation of Antigen Coupling

Antigen coupling was confirmed by testing the antigen-coupled microspheres with dilutions of rabbit anti-SNAP-tag polyclonal antibody (GenScript). The fluorescence immunoassays were performed in singleplex format, as described above. A two-fold dilution series of anti-SNAP antibody starting at 4000 ng/mL and ending at 3.9 ng/mL was performed in PBS-BSA, and volumes of each dilution were added to the test wells containing the beads. A biotin-conjugated goat anti-rabbit IgG (2 µg/mL in 50 µL PBS-BSA) was used as secondary antibody to detect bound anti-SNAP antibodies.

Figure 2:
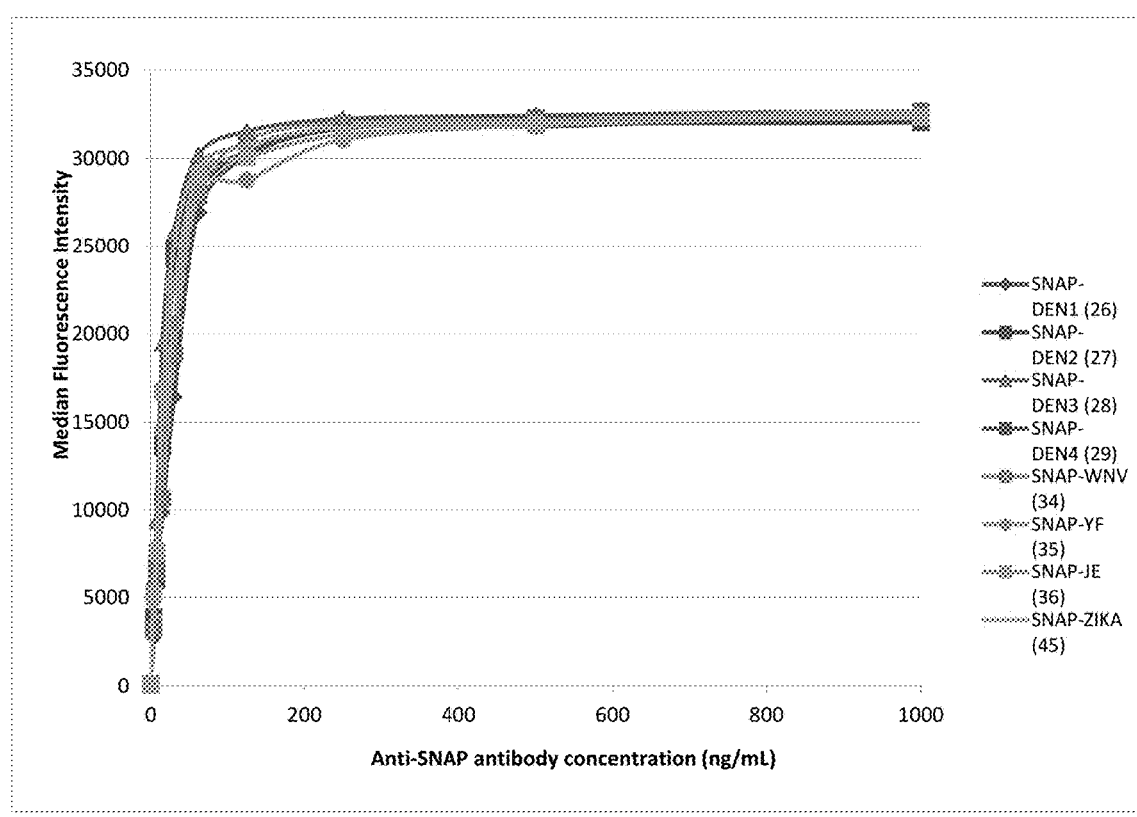

FIG. 2 shows the fluorescence results observed for the detection of anti-SNAP antibody on 8 different sets of microspheres coupled to chimeric SNAP-viral antigens proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE).

4.2 Detection of Specific Antibodies

The capture and detection of specific antibodies by the antigen-conjugated microspheres was assessed using purified monoclonal mouse antibodies (anti-WNV, anti-DV1 and anti-DV2) and polyclonal mouse sera (anti-DV3, anti-DV4, anti-YF and anti-JE) or human sera (anti-DV1). The fluorescence immunoassays were performed in singleplex and multiplex format, as described above. A four-fold dilution series of purified mouse monoclonal antibodies starting at 400 ng/mL and ending at 0.1 ng/mL, and of mouse and human sera starting at 1:25 and ending at 1:102400, was performed in PBS-BSA, and volumes of each dilution were added to the test wells containing the beads. A biotin-conjugated goat anti-mouse IgG (2 µg/mL in 50 µL PBS-BSA), was used as secondary antibody to detect bound monoclonal and polyclonal mouse antibodies. A biotin-conjugated goat anti-human IgM (2 µg/mL in 50 µL PBS- BSA) or a biotin-conjugated goat anti-human IgG (2 μg/mL in 50 μL PBS-BSA), was used to detect bound IgM or IgG antibodies in human serum, respectively.

Figure 3:
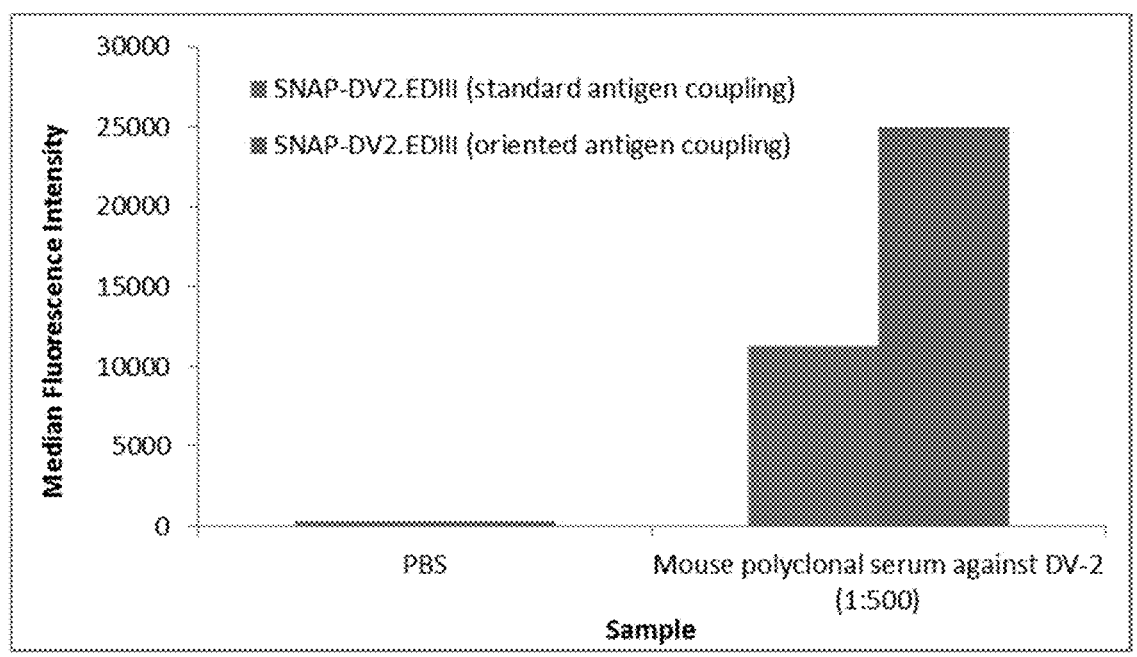

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through Bio-Plex Amine Coupling Kit, BIORAD.

Figure 4:
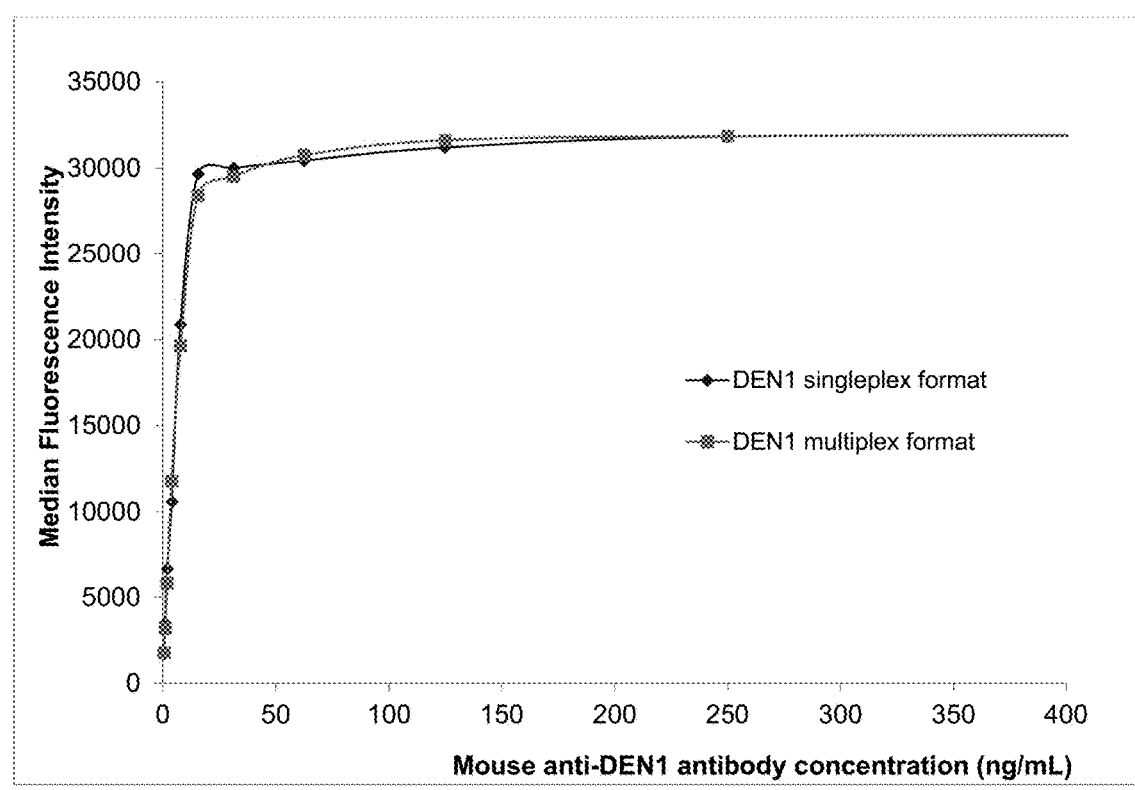

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex format with other chimeric SNAP-viral Ags proteins (SNAP-DV2.EDIII, SNAP.DV3.EDIII, SNAP.DV4.EDIII, SNAP-WNV, SNAP-YF, SNAP-JE, SNAP-TBE) coupled to microspheres.

Figure 5:
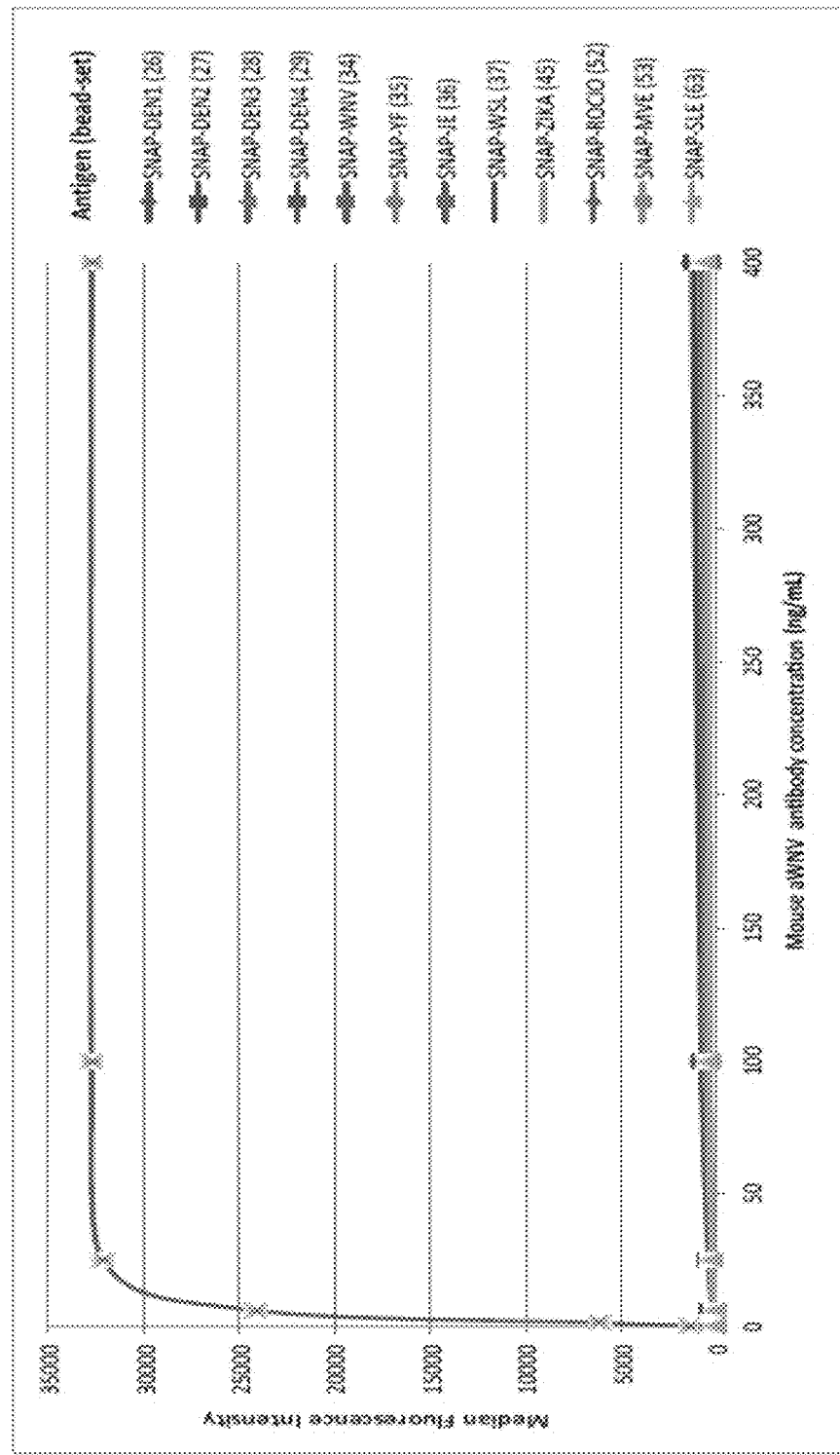
FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE) coupled to microspheres.

FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE) coupled to microspheres.

Figure 6A:
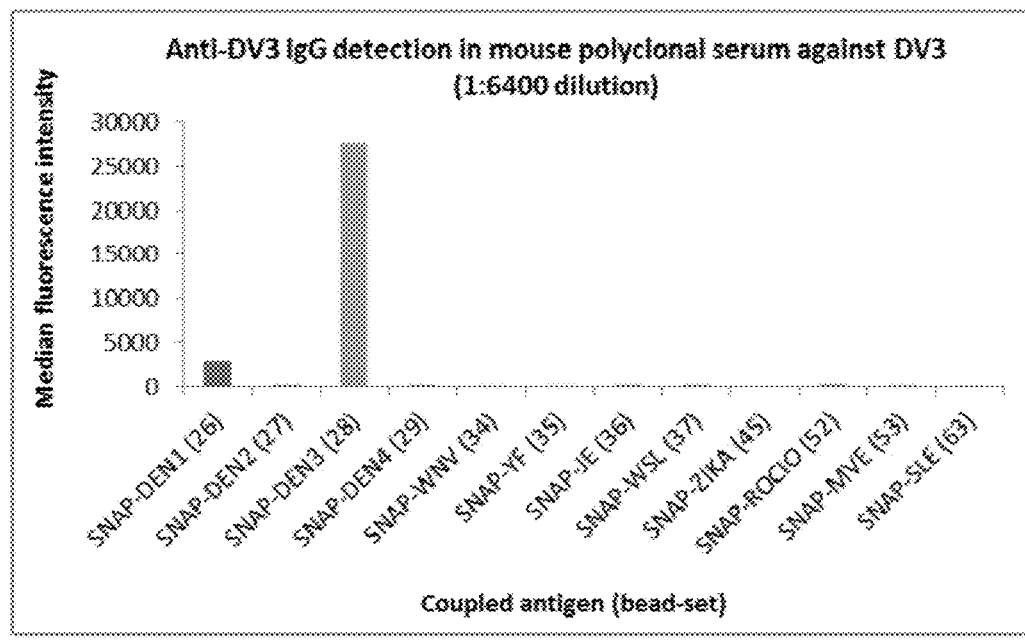
FIGS. 6A-6B show the reactivity and specificity of anti-DV3 IgG detection in mouse polyclonal serum against DV3
Figure 6:
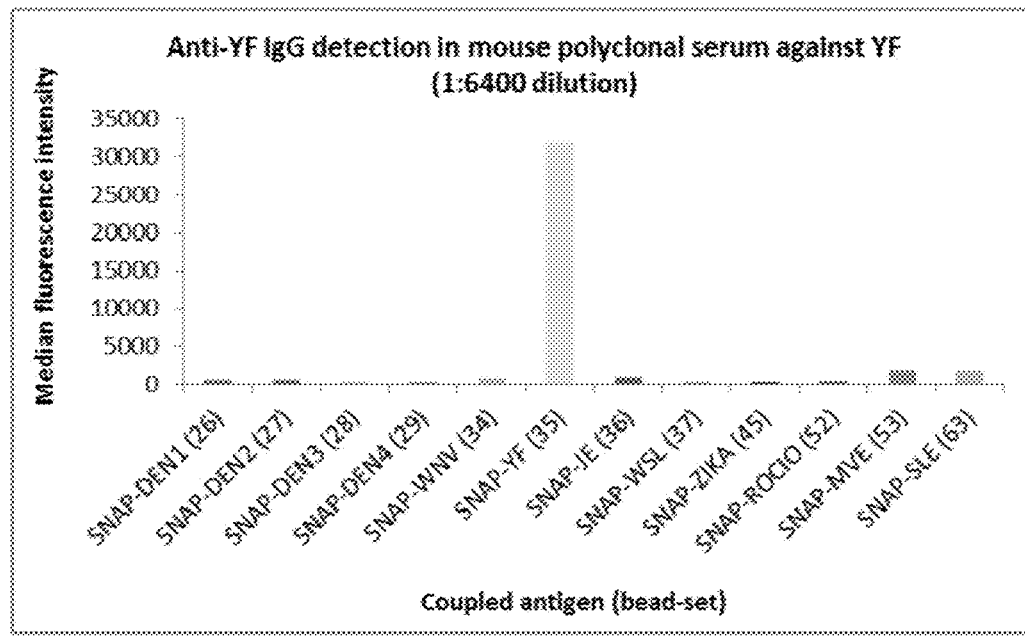

FIG. 6 shows the reactivity and specificity of anti-DV3 IgG detection in mouse polyclonal serum against DV3 (A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA) coupled to microspheres.

FIG. 7 shows the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA, SNAP-TBE) coupled to microspheres.

II. Results

The system of the invention uses a mixture of antigen-coated Magplex microspheres (Luminex Corporation) as capture reagents for specific human immunoglobulins. Each set of internally color-coded microspheres have been coupled to a specific recombinant antigen and mixed with other types of microspheres in a small sample volume. The power of this system lies in the fact that it is possible to simultaneously analyze up to 100 types of coupled microspheres per well using a flow analysis tool. The fluorescent detection instrument is equipped with a first laser for detecting the type of bead, and a second to ensure the quantification of captured IgM or IgG by exciting the fluorophore (phycoerythrin) conjugated to the specific detection antibody. With its extensive multiplexing capabilities and lower limit of detection, this approach offers substantial cost and sample savings over traditional ELISA measurements.

Presently, 16 distinct sets of microspheres have been coupled with purified chimeric SNAP-viral Ags proteins, allowing titration of serum antibodies specific to dengue serotypes 1 to 4, West Nile, Yellow fever, Japanese encephalitis, tick-borne encephalitis, Saint-Louis encephalitis, Murray Valley encephalitis, Wesselsbron, Zika, Rocio, Usutu, Rift Valley fever, and Chikungunya virus. The production of the system is highly time- and cost-effective, as only a very small amount of recombinant antigen (<50 μg) is required to produce one set of antigen-coupled microspheres (~1.25× $10^6$ microspheres), sufficient to perform 500 individual assays. Moreover, the selected sets of microspheres are adaptable to an affordable, compact, and robust fluorescent detection system such as the MagPix (Luminex Corporation).

The evaluation of antigen coupling using an anti-SNAP antibody (FIG. 2) confirmed the coupling efficiency and demonstrated that the relative quantities of bound antigens are comparable between the different coupled microsphere sets. The assessment of antibody capture and detection using purified mouse antibodies showed enhanced capture of specific antibodies by the produced antigen-coupled microspheres as compared to antigen-coupled microspheres obtained by standard amine coupling procedures (FIG. 3). In addition, it demonstrated the low detection limit of the method and confirmed that multiplexing does not affect antibody detection (FIG. 4). Additionally, the antigen-conjugated microspheres exhibited long-term stability when stored at 4° C. (>6 months). Finally, the specificity of each set of coupled microspheres in multiplex immunoassays was demonstrated for purified mouse monoclonal antibodies (FIG. 5), for IgG antibodies in polyclonal mouse sera (FIG. 6A-B) and for both IgM and IgG antibodies in polyclonal sera from infected humans (FIG. 7).

With its extensive multiplexing capabilities (up to 100 types of coupled microspheres per well) and lower limit of detection, this approach offers substantial cost and sample savings over traditional ELISA measurements.

III. Generation of a Fusion Protein Comprising SNAP and the N Nucleoprotein of the Schmallenberg Virus 1. Construction of the Vectors Encoding the Fusion Protein SNAP-SBV.N The chimeric fusion protein comprising SNAP and the N nucleoprotein of the Schmallenberg virus has been obtained as follows:

In a first step, the sequence of the open reading frame of the S segment encoding the N nucleoprotein and the NSs protein of the BH80/11-4 strain was mutated by inserting an EcoRV restriction site at its 5' terminus and an XmaI restriction site at its 3' terminus. In addition, the internal EcoRV restriction site was removed by mutating the 294T nucleotide into 294A. This mutated sequence is shown on SEQ ID NO: 17.

This mutated sequence was then inserted into the EcoRV and XmaI restriction sites of the pDeSNAP Univ cassette of SEQ ID NO: 34, generating the "pDeSNAP Univ/SBV.N" DNA cassette of SEQ ID NO: 36.

The so-called "pDeSNAP Univ/SBV.N" DNA cassette comprises (see FIG. 9 and SEQ ID NO: 36):
  the insect BiP-like sequence of SEQ ID NO: 23,
  the SNAP-like sequence of SEQ ID NO: 31,
  a first DNA sequence SEQ ID NO: 26 encoding the spacer sequence GGGS (SEQ ID NO: 25),
  a DNA sequence SEQ ID NO: 29 encoding a pro-TEV1 cleavage site of sequence ENLYFQS (SEQ ID NO: 32),
  the SBV.N DNA sequence SEQ ID NO: 17 (which corresponds to the natural SBV.N sequence, in which the internal EcoRV site has been deleted and two EcoRV and XmaI sites have been added at the extremities),
  a DNA sequence SEQ ID NO: 30 encoding a pro-TEV2 cleavage site of sequence ENLYFQG (SEQ ID NO: 33),
  a DNA sequence SEQ ID NO: 28 encoding a HisTag sequence.

Note that this cassette comprises in addition an NheI site upstream of the ATG, a BglII site between the BiP-like sequence and the SNAP-like sequence, and an AgeI site and a HindIII site which are both located downstream of the stop codon.

The sequence comprised between the BglII and AgeI restriction sites of the pDeSNAPUniv/SBV.N cassette (see FIG. 9) was excised by enzymatic digestion, then cloned into the pMT/BiP/V5-A plasmid (Invitrogen) to generate the pMT/BiP/SNAP-SBV.N vector. This vector has been used to generate stable S2 cells secreting the SNAP-SBV.N fusion protein.

The sequence comprised between the NheI and NotI restriction sites of the pDeSNAPUniv/SBV.N cassette is then cloned into the pcDNA3 plasmid (Invitrogen) to generate the pcDNA3/SNAP-SBV.N vector. This vector is then used to generate stable mammalian cells secreting the SNAP-SBV.N fusion protein.

2. Production of the Fusion Protein SNAP-SBV.N

The resulting plasmids pMT/BiP/SNAP-SBV.N that allow the production of SNAP-tagged SBV.N proteins as secreted fusion proteins, were co-transfected with selection marker pCo-Blast into S2 cells to generate the stable S2/SNAP-SBV.N cell line showing resistance to blasticidine.

This cell line has been deposited to the Collection Nationale de Cultures de Microorganismes (CNCM) of the Institut Pasteur, 25, rue du Docteur Roux, 75724 PARIS CEDEX 15, under the number CNCM I-4616.

Stable S2 cell lines grown in spinner (1000 ml) were stimulated 10 days with heavy metal cadmium ($Cd^{2+}$).

Accumulation of secreted SNAP-SBV.N protein was observed in the supernatants of the S2/SNAP-SBV.N cells after 10 days of induction with heavy metal cadmium.

0.01 mL from 4 mL of supernatant of S2/SNAP-SBV.N cells induced 10 days with $Cd^{2+}$ were tested by immunoblot assay using anti-Histag antibody (dilution 1:1,000) (see FIG. 10).

The chimeric protein SNAP-SBV.N was compared with defined amounts of the SNAP-TOS.N chimeric protein (corresponding to the fusion protein comprising SNAP and the N nucleoprotein from the Toscana virus, which is a phlebovirus).

The production of purified SNAP-SBV.N from induced S2/SNAP+SBV.N cells for 10 days is 18 mg per liter of cell culture (FIG. 10B).

BIBLIOGRAPHIC REFERENCES

Avrameas S. *Immunol. Today* 1991 May; 12(5):154-9.
Zimmerman C W, *Electrophoresis* 1995; June; 16(6):941-7.
Kim H-J. *The Journal of Veterinary Medical Science*, 2011
Damoiseaux et al., *ChemBiochem*. 4:285-287, 2001
Xu-Welliver et al., Biochemical Pharmacology 58: 1279-85, 1999
Lim A. et al, *EMBO J*. 15: 4050-4060, 1996;
Daniels D. S. et al, *EMBO J*. 19: 1719-1730, 2000;
Juillerat A. et al, *Chemistry & Biology*, vol. 10, 313-317, 2003
Wong et al Journal of Clinical Microbiology 42, no. 1 (January 2004): 65-72
Wibley J. E. A. et al, 2000
Felgner et al., *Proc. Natl. Acad. Sci. U.S.A.*, 84:7413-7417, 1987
Mackey et al., *Proc. Natl. Acad. Sci. U.S.A.*, 85:8027-8031, 1988
Wu et al., *J. Biol. Chem.*, 267:963-967, 1992;
Wu and Wu, *J. Biol. Chem.*, 263:14621-14624, 1988;
Williams et al., *Proc. Nat Acad. Sci. U.S.A.*, 88:2726-2730, 1991
Kolpe A. B. et al, *Virus Research* 2012; 168:64-72
Pan W. et al, *The Journal of Immunology*, 2004), 172:6167-6174
Sivakolundu S. et al, *Journal of Medical Microbiology*, 2012

The invention claimed is:

1. A method for detecting at least two target antibodies in a biological sample comprising:
   (a) contacting said biological sample selected from the group consisting of whole blood, serum, plasma, urine, seminal fluid, cerebrospinal fluid and saliva with at least one first microparticle bound to a 6-alkylguanine-DNA-alkyltransferase (AGT) substrate covalently coupled to a first fusion protein comprising:

a 6-alkylguanine-DNA-alkyltransferase (AGT) polypeptide having a O6-alkylguanine-DNA alkyltransferase activity and a first epitope that is recognized by a first target antibody;

(b) contacting said biological sample with at least one second microparticle bound to a 6-alkylguanine-DNA-alkyltransferase (AGT) substrate covalently coupled to a second fusion protein comprising:

a 6-alkylguanine-DNA-alkyltransferase (AGT) polypeptide having a O6-alkylguanine-DNA alkyltransferase activity and a second epitope that is recognized by a second target antibody, but not by said first target antibody; and (c) detecting the presence or absence of the two target antibodies by detecting the binding or lack of binding of the two target antibodies to the two fusion proteins.

2. The method of claim 1, wherein each of said microparticles is covalently coupled to said substrate of 6-alkylguanine-DNA-alkyltransferase (AGT) polypeptide.

3. The method of claim 2, wherein each of said microparticles is a magnetic microparticle internally labeled with a fluorescent dye.

4. The method of claim 3, wherein said biological sample is serum.

5. The method of claim 1, wherein each of said microparticles is magnetic.

6. The method of claim 1, wherein each of said microparticles is labeled with a label selected from the group consisting of a fluorochrome, a chromophore, a radioisotope, and a mass tag.

7. The method of claim 1, wherein each of said microparticles is a microparticle internally labeled with a fluorescent dye with magnetite encapsulated in a functional polymer outer coat containing surface carboxyl groups for covalent coupling of ligands.

8. The method of claim 1, comprising contacting said biological sample with at least 10 differently coupled microparticles.

9. The method of claim 1, further comprising detecting the presence or absence of the two target antibodies with secondary antibodies recognizing the constant part of the target antibodies.

10. The method of claim 1, wherein said first and second fusion proteins comprise a 6-alkylguanine-DNA-alkyltransferase (AGT) polypeptide having at least 85% identity with the amino acid sequence of SEQ ID NO:2.

11. The method of claim 1, wherein said first and second fusion proteins comprise a 6-alkylguanine-DNA-alkyltransferase (AGT) polypeptide having at least 90% identity with the amino acid sequence of SEQ ID NO:2.

12. The method of claim 1, wherein said first or second epitope is selected from the group consisting of the amino acid sequences encoded by nucleotide sequences: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:54, SEQ ID NO:55, SEQ ID NO:56, SEQ ID NO:57, and SEQ ID NO:58.

13. The method of claim 1, wherein said first and second fusion proteins that are coupled with said first and second microparticles are selected from the group consisting of: SEQ ID NO:21, SEQ ID NO:42, SEQ ID NO:49, SEQ ID NO:51, SEQ ID NO:53, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149 and SEQ ID NO:151.

\* \* \* \* \*

SEQUENCE LISTING

<160> NUMBER OF SEQ ID NOS: 153

<210> SEQ ID NO 1
<211> LENGTH: 238
<212> TYPE: PRT
<213> ORGANISM: homo sapiens

<400> SEQUENCE: 1

```
Met Leu Gly Gln Pro Ala Pro Leu Glu Arg Phe Ala Ser Arg Arg Pro
1               5                   10                  15

Gln Val Leu Ala Val Arg Thr Val Cys Asp Leu Val Leu Gly Lys Met
            20                  25                  30

Asp Lys Asp Cys Glu Met Lys Arg Thr Thr Leu Asp Ser Pro Leu Gly
        35                  40                  45

Lys Leu Glu Leu Ser Gly Cys Glu Gln Gly Leu His Glu Ile Lys Leu
    50                  55                  60

Leu Gly Lys Gly Thr Ser Ala Ala Asp Ala Val Glu Val Pro Ala Pro
65                  70                  75                  80

Ala Ala Val Leu Gly Gly Pro Glu Pro Leu Met Gln Cys Thr Ala Trp
                85                  90                  95

Leu Asn Ala Tyr Phe His Gln Pro Glu Ala Ile Glu Glu Phe Pro Val
            100                 105                 110
```

```
Pro Ala Leu His His Pro Val Phe Gln Gln Glu Ser Phe Thr Arg Gln
            115                 120                 125

Val Leu Trp Lys Leu Leu Lys Val Val Lys Phe Gly Glu Val Ile Ser
    130                 135                 140

Tyr Gln Gln Leu Ala Ala Leu Ala Gly Asn Pro Lys Ala Ala Arg Ala
145                 150                 155                 160

Val Gly Gly Ala Met Arg Gly Asn Pro Val Pro Ile Leu Ile Pro Cys
                165                 170                 175

His Arg Val Val Cys Ser Ser Gly Ala Val Gly Asn Tyr Ser Gly Gly
            180                 185                 190

Leu Ala Val Lys Glu Trp Leu Leu Ala His Glu Gly His Arg Leu Gly
        195                 200                 205

Lys Pro Gly Leu Gly Gly Ser Ser Gly Leu Ala Gly Ala Trp Leu Lys
    210                 215                 220

Gly Ala Gly Ala Thr Ser Gly Ser Pro Pro Ala Gly Arg Asn
225                 230                 235

<210> SEQ ID NO 2
<211> LENGTH: 193
<212> TYPE: PRT
<213> ORGANISM: artificial
<220> FEATURE:
<223> OTHER INFORMATION: Amino acid sequence of SNAP

<400> SEQUENCE: 2

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu

<210> SEQ ID NO 3
<211> LENGTH: 404
<212> TYPE: DNA
<213> ORGANISM: Dengue virus 1

<400> SEQUENCE: 3
```

```
taggcgcgcc agggtccctg gagggaggtg gcgggtctct gactttaaaa gggatgtcat    60
atgtgatgtg cacaggctca tttaagctag agaaggaagt ggctgagacc cagcatggaa   120
ctgtcctagt gcaggttaaa tacgaaggaa cagatgcgcc atgcaagatc ccttttcga    180 cccaagatga gaaggagtg acccagaatg ggagattgat aacagccaat cccatagtta    240
ctgacaaaga aaaccaatc aacattgaga cagaaccacc ttttggtgag agctacatca    300
tagtaggggc aggtgaaaaa gctttgaaac taagctggtt caagaaagga agcagcatag   360
ggaaaggagg tggccatcac catcaccatc actgatgacc ggtt                    404
```

<210> SEQ ID NO 4
<211> LENGTH: 404
<212> TYPE: DNA
<213> ORGANISM: Dengue virus 2

<400> SEQUENCE: 4

```
taggcgcgcc agggtccctg gagggaggtg gcgggtctct acagctcaaa ggaatgtcat    60
attctatgtg tacaggaaag tttaaagttg tgaaggaaat agcagaaaca caacatggaa   120
caatagttct cagagtacaa tatgaagggg acggttctcc gtgcaagatc ccttttgaaa   180
taatggattt ggaaaaaaga catgtcttag gtcgcttgat cacagtcaac ccaattgtta   240
cagaaataga cagcccagtc aacatagaag cagaacctcc attcggagac agctacatca   300
ttataggagt agaaccggga caactgaagc tcagctggtt taagaaagga agttccattg   360
gccaaggagg tggccatcac catcaccatc actgatgacc ggtt                    404
```

<210> SEQ ID NO 5
<211> LENGTH: 401
<212> TYPE: DNA
<213> ORGANISM: Dengue virus 3

<400> SEQUENCE: 5

```
taggcgcgcc agggtccctg gagggaggtg gcgggtctga actcaagggg atgagctatg    60
caatgtgctt gaataccttt gtgttgaaga aagaagtctc cgaaacgcag catgggacaa   120
tactcattaa ggttgagtac aaaggggaag atgcaccttg caagattcct ttctccacag   180
aggatggaca agggaaagcc acaatggta gactgatcac agccaaccca gtggttacta   240
agaaggagga gcctgtcaac attgaggctg aacctcctt tggggaaagc aacatagtga   300
ttggagttgg agacaaagcc ttgaaaatta actggtacaa gaagggaagc tcgattggga   360
agggaggtgg ccatcaccat caccatcact gatgaccggt t                       401
```

<210> SEQ ID NO 6
<211> LENGTH: 401
<212> TYPE: DNA
<213> ORGANISM: Dengue virus 4

<400> SEQUENCE: 6

```
taggcgcgcc agggtccctg gagggaggtg gcgggtctag aatcaaggga atgtcataca    60
cgatgtgctc aggaaagttc tcaattgaca aagagatggc agaaacacag catgggacaa   120
cagtggtgaa agtcaagtat gaaggtgctg agctccgtg taaagtcccc atagagatac    180
gagatgtaaa taaggaaaaa gtggttgggc gtgtcatctc atccacccct ctagctgaga   240
ataccaacag tgtgaccaac atagaactgg aaccccctt tggggacagt acatagtca    300 taggtgttgg gaacagtgca ttgacactcc attggttcag gaaggaagt tctattggca   360
```
agggaggtgg ccatcaccat caccatcact gatgaccggt t            401

<210> SEQ ID NO 7
<211> LENGTH: 398
<212> TYPE: DNA
<213> ORGANISM: West Nile Virus

<400> SEQUENCE: 7
taggcgcgcc aggaggtggc gggtctcagt tgaagggaac aacctatggc gtctgttcaa    60
aggctttcaa gtttcttggg actcccgcag acacaggtca cggcactgtg gtgttggaat   120
tgcagtacac tggcacggat ggaccttgca aagttcctat ctcgtcagtg gcttcattga   180
acgacctaac gccagtgggc agattggtca ctgtcaaccc ttttgtttca gtggccacgg   240
ccaacgctaa ggtcctgatt gaattggaac cacccctttgg agactcatac atagtggtgg   300
gcagaggaga acaacagatc aatcaccatt ggcacaagtc tggaagcagc attggcaaag   360
gaggtggcca tcaccatcac catcactgat gaccggtt                            398

<210> SEQ ID NO 8
<211> LENGTH: 410
<212> TYPE: DNA
<213> ORGANISM: Yellow fever virus

<400> SEQUENCE: 8
taggcgcgcc agggtccctg agggaggtg gcgggtcttc agctttgaca ctcaagggga    60
catcctacaa aatgtgcact gacaaaatgt cttttgtcaa gaacccaact gacactggcc   120
atggcactgt tgtgatgcag gtgaaagtgc caaaggagc cccctgcaag attccagtga   180
tagtagctga tgatcttaca gcggcaatca ataaaggcat tttggttaca gttaaccca    240
tcgcctcaac caatgatgat gaagtgctga ttgaggtgaa cccacctttt ggagacagct   300
acattatcgt tgggacagga gattcacgtc tcacttacca gtggcacaaa gagggaagct   360
caataggaaa gggaggtggc catcaccatc accatcactg atgaccggtt              410

<210> SEQ ID NO 9
<211> LENGTH: 410
<212> TYPE: DNA
<213> ORGANISM: Japanese encephalitis virus

<400> SEQUENCE: 9
taggcgcgcc agggtccctg agggaggtg gcgggtctgc tctgaaaggc acaacctatg    60
gcatgtgtac agaaaaattc tcgttcgcga aaaatccggc ggacactggt cacgaacag   120
ttgtcattga actctcctac tctgggagtg atggcccctg caaaattccg attgtctccg   180
tcgcgagcct caatgacatg actcctgttg ggcggctggt gacagtgaac ccctttgtcg   240
cggcttccag tgccaactca aaggtgctgg tcgagatgga accccccttc ggagactcct   300
atatcgtggt tggaagggga gacaagcaga tcaaccacca ttggcacaga gctggaagca   360
cgctgggcaa gggaggtggc catcaccatc accatcactg atgaccggtt              410

<210> SEQ ID NO 10
<211> LENGTH: 397
<212> TYPE: DNA
<213> ORGANISM: Zika virus

<400> SEQUENCE: 10
gcgcgccagg aggtggcggg tctcttagat tgaagggcgt gtcatactcc ttgtgtaccg    60
cagcgttcac attcaccaag atcccggctg aaacactgca cgggacagtc acagtggagg   120

```
tacagtacgc agggacagat ggaccctgca aggttccagc tcagatggcg gtggacatgc    180
aaactctgac cccagttggg aggctgataa ccgctaaccc tgtaatcact gaaagcactg    240
agaactctaa gatgatgctg gaacttgatc caccatttgg ggactcttac attgtcatag    300
gagtcgggga gaagaagatc acccatcact ggcacaggag tggcagcacc attggaaaag    360
gaggtggcca tcaccatcac catcactgat gaccggt                             397
```

```
<210> SEQ ID NO 11
<211> LENGTH: 385
<212> TYPE: DNA
<213> ORGANISM: Wesselbron virus

<400> SEQUENCE: 11
gcgcgccagg aggtggcggg ctcatcctga aaggttcaac ctactcaatg tgcaaaagag     60
ggatgtcctt tgctaagcaa ccagttgaga cagaccatgg aacagcagtg atgcagataa    120
aagttacaac tggagctccg tgcagaattc cagtgattgc agcagattcc atggcgggaa    180
cagaaaaccg tggaagcgtc atcacaacca atcctattgc tgcgtcaaac aatgatgaag    240
tgttggtgga gatcagtcca ccatttggag agagttacat catcgttggt aatggagatg    300
ataaacttac ataccactgg caaagatcag gaagcaccat cgggaatgga ggtggccatc    360
accatcacca tcactgatga ccggt                                          385
```

```
<210> SEQ ID NO 12
<211> LENGTH: 397
<212> TYPE: DNA
<213> ORGANISM: Rocio virus

<400> SEQUENCE: 12
gcgcgccagg aggtggcggg tctctcaaaa tcaaagggtc aacatacctg atgtgcaagg     60
acaaatttgc ttttgccaag aacccagttg acacaggaca cggcacaatc gtgacggagg    120
tacagtacgc tggttctgat gggccatgca ggattccaat caccatgacc gagaacctac    180
atgatctcac tcccatcgga cgattggtga cggtcaatcc atttgttccc tcatccgaga    240
cggcacaaaa aattttgatt gaactcgagc ccccctttgg gacatccttc atactggtgg    300
gtacaggtcc caaccaggtg aaataccagt ggcataagtc tggtagtgtg atcggaaaag    360
gaggtggcca tcaccatcac catcactgat gaccggt                             397
```

```
<210> SEQ ID NO 13
<211> LENGTH: 397
<212> TYPE: DNA
<213> ORGANISM: Murray encephalitis virus

<400> SEQUENCE: 13
gcgcgccagg aggtggcggg tctttgaaac tgaaaggaac cacttatggg atgtgcacag     60
aaaaatttac tttctcaaag aatccagccg cacccggaca tggcacggta gtactagaac    120
tgcagtacac cgggagtgat ggaccatgca aaattccaat atcctctgta gcaagtctca    180
atgacatgac gcctgtcgga agaatggtga cagctaatcc atatgtagct tcatcaactg    240
ccaatgctaa agttctggtg gagattgaac caccccttcgg agactcatac attgtggtag    300
gcagggagaa caagcagatc aatcaccact ggcataagga gggtagttca attggcaaag    360
gaggtggcca tcaccatcac catcactgat gaccggt                             397
```

```
<210> SEQ ID NO 14
```

<211> LENGTH: 397
<212> TYPE: DNA
<213> ORGANISM: Saint-Louis encephalitis virus

<400> SEQUENCE: 14

```
gcgcgccagg aggtggcggg tctgttaaaa tcaaggggac gacatatggt atgtgtgact      60
ctgctttcac cttcagcaag aaccctgctg acacagggca tgggacagtg atcgtggaac     120
tgcagtacac tggaagcaac ggaccatgcc gggttcccat ttctgtgact gcaaacctca     180
tggacttgac accagttgga agactggtca cggtcaatcc ctttattagc acaggggag      240
cgaacaacaa ggtcatgatc gaagttgaac caccctttgg cgactcttac atcgtcgtcg     300
gaagaggcac cacccagatc aactaccact ggcacaaaga gggaagcagc attgggaagg     360
gaggtggcca tcaccatcac catcactgat gaccggt                              397
```

<210> SEQ ID NO 15
<211> LENGTH: 579
<212> TYPE: DNA
<213> ORGANISM: artificial
<220> FEATURE:
<223> OTHER INFORMATION: DNA encoding original SNAP (normal G/C content)

<400> SEQUENCE: 15

```
agatctgaca aagactgcga aatgaagcgc accaccctgg atagccctct gggcaagctg      60
gaactgtctg gtgcgaaca gggcctgcac agatcaagc tgctgggcaa aggaacatct      120
gccgccgacg ccgtggaagt gcctgcccca gccgccgtgc tgggcggacc agagccactg     180
atgcaggcca ccgcctggct caacgcctac tttcaccagc tgaggccat cgaggagttc      240
cctgtgccag ccctgcacca cccagtgttc cagcaggaga gctttacccg ccaggtgctg     300
tggaaactgc tgaaagtggt gaagttcgga gaggtcatca gctaccagca gctggccgcc     360
ctggccggca atcccgccgc caccgccgcc gtgaaaaccg ccctgagcgg aaatcccgtg     420
cccattctga tccctgcca ccgggtggtg tctagctctg cgccgtggg gggctacgag       480
ggcgggctcg ccgtgaaaga gtggctgctg cccacgagg ccacagact gggcaagcct       540
gggctgggtc ctgcaggtat aggcgcgcca gggtcccta                             579
```

<210> SEQ ID NO 16
<211> LENGTH: 235
<212> TYPE: PRT
<213> ORGANISM: artificial
<220> FEATURE:
<223> OTHER INFORMATION: mutated N protein of schmallenberg virus

<400> SEQUENCE: 16

```
Asp Ile Ser Ser Gln Phe Ile Phe Glu Asp Val Pro Gln Arg Asn Ala
1               5                   10                  15

Ala Thr Phe Asn Pro Glu Val Gly Tyr Val Ala Phe Ile Gly Lys Tyr
            20                  25                  30

Gly Gln Gln Leu Asn Phe Gly Val Ala Arg Val Phe Phe Leu Asn Gln
        35                  40                  45

Lys Lys Ala Lys Met Val Leu His Lys Thr Ala Gln Pro Ser Val Asp
    50                  55                  60

Leu Thr Phe Gly Gly Val Lys Phe Thr Val Val Asn Asn His Phe Pro
65                  70                  75                  80

Gln Tyr Val Ser Asn Pro Val Pro Asp Asn Ala Ile Thr Leu His Arg
                85                  90                  95

Met Ser Gly Tyr Leu Ala Arg Trp Ile Ala Asp Thr Cys Lys Ala Ser
```

```
                100                 105                 110
Val Leu Lys Leu Ala Glu Ala Ser Ala Gln Ile Val Met Pro Leu Ala
            115                 120                 125

Glu Val Lys Gly Cys Thr Trp Ala Asp Gly Tyr Thr Met Tyr Leu Gly
        130                 135                 140

Phe Ala Pro Gly Ala Glu Met Phe Leu Asp Ala Asp Phe Tyr Pro
145                 150                 155                 160

Leu Val Ile Glu Met His Arg Val Leu Lys Asp Asn Met Asp Val Asn
                165                 170                 175

Phe Met Lys Lys Val Leu Arg Gln Arg Tyr Gly Thr Met Thr Ala Glu
            180                 185                 190

Glu Trp Met Thr Gln Lys Ile Thr Glu Ile Lys Ala Ala Phe Asn Ser
        195                 200                 205

Val Gly Gln Leu Ala Trp Ala Lys Ser Gly Phe Ser Pro Ala Ala Arg
    210                 215                 220

Thr Phe Leu Gln Gln Phe Gly Ile Asn Ile Pro
225                 230                 235
```

<210> SEQ ID NO 17
<211> LENGTH: 707
<212> TYPE: DNA
<213> ORGANISM: artificial
<220> FEATURE:
<223> OTHER INFORMATION: Mutated DNA sequence encoding the N protein of
      schmallenberg virus

<400> SEQUENCE: 17

```
gatatctcaa gccaattcat ttttgaagat gtaccacaac ggaatgcagc tacatttaac      60
ccggaggtcg ggtatgtggc atttattggt aagtatgggc aacaactcaa cttcggtgtt     120
gctagagtct tcttcctcaa ccagaagaag gccaagatgg tcctacataa gacggcacaa     180
ccaagtgtcg atcttacttt tggtggggtc aaatttacag tggttaataa ccatttttccc    240
caatatgtct caaatcctgt gccagacaat gccattacac ttcacaggat gtcaggttat     300
ctagcacgtt ggattgctga tacatgcaag gctagtgtcc tcaaactagc tgaagctagt     360
gctcagattg tcatgccccct gctgaggtt aagggatgca cctgggccga tggttataca     420
atgtatcttg gatttgcacc tggggccgaa atgttccttg atgcttttga cttctatcca     480
ctagttattg aaatgcatag ggtcctcaag gacaatatgg atgtaaattt tatgaaaaaa     540
gtcctccgcc aacgctatgg aacaatgact gctgaagaat ggatgactca gaaaataaca     600
gaaataaaag ctgcttttaa ttctgttgga cagcttgcct gggccaaatc tggattctct     660
cctgctgcta gaaccttctt gcagcaattc ggtatcaaca tcccggg                    707
```

<210> SEQ ID NO 18
<211> LENGTH: 211
<212> TYPE: PRT
<213> ORGANISM: mus musculus

<400> SEQUENCE: 18

```
Met Ala Glu Thr Cys Lys Met Lys Tyr Ser Val Leu Asp Ser Pro Leu
1               5                   10                  15

Gly Lys Met Glu Leu Ser Gly Cys Glu Arg Gly Leu His Gly Ile Arg
            20                  25                  30

Leu Leu Ser Gly Lys Thr Pro Asn Thr Asp Pro Thr Glu Ala Pro Ala
        35                  40                  45

Thr Pro Glu Val Leu Gly Gly Pro Glu Gly Val Pro Glu Pro Leu Val
```

```
            50                 55                  60
Gln Cys Thr Ala Trp Leu Glu Ala Tyr Phe Arg Glu Pro Ala Ala Thr
 65                  70                  75                  80

Glu Gly Leu Pro Leu Pro Ala Leu His His Pro Val Phe Gln Gln Asp
                 85                  90                  95

Ser Phe Thr Arg Gln Val Leu Trp Lys Leu Leu Lys Val Val Lys Phe
            100                 105                 110

Gly Glu Thr Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
130                 135                 140

Ile Leu Ile Pro Cys His Arg Val Val Arg Ser Asp Gly Ala Ile Gly
145                 150                 155                 160

His Tyr Ser Gly Gly Gln Ala Val Lys Glu Trp Leu Leu Ala His
                165                 170                 175

Glu Gly Ile Pro Thr Gly Gln Pro Ala Ser Lys Gly Leu Gly Leu Thr
            180                 185                 190

Gly Thr Trp Leu Lys Ser Ser Phe Glu Ser Thr Ser Ser Glu Pro Ser
        195                 200                 205

Gly Arg Asn
    210

<210> SEQ ID NO 19
<211> LENGTH: 209
<212> TYPE: PRT
<213> ORGANISM: Rattus norvegicus

<400> SEQUENCE: 19

Met Ala Glu Ile Cys Lys Met Lys Tyr Thr Val Leu Asp Ser Pro Leu
  1               5                  10                  15

Gly Lys Ile Glu Leu Ser Gly Cys Glu Arg Gly Leu His Gly Ile Arg
             20                  25                  30

Phe Leu Ser Gly Lys Thr Pro Asn Thr Asp Pro Thr Glu Ala Pro Ala
         35                  40                  45

Cys Pro Glu Val Leu Gly Gly Pro Glu Gly Val Pro Glu Pro Leu Val
     50                  55                  60

Gln Cys Thr Ala Trp Leu Glu Ala Tyr Phe His Glu Pro Ala Ala Thr
 65                  70                  75                  80

Glu Gly Leu Pro Leu Pro Ala Leu His His Pro Val Phe Gln Gln Asp
                 85                  90                  95

Ser Phe Thr Arg Gln Val Leu Trp Lys Leu Leu Lys Val Val Lys Phe
            100                 105                 110

Gly Glu Met Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
130                 135                 140

Ile Leu Ile Pro Cys His Arg Val Ile Arg Ser Asp Gly Ala Ile Gly
145                 150                 155                 160

Asn Tyr Ser Gly Gly Gln Thr Val Lys Glu Trp Leu Leu Ala His
                165                 170                 175

Glu Gly Ile Pro Thr Gly Gln Pro Ala Ser Lys Gly Leu Gly Leu Ile
            180                 185                 190

Gly Ser Trp Leu Lys Pro Ser Phe Glu Ser Ser Ser Pro Lys Pro Ser
        195                 200                 205
```

Gly

<210> SEQ ID NO 20
<211> LENGTH: 963
<212> TYPE: DNA
<213> ORGANISM: artificial
<220> FEATURE:
<223> OTHER INFORMATION: DNA sequence coding for SNAP - linker - DEN1
      EDIII - linker- Histag

<400> SEQUENCE: 20

```
agatctgaca aagactgcga atgaagcgc accaccctgg atagccctct gggcaagctg      60
gaactgtctg gtgcgaaca gggcctgcac gagatcaagc tgctgggcaa aggaacatct    120
gccgccgacg ccgtggaagt gcctgcccca gccgccgtgc tgggcggacc agagccactg    180
atgcaggcca ccgcctggct caacgcctac tttcaccagc ctgaggccat cgaggagttc    240
cctgtgccag ccctgcacca cccagtgttc cagcaggaga gctttacccg ccaggtgctg    300
tggaaactgc tgaaagtggt gaagttcgga gaggtcatca gctaccagca gctggccgcc    360
ctggccggca atcccgccgc caccgccgcc gtgaaaaccg ccctgagcgg aaatcccgtg    420
cccattctga tccctgcca ccgggtggtg tctagctctg cgccgtggg gggctacgag    480
ggcgggctcg ccgtgaaaga gtggctgctg gcccacgagg ccacagact gggcaagcct    540
gggctgggtc ctgcaggtat aggcgcgcca gggtccctgg agggaggtgg cgggtctctg    600
actttaaaag ggatgtcata tgtgatgtgc acaggctcat ttaagctaga aaggaagtg    660
gctgagaccc agcatggaac tgtcctagtg caggttaaat acgaaggaac agatgcgcca    720
tgcaagatcc ccttttcgac ccaagatgag aaaggagtga cccagaatgg agagattgata    780
acagccaatc ccatagttac tgacaaagaa aaaccaatca acattgagac agaaccacct    840
tttggtgaga gctacatcat agtagggca ggtgaaaaag ctttgaaact aagctggttc    900
aagaaaggaa gcagcatagg gaaaggaggt ggccatcacc atcaccatca ctgatgaccg    960
gtt                                                                  963
```

<210> SEQ ID NO 21
<211> LENGTH: 316
<212> TYPE: PRT
<213> ORGANISM: artificial
<220> FEATURE:
<223> OTHER INFORMATION: SNAP - linker - DEN1 EDIII - linker- Histag

<400> SEQUENCE: 21

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
                20                  25                  30

Lys Leu Leu Lys Gly Thr Ser Ala Ala Asp Ala Val Glu Val Pro Ala
            35                  40                  45

Pro Ala Ala Val Leu Gly Gly Pro Glu Pro Leu Met Gln Ala Thr Ala
        50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Ala Ala Thr Ala

```
        115                 120                 125
Ala Val Lys Thr Ala Leu Ser Gly Asn Pro Val Pro Ile Leu Ile Pro
    130                 135                 140
Cys His Arg Val Val Ser Ser Gly Ala Val Gly Gly Tyr Glu Gly
145                 150                 155                 160
Gly Leu Ala Val Lys Glu Trp Leu Leu Ala His Glu Gly His Arg Leu
                165                 170                 175
Gly Lys Pro Gly Leu Gly Pro Ala Gly Ile Gly Ala Pro Gly Ser Leu
            180                 185                 190
Glu Gly Gly Gly Gly Ser Leu Thr Leu Lys Gly Met Ser Tyr Val Met
                195                 200                 205
Cys Thr Gly Ser Phe Lys Leu Glu Lys Glu Val Ala Glu Thr Gln His
            210                 215                 220
Gly Thr Val Leu Val Gln Val Lys Tyr Glu Gly Thr Asp Ala Pro Cys
225                 230                 235                 240
Lys Ile Pro Phe Ser Thr Gln Asp Glu Lys Gly Val Thr Gln Asn Gly
                245                 250                 255
Arg Leu Ile Thr Ala Asn Pro Ile Val Thr Asp Lys Glu Lys Pro Ile
            260                 265                 270
Asn Ile Glu Thr Glu Pro Pro Phe Gly Glu Ser Tyr Ile Ile Val Gly
                275                 280                 285
Ala Gly Glu Lys Ala Leu Lys Leu Ser Trp Phe Lys Lys Gly Ser Ser
            290                 295                 300
Ile Gly Lys Gly Gly Gly His His His His His His
305                 310                 315

<210> SEQ ID NO 22
<211> LENGTH: 54
<212> TYPE: DNA
<213> ORGANISM: artificial
<220> FEATURE:
<223> OTHER INFORMATION: DNA sequence encoding the ssBiP sequence

<400> SEQUENCE: 22
atgaagttat gcatattact ggccgtcgtg gcctttgttg gcctctcgct cggg          54

<210> SEQ ID NO 23
<211> LENGTH: 66
<212> TYPE: DNA
<213> ORGANISM: artificial
<220> FEATURE:
<223> OTHER INFORMATION: DNA artificial encoding BiP-like signal =
      insect ssBiP signal peptide + cleavage site DEN1prM signal
      sequence

<400> SEQUENCE: 23
atgaaactat gtattctact tgcagttgtt gcgttcgtag gattgtcctt acctacagct    60
ctggca                                                              66

<210> SEQ ID NO 24
<211> LENGTH: 22
<212> TYPE: PRT
<213> ORGANISM: artificial
<220> FEATURE:
<223> OTHER INFORMATION: BiP-like signal = insect ssBiP signal peptide +
      cleavage site DEN1prM signal sequence

<400> SEQUENCE: 24

Met Lys Leu Cys Ile Leu Leu Ala Val Val Ala Phe Val Gly Leu Ser
1               5                   10                  15
```

Leu Pro Thr Ala Leu Ala
            20

<210> SEQ ID NO 25
<211> LENGTH: 4
<212> TYPE: PRT
<213> ORGANISM: artificial
<220> FEATURE:
<223> OTHER INFORMATION: Amino acid sequence of the spacer

<400> SEQUENCE: 25

Gly Gly Gly Ser
1

<210> SEQ ID NO 26
<211> LENGTH: 12
<212> TYPE: DNA
<213> ORGANISM: artificial
<220> FEATURE:
<223> OTHER INFORMATION: DNA sequence of the spacer

<400> SEQUENCE: 26
ggtggcggat ct                                                          12

<210> SEQ ID NO 27
<211> LENGTH: 6
<212> TYPE: PRT
<213> ORGANISM: artificial
<220> FEATURE:
<223> OTHER INFORMATION: Amino acid sequence of HIS TAG

<400> SEQUENCE: 27

His His His His His His
1               5

<210> SEQ ID NO 28
<211> LENGTH: 18
<212> TYPE: DNA
<213> ORGANISM: artificial
<220> FEATURE:
<223> OTHER INFORMATION: DNA sequence encoding His Tag

<400> SEQUENCE: 28
catcatcatc atcatcat                                                    18

<210> SEQ ID NO 29
<211> LENGTH: 21
<212> TYPE: DNA
<213> ORGANISM: artificial
<220> FEATURE:
<223> OTHER INFORMATION: DNA encoding pro-TEV cleavage site 1

<400> SEQUENCE: 29
gaaaacctgt acttccagag c                                                21

<210> SEQ ID NO 30
<211> LENGTH: 21
<212> TYPE: DNA
<213> ORGANISM: artificial
<220> FEATURE:
<223> OTHER INFORMATION: DNA encoding pro-TEV cleavage site 2

<400> SEQUENCE: 30
gagaatctat attttcaagg g                                                21

<210> SEQ ID NO 31
<211> LENGTH: 530
<212> TYPE: DNA
<213> ORGANISM: artificial
<220> FEATURE:
<223> OTHER INFORMATION: SNAP-like sequence G/C low content

<400> SEQUENCE: 31

```
gacaaagact gcgaaatgaa aagaactaca ttggattcac cacttgggaa gttggaactg      60
agtggatgcg agcaaggatt gcatgaaatt aagctactgg gaaaaggaac ttctgctgct     120
gatgcagttg aagttccagc accagcagct gttcttggag gtcctgagcc cctcatgcaa     180
gccacagcct ggcttaacgc atatttccac cagcctgagg ccattgagga atttccagtc     240
cccgcccttc accatcctgt gtttcagcag gagagcttca cccgccaggt cctgtggaaa     300
ttgctgaagg tggtcaagtt tggtgaagtg atttcatatc agcaacttgc tgcattggcc     360
ggtaaccccg cagctacagc tgccgtgaaa actgctctca gcggaaatcc tgtgcccatc     420
ctgatccctt gtcacagagt cgtttcatct tccggagctg taggtggcta tgaaggagga     480
ctggcagtta aggagtggct gctggctcat gaaggtcata gacttggaaa                530
```

<210> SEQ ID NO 32
<211> LENGTH: 7
<212> TYPE: PRT
<213> ORGANISM: artificial
<220> FEATURE:
<223> OTHER INFORMATION: Pro-TEV cleavage site 1

<400> SEQUENCE: 32

```
Glu Asn Leu Tyr Phe Gln Ser
1               5
```

<210> SEQ ID NO 33
<211> LENGTH: 7
<212> TYPE: PRT
<213> ORGANISM: artificial
<220> FEATURE:
<223> OTHER INFORMATION: Pro-TEV cleavage site 2

<400> SEQUENCE: 33

```
Glu Asn Leu Tyr Phe Gln Gly
1               5
```

<210> SEQ ID NO 34
<211> LENGTH: 798
<212> TYPE: DNA
<213> ORGANISM: artificial
<220> FEATURE:
<223> OTHER INFORMATION: Cassette DNA pDeSNAP Univ (BIPlike - SNAPlike-
     proTEV/Histag)

<400> SEQUENCE: 34

```
gatcgcgagc tagcaccatg aaactatgta ttctacttgc agttgttgcg ttcgtaggat      60
tgtccttacc tacagctctg gcaagatctg acaaagactg cgaaatgaaa agaactacat     120
tggattcacc acttgggaag ttggaactga gtggatgcga gcaaggattg catgaaatta     180
agctactggg aaaaggaact tctgctgctg atgcagttga agttccagca ccagcagctg     240
ttcttggagg tcctgagccc ctcatgcaag ccacagcctg gcttaacgca tatttccacc     300
agcctgaggc cattgaggaa tttccagtcc ccgcccttca ccatcctgtg tttcagcagg     360
agagcttcac ccgccaggtc ctgtggaaat tgctgaaggt ggtcaagttt ggtgaagtga     420
tttcatatca gcaacttgct gcattggccg gtaaccccgc agctacagct gccgtgaaaa     480
```

```
ctgctctcag cggaaatcct gtgcccatcc tgatcccttg tcacagagtc gtttcatctt      540
ccggagctgt aggtggctat gaaggaggac tggcagttaa ggagtggctg ctggctcatg      600
aaggtcatag acttggaaag cctgggctgg gtcctgctgg tataggcgcg ccagggtccc      660
taggtggcgg atccgaaaac ctgtacttcc agagcgatat cggaggtgga ggcccgggag      720
agaatctata ttttcaaggg cccggcggag gtagtcacca tcatcaccat cactaatgac      780
cggtgcggcc gcaagctt                                                    798

<210> SEQ ID NO 35
<211> LENGTH: 1439
<212> TYPE: DNA
<213> ORGANISM: artificial
<220> FEATURE:
<223> OTHER INFORMATION: Cassette DNA pDeSNAP Univ +SBV.N (ssBIP -
      SNAPlike- SBV.N- proTEV/Histag)

<400> SEQUENCE: 35
atgaagttat gcatattact ggccgtcgtg gcctttgttg cctctcgct cgggagatct        60 gacaaagact gcgaaatgaa aagaactaca ttggattcac cacttgggaa gttggaactg      120
agtggatgcg agcaaggatt gcatgaaatt aagctactgg gaaaaggaac ttctgctgct      180
gatgcagttg aagttccagc accagcagct gttcttggag gtcctgagcc cctcatgcaa      240
gccacagcct ggcttaacgc atatttccac cagcctgagg ccattgagga atttccagtc      300
cccgcccttc accatcctgt gtttcagcag gagagcttca cccgccaggt cctgtggaaa      360
ttgctgaagg tggtcaagtt tggtgaagtg atttcatatc agcaacttgc tgcattggcc      420
ggtaaccccg cagctacagc tgccgtgaaa actgctctca gcggaaatcc tgtgcccatc      480
ctgatccctt gtcacagagt cgtttcatct tccggagctg taggtggcta tgaaggagga      540
ctggcagtta aggagtggct gctggctcat gaaggtcata gacttggaaa gcctgggctg      600
gtcctgctgg tataggcgcg ccagggtcc ctaggtggcg gatccgaaaa cctgtacttc      660
cagagcgata tctcaagcca attcattttt gaagatgtac cacaacggaa tgcagctaca      720
tttaacccgg aggtcgggta tgtggcattt attggtaagt atgggcaaca actcaacttc      780
ggtgttgcta gagtcttctt cctcaaccag aagaaggcca agatggtcct acataagacg      840
gcacaaccaa gtcgatctt tacttttggt ggggtcaaat ttacagtggt taataaccat      900
tttccccaat atgtctcaaa tcctgtgcca gacaatgcca ttacacttca caggatgtca      960
ggttatctag cacgttggat tgctgataca tgcaaggcta gtgtcctcaa actagctgaa     1020
gctagtgctc agattgtcat gccccttgct gaggttaagg gatgcacctg gccgatggt      1080 tatacaatgt atcttggatt tgcacctggg gccgaaatgt tccttgatgc ttttgacttc     1140
tatccactag ttattgaaat gcatagggtc ctcaaggaca atatggatgt aaattttatg     1200
aaaaaagtcc tccgccaacg ctatggaaca atgactgctg aagaatggat gactcagaaa     1260
ataacagaaa taaagctgc ttttaattct gttggacagc ttgcctgggc caaatctgga     1320
ttctctcctg ctgctagaac cttcttgcag caattcggta tcaacatccc gggagagaat     1380
ctatattttc aagggcccgg cggaggtagt caccatcatc accatcacta atgaccggt      1439

<210> SEQ ID NO 36
<211> LENGTH: 1480
<212> TYPE: DNA
<213> ORGANISM: artificial
<220> FEATURE:
<223> OTHER INFORMATION: Cassette DNA pDeSNAP Univ +SBV.N (BIPlike -
```

SNAPlike-SBV.N -proTEV/Histag)

<400> SEQUENCE: 36

| | | |
|---|---|---|
| tcgcgagcta gcaccatgaa actatgtatt ctacttgcag ttgttgcgtt cgtaggattg | 60 |
| tccttaccta cagctctggc aagatctgac aaagactgcg aaatgaaaag aactacattg | 120 |
| gattcaccac ttgggaagtt ggaactgagt ggatgcgagc aaggattgca tgaaattaag | 180 |
| ctactgggaa aaggaacttc tgctgctgat gcagttgaag ttccagcacc agcagctgtt | 240 |
| cttggaggtc ctgagcccct catgcaagcc acagcctggc ttaacgcata tttccaccag | 300 |
| cctgaggcca ttgaggaatt ccagtcccc gcccttcacc atcctgtgtt tcagcaggag | 360 |
| agcttcaccc gccaggtcct gtggaaattg ctgaaggtgg tcaagtttgg tgaagtgatt | 420 |
| tcatatcagc aacttgctgc attggccggt aaccccgcag ctacagctgc cgtgaaaact | 480 |
| gctctcagcg gaaatcctgt gcccatcctg atcccttgtc acagagtcgt ttcatcttcc | 540 |
| ggagctgtag gtggctatga aggaggactg gcagttaagg agtggctgct ggctcatgaa | 600 |
| ggtcatagac ttgaaagcc tgggctgggt cctgctggta taggcgcgcc agggtcccta | 660 |
| ggtggcggat ccgaaaacct gtacttccag agcgatatct caagccaatt cattttgaa | 720 |
| gatgtaccac aacggaatgc agctacattt aacccggagg tcgggtatgt ggcatttatt | 780 |
| ggtaagtatg ggcaacaact caacttcggt gttgctagag tcttcttcct caaccagaag | 840 |
| aaggccaaga tggtcctaca taagacggca caaccaagtg tcgatcttac ttttggtggg | 900 |
| gtcaaattta cagtggttaa taaccatttt ccccaatatg tctcaaatcc tgtgccagac | 960 |
| aatgccatta cacttcacag gatgtcaggt tatctagcac gttggattgc tgatacatgc | 1020 |
| aaggctagtg tcctcaaact agctgaagct agtgctcaga ttgtcatgcc ccttgctgag | 1080 |
| gttaagggat gcacctgggc cgatggttat acaatgtatc ttggatttgc acctggggcc | 1140 |
| gaaatgttcc ttgatgcttt tgacttctat ccactagtta ttgaaatgca tagggtcctc | 1200 |
| aaggacaata tggatgtaaa ttttatgaaa aaagtcctcc gccaacgcta tggaacaatg | 1260 |
| actgctgaag aatggatgac tcagaaaata acagaaataa aagctgcttt taattctgtt | 1320 |
| ggacagcttg cctgggccaa atctggattc tctcctgctg ctagaacctt cttgcagcaa | 1380 |
| ttcggtatca acatcccggg agagaatcta tattttcaag ggcccggcgg aggtagtcac | 1440 |
| catcatcacc atcactaatg accggtgcgg ccgcaagctt | 1480 |

<210> SEQ ID NO 37
<211> LENGTH: 18
<212> TYPE: PRT
<213> ORGANISM: artificial
<220> FEATURE:
<223> OTHER INFORMATION: Amino acid sequence of the ssBiP sequence

<400> SEQUENCE: 37

Met Lys Leu Cys Ile Leu Leu Ala Val Val Ala Phe Val Gly Leu Ser
1               5                   10                  15

Leu Gly

<210> SEQ ID NO 38
<211> LENGTH: 17
<212> TYPE: PRT
<213> ORGANISM: West Nile virus strain IS-98-ST1

<400> SEQUENCE: 38

Met Val Val Phe Val Val Leu Leu Leu Leu Val Ala Pro Ala Tyr Ser
1               5                   10                  15

Leu

<210> SEQ ID NO 39
<211> LENGTH: 5
<212> TYPE: PRT
<213> ORGANISM: Dengue virus

<400> SEQUENCE: 39

Pro Thr Ala Leu Ala
1               5

<210> SEQ ID NO 40
<211> LENGTH: 6
<212> TYPE: PRT
<213> ORGANISM: artificial
<220> FEATURE:
<223> OTHER INFORMATION: Cleavage site of enterokinase

<400> SEQUENCE: 40

Asp Asp Asp Asp Lys Asp
1               5

<210> SEQ ID NO 41
<211> LENGTH: 480
<212> TYPE: PRT
<213> ORGANISM: artificial
<220> FEATURE:
<223> OTHER INFORMATION: Amino acid sequence of
      BiPlike+SNAPlike+proTEV+SBV.N+proTEV+Histag

<400> SEQUENCE: 41

Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
                20                  25                  30

Thr Thr Leu Asp Ser Pro Leu Gly Lys Leu Glu Leu Ser Gly Cys Glu
            35                  40                  45

Gln Gly Leu His Glu Ile Lys Leu Leu Gly Lys Gly Thr Ser Ala Ala
        50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
                100                 105                 110

Gln Gln Glu Ser Phe Thr Arg Gln Val Leu Trp Lys Leu Leu Lys Val
            115                 120                 125

Val Lys Phe Gly Glu Val Ile Ser Tyr Gln Gln Leu Ala Ala Leu Ala
        130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Ser Gly
                165                 170                 175

Ala Val Gly Gly Tyr Glu Gly Gly Leu Ala Val Lys Glu Trp Leu Leu
                180                 185                 190

Ala His Glu Gly His Arg Leu Gly Lys Pro Gly Leu Gly Pro Ala Gly
            195                 200                 205

Ile Gly Ala Pro Gly Ser Leu Gly Gly Ser Glu Asn Leu Tyr Phe
        210                 215                 220

-continued

```
Gln Ser Asp Ile Ser Ser Gln Phe Ile Phe Glu Asp Val Pro Gln Arg
225                 230                 235                 240

Asn Ala Ala Thr Phe Asn Pro Glu Val Gly Tyr Val Ala Phe Ile Gly
            245                 250                 255

Lys Tyr Gly Gln Gln Leu Asn Phe Gly Val Ala Arg Val Phe Phe Leu
        260                 265                 270

Asn Gln Lys Lys Ala Lys Met Val Leu His Lys Thr Ala Gln Pro Ser
    275                 280                 285

Val Asp Leu Thr Phe Gly Gly Val Lys Phe Thr Val Asn Asn His
290                 295                 300

Phe Pro Gln Tyr Val Ser Asn Pro Val Pro Asp Asn Ala Ile Thr Leu
305                 310                 315                 320

His Arg Met Ser Gly Tyr Leu Ala Arg Trp Ile Ala Asp Thr Cys Lys
            325                 330                 335

Ala Ser Val Leu Lys Leu Ala Glu Ala Ser Ala Gln Ile Val Met Pro
        340                 345                 350

Leu Ala Glu Val Lys Gly Cys Thr Trp Ala Asp Gly Tyr Thr Met Tyr
    355                 360                 365

Leu Gly Phe Ala Pro Gly Ala Glu Met Phe Leu Asp Ala Phe Asp Phe
370                 375                 380

Tyr Pro Leu Val Ile Glu Met His Arg Val Leu Lys Asp Asn Met Asp
385                 390                 395                 400

Val Asn Phe Met Lys Lys Val Leu Arg Gln Arg Tyr Gly Thr Met Thr
            405                 410                 415

Ala Glu Glu Trp Met Thr Gln Lys Ile Thr Ile Lys Ala Ala Phe
        420                 425                 430

Asn Ser Val Gly Gln Leu Ala Trp Ala Lys Ser Gly Phe Ser Pro Ala
    435                 440                 445

Ala Arg Thr Phe Leu Gln Gln Phe Gly Ile Asn Ile Pro Gly Glu Asn
    450                 455                 460

Leu Tyr Phe Gln Gly Pro Gly Gly Ser His His His His His
465                 470                 475                 480
```

<210> SEQ ID NO 42
<211> LENGTH: 438
<212> TYPE: PRT
<213> ORGANISM: artificial
<220> FEATURE:
<223> OTHER INFORMATION: Amino acid sequence of the fusion protein SNAP+SCHM.N (without BiPlike + HisTag

<400> SEQUENCE: 42

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
```

```
            100                 105                 110
Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
        130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ser
        195                 200                 205

Gln Phe Ile Phe Glu Asp Val Pro Gln Arg Asn Ala Ala Thr Phe Asn
    210                 215                 220

Pro Glu Val Gly Tyr Val Ala Phe Ile Gly Lys Tyr Gly Gln Gln Leu
225                 230                 235                 240

Asn Phe Gly Val Ala Arg Val Phe Phe Leu Asn Gln Lys Lys Ala Lys
                245                 250                 255

Met Val Leu His Lys Thr Ala Gln Pro Ser Val Asp Leu Thr Phe Gly
            260                 265                 270

Gly Val Lys Phe Thr Val Asn Asn His Phe Pro Gln Tyr Val Ser
        275                 280                 285

Asn Pro Val Pro Asp Asn Ala Ile Thr Leu His Arg Met Ser Gly Tyr
    290                 295                 300

Leu Ala Arg Trp Ile Ala Asp Thr Cys Lys Ala Ser Val Leu Lys Leu
305                 310                 315                 320

Ala Glu Ala Ser Ala Gln Ile Val Met Pro Leu Ala Glu Val Lys Gly
                325                 330                 335

Cys Thr Trp Ala Asp Gly Tyr Thr Met Tyr Leu Gly Phe Ala Pro Gly
            340                 345                 350

Ala Glu Met Phe Leu Asp Ala Phe Asp Phe Tyr Pro Leu Val Ile Glu
        355                 360                 365

Met His Arg Val Leu Lys Asp Asn Met Asp Val Asn Phe Met Lys Lys
    370                 375                 380

Val Leu Arg Gln Arg Tyr Gly Thr Met Thr Ala Glu Glu Trp Met Thr
385                 390                 395                 400

Gln Lys Ile Thr Glu Ile Lys Ala Ala Phe Asn Ser Val Gly Gln Leu
                405                 410                 415

Ala Trp Ala Lys Ser Gly Phe Ser Pro Ala Ala Arg Thr Phe Leu Gln
            420                 425                 430

Gln Phe Gly Ile Asn Ile
        435

<210> SEQ ID NO 43
<211> LENGTH: 4194
<212> TYPE: DNA
<213> ORGANISM: artificial
<220> FEATURE:
<223> OTHER INFORMATION: pMT/BiP/SNAP-Histag  avec cassette DeSNAP Univ

<400> SEQUENCE: 43
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
```

-continued

| | |
|---|---|
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccag tgaattttaa cgttgcagga | 420 |
| caggatgtgg tgcccgatgt gactagctct ttgctgcagg ccgtcctatc ctctggttcc | 480 |
| gataagagac ccagaactcc ggccccccac cgcccaccgc cacccccata catatgtggt | 540 |
| acgcaagtaa gagtgcctgc gcatgcccca tgtgccccac caagagtttt gcatcccata | 600 |
| caagtcccca aagtggagaa ccgaaccaat tcttcgcggg cagaacaaaa gcttctgcac | 660 |
| acgtctccac tcgaatttgg agccggccgg cgtgtgcaaa agaggtgaat cgaacgaaag | 720 |
| acccgtgtgt aaagccgcgt ttccaaaatg tataaaaccg agagcatctg ccaatgtgc | 780 |
| atcagttgtg gtcagcagca aaatcaagtg aatcatctca gtgcaactaa aggggggatc | 840 |
| cgatctcaat atgaagttat gcatattact ggccgtcgtg gcctttgttg gcctctcgct | 900 |
| cgggagatct gacaaagact gcgaaatgaa aagaactaca ttggattcac cacttgggaa | 960 |
| gttggaactg agtggatgcg agcaaggatt gcatgaaatt aagctactgg gaaaaggaac | 1020 |
| ttctgctgct gatgcagttg aagttccagc accagcagct gttcttggag gtcctgagcc | 1080 |
| cctcatgcaa gccacagcct ggcttaacgc atatttccac cagcctgagg ccattgagga | 1140 |
| atttccagtc cccgcccttc accatcctgt gtttcagcag gagagcttca cccgccaggt | 1200 |
| cctgtggaaa ttgctgaagg tggtcaagtt tggtgaagtg atttcatatc agcaacttgc | 1260 |
| tgcattggcc ggtaaccccg cagctacagc tgccgtgaaa actgctctca gcggaaatcc | 1320 |
| tgtgcccatc ctgatccctt gtcacagagt cgtttcatct tccggagctg taggtggcta | 1380 |
| tgaaggagga ctggcagtta aggagtggct gctggctcat gaaggtcata gacttggaaa | 1440 |
| gcctgggctg ggtcctgctg gtataggcgc gccagggtcc ctaggtggcg gatccgaaaa | 1500 |
| cctgtacttc cagagcgata tcggaggtgg aggcccggga gagaatctat attttcaagg | 1560 |
| gcccggcgga ggtagtcacc atcatcacca tcactaatga ccggtcatca tcaccatcac | 1620 |
| cattgagttt aaacccgctg atcagcctcg actgtgcctt ctaaggcctg agctcgctga | 1680 |
| tcagcctcga tcgaggatcc agacatgata agatacattg atgagtttgg acaaaccaca | 1740 |
| actagaatgc agtgaaaaaa atgctttatt tgtgaaattt gtgatgctat tgctttattt | 1800 |
| gtaaccatta taagctgcaa taaacaagtt aacaacaaca attgcattca ttttatgttt | 1860 |
| caggttcagg gggaggtgtg ggaggttttt taaagcaagt aaaacctcta caaatgtggt | 1920 |
| atggctgatt atgatcagtc gacctgcagg catgcaagct tggcgtaatc atggtcatag | 1980 |
| ctgtttcctg tgtgaaattg ttatccgctc acaattccac acaacatacg agccggaagc | 2040 |
| ataaagtgta aagcctgggg tgcctaatga gtgagctaac tcacattaat tgcgttgcgc | 2100 |
| tcactgcccg ctttccagtc gggaaacctg tcgtgccagc tgcattaatg aatcggccaa | 2160 |
| cgcgcgggga gaggcggttt gcgtattggg cgctcttccg cttcctcgct cactgactcg | 2220 |
| ctgcgctcgg tcgttcggct gcggcgagcg gtatcagctc actcaaaggc ggtaatacgg | 2280 |
| ttatccacag aatcagggga taacgcagga agaacatgt gagcaaaagg ccagcaaaag | 2340 |
| gccaggaacc gtaaaaaggc cgcgttgctg gcgtttttcc ataggctccg ccccccctgac | 2400 |
| gagcatcaca aaaatcgacg ctcaagtcag aggtggcgaa acccgacagg actataaaga | 2460 |
| taccaggcgt ttccccctgg aagctccctc gtgcgctctc ctgttccgac cctgccgctt | 2520 |

```
accggatacc tgtccgcctt tctcccttcg ggaagcgtgg cgctttctca tagctcacgc   2580
tgtaggtatc tcagttcggt gtaggtcgtt cgctccaagc tgggctgtgt gcacgaaccc   2640
cccgttcagc ccgaccgctg cgccttatcc ggtaactatc gtcttgagtc caacccggta   2700
agacacgact tatcgccact ggcagcagcc actggtaaca ggattagcag agcgaggtat   2760
gtaggcggtg ctacagagtt cttgaagtgg tggcctaact acggctacac tagaaggaca   2820
gtatttggta tctgcgctct gctgaagcca gttaccttcg gaaaagagt tggtagctct   2880 tgatccggca acaaaccac cgctggtagc ggtggttttt tgtttgcaa gcagcagatt   2940 acgcgcagaa aaaaggatc tcaagaagat cctttgatct tttctacggg gtctgacgct   3000
cagtggaacg aaaactcacg ttaagggatt ttggtcatga gattatcaaa aaggatcttc   3060
acctagatcc ttttaaatta aaatgaagt tttaaatcaa tctaaagtat atatgagtaa   3120
acttggtctg acagttacca atgcttaatc agtgaggcac ctatctcagc gatctgtcta   3180
tttcgttcat ccatagttgc ctgactcccc gtcgtgtaga taactacgat acgggagggc   3240
ttaccatctg gccccagtgc tgcaatgata ccgcgagacc cacgctcacc ggctccagat   3300
ttatcagcaa taaaccagcc agccggaagg gccgagcgca gaagtggtcc tgcaacttta   3360
tccgcctcca tccagtctat taattgttgc cgggaagcta gagtaagtag ttcgccagtt   3420
aatagtttgc gcaacgttgt tgccattgct acaggcatcg tggtgtcacg ctcgtcgttt   3480
ggtatggctt cattcagctc cggttcccaa cgatcaaggc gagttacatg atccccatg   3540 ttgtgcaaaa aagcggttag ctccttcggt cctccgatcg ttgtcagaag taagttggcc   3600
gcagtgttat cactcatggt tatggcagca ctgcataatt ctcttactgt catgccatcc   3660
gtaagatgct tttctgtgac tggtgagtac tcaaccaagt cattctgaga atagtgtatg   3720
cggcgaccga gttgctcttg cccggcgtca atacgggata taccgcgcc acatagcaga   3780 actttaaaag tgctcatcat tggaaaacgt tcttcggggc gaaaactctc aaggatctta   3840
ccgctgttga gatccagttc gatgtaaccc actcgtgcac ccaactgatc ttcagcatct   3900
tttactttca ccagcgtttc tgggtgagca aaaacaggaa ggcaaaatgc cgcaaaaaag   3960
ggaataaggg cgacacggaa atgttgaata ctcatactct ccttttttca atattattga   4020
agcatttatc agggttattg tctcatgagc ggatacatat ttgaatgtat ttagaaaaat   4080
aaacaaatag gggttccgcg cacatttccc cgaaaagtgc cacctgacgt ctaagaaacc   4140
attattatca tgacattaac ctataaaaat aggcgtatca cgaggccctt tcgt         4194
```

<210> SEQ ID NO 44
<211> LENGTH: 3458
<212> TYPE: DNA
<213> ORGANISM: artificial
<220> FEATURE:
<223> OTHER INFORMATION: pUC57 with DeSNAP Univ cassette

<400> SEQUENCE: 44

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
```

```
tttcccagtc acgacgttgt aaaacgacgg ccagtgaatt cgagctcggt acctcgcgaa    420
tgcatctaga tcgagctagc accatgaaac tatgtattct acttgcagtt gttgcgttcg    480
taggattgtc cttacctaca gctctggcaa gatctgacaa agactgcgaa atgaaaagaa    540
ctacattgga ttcaccactt gggaagttgg aactgagtgg atgcgagcaa ggattgcatg    600
aaattaagct actgggaaaa ggaacttctg ctgctgatgc agttgaagtt ccagcaccag    660
cagctgttct tggaggtcct gagcccctca tgcaagccac agcctggctt aacgcatatt    720
tccaccagcc tgaggccatt gaggaatttc cagtccccgc ccttcaccat cctgtgtttc    780
agcaggagag cttcacccgc caggtcctgt ggaaattgct gaaggtggtc aagtttggtg    840
aagtgatttc atatcagcaa cttgctgcat tggccggtaa ccccgcagct acagctgccg    900
tgaaaactgc tctcagcgga aatcctgtgc catcctgat cccttgtcac agagtcgttt    960
catcttccgg agctgtaggt ggctatgaag gaggactggc agttaaggag tggctgctgg    1020
ctcatgaagg tcatagactt ggaaagcctg gctgggtcc tgctggtata ggcgcgccag    1080
ggtccctagg tggcggatcc gaaaacctgt acttccagag cgatatcgga ggtggaggcc    1140
cgggagagaa tctatatttt caagggcccg gcggaggtag tcaccatcat caccatcact    1200
aatgaccggt gcggccgcaa gcttggcgta atcatggtca tagctgtttc ctgtgtgaaa    1260
ttgttatccg ctcacaattc cacacaacat acgagccgga agcataaagt gtaaagcctg    1320
gggtgcctaa tgagtgagct aactcacatt aattgcgttg cgctcactgc ccgctttcca    1380
gtcgggaaac ctgtcgtgcc agctgcatta atgaatcggc caacgcgcgg ggagaggcgg    1440
tttgcgtatt gggcgctctt ccgcttcctc gctcactgac tcgctgcgct cggtcgttcg    1500
gctgcggcga gcggtatcag ctcactcaaa ggcggtaata cggttatcca gaatcagg    1560 ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta ctagaagaa cagtatttg gtatctgcgc    2100 tctgctgaag ccagttacct tcggaaaaag agttggtagc tcttgatccg gcaaacaaac    2160
caccgctggt agcggtggtt tttgtttg caagcagcag attacgcgca gaaaaaaagg    2220
atctcaagaa gatcctttga tcttttctac ggggtctgac gctcagtgga acgaaaactc    2280
acgttaaggg attttggtca tgagattatc aaaaaggatc ttcacctaga tccttttaaa    2340
ttaaaaatga agttttaaat caatctaaag tatatatgag taaacttggt ctgacagtta    2400
ccaatgctta atcagtgagg cacctatctc agcgatctgt ctatttcgtt catccatagt    2460
tgcctgactc cccgtcgtgt agataactac gatacgggag gcttaccat ctggccccag    2520 tgctgcaatg ataccgcgag acccacgctc accggctcca gatttatcag caataaacca    2580
gccagccgga agggccgagc gcagaagtgg tcctgcaact ttatccgcct ccatccagtc    2640
tattaattgt tgccgggaag ctagagtaag tagttcgcca gttaatagtt tgcgcaacgt    2700
tgttgccatt gctacaggca tcgtggtgtc acgctcgtcg tttggtatgg cttcattcag    2760
```

```
ctccggttcc caacgatcaa ggcgagttac atgatccccc atgttgtgca aaaaagcggt    2820
tagctccttc ggtcctccga tcgttgtcag aagtaagttg gccgcagtgt tatcactcat    2880
ggttatggca gcactgcata attctcttac tgtcatgcca tccgtaagat gcttttctgt    2940
gactggtgag tactcaacca agtcattctg agaatagtgt atgcggcgac cgagttgctc    3000
ttgcccggcg tcaatacggg ataataccgc gccacatagc agaactttaa aagtgctcat    3060
cattggaaaa cgttcttcgg ggcgaaaact ctcaaggatc ttaccgctgt tgagatccag    3120
ttcgatgtaa cccactcgtg cacccaactg atcttcagca tcttttactt tcaccagcgt    3180
ttctgggtga gcaaaaacag gaaggcaaaa tgccgcaaaa aagggaataa gggcgacacg    3240
gaaatgttga atactcatac tcttcctttt tcaatattat tgaagcattt atcagggtta    3300
ttgtctcatg agcggataca tatttgaatg tatttagaaa aataaacaaa taggggttcc    3360
gcgcacattt ccccgaaaag tgccacctga cgtctaagaa accattatta tcatgacatt    3420
aacctataaa aataggcgta tcacgaggcc ctttcgtc                            3458
```

<210> SEQ ID NO 45  
<211> LENGTH: 6365  
<212> TYPE: DNA  
<213> ORGANISM: artificial  
<220> FEATURE:  
<223> OTHER INFORMATION: pcDNA3 with DeSNAP Univ cassette

<400> SEQUENCE: 45

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacg caaatgggcg     780 gtaggcgtgt acggtgggag gtctatataa gcagagctct ctggctaact agagaaccca     840
ctgcttactg gcttatcgaa attaatacga ctcactatag ggagacccaa gctggctagc     900
accatgaaac tatgtattct acttgcagtt gttgcgttcg taggattgtc cttacctaca     960
gctctggcaa gatctgacaa agactgcgaa atgaaaagaa ctacattgga ttcaccactt    1020
gggaagttgg aactgagtgg atgcgagcaa ggattgcatg aaattaagct actgggaaaa    1080
ggaacttctg ctgctgatgc agttgaagtt ccagcaccag cagctgttct ggaggtcct    1140 gagcccctca tgcaagccac agcctggctt aacgcatatt ccaccagcc tgaggccatt    1200 gaggaatttc cagtccccgc ccttcaccat cctgtgtttc agcaggagag cttcacccgc    1260
caggtcctgt ggaaattgct gaaggtggtc aagtttggtg aagtgattc atatcagcaa    1320
```

```
cttgctgcat tggccggtaa ccccgcagct acagctgccg tgaaaactgc tctcagcgga   1380
aatcctgtgc ccatcctgat cccttgtcac agagtcgttt catcttccgg agctgtaggt   1440
ggctatgaag gaggactggc agttaaggag tggctgctgg ctcatgaagg tcatagactt   1500
ggaaagcctg gctgggtcc tgctggtata ggcgcgccag ggtccctagg tggcggatcc    1560
gaaaacctgt acttccagag cgatatcgga ggtggaggcc cgggagagaa tctatatttt   1620
caagggcccg cggaggtag tcaccatcat caccatcact aatgaccggt gcggccgcaa    1680
gcttggtacc gagctcggat ccactagtcc agtgtggtgg aattctgcag atatccagca   1740
cagtggcggc cgctcgagtc tagagggccc gtttaaaccc gctgatcagc ctcgactgtg   1800
ccttctagtt gccagccatc tgttgtttgc cctcccccg tgccttcctt gaccctggaa    1860
ggtgccactc ccactgtcct ttcctaataa aatgaggaaa ttgcatcgca ttgtctgagt   1920
aggtgtcatt ctattctggg gggtggggtg ggcaggaca gcaaggggga ggattgggaa    1980
gacaatagca ggcatgctgg ggatgcggtg ggctctatgg cttctgaggc ggaaagaacc   2040
agctggggct ctaggggta tccccacgcg ccctgtagcg cgcattaag cgcggcgggt     2100
gtggtggtta cgcgcagcgt gaccgctaca cttgccagcg ccctagcgcc cgctcctttc   2160
gctttcttcc cttcctttct cgccacgttc gccggctttc cccgtcaagc tctaaatcgg   2220
gggctccctt tagggttccg atttagtgct ttacggcacc tcgaccccaa aaaacttgat   2280
tagggtgatg gttcacgtag tgggccatcg cccgatagac ggttttttcg ccctttgacg   2340
ttggagtcca cgttctttaa tagtggactc ttgttccaaa ctggaacaac actcaaccct   2400
atctcggtct attcttttga tttataaggg attttgccga tttcggccta ttggttaaaa   2460
aatgagctga tttaacaaaa atttaacgcg aattaattct gtggaatgtg tgtcagttag   2520
ggtgtggaaa gtccccaggc tccccagcag gcagaagtat gcaaagcatg catctcaatt   2580
agtcagcaac caggtgtgga aagtccccag gctccccagc aggcagaagt atgcaaagca   2640
tgcatctcaa ttagtcagca accatagtcc gccccctaac tccgcccatc ccgcccctaa   2700
ctccgcccag ttccgcccat tctccgcccc atggctgact aatttttttt atttatgcag   2760
aggccgaggc cgcctctgcc tctgagctat tccagaagta gtgaggaggc ttttttggag   2820
gcctaggctt ttgcaaaaag ctcccgggag cttgtatatc cattttcgga tctgatcagc   2880
acgtgatgaa aaagcctgaa ctcaccgcga cgtctgtcga agtttctg atcgaaaagt     2940
tcgacagcgt ctccgacctg atgcagctct cggagggcga agaatctcgt gctttcagct   3000
tcgatgtagg agggcgtgga tatgtcctgc gggtaaatag ctgcgccgat ggtttctaca   3060
aagatcgtta tgtttatcgg cactttgcat cggccgcgct cccgattccg aagtgcttg    3120
acattgggga attcagcgag agcctgacct attgcatctc ccgccgtgca cagggtgtca   3180
cgttgcaaga cctgcctgaa accgaactgc ccgctgttct gcagccggtc gcggaggcca   3240
tggatgcgat cgctgcggcc gatcttagcc agacgagcgg gttcggccca ttcggaccgc   3300
aaggaatcgg tcaatacact acatggcgtg atttcatatg cgcgattgct gatccccatg   3360
tgtatcactg gcaaactgtg atggacgaca ccgtcagtgc gtccgtcgcg caggctctcg   3420
atgagctgat gctttgggcc gaggactgcc ccgaagtccg gcaccgtgtg cacgcggatt   3480
tcggctccaa caatgtcctg acggacaatg gccgcataac agcggtcatt gactggagcg   3540
aggcgatgtt cggggattcc caatacgagg tcgccaacat cttcttctgg aggccgtggt   3600
tggcttgtat ggagcagcag acgcgctact tcgagcggag gcatccggag cttgcaggat   3660
cgccgcggct ccgggcgtat atgctccgca ttggtcttga ccaactctat cagagcttgg   3720
```

```
ttgacggcaa tttcgatgat gcagcttggg cgcagggtcg atgcgacgca atcgtccgat    3780
ccggagccgg gactgtcggg cgtacacaaa tcgcccgcag aagcgcggcc gtctggaccg    3840
atggctgtgt agaagtactc gccgatagtg gaaaccgacg ccccagcact cgtccgaggg    3900
caaaggaata gcacgtgcta cgagatttcg attccaccgc cgccttctat gaaaggttgg    3960
gcttcggaat cgttttccgg gacgccggct ggatgatcct ccagcgcggg gatctcatgc    4020
tggagttctt cgcccacccc aacttgttta ttgcagctta taatggttac aaataaagca    4080
atagcatcac aaatttcaca aataaagcat ttttttcact gcattctagt tgtggtttgt    4140
ccaaactcat caatgtatct tatcatgtct gtataccgtc gacctctagc tagagcttgg    4200
cgtaatcatg gtcatagctg tttcctgtgt gaaattgtta tccgctcaca attccacaca    4260
acatacgagc cggaagcata aagtgtaaag cctggggtgc ctaatgagtg agctaactca    4320
cattaattgc gttgcgctca ctgcccgctt tccagtcggg aaacctgtcg tgccagctgc    4380
attaatgaat cggccaacgc gcggggagag gcggtttgcg tattgggcgc tcttccgctt    4440
cctcgctcac tgactcgctg cgctcggtcg ttcggctgcg gcgagcggta tcagctcact    4500
caaaggcggt aatacggtta tccacagaat caggggataa cgcaggaaag aacatgtgag    4560
caaaaggcca gcaaaaggcc aggaaccgta aaaaggccgc gttgctggcg ttttttccata    4620
ggctccgccc ccctgacgag catcacaaaa atcgacgctc aagtcagagg tggcgaaacc    4680
cgacaggact ataaagatac caggcgtttc cccctggaag ctccctcgtg cgctctcctg    4740
ttccgaccct gccgcttacc ggatacctgt ccgcctttct cccttcggga agcgtggcgc    4800
tttctcatag ctcacgctgt aggtatctca gttcggtgta ggtcgttcgc tccaagctgg    4860
gctgtgtgca cgaacccccc gttcagcccg accgctgcgc cttatccggt aactatcgtc    4920
ttgagtccaa cccggtaaga cacgacttat cgccactggc agcagccact ggtaacagga    4980
ttagcagagc gaggtatgta ggcggtgcta cagagttctt gaagtggtgg cctaactacg    5040
gctacactag aagaacagta tttggtatct gcgctctgct gaagccagtt accttcggaa    5100
aaagagttgg tagctcttga tccggcaaac aaaccaccgc tggtagcggt ttttttgttt    5160
gcaagcagca gattacgcgc agaaaaaaag gatctcaaga agatcctttg atcttttcta    5220
cggggtctga cgctcagtgg aacgaaaact cacgttaagg gattttggtc atgagattat    5280
caaaaaggat cttcacctag atccttttaa attaaaaatg aagttttaaa tcaatctaaa    5340
gtatatatga gtaaacttgg tctgacagtt accaatgctt aatcagtgag gcacctatct    5400
cagcgatctg tctatttcgt tcatccatag ttgcctgact ccccgtcgtg tagataacta    5460
cgatacggga gggcttacca tctggcccca gtgctgcaat gataccgcga cccacgct    5520
caccggctcc agatttatca gcaataaacc agccagccgg aagggccgag cgcagaagtg    5580
gtcctgcaac tttatccgcc tccatccagt ctattaattg ttgccgggaa gctagagtaa    5640
gtagttcgcc agttaatagt ttgcgcaacg ttgttgccat tgctacaggc atcgtggtgt    5700
cacgctcgtc gtttggtatg gcttcattca gctccggttc ccaacgatca aggcgagtta    5760
catgatcccc catgttgtgc aaaaaagcgg ttagctcctt cggtcctccg atcgttgtca    5820
gaagtaagtt ggccgcagtg ttatcactca tggttatggc agcactgcat aattctctta    5880
ctgtcatgcc atccgtaaga tgcttttctg tgactggtga gtactcaacc aagtcattct    5940
gagaatagtg tatgcggcga ccgagttgct cttgcccggc gtcaatacgg gataataccg    6000
cgccacatag cagaacttta aaagtgctca tcattggaaa acgttcttcg gggcgaaaac    6060
```

-continued

```
tctcaaggat cttaccgctg ttgagatcca gttcgatgta acccactcgt gcacccaact    6120
gatcttcagc atcttttact ttcaccagcg tttctgggtg agcaaaaaca ggaaggcaaa    6180
atgccgcaaa aagggaata agggcgacac ggaaatgttg aatactcata ctcttccttt    6240
ttcaatatta ttgaagcatt tatcagggtt attgtctcat gagcggatac atatttgaat    6300
gtatttagaa aaataaacaa ataggggttc cgcgcacatt tccccgaaaa gtgccacctg    6360
acgtc                                                                 6365
```

<210> SEQ ID NO 46
<211> LENGTH: 476
<212> TYPE: PRT
<213> ORGANISM: artificial
<220> FEATURE:
<223> OTHER INFORMATION: Amino acid sequence of
    ssBiP+SNAPlike+proTEV+SBV.N+proTEV+Histag (encoded by SEQ ID
    NO:35)

<400> SEQUENCE: 46

```
Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Gly Ser Glu Asn Leu Tyr Phe Gln Ser Asp Ile
    210                 215                 220

Ser Ser Gln Phe Ile Phe Glu Asp Val Pro Gln Arg Asn Ala Ala Thr
225                 230                 235                 240

Phe Asn Pro Glu Val Gly Tyr Val Ala Phe Ile Gly Lys Tyr Gly Gln
                245                 250                 255

Gln Leu Asn Phe Gly Val Ala Arg Val Phe Phe Leu Asn Gln Lys Lys
            260                 265                 270

Ala Lys Met Val Leu His Lys Thr Ala Gln Pro Ser Val Asp Leu Thr
        275                 280                 285

Phe Gly Gly Val Lys Phe Thr Val Val Asn Asn His Phe Pro Gln Tyr
```

```
                   290                 295                 300
Val Ser Asn Pro Val Pro Asp Asn Ala Ile Thr Leu His Arg Met Ser
305                 310                 315                 320

Gly Tyr Leu Ala Arg Trp Ile Ala Asp Thr Cys Lys Ala Ser Val Leu
            325                 330                 335

Lys Leu Ala Glu Ala Ser Ala Gln Ile Val Met Pro Leu Ala Glu Val
                340                 345                 350

Lys Gly Cys Thr Trp Ala Asp Gly Tyr Thr Met Tyr Leu Gly Phe Ala
            355                 360                 365

Pro Gly Ala Glu Met Phe Leu Asp Ala Phe Asp Phe Tyr Pro Leu Val
        370                 375                 380

Ile Glu Met His Arg Val Leu Lys Asp Asn Met Asp Val Asn Phe Met
385                 390                 395                 400

Lys Lys Val Leu Arg Gln Arg Tyr Gly Thr Met Thr Ala Glu Glu Trp
                405                 410                 415

Met Thr Gln Lys Ile Thr Glu Ile Lys Ala Ala Phe Asn Ser Val Gly
            420                 425                 430

Gln Leu Ala Trp Ala Lys Ser Gly Phe Ser Pro Ala Ala Arg Thr Phe
        435                 440                 445

Leu Gln Gln Phe Gly Ile Asn Ile Pro Gly Glu Asn Leu Tyr Phe Gln
        450                 455                 460

Gly Pro Gly Gly Gly Ser His His His His His His
465                 470                 475

<210> SEQ ID NO 47
<211> LENGTH: 891
<212> TYPE: DNA
<213> ORGANISM: artificial
<220> FEATURE:
<223> OTHER INFORMATION: Modified DNA sequence encoding enterovirus 71
      VP1 (strain JL-AFP-EV71-07-03)

<400> SEQUENCE: 47
ggagataggg tggcagacgt gattgaaagt tccaaggaa atagtgtgag cagagccctc     60
actcaagctc taccagcacc cacaggtcag aacacacagg tgagcagtca tcgactggat   120
acaggcaagg ttccagcact ccaagctgct gaaattggag catcatcaaa tgctagtgat   180
gagagcatga tcgagacacg ctgtgttctt aactcgcata gcacagctga ccactctt     240 gatagtttct tcagcagagc ggggttagtt ggagagattg atctccctct tgaaggcaca   300
actaacccaa atggttatgc caactgggac atagatataa caggttacgc gcaaatgcgt   360
agaaaggtgg agctattcac ctacatgcgc tttgatgcag agttcacttt tgttgcgtgc   420
acacccaccg gggaagttgt cccacaattg ctccaataca tgtttgtgcc acctggagcc   480
cctaagccag attccaggga atccctcgca tggcaaactg ccaccaaccc ctcagttttt   540
gtcaagctgt cagaccctcc agcacaagtt tcagtaccat tcatgtcacc tgcgagtgct   600
taccaatggt tttatgacgg ttatcccaca ttcggagaac acaaacagga gaaggatctc   660
gaatatgggg catgtcctaa caacatgatg ggcacgttct cagtgcggac tgtagggacc   720
tccaagtcca agtacccttt agtggttagg atttacatga gaatgaagca cgtcagggcg   780
tggataccct gcccgatgcg caaccaaaac tacctattca aagccaaccc aaattatgct   840
ggcaactcca ttaagccaac tggtaccagt cgcacagcga tcactactct c             891

<210> SEQ ID NO 48
<211> LENGTH: 1643
```

<212> TYPE: DNA
<213> ORGANISM: artificial
<220> FEATURE:
<223> OTHER INFORMATION: DNA Sequence of chimeric DeSNAPuniv-EV71.VP1
    (ssBiP-SNAPlike- proTEVcleavage site - modified
    EV71-VP1-proTEVcleavage site -Histag) for expression in S2 cells

<400> SEQUENCE: 48

```
atgaagttat gcatattact ggccgtcgtg gtggcctttg ttggcctctc gctcgggaga     60
tctagatctg acaaagactg cgaaatgaaa agaactacat tggattcacc acttgggaag    120
ttggaactga gtggatgcga gcaaggattg catgaaatta agctactggg aaaaggaact    180
tctgctgctg atgcagttga agttccagca ccagcagctt tcttggagg tcctgagccc     240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat gctgaaggt ggtcaagttt ggtgaagtga tttcatatca gcaacttgct     420
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cggagatagg gtggcagacg tgattgaaag ttccaaagga    720
aatagtgtga gcagagccct cactcaagct ctaccagcac ccacaggtca gaacacacag    780
gtgagcagtc atcgactgga tacaggcaag gttccagcac tccaagctgc tgaaattgga    840
gcatcatcaa atgctagtga tgagagcatg atcgagacac gctgtgttct taactcgcat    900
agcacagctg agaccactct tgatagtttc ttcagcagag cggggttagt ggagagatt      960
gatctccctc ttgaaggcac aactaaccca atggttatg ccaactggga catagatata    1020
acaggttacg cgcaaatgcg tagaaaggtg gagctattca cctacatgcg ctttgatgca    1080
gagttcactt tgttgcgtg cacacccacc ggggaagttg tcccacaatt gctccaatac    1140
atgtttgtgc acctggagc ccctaagcca gattccaggg aatccctcgc atggcaaact    1200
gccaccaacc cctcagtttt tgtcaagctg tcagacctc cagcacaagt ttcagtacca    1260
ttcatgtcac ctgcgagtgc ttaccaatgg ttttatgacg ttatccac attcggagaa    1320
cacaaacagg agaaggatct cgaatatggg gcatgtccta caacatgat gggcacgttc    1380
tcagtgcgga ctgtagggac ctccaagtcc aagtaccctt tagtggttag gatttacatg    1440
agaatgaagac acgtcagggc gtggatacct cgcccgatgc gcaaccaaaa ctacctattc    1500
aaagccaacc caaattatgc tggcaactcc attaagccaa ctggtaccag tcgcacagcg    1560
atcactactc tcccgggaga gaatctatat tttcaagggc ccggcggagg tagtcaccat    1620
catcaccatc actaatgacc ggt                                          1643
```

<210> SEQ ID NO 49
<211> LENGTH: 523
<212> TYPE: PRT
<213> ORGANISM: artificial
<220> FEATURE:
<223> OTHER INFORMATION: Amino acid sequence of fusion protein
    [SNAPlike - proTEV - VP1 EV71 - proTEV- Histag]

<400> SEQUENCE: 49

```
Arg Ser Asp Lys Asp Cys Glu Met Lys Arg Thr Thr Leu Asp Ser Pro
 1               5                  10                  15
```

-continued

```
Leu Gly Lys Leu Glu Leu Ser Gly Cys Glu Gln Gly Leu His Glu Ile
            20                  25                  30
Lys Leu Leu Gly Lys Gly Thr Ser Ala Ala Asp Ala Val Glu Val Pro
            35                  40                  45
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Leu Lys Val Val Lys Phe Gly Glu Val
            100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
            130                 135                 140
Pro Cys His Arg Val Val Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Ser Glu Asn Leu Tyr Phe Gln Ser Asp Ile Gly Asp
            195                 200                 205
Arg Val Ala Asp Val Ile Glu Ser Ser Lys Gly Asn Ser Val Ser Arg
210                 215                 220
Ala Leu Thr Gln Ala Leu Pro Ala Pro Thr Gly Gln Asn Thr Gln Val
225                 230                 235                 240
Ser Ser His Arg Leu Asp Thr Gly Lys Val Pro Ala Leu Gln Ala Ala
                245                 250                 255
Glu Ile Gly Ala Ser Ser Asn Ala Ser Asp Glu Ser Met Ile Glu Thr
            260                 265                 270
Arg Cys Val Leu Asn Ser His Ser Thr Ala Glu Thr Thr Leu Asp Ser
            275                 280                 285
Phe Phe Ser Arg Ala Gly Leu Val Gly Glu Ile Asp Leu Pro Leu Glu
            290                 295                 300
Gly Thr Thr Asn Pro Asn Gly Tyr Ala Asn Trp Asp Ile Asp Ile Thr
305                 310                 315                 320
Gly Tyr Ala Gln Met Arg Arg Lys Val Glu Leu Phe Thr Tyr Met Arg
                325                 330                 335
Phe Asp Ala Glu Phe Thr Phe Val Ala Cys Thr Pro Thr Gly Glu Val
            340                 345                 350
Val Pro Gln Leu Leu Gln Tyr Met Phe Val Pro Pro Gly Ala Pro Lys
            355                 360                 365
Pro Asp Ser Arg Glu Ser Leu Ala Trp Gln Thr Ala Thr Asn Pro Ser
            370                 375                 380
Val Phe Val Lys Leu Ser Asp Pro Pro Ala Gln Val Ser Val Pro Phe
385                 390                 395                 400
Met Ser Pro Ala Ser Ala Tyr Gln Trp Phe Tyr Asp Gly Tyr Pro Thr
                405                 410                 415
Phe Gly Glu His Lys Gln Glu Lys Asp Leu Glu Tyr Gly Ala Cys Pro
            420                 425                 430
Asn Asn Met Met Gly Thr Phe Ser Val Arg Thr Val Gly Thr Ser Lys
```

```
                 435                 440                 445

Ser Lys Tyr Pro Leu Val Val Arg Ile Tyr Met Arg Met Lys His Val
    450                 455                 460

Arg Ala Trp Ile Pro Arg Pro Met Arg Asn Gln Asn Tyr Leu Phe Lys
465                 470                 475                 480

Ala Asn Pro Asn Tyr Ala Gly Asn Ser Ile Lys Pro Thr Gly Thr Ser
                485                 490                 495

Arg Thr Ala Ile Thr Thr Leu Pro Gly Glu Asn Leu Tyr Phe Gln Gly
            500                 505                 510

Pro Gly Gly Gly Ser His His His His His His
            515                 520

<210> SEQ ID NO 50
<211> LENGTH: 2386
<212> TYPE: DNA
<213> ORGANISM: artificial
<220> FEATURE:
<223> OTHER INFORMATION: DNA Sequence encoding chimeric DeSNAPuniv-JE.
      -sE (ssBiP- sE from JEV strain SA-14 -SNAPlike) for expression in
      S2 cells

<400> SEQUENCE: 50
```

| | | | | | |
|---|---|---|---|---|---|
| atgaagttat | gcatattact | ggccgtcgtg | gcctttgttg | gcctctcgct | cgggagatct | 60 |
| atgaagttgt | cgaatttcca | ggggaagctt | tgatgacca | tcaacaacac | ggacattgca | 120 |
| gacgttatcg | tgattcccac | ctcaaaagga | gagaacagat | gctgggtccg | ggcaatcgac | 180 |
| gtcggctaca | tgtgtgagga | cactatcacg | tacgaatgtc | ctaagcttac | catgggcaat | 240 |
| gatccagagg | atgtggattg | ctggtgtgac | aaccaagaag | tctacgtcca | atatggacgg | 300 |
| tgcacgcgga | ccaggcattc | caagcgaagc | aggagatccg | tgtcggtcca | aacacatggg | 360 |
| gagagttcac | tagtgaataa | aaagaggct | tggctggatt | caacgaaagc | cacacgatat | 420 |
| ctcatgaaaa | ctgagaactg | gatcataagg | aatcctggct | atgctttcct | ggcggcggta | 480 |
| cttggctgga | tgcttggcag | taacaacggt | caacgcgtgg | tatttaccat | cctcctgctg | 540 |
| ttggtcgctc | cggcttacag | tttttaattgt | ctgggaatgg | gcaatcgtga | cttcatagaa | 600 |
| ggagccagtg | gagccacttg | ggtggacttg | gtgctagaag | gagatagctg | cttgacaatc | 660 |
| atggcaaacg | acaaaccaac | attggacgtc | gcatgatta | acatcgaagc | tagccaactt | 720 |
| gctgaggtca | gaagttactg | ctatcatgct | tcagtcactg | acatctcgac | ggtggctcgg | 780 |
| tgccccacga | ctggagaagc | tcacaacgag | aagcgagctg | atagtagcta | tgtgtgcaaa | 840 |
| caaggcttca | ctgaccgtgg | gtggggcaac | ggatgtggac | ttttcgggaa | gggaagcatt | 900 |
| gacacatgtg | caaaattctc | ctgcaccagt | aaagcgattg | ggagaacaat | ccagccagaa | 960 |
| aacatcaaat | acgaagttgg | cattttgtg | catggaacca | ccacttcgga | aaaccatggg | 1020 |
| aattattcag | cgcaagttgg | ggcgtcccag | gcggcaaagt | ttacagtaac | acccaatgct | 1080 |
| ccttcgataa | ccctcaaact | tggtgactac | ggagaagtca | cactgactg | tgagccaagg | 1140 |
| agtggactga | acactgaagc | gttttacgtc | atgaccgtgg | ggtcaaagtc | atttctggtc | 1200 |
| catagggagt | ggtttcatga | cctcgctctc | ccctggacgt | ccccttcgag | cacagcgtgg | 1260 |
| agaaacagag | aactcctcat | ggaattgaa | ggggcgcacg | ccacaaaaca | gtccgttgtt | 1320 |
| gctcttgggt | cacaggaagg | aggcctccat | caggcgttgg | caggagccat | cgtggtggag | 1380 |
| tactcaagct | cagtgaagtt | aacatcaggc | caccctgaaat | gtaggctgaa | aatggacaaa | 1440 |
| ctggctctga | aaggcacaac | ctatggcatg | tgtacagaaa | aattctcgtt | cgcgaaaaat | 1500 |

```
ccggcggaca ctggtcacgg aacagttgtc attgaactct cctactctgg gagtgatggc   1560
tcctgcaaaa ttccgattgt ttccgttgcg agcctcaatg acatgacccc cgttgggcgg   1620
ctggtgacag tgaaccccct cgtcgcgact tccagtgcca actcaaaggt gctggtcgag   1680
atggaacccc ccttcggaga ctcctacatc gtagttggaa ggggagacaa gcagatcaac   1740
caccattggc acaaagctgg gcggccgcac ggcggaggta gcaaagactg cgaaatgaag   1800
cgcaccaccc tggatagccc tctgggcaag ctggaactgt ctgggtgcga acagggcctg   1860
cacgagatca agctgctggg caaggaaca  tctgccgccg acgccgtgga agtgcctgcc   1920
ccagccgccg tgctgggcgg accagagcca ctgatgcagg ccaccgcctg gctcaacgcc   1980
tactttcacc agcctgaggc catcgaggag ttccctgtgc agccctgca ccacccagtg    2040 ttccagcagg agagctttac ccgccaggtg ctgtggaaac tgctgaaagt ggtgaagttc   2100
ggagaggtca tcagctacca gcagctggcc gccctggccg gcaatcccgc cgccaccgcc   2160
gccgtgaaaa ccgccctgag cggaaatccc gtgcccattc tgatcccctg ccaccgggtg   2220
gtgtctagct ctggcgccgt gggggctac gagggcgggc tcgccgtgaa agagtggctg   2280
ctggcccacg agggccacag actgggcaag cctgggctgg gtcctgcagg tataggcgcg   2340
ccagggtccc tggagcatca tcatcatcat cattgatgac gggccc                 2386
```

<210> SEQ ID NO 51
<211> LENGTH: 773
<212> TYPE: PRT
<213> ORGANISM: artificial
<220> FEATURE:
<223> OTHER INFORMATION: Amino acid Sequence of fusion protein [sE from
      JEV strain SA-14 - SNAPlike - Histag]

<400> SEQUENCE: 51

```
Arg Ser Met Lys Leu Ser Asn Phe Gln Gly Lys Leu Leu Met Thr Ile
  1               5                  10                  15

Asn Asn Thr Asp Ile Ala Asp Val Ile Val Ile Pro Thr Ser Lys Gly
             20                  25                  30

Glu Asn Arg Cys Trp Val Arg Ala Ile Asp Val Gly Tyr Met Cys Glu
         35                  40                  45

Asp Thr Ile Thr Tyr Glu Cys Pro Lys Leu Thr Met Gly Asn Asp Pro
     50                  55                  60

Glu Asp Val Asp Cys Trp Cys Asp Asn Gln Glu Val Tyr Val Gln Tyr
 65                  70                  75                  80

Gly Arg Cys Thr Arg Thr Arg His Ser Lys Arg Ser Arg Ser Val
                 85                  90                  95

Ser Val Gln Thr His Gly Glu Ser Ser Leu Val Asn Lys Lys Glu Ala
            100                 105                 110

Trp Leu Asp Ser Thr Lys Ala Thr Arg Tyr Leu Met Lys Thr Glu Asn
        115                 120                 125

Trp Ile Ile Arg Asn Pro Gly Tyr Ala Phe Leu Ala Ala Val Leu Gly
    130                 135                 140

Trp Met Leu Gly Ser Asn Asn Gly Gln Arg Val Val Phe Thr Ile Leu
145                 150                 155                 160

Leu Leu Leu Val Ala Pro Ala Tyr Ser Phe Asn Cys Leu Gly Met Gly
                165                 170                 175

Asn Arg Asp Phe Ile Glu Gly Ala Ser Gly Ala Thr Trp Val Asp Leu
            180                 185                 190

Val Leu Glu Gly Asp Ser Cys Leu Thr Ile Met Ala Asn Asp Lys Pro
        195                 200                 205
```

```
Thr Leu Asp Val Arg Met Ile Asn Ile Glu Ala Ser Gln Leu Ala Glu
    210                 215                 220

Val Arg Ser Tyr Cys Tyr His Ala Ser Val Thr Asp Ile Ser Thr Val
225                 230                 235                 240

Ala Arg Cys Pro Thr Thr Gly Glu Ala His Asn Glu Lys Arg Ala Asp
                245                 250                 255

Ser Ser Tyr Val Cys Lys Gln Gly Phe Thr Asp Arg Gly Trp Gly Asn
                260                 265                 270

Gly Cys Gly Leu Phe Gly Lys Gly Ser Ile Asp Thr Cys Ala Lys Phe
                275                 280                 285

Ser Cys Thr Ser Lys Ala Ile Gly Arg Thr Ile Gln Pro Glu Asn Ile
    290                 295                 300

Lys Tyr Glu Val Gly Ile Phe Val His Gly Thr Thr Thr Ser Glu Asn
305                 310                 315                 320

His Gly Asn Tyr Ser Ala Gln Val Gly Ala Ser Gln Ala Ala Lys Phe
                325                 330                 335

Thr Val Thr Pro Asn Ala Pro Ser Ile Thr Leu Lys Leu Gly Asp Tyr
                340                 345                 350

Gly Glu Val Thr Leu Asp Cys Glu Pro Arg Ser Gly Leu Asn Thr Glu
                355                 360                 365

Ala Phe Tyr Val Met Thr Val Gly Ser Lys Ser Phe Leu Val His Arg
    370                 375                 380

Glu Trp Phe His Asp Leu Ala Leu Pro Trp Thr Ser Pro Ser Ser Thr
385                 390                 395                 400

Ala Trp Arg Asn Arg Glu Leu Leu Met Glu Phe Glu Gly Ala His Ala
                405                 410                 415

Thr Lys Gln Ser Val Val Ala Leu Gly Ser Gln Glu Gly Gly Leu His
                420                 425                 430

Gln Ala Leu Ala Gly Ala Ile Val Val Glu Tyr Ser Ser Ser Val Lys
            435                 440                 445

Leu Thr Ser Gly His Leu Lys Cys Arg Leu Lys Met Asp Lys Leu Ala
    450                 455                 460

Leu Lys Gly Thr Thr Tyr Gly Met Cys Thr Glu Lys Phe Ser Phe Ala
465                 470                 475                 480

Lys Asn Pro Ala Asp Thr Gly His Gly Thr Val Val Ile Glu Leu Ser
                485                 490                 495

Tyr Ser Gly Ser Asp Gly Ser Cys Lys Ile Pro Ile Val Ser Val Ala
                500                 505                 510

Ser Leu Asn Asp Met Thr Pro Val Gly Arg Leu Val Thr Val Asn Pro
    515                 520                 525

Phe Val Ala Thr Ser Ser Ala Asn Ser Lys Val Leu Val Glu Met Glu
530                 535                 540

Pro Pro Phe Gly Asp Ser Tyr Ile Val Val Gly Arg Gly Asp Lys Gln
545                 550                 555                 560

Ile Asn His His Trp His Lys Ala Gly Arg Pro His Gly Gly Gly Ser
                565                 570                 575

Lys Asp Cys Glu Met Lys Arg Thr Thr Leu Asp Ser Pro Leu Gly Lys
                580                 585                 590

Leu Glu Leu Ser Gly Cys Glu Gln Gly Leu His Glu Ile Lys Leu Leu
            595                 600                 605

Gly Lys Gly Thr Ser Ala Ala Asp Ala Val Glu Val Pro Ala Pro Ala
    610                 615                 620
```

```
Ala Val Leu Gly Gly Pro Glu Pro Leu Met Gln Thr Ala Trp Leu
625                 630                 635                 640

Asn Ala Tyr Phe His Gln Pro Glu Ala Ile Glu Glu Phe Pro Val Pro
            645                 650                 655

Ala Leu His His Pro Val Phe Gln Gln Glu Ser Phe Thr Arg Gln Val
            660                 665                 670

Leu Trp Lys Leu Leu Lys Val Val Lys Phe Gly Glu Val Ile Ser Tyr
            675                 680                 685

Gln Gln Leu Ala Ala Leu Ala Gly Asn Pro Ala Thr Ala Ala Val
        690                 695                 700

Lys Thr Ala Leu Ser Gly Asn Pro Val Pro Ile Leu Ile Pro Cys His
705                 710                 715                 720

Arg Val Val Ser Ser Ser Gly Ala Val Gly Gly Tyr Glu Gly Gly Leu
                725                 730                 735

Ala Val Lys Glu Trp Leu Leu Ala His Glu Gly His Arg Leu Gly Lys
            740                 745                 750

Pro Gly Leu Gly Pro Ala Gly Ile Gly Ala Pro Gly Ser Leu Glu His
        755                 760                 765

His His His His His
    770

<210> SEQ ID NO 52
<211> LENGTH: 1020
<212> TYPE: DNA
<213> ORGANISM: artificial
<220> FEATURE:
<223> OTHER INFORMATION: DNA Sequence encoding the fusion protein
      BiPlike-SNAPlike-EDIII from Japanese encephalitis virus genotype I
      cloned into pMT/BiP/SNAP for expression in S2 cells

<400> SEQUENCE: 52
atgaaactat gtattctact tgcagttgtt gcgttcgtag gattgtcctt aagatctgac    60
aaagactgcg aaatgaaaag aactacattg gattcaccac ttgggaagtt ggaactgagt   120
ggatgcgagc aaggattgca tgaaattaag ctactgggaa aaggaacttc tgctgctgat   180
gcagttgaag ttccagcacc agcagctgtt cttggaggtc ctgagcccct catgcaagcc   240
acagcctggc ttaacgcata tttccaccag cctgaggcca ttgaggaatt tccagtcccc   300
gcccttcacc atcctgtgtt tcagcaggag agcttcaccc gccaggtcct gtggaaattg   360
ctgaaggtgg tcaagtttgg tgaagtgatt tcatatcagc aacttgctgc attggccggt   420
aaccccgcag ctacagctgc cgtgaaaact gctctcagcg gaaatcctgt gcccatcctg   480
atcccttgtc acagagtcgt ttcatcttcc ggagctgtag gtggctatga aggaggactg   540
gcagttaagg agtggctgct ggctcatgaa ggtcatagac ttggaaagcc tgggctgggt   600
cctgctggta taggcgcgcc agggtccctg gagggaggtg gcgggtctgc tctgaagggc   660
acgacttacg gcatgtgtac agaaaaattc tcgttcgcga aaatccagc ggacacaggc   720 catggaacag ttgtcattga gctcacatac tctggaagcg atggtccctg taaaattccg   780
attgtctcag tcgcgagttt aaacgacatg acccctgtgg ggaggctggt aacagtaaac   840
cccttcgtcg cgacatctag ctccaactca aaggtgctgg ttgagatgga acctccttc    900 ggagactctt acatcgtggt tggaagaggg gataagcaga ttaaccatca ctggcacaaa   960
gctggaagca cgctgggtaa aggaggtggc catcaccatc accatcactg atgaccggtt  1020

<210> SEQ ID NO 53
<211> LENGTH: 319
```

```
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype I -
      Histag

<400> SEQUENCE: 53
```

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Ser Ala Leu Lys Gly Thr Thr Tyr Gly Met
        195                 200                 205

Cys Thr Glu Lys Phe Ser Phe Ala Lys Asn Pro Ala Asp Thr Gly His
210                 215                 220

Gly Thr Val Val Ile Glu Leu Thr Tyr Ser Gly Ser Asp Gly Pro Cys
225                 230                 235                 240

Lys Ile Pro Ile Val Ser Val Ala Ser Leu Asn Asp Met Thr Pro Val
                245                 250                 255

Gly Arg Leu Val Thr Val Asn Pro Phe Val Ala Thr Ser Ser Ser Asn
            260                 265                 270

Ser Lys Val Leu Val Glu Met Glu Pro Pro Phe Gly Asp Ser Tyr Ile
        275                 280                 285

Val Val Gly Arg Gly Asp Lys Gln Ile Asn His His Trp His Lys Ala
290                 295                 300

Gly Ser Thr Leu Gly Lys Gly Gly His His His His His
305                 310                 315

```
<210> SEQ ID NO 54
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 1
      (JE-1.EDIII)
```

<400> SEQUENCE: 54

```
gcgcgccagg gtccctggag ggaggtggcg ggtctgctct gaagggcacg acttacggca    60
tgtgtacaga aaaattctcg ttcgcgaaaa atccagcgga cacaggccat ggaacagttg   120
tcattgagct cacatactct ggaagcgatg gtccctgtaa aattccgatt gtctcagtcg   180
cgagtttaaa cgacatgacc cctgtgggga ggctggtaac agtaaacccc ttcgtcgcga   240
catctagctc caactcaaag gtgctggttg agatggaacc tcccttcgga gactcttaca   300
tcgtggttgg aagaggggat aagcagatta accatcactg gcacaaagct ggaagcacgc   360
tgggtaaagg aggtggccat caccatcacc atcactgatg accggt               406
```

<210> SEQ ID NO 55
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 2
      (JE-2.EDIII)

<400> SEQUENCE: 55

```
gcgcgccagg gtccctggag ggaggtggcg ggtctgctct gaaaggcaca acctatggta    60
tgtgcacaga aaactcctcg ttccgaaaaa atccagcgga cacaggccat ggaacagttg   120
tcattgagct cacatactct gggagtgatg gtccctgtaa gattccaaat gtctccgttg   180
cgagcctgaa tgacatgacc cctgtaggga ggctggtaac agtaaacccc tttgtcgcga   240
catccagcgc caactcaaaa gtgctggttg aaatggaacc cccttttgga gattcttaca   300
tcgtggtcgg aagaggtgac aagcagatca atcatcactg gcacaaagct ggaagcacgc   360
tgggcaaagg aggtggccat caccatcacc atcactgatg accggt               406
```

<210> SEQ ID NO 56
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 4
      (JE-4.EDIII)

<400> SEQUENCE: 56

```
gcgcgccagg gtccctggag ggaggtggcg ggtctgctct gaaaggcaca acctatggaa    60
tgtgcacaga aaagttctcg tttgcaaaga atccagcaga cactggtcat ggaacagttg   120
tcattgaact cctgtattct ggaagtgacg gcccctgtaa catcccaatt gtctcagtgg   180
tcagtctaaa cgacatgact ccagttgaa ggttggtgac agtgaacccc ttcgttgcca   240
catccagttc caattcaaag gtcttagttg agatggaacc tccttttgga gactcctaca   300
ttgtggtcgg gagaggagaa aaacaaatca accaccactg gcacaaacct ggaagcacat   360
tgggcaaagg aggtggccat caccatcacc atcactgatg accggt               406
```

<210> SEQ ID NO 57
<211> LENGTH: 406
<212> TYPE: DNA
<213> ORGANISM: artificial
<220> FEATURE:
<223> OTHER INFORMATION: DNA sequence encoding Domain III of envelope E
      protein from Japanese encephalitis virus of genotype 5
      (JE-5.EDIII)

<400> SEQUENCE: 57

```
gcgcgccagg gtccctggag ggaggtggcg ggtctgcgtt gaaagggacc acctatggta      60
tgtgcacaga gaagttctct ttttccaaga atccagctga cactggtcat ggtacggttg     120
tcatagaatt gcagtacacc ggcactgacg gaccttgcaa gatacccatc tcttcggtgg     180
ccagtctgaa tgatttaact ccagttggta gattggtgac agtcaatcct tttgttgcca     240
catccaccgc caattcgaag gttttggtag aattggaacc accatttgga gattcattca     300
ttgttgtcgg aagaggagat aagcagatca atcaccattg gcacaaggct ggcagttcac     360
tgggaaaggg aggtggccat caccatcacc atcactgatg accggt                    406

<210> SEQ ID NO 58
<211> LENGTH: 394
<212> TYPE: DNA
<213> ORGANISM: artificial
<220> FEATURE:
<223> OTHER INFORMATION: DNA sequence of Domain III encoding envelope E
      protein from Rabensburg virus (RabV.EDIII)

<400> SEQUENCE: 58
gcgcgccagg aggtggcggg tctcagctca aggaacgac ctatggagta tgcgcaaaag       60
ccttcaagtt ttctgggaat ccagctgaca cagggcatgg caccgtggtc ttagagttgc     120
aatacaccgg aaccgatggt ccttgtaagg tgcctgtctc ttccgtggct tcactcaacg     180
acctaactcc cgttgggaga ctggtgacag tgaatccctt tgttgctgca gctactgcta     240
attcaaaggt tctgatagaa ctggaacctc cattcggtga ctcatacatt gtggtaggta     300
gaggagaaca ccagataaac caccattggc acaagtctgg aagcagtatt ggaaagggag     360
gtggccatca ccatcaccat cactgatgac cggt                                 394

<210> SEQ ID NO 59
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      2 cloned into pMT/BiP/SNAP for expression in S2 cells

<400> SEQUENCE: 59
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aggaacttc tgctgctgat     180 gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg gaaatcctgt gcccatcctg     480
atcccttgtc acagagtcgt ttcatcttcc ggagctgtag gtggctatga aggaggactg     540
gcagttaagg agtggctgct ggctcatgaa ggtcatagac ttgaaaagcc tgggctgggt     600
cctgctggta taggcgcgcc agggtccctg gagggaggtg gcgggtctgc tctgaaaggc     660
acaacctatg gtatgtgcac agaaaactcc tcgttccgaa aaatccagc ggacacaggc      720 catgaacag ttgtcattga gctcacatac tctgggagta atggtccctg taagattcca     780
aatgtctccg ttgcgagcct gaatgacatg accctgtag ggaggctggt aacagtaaac     840
```

```
cccctttgtcg cgacatccag cgccaactca aaagtgctgg ttgaaatgga accccctttt      900
ggagattctt acatcgtggt cggaagaggt gacaagcaga tcaatcatca ctggcacaaa      960
gctggaagca cgctgggcaa aggaggtggc catcaccatc accatcactg atgaccggtt     1020
```

<210> SEQ ID NO 60
<211> LENGTH: 319
<212> TYPE: PRT
<213> ORGANISM: artificial
<220> FEATURE:
<223> OTHER INFORMATION: Amino acid Sequence of the fusion protein SNAPlike-EDIII from Japanese encephalitis virus genotype 2 - Histag

<400> SEQUENCE: 60

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Asn Ser Ser Phe Arg Lys Asn Pro Ala Asp Thr Gly His
    210                 215                 220

Gly Thr Val Val Ile Glu Leu Thr Tyr Ser Gly Ser Asp Gly Pro Cys
225                 230                 235                 240

Lys Ile Pro Asn Val Ser Val Ala Ser Leu Asn Asp Met Thr Pro Val
                245                 250                 255

Gly Arg Leu Val Thr Val Asn Pro Phe Val Ala Thr Ser Ser Ala Asn
            260                 265                 270

Ser Lys Val Leu Val Glu Met Glu Pro Pro Phe Gly Asp Ser Tyr Ile
        275                 280                 285

Val Val Gly Arg Gly Asp Lys Gln Ile Asn His His Trp His Lys Ala
    290                 295                 300

Gly Ser Thr Leu Gly Lys Gly Gly Gly His His His His His His
305                 310                 315
```

<210> SEQ ID NO 61
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      4 cloned into pMT/BiP/SNAP for expression in S2 cells

<400> SEQUENCE: 61

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg aaatcctgt gcccatcctg       480
atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc agggtccctg gagggaggtg gcgggtctgc tctgaaaggc     660
acaacctatg gaatgtgcac agaaaagttc tcgtttgcaa gaatccagc agacactggt      720
catggaacag ttgtcattga actcctgtat tctggaagtg acggcccctg taacatccca     780
attgtctcag tggtcagtct aaacgacatg actccagttg gaaggttggt gacagtgaac     840
cccttcgttg ccacatccag ttccaattca aaggtcttag ttgagatgga acctcctttt     900
ggagactcct acattgtggt cgggagagga gaaaaacaaa tcaaccacca ctggcacaaa     960
cctggaagca cattgggcaa aggaggtggc catcaccatc accatcactg atgaccggtt    1020
```

<210> SEQ ID NO 62
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype 4 -
      Histag

<400> SEQUENCE: 62

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Lys Val Val Lys Phe Gly Glu Val
            100                 105                 110
```

```
Ile Ser Tyr Gln Gln Leu Ala Ala Leu Ala Gly Asn Pro Ala Ala Thr
    115                 120                 125

Ala Ala Val Lys Thr Ala Leu Ser Gly Asn Pro Val Pro Ile Leu Ile
130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
                180                 185                 190

Leu Glu Gly Gly Gly Ser Ala Leu Lys Gly Thr Thr Tyr Gly Met
            195                 200                 205

Cys Thr Glu Lys Phe Ser Phe Ala Lys Asn Pro Ala Asp Thr Gly His
    210                 215                 220

Gly Thr Val Val Ile Glu Leu Leu Tyr Ser Gly Ser Asp Gly Pro Cys
225                 230                 235                 240

Asn Ile Pro Ile Val Ser Val Val Ser Leu Asn Asp Met Thr Pro Val
                245                 250                 255

Gly Arg Leu Val Thr Val Asn Pro Phe Val Ala Thr Ser Ser Ser Asn
                260                 265                 270

Ser Lys Val Leu Val Glu Met Glu Pro Pro Phe Gly Asp Ser Tyr Ile
    275                 280                 285

Val Val Gly Arg Gly Glu Lys Gln Ile Asn His His Trp His Lys Pro
    290                 295                 300

Gly Ser Thr Leu Gly Lys Gly Gly His His His His His
305                 310                 315

<210> SEQ ID NO 63
<211> LENGTH: 1020
<212> TYPE: DNA
<213> ORGANISM: artificial
<220> FEATURE:
<223> OTHER INFORMATION: DNA Sequence encoding the fusion protein
      BiPlike -SNAPlike-EDIII from Japanese encephalitis virus genotype
      5 cloned into pMT/BiP/SNAP for expression in S2 cells

<400> SEQUENCE: 63
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca tgaggaatt ccagtcccc      300 gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg gaaatcctgt gcccatcctg     480
atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc agggtccctg gaggaggtg gcgggtctgc gttgaaaggg     660
accacctatg gtatgtgcac agagaagttc tcttttttcca agaatccagc tgacactggt     720
catggtacgg ttgtcataga attgcagtac accggcactg acggaccttg caagataccc     780
atctcttcgg tggccagtct gaatgattta actccagttg gtagattggt gacagtcaat     840
```

```
cctttgttg ccacatccac cgccaattcg aaggttttgg tagaattgga accaccattt    900
ggagattcat tcattgttgt cggaagagga gataagcaga tcaatcacca ttggcacaag    960
gctggcagtt cactgggaaa gggaggtggc catcaccatc accatcactg atgaccggtt   1020
```

<210> SEQ ID NO 64
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype 5 -
      Histag

<400> SEQUENCE: 64

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
                20                  25                  30

Lys Leu Leu Gly Lys Gly Thr Ser Ala Ala Asp Ala Val Glu Val Pro
            35                  40                  45

Ala Pro Ala Ala Val Leu Gly Gly Pro Glu Pro Leu Met Gln Ala Thr
50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
                100                 105                 110

Ile Ser Tyr Gln Gln Leu Ala Ala Leu Ala Gly Asn Pro Ala Ala Thr
            115                 120                 125

Ala Ala Val Lys Thr Ala Leu Ser Gly Asn Pro Val Pro Ile Leu Ile
130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Ser Ala Leu Lys Gly Thr Thr Tyr Gly Met
        195                 200                 205

Cys Thr Glu Lys Phe Ser Phe Ser Lys Asn Pro Ala Asp Thr Gly His
210                 215                 220

Gly Thr Val Val Ile Glu Leu Gln Tyr Thr Gly Thr Asp Gly Pro Cys
225                 230                 235                 240

Lys Ile Pro Ile Ser Ser Val Ala Ser Leu Asn Asp Leu Thr Pro Val
                245                 250                 255

Gly Arg Leu Val Thr Val Asn Pro Phe Val Ala Thr Ser Thr Ala Asn
            260                 265                 270

Ser Lys Val Leu Val Glu Leu Glu Pro Pro Phe Gly Asp Ser Phe Ile
        275                 280                 285

Val Val Gly Arg Gly Asp Lys Gln Ile Asn His His Trp His Lys Ala
290                 295                 300

Gly Ser Ser Leu Gly Lys Gly Gly Gly His His His His His
305                 310                 315
```

<210> SEQ ID NO 65
<211> LENGTH: 1008
<212> TYPE: DNA
<213> ORGANISM: artificial
<220> FEATURE:
<223> OTHER INFORMATION: DNA Sequence encoding the fusion protein BiPlike -SNAPlike-EDIII from Rabensburg virus cloned into pMT/BiP/SNAP for expression in S2 cells

<400> SEQUENCE: 65

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt ccagtcccc      300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg aaatcctgt gcccatcctg       480
atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc aggaggtggc gggtctcagc tcaaaggaac gacctatgga    660
gtatgcgcaa aagccttcaa gttttctggg aatccagctg acacagggca tggcaccgtg     720
gtcttagagt tgcaatacac cggaaccgat ggtccttgta aggtgcctgt ctcttccgtg     780
gcttcactca acgacctaac tcccgttggg agactggtga cagtgaatcc ctttgttgct     840
gcagctactg ctaattcaaa ggttctgata gaactggaac ctccattcgg tgactcatac     900
attgtggtag gtagaggaga acaccagata aaccaccatt ggcacaagtc tggaagcagt     960
attggaaagg gaggtggcca tcaccatcac catcactgat gaccggtt                 1008
```

<210> SEQ ID NO 66
<211> LENGTH: 314
<212> TYPE: PRT
<213> ORGANISM: artificial
<220> FEATURE:
<223> OTHER INFORMATION: Amino acid Sequence of the fusion protein SNAPlike-EDIII from Rabensburg virus - Histag

<400> SEQUENCE: 66

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125
```

```
Ala Ala Val Lys Thr Ala Leu Ser Gly Asn Pro Val Pro Ile Leu Ile
    130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Gly
                180                 185                 190
Gly Ser Gln Leu Lys Gly Thr Thr Tyr Gly Val Cys Ala Lys Ala
        195                 200                 205
Phe Lys Phe Ser Gly Asn Pro Ala Asp Thr Gly His Gly Thr Val Val
    210                 215                 220
Leu Glu Leu Gln Tyr Thr Gly Thr Asp Gly Pro Cys Lys Val Pro Val
225                 230                 235                 240
Ser Ser Val Ala Ser Leu Asn Asp Leu Thr Pro Val Gly Arg Leu Val
                245                 250                 255
Thr Val Asn Pro Phe Val Ala Ala Ala Thr Ala Asn Ser Lys Val Leu
                260                 265                 270
Ile Glu Leu Glu Pro Pro Phe Gly Asp Ser Tyr Ile Val Val Gly Arg
                275                 280                 285
Gly Glu His Gln Ile Asn His His Trp His Lys Ser Gly Ser Ser Ile
    290                 295                 300
Gly Lys Gly Gly Gly His His His His
305                 310

<210> SEQ ID NO 67
<211> LENGTH: 977
<212> TYPE: DNA
<213> ORGANISM: artificial
<220> FEATURE:
<223> OTHER INFORMATION: DNA Sequence encoding the fusion protein
      ssBiP-SNAPlike-EDIII from an insect flavivirus virus cloned into
      pMT/BiP/SNAP for expression in S2 cells

<400> SEQUENCE: 67
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg aaatcctgt gcccatcctg      480 atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc aggaggtggc ggggaagcgc agacagtgtt ctctcaatcc     660
ccttgggggt tcgaaggaat agcggagata acactaaaag aggcccaaaa gagcatttgt     720
tcactacctt tgtcttgtgt gggctgtagc ttgttgtctt ccaaggtcgt tttccttgag     780
acaacaacga agctgccgt ccacgttgga tgtgggaatg aacttctgt tctaacagtt      840 ggaactactc ctgtgagtat cgactgtgta gtaacgcccc gtcgcaggt gtggaggctc      900
```

```
gtgtcgcacg tcaccggaag atacaccaaa cttgggtttg gaggtggcca tcaccatcac        960
catcactgat gaccggt                                                        977
```

<210> SEQ ID NO 68
<211> LENGTH: 305
<212> TYPE: PRT
<213> ORGANISM: artificial
<220> FEATURE:
<223> OTHER INFORMATION: Amino acid Sequence of the fusion protein
      SNAPlike-EDIII from a insect flavivirus - Histag

<400> SEQUENCE: 68

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Glu Ala Gln Thr Val Phe Ser Gln Ser Pro Trp Gly Phe Glu
        195                 200                 205

Gly Ile Ala Glu Ile Thr Leu Lys Glu Ala Gln Lys Ser Ile Cys Ser
    210                 215                 220

Leu Pro Leu Ser Cys Val Gly Cys Ser Leu Leu Ser Ser Lys Val Val
225                 230                 235                 240

Phe Leu Glu Thr Thr Thr Lys Ala Ala Val His Val Gly Cys Gly Asn
                245                 250                 255

Gly Thr Ser Val Leu Thr Val Gly Thr Thr Pro Val Ser Ile Asp Cys
            260                 265                 270

Val Val Thr Pro Leu Ser Gln Val Trp Arg Leu Val Ser His Val Thr
        275                 280                 285

Gly Arg Tyr Thr Lys Leu Gly Phe Gly Gly Gly His His His His
    290                 295                 300

His
305
```

<210> SEQ ID NO 69
<211> LENGTH: 1783
<212> TYPE: DNA

<213> ORGANISM: artificial
<220> FEATURE:
<223> OTHER INFORMATION: DNA sequence encoding ssBiP-sE2 from Ross River
      virus strain QML-1 -SNAPlike-Histag for expression in S2 cells

<400> SEQUENCE: 69

| | | | | | |
|---|---|---|---|---|---|
| atgaagttat | gcatattact | ggccgtcgtg | gcctttgttg | gcctctcgct | cgggagatct | 60 |
| agtgtaacag | agcacttcaa | tgtgtataag | gctactagac | catacctagc | acattgcgct | 120 |
| gattgcgggg | acgggtactt | ctgctatagc | ccagttgcca | tcgagaagat | ccagatgag | 180 |
| gcgtctgatg | gcatgctcaa | gatccaagtc | tccgcccaaa | taggtctgga | caaggcaggc | 240 |
| acccacgccc | acacgaagct | ccgatatatg | gctggtcacg | atgttcagga | atctaagaga | 300 |
| gattccttga | gggtgtacac | gtccgcagcg | tgctccatac | atgggacgat | gggacacttc | 360 |
| atcgtcgcac | actgtccacc | aggcgactac | ctcaaggttt | cgttcgagga | cgcagattcg | 420 |
| cacgtgaagg | catgtaaggt | ccaatacaag | cacaatccat | gccggtggg | tagagagaag | 480 |
| ttcgtggtta | gaccacactt | tggcgtagag | ctgccatgca | cctcatacca | gctgacaacg | 540 |
| gctcccaccg | acgaggagat | tgacatgcat | acaccgccag | atataccgga | tcgcaccctg | 600 |
| ctatcacaga | cggcgggcaa | cgtcaaaata | acagcaggcg | gcaggactat | caggtacaat | 660 |
| tgtacctgcg | gccgtgacaa | cgtaggcact | accagtactg | acaagaccat | caacacatgc | 720 |
| aagattgacc | aatgccatgc | tgccgtcacc | agccatgaca | aatggcaatt | tacctctcca | 780 |
| tttgttccca | gggctgatca | gacagctagg | aaaggcaagg | tacacgttcc | gttccctctg | 840 |
| actaacgtca | cctgccgagt | gccgttggct | cgagcgccgg | atgtcaccta | tggtaagaag | 900 |
| gaggtgaccc | tgagattaca | cccagatcat | ccgacactct | tctcctatag | gagtttagga | 960 |
| gccgaaccgc | acccgtacga | ggaatgggtt | gacaagttct | ctgagcgcat | catcccagtg | 1020 |
| acggaagaag | ggattgaata | ccagtggggc | aacaacccgc | cggtccgcct | gtgggcgcaa | 1080 |
| ctgacgaccg | agggcaaacc | ccatggatgg | ccacatgaaa | tcattcagta | ctattatgga | 1140 |
| ctatacccgg | ccgccacgcg | gccgcacggc | ggaggtagca | aagactgcga | aatgaagcgc | 1200 |
| accacctggg | atagccctct | gggcaagctg | gaactgtctg | ggtgcgaaca | gggcctgcac | 1260 |
| gagatcaagc | tgctgggcaa | aggaacatct | gccgccgacg | ccgtgaagt | gcctgcccca | 1320 |
| gccgccgtgc | tgggcggacc | agagccactg | atgcaggcca | ccgcctggct | caacgcctac | 1380 |
| tttcaccagc | ctgaggccat | cgaggagttc | cctgtgccag | ccctgcacca | cccagtgttc | 1440 |
| cagcaggaga | gctttacccg | ccaggtgctg | tggaaactgc | tgaaagtggt | gaagttcgga | 1500 |
| gaggtcatca | gctaccagca | gctggccgcc | ctggccggca | tcccgccgc | caccgccgcc | 1560 |
| gtgaaaaccg | ccctgagcgg | aaatcccgtg | cccattctga | tccccctgcca | ccgggtggtg | 1620 |
| tctagctctg | gcgccgtggg | gggctacgag | ggcgggctcg | ccgtgaaaga | gtggctgctg | 1680 |
| gcccacgagg | gccacagact | gggcaagcct | gggctgggtc | ctgcaggtat | aggcgcgcca | 1740 |
| gggtccctgg | agcatcatca | tcatcatcat | tgatgacggg | ccc | | 1783 |

<210> SEQ ID NO 70
<211> LENGTH: 572
<212> TYPE: PRT
<213> ORGANISM: artificial
<220> FEATURE:
<223> OTHER INFORMATION: Amino acid sequence of the fusion protein [sE2
      from Ross River virus strain QML-1 -SNAPlike-Histag]

<400> SEQUENCE: 70

Arg Ser Ser Val Thr Glu His Phe Asn Val Tyr Lys Ala Thr Arg Pro

-continued

```
1               5                   10                  15
Tyr Leu Ala His Cys Ala Asp Cys Gly Asp Gly Tyr Phe Cys Tyr Ser
                20                  25                  30

Pro Val Ala Ile Glu Lys Ile Arg Asp Glu Ala Ser Asp Gly Met Leu
                35                  40                  45

Lys Ile Gln Val Ser Ala Gln Ile Gly Leu Asp Lys Ala Gly Thr His
50                  55                  60

Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
                100                 105                 110

Leu Lys Val Ser Phe Glu Asp Ala Asp Ser His Val Lys Ala Cys Lys
                115                 120                 125

Val Gln Tyr Lys His Asn Pro Leu Pro Val Gly Arg Glu Lys Phe Val
                130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
                180                 185                 190

Thr Ala Gly Gly Arg Thr Ile Arg Tyr Asn Cys Thr Cys Gly Arg Asp
                195                 200                 205

Asn Val Gly Thr Thr Ser Thr Asp Lys Thr Ile Asn Thr Cys Lys Ile
210                 215                 220

Asp Gln Cys His Ala Ala Val Thr Ser His Asp Lys Trp Gln Phe Thr
225                 230                 235                 240

Ser Pro Phe Val Pro Arg Ala Asp Gln Thr Ala Arg Lys Gly Lys Val
                245                 250                 255

His Val Pro Phe Pro Leu Thr Asn Val Thr Cys Arg Val Pro Leu Ala
                260                 265                 270

Arg Ala Pro Asp Val Thr Tyr Gly Lys Lys Glu Val Thr Leu Arg Leu
                275                 280                 285

His Pro Asp His Pro Thr Leu Phe Ser Tyr Arg Ser Leu Gly Ala Glu
                290                 295                 300

Pro His Pro Tyr Glu Glu Trp Val Asp Lys Phe Ser Glu Arg Ile Ile
305                 310                 315                 320

Pro Val Thr Glu Glu Gly Ile Glu Tyr Gln Trp Gly Asn Asn Pro Pro
                325                 330                 335

Val Arg Leu Trp Ala Gln Leu Thr Thr Glu Gly Lys Pro His Gly Trp
                340                 345                 350

Pro His Glu Ile Ile Gln Tyr Tyr Tyr Gly Leu Tyr Pro Ala Ala Thr
                355                 360                 365

Arg Pro His Gly Gly Ser Lys Asp Cys Glu Met Lys Arg Thr Thr
                370                 375                 380

Leu Asp Ser Pro Leu Gly Lys Leu Glu Leu Ser Gly Cys Glu Gln Gly
385                 390                 395                 400

Leu His Glu Ile Lys Leu Leu Gly Lys Gly Thr Ser Ala Ala Asp Ala
                405                 410                 415

Val Glu Val Pro Ala Pro Ala Ala Val Leu Gly Gly Pro Glu Pro Leu
                420                 425                 430
```

```
Met Gln Ala Thr Ala Trp Leu Asn Ala Tyr Phe His Gln Pro Glu Ala
        435                 440                 445
Ile Glu Glu Phe Pro Val Pro Ala Leu His His Pro Val Phe Gln Gln
    450                 455                 460
Glu Ser Phe Thr Arg Gln Val Leu Trp Lys Leu Leu Lys Val Val Lys
465                 470                 475                 480
Phe Gly Glu Val Ile Ser Tyr Gln Gln Leu Ala Ala Leu Ala Gly Asn
                485                 490                 495
Pro Ala Ala Thr Ala Ala Val Lys Thr Ala Leu Ser Gly Asn Pro Val
            500                 505                 510
Pro Ile Leu Ile Pro Cys His Arg Val Val Ser Ser Gly Ala Val
        515                 520                 525
Gly Gly Tyr Glu Gly Gly Leu Ala Val Lys Glu Trp Leu Leu Ala His
    530                 535                 540
Glu Gly His Arg Leu Gly Lys Pro Gly Leu Gly Pro Ala Gly Ile Gly
545                 550                 555                 560
Ala Pro Gly Ser Leu Glu His His His His His His
                565                 570
```

<210> SEQ ID NO 71
<211> LENGTH: 1783
<212> TYPE: DNA
<213> ORGANISM: artificial
<220> FEATURE:
<223> OTHER INFORMATION: DNA sequence encoding ssBiP-sE2 from Mayaro
      virus strain IQD2668 -SNAPlike-Histag for expression in S2 cells

<400> SEQUENCE: 71

```
atgaagttat gcatattact ggccgtcgtg gcctttgttg gcctctcgct cgggagatct      60
agtgtaacag agcacttcaa tgtgtataag gctactagac atacctagc acattgcgct     120
gattgcgggg acgggtactt ctgctatagc ccagttgcca tcgagaagat ccgagatgag     180
gcgtctgatg gcatgctcaa gatccaagtc tccgcccaaa taggtctgga caaggcaggc     240
acccacgccc acacgaagct ccgatatatg gctggtcacg atgttcagga atctaagaga     300
gattccttga gggtgtacac gtccgcagcg tgctccatac atgggacgat gggacacttc     360
atcgtcgcac actgtccacc aggcgactac ctcaaggttt cgttcgagga cgcagattcg     420
cacgtgaagg catgtaaggt ccaatacaag cacaatccat tgccggtggg tagagagaag     480
ttcgtggtta gaccacactt tggcgtagag ctgccatgca cctcatacca gctgacaacg     540
gctcccaccg acgaggagat tgacatgcat acaccgccag atataccgga tcgcaccctg     600
ctatcacaga cggcgggcaa cgtcaaaata acagcaggcg gcaggactat caggtacaat     660
tgtacctgcg gccgtgacaa cgtaggcact accagtactg acaagaccat caacacatgc     720
aagattgacc aatgccatgc tgccgtcacc agccatgaca atggcaatt tacctctcca     780
tttgttccca gggctgatca gacagctagg aaaggcaagg tacacgttcc gttccctctg     840
actaacgtca cctgccgagt gccgttggct cgagcgccgg atgtcaccta tggtaagaag     900
gaggtgaccc tgagattaca cccagatcat ccgacactct ctcctatag gagtttagga     960
gccgaaccgc acccgtacga ggaatgggtt gacaagttct ctgagcgcat catcccagtg    1020
acggaagaag ggattgaata ccagtggggc aacaaccgc cggtccgcct gtgggcgcaa    1080
ctgacgaccg aggcaaaacc ccatggatgg ccacatgaaa tcattcagta ctattatgga    1140
ctataccccg ccgccacgcg gccgcacggc ggaggtagca aagactgcga aatgaagcgc    1200
```

```
accaccctgg atagccctct gggcaagctg gaactgtctg ggtgcgaaca gggcctgcac    1260
gagatcaagc tgctgggcaa aggaacatct gccgccgacg ccgtggaagt gcctgcccca    1320
gccgccgtgc tggcggacc agagccactg atgcaggcca ccgcctggct caacgcctac    1380
tttcaccagc tgaggccat cgaggagttc cctgtgccag ccctgcacca cccagtgttc    1440
cagcaggaga gctttacccg ccaggtgctg tggaaactgc tgaaagtggt gaagttcgga    1500
gaggtcatca gctaccagca gctggccgcc ctggccggca atcccgccgc caccgccgcc    1560
gtgaaaaccg ccctgagcgg aaatcccgtg cccattctga tcccctgcca ccgggtggtg    1620
tctagctctg cgccgtggg gggctacgag ggcgggctcg ccgtgaaaga gtggctgctg    1680
gcccacgagg ccacagact gggcaagcct gggctgggtc ctgcaggtat aggcgcgcca    1740
gggtccctgg agcatcatca tcatcatcat tgatgacggg ccc    1783
```

<210> SEQ ID NO 72
<211> LENGTH: 572
<212> TYPE: PRT
<213> ORGANISM: artificial
<220> FEATURE:
<223> OTHER INFORMATION: Amino acid sequence of the fusion protein [sE2 from Mayaro virus strain IQD2668 -SNAPlike-Histag]

<400> SEQUENCE: 72

```
Arg Ser Ser Val Thr Glu His Phe Asn Val Tyr Lys Ala Thr Arg Pro
1               5                   10                  15

Tyr Leu Ala His Cys Ala Asp Cys Gly Asp Gly Tyr Phe Cys Tyr Ser
            20                  25                  30

Pro Val Ala Ile Glu Lys Ile Arg Asp Glu Ala Ser Asp Gly Met Leu
        35                  40                  45

Lys Ile Gln Val Ser Ala Gln Ile Gly Leu Asp Lys Ala Gly Thr His
    50                  55                  60

Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
            100                 105                 110

Leu Lys Val Ser Phe Glu Asp Ala Asp Ser His Val Lys Ala Cys Lys
        115                 120                 125

Val Gln Tyr Lys His Asn Pro Leu Pro Val Gly Arg Glu Lys Phe Val
    130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
            180                 185                 190

Thr Ala Gly Gly Arg Thr Ile Arg Tyr Asn Cys Thr Cys Gly Arg Asp
        195                 200                 205

Asn Val Gly Thr Thr Ser Thr Asp Lys Thr Ile Asn Thr Cys Lys Ile
    210                 215                 220

Asp Gln Cys His Ala Ala Val Thr Ser His Asp Lys Trp Gln Phe Thr
225                 230                 235                 240

Ser Pro Phe Val Pro Arg Ala Asp Gln Thr Ala Arg Lys Gly Lys Val
                245                 250                 255
```

```
His Val Pro Phe Pro Leu Thr Asn Val Thr Cys Arg Val Pro Leu Ala
            260                 265                 270
Arg Ala Pro Asp Val Thr Tyr Gly Lys Lys Glu Val Thr Leu Arg Leu
        275                 280                 285
His Pro Asp His Pro Thr Leu Phe Ser Tyr Arg Ser Leu Gly Ala Glu
    290                 295                 300
Pro His Pro Tyr Glu Glu Trp Val Asp Lys Phe Ser Glu Arg Ile Ile
305                 310                 315                 320
Pro Val Thr Glu Glu Gly Ile Glu Tyr Gln Trp Gly Asn Asn Pro Pro
                325                 330                 335
Val Arg Leu Trp Ala Gln Leu Thr Thr Glu Gly Lys Pro His Gly Trp
            340                 345                 350
Pro His Glu Ile Ile Gln Tyr Tyr Tyr Gly Leu Tyr Pro Ala Ala Thr
        355                 360                 365
Arg Pro His Gly Gly Gly Ser Lys Asp Cys Glu Met Lys Arg Thr Thr
    370                 375                 380
Leu Asp Ser Pro Leu Gly Lys Leu Glu Leu Ser Gly Cys Glu Gln Gly
385                 390                 395                 400
Leu His Glu Ile Lys Leu Leu Gly Lys Gly Thr Ser Ala Ala Asp Ala
                405                 410                 415
Val Glu Val Pro Ala Pro Ala Ala Val Leu Gly Gly Pro Glu Pro Leu
            420                 425                 430
Met Gln Ala Thr Ala Trp Leu Asn Ala Tyr Phe His Gln Pro Glu Ala
        435                 440                 445
Ile Glu Glu Phe Pro Val Pro Ala Leu His His Pro Val Phe Gln Gln
    450                 455                 460
Glu Ser Phe Thr Arg Gln Val Leu Trp Lys Leu Leu Lys Val Val Lys
465                 470                 475                 480
Phe Gly Glu Val Ile Ser Tyr Gln Gln Leu Ala Ala Leu Ala Gly Asn
                485                 490                 495
Pro Ala Ala Thr Ala Ala Val Lys Thr Ala Leu Ser Gly Asn Pro Val
            500                 505                 510
Pro Ile Leu Ile Pro Cys His Arg Val Val Ser Ser Ser Gly Ala Val
        515                 520                 525
Gly Gly Tyr Glu Gly Gly Leu Ala Val Lys Glu Trp Leu Leu Ala His
    530                 535                 540
Glu Gly His Arg Leu Gly Lys Pro Gly Leu Gly Pro Ala Gly Ile Gly
545                 550                 555                 560
Ala Pro Gly Ser Leu Glu His His His His His His
                565                 570

<210> SEQ ID NO 73
<211> LENGTH: 1786
<212> TYPE: DNA
<213> ORGANISM: artificial
<220> FEATURE:
<223> OTHER INFORMATION: DNA sequence encoding ssBiP-sE2 from Western
      Equine Encephalitis virus -SNAPlike-Histag for expression in S2
      cells

<400> SEQUENCE: 73
atgaagttat gcatattact ggccgtcgtg gcctttgttg gcctctcgct cgggagatct      60
agcattaccg atgacttcac actgaccagt ccctacctgg ggttctgccc gtattgcaga     120
cactcaacgc cgtgtttcag cccaataaaa attgagaacg tgtgggacga atctgatgat     180
ggatcgatta gaatccaggt ctcggcacaa ttcggctaca atcaggcagg cactgcggat     240
```

-continued

```
gtcaccaaat tccgttacat gtctttcgac cacgaccatg acatcaagga agacagtatg    300
gagaaaatag ctatcagcac atctggaccc tgccgtcgtc ttggccacaa agggtacttc    360
ctgttagctc aatgtcctcc aggtgacagt gtaaccgtca gtatcacgag cggagcatct    420
gagaattcat gcaccgtgga gaaaaagatc aggaggaagt tgtcggtag agaggagtac     480 ttgttcccac ccgtccatgg aaagctggta aagtgccacg tttacgatca cttgaaggag    540
acgtctgccg ggtacataac catgcacagg ccaggcccac acgcgtataa gtcctatctg    600
gaggaagcgt caggcgaagt gtacattaaa ccaccttctg caagaacgt cacctacgaa     660 tgtaagtgtg cgactacag cacaggtatc gtgagcacgc gaacgaagat gaacggctgc    720
actaaagcaa acagtgcat tgcctacaag agcgaccaaa cgaaatgggt cttcaactcg    780
ccggatctta ttaggcacac agaccactca gtgcaaggta aattgcacat tccattccgc    840
ttgacaccga cagtctgccc ggttccgtta gctcacacgc ctacagtcac gaagtggttc    900
aaaggcatca ccctccacct gactgcaatg cgaccaacat tgctgacaac gagaaaattg    960
gggctgcgag cagacgcaac agcagaatgg attacagggt ctacatccag gaattttct    1020 gtggggcgag aagggctgga gtacgtatgg ggtaaccatg aaccagtcag agtctgggcc    1080
caggagtcgg caccaggcga cccacatgga tggccgcatg agatcatcat ccactattat    1140
catcggcatc cagtctacac gcggccgcac ggcggaggta gcaaagactg cgaaatgaag    1200
cgcaccaccc tggatagccc tctgggcaag ctggaactgt ctgggtgcga cagggcctg    1260 cacgagatca agctgctggg caaaggaaca tctgccgccg acgccgtgga agtgcctgcc    1320
ccagccgccg tgctgggcgg accagagcca ctgatgcagg ccaccgcctg gctcaacgcc    1380
tactttcacc agcctgaggc catcgaggag ttccctgtgc cagccctgca ccacccagtg    1440
ttccagcagg agagctttac ccgccaggtg ctgtggaaac tgctgaaagt ggtgaagttc    1500
ggagaggtca tcagctacca gcagctggcc gccctggccg gcaatcccgc cgccaccgcc    1560
gccgtgaaaa ccgccctgag cggaaatccc gtgcccattc tgatcccctg ccaccgggtg    1620
gtgtctagct ctggcgccgt gggggggctac gagggcgggc tcgccgtgaa agagtggctg    1680
ctggcccacg agggccacag actgggcaag cctgggctgg gtcctgcagg tataggcgcg    1740
ccagggtccc tggagcatca tcatcatcat cattgatgac gggccc                  1786
```

<210> SEQ ID NO 74
<211> LENGTH: 573
<212> TYPE: PRT
<213> ORGANISM: artificial
<220> FEATURE:
<223> OTHER INFORMATION: Amino acid sequence of the fusion protein [sE2 from Western Equine Encephalitis -SNAPlike-Histag]

<400> SEQUENCE: 74

```
Arg Ser Ser Ile Thr Asp Asp Phe Thr Leu Thr Ser Pro Tyr Leu Gly
1               5                   10                  15

Phe Cys Pro Tyr Cys Arg His Ser Thr Pro Cys Phe Ser Pro Ile Lys
            20                  25                  30

Ile Glu Asn Val Trp Asp Glu Ser Asp Asp Gly Ser Ile Arg Ile Gln
        35                  40                  45

Val Ser Ala Gln Phe Gly Tyr Asn Gln Ala Gly Thr Ala Asp Val Thr
    50                  55                  60

Lys Phe Arg Tyr Met Ser Phe Asp His Asp His Asp Ile Lys Glu Asp
65                  70                  75                  80
```

```
Ser Met Glu Lys Ile Ala Ile Ser Thr Ser Gly Pro Cys Arg Arg Leu
                85                  90                  95

Gly His Lys Gly Tyr Phe Leu Leu Ala Gln Cys Pro Pro Gly Asp Ser
            100                 105                 110

Val Thr Val Ser Ile Thr Ser Gly Ala Ser Glu Asn Ser Cys Thr Val
            115                 120                 125

Glu Lys Lys Ile Arg Arg Lys Phe Val Gly Arg Glu Glu Tyr Leu Phe
            130                 135                 140

Pro Pro Val His Gly Lys Leu Val Lys Cys His Val Tyr Asp His Leu
145                 150                 155                 160

Lys Glu Thr Ser Ala Gly Tyr Ile Thr Met His Arg Pro Gly Pro His
                165                 170                 175

Ala Tyr Lys Ser Tyr Leu Glu Glu Ala Ser Gly Glu Val Tyr Ile Lys
                180                 185                 190

Pro Pro Ser Gly Lys Asn Val Thr Tyr Glu Cys Lys Cys Gly Asp Tyr
                195                 200                 205

Ser Thr Gly Ile Val Ser Thr Arg Thr Lys Met Asn Gly Cys Thr Lys
            210                 215                 220

Ala Lys Gln Cys Ile Ala Tyr Lys Ser Asp Gln Thr Lys Trp Val Phe
225                 230                 235                 240

Asn Ser Pro Asp Leu Ile Arg His Thr Asp His Ser Val Gln Gly Lys
                245                 250                 255

Leu His Ile Pro Phe Arg Leu Thr Pro Thr Val Cys Pro Val Pro Leu
                260                 265                 270

Ala His Thr Pro Thr Val Thr Lys Trp Phe Lys Gly Ile Thr Leu His
                275                 280                 285

Leu Thr Ala Met Arg Pro Thr Leu Leu Thr Thr Arg Lys Leu Gly Leu
            290                 295                 300

Arg Ala Asp Ala Thr Ala Glu Trp Ile Thr Gly Ser Thr Ser Arg Asn
305                 310                 315                 320

Phe Ser Val Gly Arg Glu Gly Leu Glu Tyr Val Trp Gly Asn His Glu
                325                 330                 335

Pro Val Arg Val Trp Ala Gln Glu Ser Ala Pro Gly Asp Pro His Gly
                340                 345                 350

Trp Pro His Glu Ile Ile Ile His Tyr Tyr His Arg His Pro Val Tyr
                355                 360                 365

Thr Arg Pro His Gly Gly Gly Ser Lys Asp Cys Glu Met Lys Arg Thr
            370                 375                 380

Thr Leu Asp Ser Pro Leu Gly Lys Leu Glu Leu Ser Gly Cys Glu Gln
385                 390                 395                 400

Gly Leu His Glu Ile Lys Leu Leu Gly Lys Gly Thr Ser Ala Ala Asp
                405                 410                 415

Ala Val Glu Val Pro Ala Pro Ala Ala Val Leu Gly Gly Pro Glu Pro
                420                 425                 430

Leu Met Gln Ala Thr Ala Trp Leu Asn Ala Tyr Phe His Gln Pro Glu
                435                 440                 445

Ala Ile Glu Glu Phe Pro Val Pro Ala Leu His His Pro Val Phe Gln
                450                 455                 460

Gln Glu Ser Phe Thr Arg Gln Val Leu Trp Lys Leu Leu Lys Val Val
465                 470                 475                 480

Lys Phe Gly Glu Val Ile Ser Tyr Gln Gln Leu Ala Ala Leu Ala Gly
                485                 490                 495

Asn Pro Ala Ala Thr Ala Ala Val Lys Thr Ala Leu Ser Gly Asn Pro
```

```
              500             505             510
Val Pro Ile Leu Ile Pro Cys His Arg Val Val Ser Ser Ser Gly Ala
        515             520             525

Val Gly Gly Tyr Glu Gly Gly Leu Ala Val Lys Glu Trp Leu Leu Ala
        530             535             540

His Glu Gly His Arg Leu Gly Lys Pro Gly Leu Gly Pro Ala Gly Ile
545             550             555             560

Gly Ala Pro Gly Ser Leu Glu His His His His His His
                565             570
```

<210> SEQ ID NO 75
<211> LENGTH: 1786
<212> TYPE: DNA
<213> ORGANISM: artificial
<220> FEATURE:
<223> OTHER INFORMATION: DNA sequence encoding ssBiP-sE2 from Eastern
      Equine Encephalitis virus -SNAPlike-Histag for expression in S2
      cells

<400> SEQUENCE: 75

| | |
|---|---|
| atgaagttat gcatattact ggccgtcgtg gcctttgttg gcctctcgct cgggagatct | 60 |
| gatttggaca ctcatttcac ccagtataag ttggcacgcc cgtatattgc tgattgccct | 120 |
| aactgtgggc atagtcggtg cgacagccct atagctatag aagaagtcag aggggatgcg | 180 |
| cacgcaggag tcatccgcat ccagacatca gctatgttcg gtctgaagac ggatggagtc | 240 |
| gatttggcct acatgagttt catgaacggc aaaacgcaga atcaataaa gatcgacaac | 300 |
| ctgcatgtgc gcacctcagc cccttgttcc tcgtgtcgc accacggcta ttacatcctg | 360 |
| gctcaatgcc caccagggga cacggttaca gttgggtttc acgacgggcc taaccgccat | 420 |
| acgtgcacag ttgcccataa ggtagaattc aggccagtgg gtagagagaa ataccgtcac | 480 |
| ccacctgaac atggagttga attaccgtgt aaccgttaca ctcacaagcg tgcagaccaa | 540 |
| ggacactatg ttgagatgca tcaacccggg ctagttgccg accactctct ccttagcatc | 600 |
| cacagtgcca aggtgaaaat tacggtaccg agcggcgccc aagtgaaata ctactgcaag | 660 |
| tgcccagatg tacgagaggg aattaccagc agcgaccata caaccacctg cacggatgtc | 720 |
| aaacaatgca gggcttacct gattgacaac aaaaaatggg tgtacaactc tggaagactg | 780 |
| cctcgaggag agggcgacac ttttaaagga aaacttcatg tgcccttttgt gcctgttaag | 840 |
| gccaagtgca tcgccacgct ggcaccggag cctctagttg agcacaaaca ccgcaccctg | 900 |
| attttacacc tgcacccgga ccatccgacc ttgctgacga ccaggtcact tggaagtgat | 960 |
| gcaaatccaa ctcgacaatg gattgagcga ccaacaactg tcaatttcac agtcaccgga | 1020 |
| gaagggttgg agtatacctg ggaaaccat ccaccaaaaa gagtatggc tcaagagtca | 1080 |
| ggagaaggga atccacatgg atggccgcac gaagtggtag tctattacta caacaggtac | 1140 |
| ccgttaacca caattatcgg gcggccgcac ggcggaggta gcaaagactg cgaaatgaag | 1200 |
| cgcaccaccc tggatagccc tctgggcaag ctggaactgt ctgggtgcga acagggcctg | 1260 |
| cacgagatca agctgctggg caaaggaaca tctgccgccg acgccgtgga agtgcctgcc | 1320 |
| ccagccgccg tgctgggcgg accagagcca ctgatgcagg ccaccgcctg gctcaacgcc | 1380 |
| tactttcacc agcctgaggc catcgaggag ttccctgtgc agccctgca ccacccagtg | 1440 |
| ttccagcagg agagctttac cgccaggtg ctgtggaaac tgctgaaagt ggtgaagttc | 1500 |
| ggagaggtca tcagctacca gcagctggcc gccctggccg caatcccgc cgccaccgcc | 1560 |
| gccgtgaaaa ccgccctgag cggaaatccc gtgcccattc tgatcccctg ccaccggtg | 1620 |

```
gtgtctagct ctggcgccgt ggggggctac gagggcgggc tcgccgtgaa agagtggctg    1680
ctggcccacg agggccacag actgggcaag cctgggctgg gtcctgcagg tataggcgcg    1740
ccagggtccc tggagcatca tcatcatcat cattgatgac gggccc                   1786
```

<210> SEQ ID NO 76
<211> LENGTH: 573
<212> TYPE: PRT
<213> ORGANISM: artificial
<220> FEATURE:
<223> OTHER INFORMATION: Amino acid sequence of the fusion protein [sE2 from Eastern Equine Encephalitis -SNAPlike-Histag]

<400> SEQUENCE: 76

```
Arg Ser Asp Leu Asp Thr His Phe Thr Gln Tyr Lys Leu Ala Arg Pro
1               5                   10                  15

Tyr Ile Ala Asp Cys Pro Asn Cys Gly His Ser Arg Cys Asp Ser Pro
            20                  25                  30

Ile Ala Ile Glu Glu Val Arg Gly Asp Ala His Ala Gly Val Ile Arg
        35                  40                  45

Ile Gln Thr Ser Ala Met Phe Gly Leu Lys Thr Asp Gly Val Asp Leu
    50                  55                  60

Ala Tyr Met Ser Phe Met Asn Gly Lys Thr Gln Lys Ser Ile Lys Ile
65                  70                  75                  80

Asp Asn Leu His Val Arg Thr Ser Ala Pro Cys Ser Leu Val Ser His
                85                  90                  95

His Gly Tyr Tyr Ile Leu Ala Gln Cys Pro Pro Gly Asp Thr Val Thr
            100                 105                 110

Val Gly Phe His Asp Gly Pro Asn Arg His Thr Cys Thr Val Ala His
        115                 120                 125

Lys Val Glu Phe Arg Pro Val Gly Arg Glu Lys Tyr Arg His Pro Pro
    130                 135                 140

Glu His Gly Val Glu Leu Pro Cys Asn Arg Tyr Thr His Lys Arg Ala
145                 150                 155                 160

Asp Gln Gly His Tyr Val Glu Met His Gln Pro Gly Leu Val Ala Asp
                165                 170                 175

His Ser Leu Leu Ser Ile His Ser Ala Lys Val Lys Ile Thr Val Pro
            180                 185                 190

Ser Gly Ala Gln Val Lys Tyr Tyr Cys Lys Cys Pro Asp Val Arg Glu
        195                 200                 205

Gly Ile Thr Ser Ser Asp His Thr Thr Thr Cys Thr Asp Val Lys Gln
    210                 215                 220

Cys Arg Ala Tyr Leu Ile Asp Asn Lys Lys Trp Val Tyr Asn Ser Gly
225                 230                 235                 240

Arg Leu Pro Arg Gly Glu Gly Asp Thr Phe Lys Gly Lys Leu His Val
                245                 250                 255

Pro Phe Val Pro Val Lys Ala Lys Cys Ile Ala Thr Leu Ala Pro Glu
            260                 265                 270

Pro Leu Val Glu His Lys His Arg Thr Leu Ile Leu His Leu His Pro
        275                 280                 285

Asp His Pro Thr Leu Leu Thr Thr Arg Ser Leu Gly Ser Asp Ala Asn
    290                 295                 300

Pro Thr Arg Gln Trp Ile Glu Arg Pro Thr Thr Val Asn Phe Thr Val
305                 310                 315                 320

Thr Gly Glu Gly Leu Glu Tyr Thr Trp Gly Asn His Pro Pro Lys Arg
```

```
              325                 330                 335
Val Trp Ala Gln Glu Ser Gly Glu Gly Asn Pro His Gly Trp Pro His
            340                 345                 350
Glu Val Val Tyr Tyr Asn Arg Tyr Pro Leu Thr Thr Ile Ile
        355                 360                 365
Gly Arg Pro His Gly Gly Ser Lys Asp Cys Glu Met Lys Arg Thr
    370                 375                 380
Thr Leu Asp Ser Pro Leu Gly Lys Leu Glu Leu Ser Gly Cys Glu Gln
385                 390                 395                 400
Gly Leu His Glu Ile Lys Leu Leu Gly Lys Gly Thr Ser Ala Ala Asp
                405                 410                 415
Ala Val Glu Val Pro Ala Pro Ala Ala Val Leu Gly Gly Pro Glu Pro
            420                 425                 430
Leu Met Gln Ala Thr Ala Trp Leu Asn Ala Tyr Phe His Gln Pro Glu
            435                 440                 445
Ala Ile Glu Glu Phe Pro Val Pro Ala Leu His His Pro Val Phe Gln
450                 455                 460
Gln Glu Ser Phe Thr Arg Gln Val Leu Trp Lys Leu Leu Lys Val Val
465                 470                 475                 480
Lys Phe Gly Glu Val Ile Ser Tyr Gln Gln Leu Ala Ala Leu Ala Gly
                485                 490                 495
Asn Pro Ala Ala Thr Ala Ala Val Lys Thr Ala Leu Ser Gly Asn Pro
                500                 505                 510
Val Pro Ile Leu Ile Pro Cys His Arg Val Val Ser Ser Ser Gly Ala
            515                 520                 525
Val Gly Gly Tyr Glu Gly Gly Leu Ala Val Lys Glu Trp Leu Leu Ala
        530                 535                 540
His Glu Gly His Arg Leu Gly Lys Pro Gly Leu Gly Pro Ala Gly Ile
545                 550                 555                 560
Gly Ala Pro Gly Ser Leu Glu His His His His His His
                565                 570

<210> SEQ ID NO 77
<211> LENGTH: 1792
<212> TYPE: DNA
<213> ORGANISM: artificial
<220> FEATURE:
<223> OTHER INFORMATION: DNA sequence encoding ssBiP-sE2 from Venezuelan
      Equine Encephalitis virus -SNAPlike-Histag for expression in S2
      cells

<400> SEQUENCE: 77
atgaagttat gcatattact ggccgtcgtg gcctttgttg gcctctcgct cgggagatct      60
agatcttcta ccgaggagct gtttaaggag tataagctaa cgcgccctta catgccaga     120 tgcatcagat gtgccgttgg gagctgccat agtccaatag caattgaggc agtgaagagc     180
gacgggcacg acggctatgt tagacttcag acttcctcgc agtatggcct ggattcctct     240
ggcaacttaa agggaaggac tatgcggtat gatatgcacg ggaccattga agagatacca     300
ctacatcaag tgtcactcca cacatctcgc ccgtgtcaca ttgtggatgg catggttat     360 tttctgcttg ctaggtgccc ggcagggac tccatcacca tggaatttaa gaaaggttca     420
gtcacacact cctgctcagt gccgtatgaa gtgaaattta atcctgtagg cagagaactc     480
tacactcatc caccagaaca cggagcagag caagcgtgcc aagtctacgc gcacgatgca     540
cagaacagag gagcttatgt cgagatgcac ctcccgggct cagaagtgga cagcagtttg     600
```

```
atttccttga gcggcagttc agtcaccgtg cacctcctg tcgggactag cgccttggtg      660
aaatgcaagt gcggcggcac aaagatctcc gaaaccatca acaaggcaaa acagttcagc    720
cagtgcacaa agaaggagca gtgcagagca tatcgactgc agaatgacaa gtgggtgtat    780
aattctgaca aactgcccaa agcagcggga gccacccta aaggaaaact acacgtcccg     840
ttcttgctgg cagacggcaa atgcaccgtg cctctagcac cggaacctat gataaccttc    900
ggtttccgat cagtgtcact gaaactgcac cctaagaatc ccacatatct gaccactcgc    960
caacttgctg atgagcctca ttacacgcac gagctcatat ctgaaccagc tgttaggaat   1020
tttaccgtca ctgaaaaggg gtgggagttt gtatggggaa accatccgcc gaaaaggttt   1080
tgggcacagg aaacagcacc cggaaatcca catgggctgc acatgaggt gataactcat    1140 tattaccaca gataccctat gtccacgcgg ccgcacggcg gaggtagcaa agactgcgaa   1200
atgaagcgca ccaccctgga tagccctctg ggcaagctgg aactgtctgg gtgcgaacag   1260
ggcctgcacg agatcaagct gctgggcaaa ggaacatctg ccgccgacgc cgtggaagtg   1320
cctgccccag ccgccgtgct gggcggacca gagccactga tgcaggccac cgcctggctc   1380
aacgcctact tcaccagcc tgaggccatc gaggagttcc ctgtgccagc cctgcaccac   1440
ccagtgttcc agcaggagag ctttacccgc caggtgctgt ggaaactgct gaaagtggtg   1500
aagttcggag aggtcatcag ctaccagcag ctggccgccc tggccggcaa tcccgccgcc   1560
accgccgccg tgaaaaccgc cctgagcgga atcccgtgc ccattctgat ccctgccac     1620 cgggtggtgt ctagctctgg cgccgtgggg ggctacgagg gcgggctcgc cgtgaaagag   1680
tggctgctgg cccacgaggg ccacagactg ggcaagcctg ggctgggtcc tgcaggtata   1740
ggcgcgccag ggtccctgga gcatcatcat catcatcatt gatgacgggc cc           1792
```

<210> SEQ ID NO 78
<211> LENGTH: 575
<212> TYPE: PRT
<213> ORGANISM: artificial
<220> FEATURE:
<223> OTHER INFORMATION: Amino acid sequence of the fusion protein [sE2 from Venezuelan Equine Encephalitis -SNAPlike-Histag]

<400> SEQUENCE: 78

```
Arg Ser Arg Ser Ser Thr Glu Glu Leu Phe Lys Glu Tyr Lys Leu Thr
1               5                  10                  15

Arg Pro Tyr Met Ala Arg Cys Ile Arg Cys Ala Val Gly Ser Cys His
                20                  25                  30

Ser Pro Ile Ala Ile Glu Ala Val Lys Ser Asp Gly His Asp Gly Tyr
            35                  40                  45

Val Arg Leu Gln Thr Ser Ser Gln Tyr Gly Leu Asp Ser Ser Gly Asn
        50                  55                  60

Leu Lys Gly Arg Thr Met Arg Tyr Asp Met His Gly Thr Ile Glu Glu
65                  70                  75                  80

Ile Pro Leu His Gln Val Ser Leu His Thr Ser Arg Pro Cys His Ile
                85                  90                  95

Val Asp Gly His Gly Tyr Phe Leu Leu Ala Arg Cys Pro Ala Gly Asp
            100                 105                 110

Ser Ile Thr Met Glu Phe Lys Lys Gly Ser Val Thr His Ser Cys Ser
        115                 120                 125

Val Pro Tyr Glu Val Lys Phe Asn Pro Val Gly Arg Glu Leu Tyr Thr
    130                 135                 140

His Pro Pro Glu His Gly Ala Glu Gln Ala Cys Gln Val Tyr Ala His
```

```
            145                 150                 155                 160
        Asp Ala Gln Asn Arg Gly Ala Tyr Val Glu Met His Leu Pro Gly Ser
                        165                 170                 175
        Glu Val Asp Ser Ser Leu Ile Ser Leu Ser Gly Ser Ser Val Thr Val
                        180                 185                 190
        Thr Pro Pro Val Gly Thr Ser Ala Leu Val Lys Cys Lys Cys Gly Gly
                        195                 200                 205
        Thr Lys Ile Ser Glu Thr Ile Asn Lys Ala Lys Gln Phe Ser Gln Cys
                        210                 215                 220
        Thr Lys Lys Glu Gln Cys Arg Ala Tyr Arg Leu Gln Asn Asp Lys Trp
        225                 230                 235                 240
        Val Tyr Asn Ser Asp Lys Leu Pro Lys Ala Gly Ala Thr Leu Lys
                        245                 250                 255
        Gly Lys Leu His Val Pro Phe Leu Leu Ala Asp Gly Lys Cys Thr Val
                        260                 265                 270
        Pro Leu Ala Pro Glu Pro Met Ile Thr Phe Gly Phe Arg Ser Val Ser
                        275                 280                 285
        Leu Lys Leu His Pro Lys Asn Pro Thr Tyr Leu Thr Thr Arg Gln Leu
                        290                 295                 300
        Ala Asp Glu Pro His Tyr Thr His Glu Leu Ile Ser Glu Pro Ala Val
        305                 310                 315                 320
        Arg Asn Phe Thr Val Thr Glu Lys Gly Trp Glu Phe Val Trp Gly Asn
                        325                 330                 335
        His Pro Pro Lys Arg Phe Trp Ala Gln Glu Thr Ala Pro Gly Asn Pro
                        340                 345                 350
        His Gly Leu Pro His Glu Val Ile Thr His Tyr Tyr His Arg Tyr Pro
                        355                 360                 365
        Met Ser Thr Arg Pro His Gly Gly Ser Lys Asp Cys Glu Met Lys
                        370                 375                 380
        Arg Thr Thr Leu Asp Ser Pro Leu Gly Lys Leu Glu Leu Ser Gly Cys
        385                 390                 395                 400
        Glu Gln Gly Leu His Glu Ile Lys Leu Leu Gly Lys Gly Thr Ser Ala
                        405                 410                 415
        Ala Asp Ala Val Glu Val Pro Ala Pro Ala Ala Val Leu Gly Gly Pro
                        420                 425                 430
        Glu Pro Leu Met Gln Ala Thr Ala Trp Leu Asn Ala Tyr Phe His Gln
                        435                 440                 445
        Pro Glu Ala Ile Glu Glu Phe Pro Val Pro Ala Leu His His Pro Val
                        450                 455                 460
        Phe Gln Gln Glu Ser Phe Thr Arg Gln Val Leu Trp Lys Leu Leu Lys
        465                 470                 475                 480
        Val Val Lys Phe Gly Glu Val Ile Ser Tyr Gln Gln Leu Ala Ala Leu
                        485                 490                 495
        Ala Gly Asn Pro Ala Ala Thr Ala Ala Val Lys Thr Ala Leu Ser Gly
                        500                 505                 510
        Asn Pro Val Pro Ile Leu Ile Pro Cys His Arg Val Val Ser Ser Ser
                        515                 520                 525
        Gly Ala Val Gly Gly Tyr Glu Gly Gly Leu Ala Val Lys Glu Trp Leu
                        530                 535                 540
        Leu Ala His Glu Gly His Arg Leu Gly Lys Pro Gly Leu Gly Pro Ala
        545                 550                 555                 560
        Gly Ile Gly Ala Pro Gly Ser Leu Glu His His His His His His
                        565                 570                 575
```

<210> SEQ ID NO 79
<211> LENGTH: 1442
<212> TYPE: DNA
<213> ORGANISM: artificial
<220> FEATURE:
<223> OTHER INFORMATION: DNA sequence encoding ssBiP- SNAPlike-Akabane N
    protein-proTEV cleavage site-Histag for expression in S2 cells

<400> SEQUENCE: 79

```
atgaagttat gcatattact ggccgtcgtg gtggcctttg ttggcctctc gctcgggaga      60
tctgacaaag actgcgaaat gaaaagaact acattggatt caccacttgg aagttggaa     120
ctgagtggat gcgagcaagg attgcatgaa attaagctac tgggaaaagg aacttctgct    180
gctgatgcag ttgaagttcc agcaccagca gctgttcttg aggtcctga gcccctcatg     240
caagccacag cctggcttaa cgcatatttc caccagcctg aggccattga ggaatttcca    300
gtccccgccc ttcaccatcc tgtgtttcag caggagagct tcacccgcca ggtcctgtgg    360
aaattgctga aggtggtcaa gtttggtgaa gtgatttcat atcagcaact tgctgcattg    420
gccggtaacc cgcagctac agctgccgtg aaaactgctc tcagcggaaa tcctgtgccc     480
atcctgatcc cttgtcacag agtcgtttca tcttccggag ctgtaggtgg ctatgaagga    540
ggactggcag ttaaggagtg gctgctggct catgaaggtc atagacttgg aaagcctggg    600
ctgggtcctg ctggtatagg cgcgccaggg tccctaggtg gcggatccga aaacctgtac    660
ttccagagcg atatcgcaaa tcaatttatt ttcaacgatg ttccacaacg gaatgcagct    720
acatttaatc cggatgcagg gtatgtggca tttatcagta agtatgggca gcagctcaac    780
tttactgttg ctagagtctt cttcctcaac cagaagaagg ccaagatggt cttacataag    840
acgccacaac caagtgtcga tcttactttt gcaggggtca aatttacagt ggttaataac    900
cattttcccc agtatactgc aaatccggtg tcagacactg cctttacgct ccatcgcatc    960
tcgggctact agctcgatgg gttgctgag cagtgcaagg ctaatcagat caaacttgca    1020
gaggcagctg ctacaatcgt aatgccgctg gctgaagtga agggctgcac ctggagtgat   1080
gggtacgcaa tgtacctagg cttgccccct ggtgctgaga tgtttctgga aacctttgag   1140
ttttacccat tggttattga catgcaccgt gtgataaagg atgggatgga tgtcaacttc   1200
atgaggaagg tcttacgcca gagatatggg cagctgactg cagaagaatg gatgacatct   1260
aagttggacg cagtcaaggc tgcatttagc tcagttgccc aaatatcctg gccaaatct   1320
ggcttctcac ctgcagctag agcttttcctg gctcaattg gtattcagat cccgggagag   1380
aatctatatt ttcaagggcc cggcggaggt agtcaccatc atcaccatca ctaatgaccg   1440
gt                                                                  1442
```

<210> SEQ ID NO 80
<211> LENGTH: 458
<212> TYPE: PRT
<213> ORGANISM: artificial
<220> FEATURE:
<223> OTHER INFORMATION: Amino acid sequence of fusion protein
    [SNAPlike-Akabane N protein-Histag]

<400> SEQUENCE: 80

```
Arg

```
Lys Leu Leu Gly Lys Gly Thr Ser Ala Ala Asp Ala Val Glu Val Pro
            35                  40                  45
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Leu Lys Val Val Lys Phe Gly Glu Val
            100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
130                 135                 140
Pro Cys His Arg Val Val Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Gly Ser Glu Asn Leu Tyr Phe Gln Ser Asp Ile Ala Asn
            195                 200                 205
Gln Phe Ile Phe Asn Asp Val Pro Gln Arg Asn Ala Ala Thr Phe Asn
            210                 215                 220
Pro Asp Ala Gly Tyr Val Ala Phe Ile Ser Lys Tyr Gly Gln Gln Leu
225                 230                 235                 240
Asn Phe Thr Val Ala Arg Val Phe Phe Leu Asn Gln Lys Lys Ala Lys
                245                 250                 255
Met Val Leu His Lys Thr Pro Gln Pro Ser Val Asp Leu Thr Phe Ala
                260                 265                 270
Gly Val Lys Phe Thr Val Val Asn Asn His Phe Pro Gln Tyr Thr Ala
            275                 280                 285
Asn Pro Val Ser Asp Thr Ala Phe Thr Leu His Arg Ile Ser Gly Tyr
            290                 295                 300
Leu Ala Arg Trp Val Ala Glu Gln Cys Lys Ala Asn Gln Ile Lys Leu
305                 310                 315                 320
Ala Glu Ala Ala Ala Thr Ile Val Met Pro Leu Ala Glu Val Lys Gly
                325                 330                 335
Cys Thr Trp Ser Asp Gly Tyr Ala Met Tyr Leu Gly Phe Ala Pro Gly
                340                 345                 350
Ala Glu Met Phe Leu Glu Thr Phe Glu Phe Tyr Pro Leu Val Ile Asp
            355                 360                 365
Met His Arg Val Ile Lys Asp Gly Met Asp Val Asn Phe Met Arg Lys
            370                 375                 380
Val Leu Arg Gln Arg Tyr Gly Gln Leu Thr Ala Glu Glu Trp Met Thr
385                 390                 395                 400
Ser Lys Leu Asp Ala Val Lys Ala Ala Phe Ser Ser Val Ala Gln Ile
                405                 410                 415
Ser Trp Ala Lys Ser Gly Phe Ser Pro Ala Ala Arg Ala Phe Leu Ala
            420                 425                 430
Gln Phe Gly Ile Gln Ile Pro Gly Glu Asn Leu Tyr Phe Gln Gly Pro
            435                 440                 445
Gly Gly Gly Ser His His His His His His
```

<210> SEQ ID NO 81
<211> LENGTH: 1451
<212> TYPE: DNA
<213> ORGANISM: artificial
<220> FEATURE:
<223> OTHER INFORMATION: DNA sequence encoding ssBiP- SNAPlike-Aino N
      protein-proTEV cleavage site-Histag for expression in S2 cells

<400> SEQUENCE: 81

```
atgaagttat gcatattact ggccgtcgtg gtggcctttg ttggcctctc gctcgggaga        60
tctagatctg acaaagactg cgaaatgaaa agaactacta tggattcacc acttgggaag      120
ttggaactga gtggatgcga gcaaggattg catgaaatta agctactggg aaaaggaact      180
tctgctgctg atgcagttga agttccagca ccagcagctg ttcttggagg tcctgagccc      240
ctcatgcaag ccacagcctg gcttaacgca tatttccacc agcctgaggc cattgaggaa      300
tttccagtcc ccgcccttca ccatcctgtg tttcagcagg agagcttcac ccgccaggtc      360
ctgtggaaat gctgaaggt ggtcaagttt ggtgaagtga tttcatatca gcaacttgct       420
gcattggccg taaccccgc agctacagct gccgtgaaaa ctgctctcag cggaaatcct       480
gtgcccatcc tgatcccttg tcacagagtc gtttcatctt ccggagctgt aggtggctat      540
gaaggaggac tggcagttaa ggagtggctg ctggctcatg aaggtcatag acttggaaag      600
cctgggctgg tcctgctgg tataggcgcg ccagggtccc taggtggcgg atccgaaaac      660
ctgtacttcc agagcgatat cgcaaaccaa tttattttcc aagatgttcc tcaacggaat      720
ctcgctacat ttaacccgga ggtcgggtat gtggcattta ttgctaaaca tgggtcccaa      780
ctcaatttcg ataccgttag agtcttcttc ctcaatcaga gaaaggccaa gatggtgctc      840
agtaagacgg cacaaccaag tgttgatctt acatttggtg gcatcaaatt tacactggtt      900
aataaccatt tccccaata cacagcaaat cctgtgccag acactgccct cactctccac      960
cgtctctcag gttatctagc aaaatgggtt gcagaccaat gcaaaacaaa tcagattaaa    1020
ctggctgagg ccatggaaaa aattgtcatg ccacttgctg aagtgaaagg ttgcacctgg     1080
actgaaggac tgactatgta tctgggattt gcaccaggcg ctgaaatgtt tttagaaaca     1140
tttgagttct acccttttggt tattgacatg cacagagtgc tgaaagatgg aatggatgtc    1200
aactttatga gaaaggtcct tcgccagcgc tatggcacat tgactgcaga acagtggatg     1260
actcaaaaaa tagatgctgt ccgtgcagcc ttcaatgctg ttgggcagct aagttgggct     1320 aaaatcaggat tctcaccagc tgccagagcc ttccttgccc aattcggcat aaacatgatc    1380
ccgggagaga atctatattt tcaagggccc ggcggaggta gtcaccatca tcaccatcac    1440
taatgaccgg t                                                           1451
```

<210> SEQ ID NO 82
<211> LENGTH: 459
<212> TYPE: PRT
<213> ORGANISM: artificial
<220> FEATURE:
<223> OTHER INFORMATION: Amino acid sequence of fusion protein
      [SNAPlike-Aino N protein-Histag]

<400> SEQUENCE: 82

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

```
Lys Leu Leu Gly Lys Gly Thr Ser Ala Ala Asp Ala Val Glu Val Pro
         35                  40                  45

Ala Pro Ala Ala Val Leu Gly Gly Pro Glu Pro Leu Met Gln Ala Thr
     50                  55                  60

Ala Trp Leu Asn Ala Tyr Phe His Gln Pro Glu Ala Ile Glu Glu Phe
 65                  70                  75                  80

Pro Val Pro Ala Leu His His Pro Val Phe Gln Gln Glu Ser Phe Thr
                 85                  90                  95

Arg Gln Val Leu Trp Lys Leu Leu Lys Val Val Lys Phe Gly Glu Val
             100                 105                 110

Ile Ser Tyr Gln Gln Leu Ala Ala Leu Ala Gly Asn Pro Ala Ala Thr
             115                 120                 125

Ala Ala Val Lys Thr Ala Leu Ser Gly Asn Pro Val Pro Ile Leu Ile
         130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Gly His Arg
             165                 170                 175

Leu Gly Lys Pro Gly Leu Gly Pro Ala Gly Ile Gly Ala Pro Gly Ser
             180                 185                 190

Leu Gly Gly Gly Ser Glu Asn Leu Tyr Phe Gln Ser Asp Ile Ala Asn
             195                 200                 205

Gln Phe Ile Phe Gln Asp Val Pro Gln Arg Asn Leu Ala Thr Phe Asn
             210                 215                 220

Pro Glu Val Gly Tyr Val Ala Phe Ile Ala Lys His Gly Ser Gln Leu
225                 230                 235                 240

Asn Phe Asp Thr Val Arg Val Phe Phe Leu Asn Gln Lys Lys Ala Lys
                 245                 250                 255

Met Val Leu Ser Lys Thr Ala Gln Pro Ser Val Asp Leu Thr Phe Gly
             260                 265                 270

Gly Ile Lys Phe Thr Leu Val Asn Asn His Phe Pro Gln Tyr Thr Ala
             275                 280                 285

Asn Pro Val Pro Asp Thr Ala Leu Thr Leu His Arg Leu Ser Gly Tyr
         290                 295                 300

Leu Ala Lys Trp Val Ala Asp Gln Cys Lys Thr Asn Gln Ile Lys Leu
305                 310                 315                 320

Ala Glu Ala Met Glu Lys Ile Val Met Pro Leu Ala Glu Val Lys Gly
                 325                 330                 335

Cys Thr Trp Thr Glu Gly Leu Thr Met Tyr Leu Gly Phe Ala Pro Gly
             340                 345                 350

Ala Glu Met Phe Leu Glu Thr Phe Glu Phe Tyr Pro Leu Val Ile Asp
             355                 360                 365

Met His Arg Val Leu Lys Asp Gly Met Asp Val Asn Phe Met Arg Lys
370                 375                 380

Val Leu Arg Gln Arg Tyr Gly Thr Leu Thr Ala Glu Gln Trp Met Thr
385                 390                 395                 400

Gln Lys Ile Asp Ala Val Arg Ala Ala Phe Asn Ala Val Gly Gln Leu
             405                 410                 415

Ser Trp Ala Lys Ser Gly Phe Ser Pro Ala Ala Arg Ala Phe Leu Ala
             420                 425                 430

Gln Phe Gly Ile Asn Met Ile Pro Gly Glu Asn Leu Tyr Phe Gln Gly
             435                 440                 445
```

Pro Gly Gly Gly Ser His His His His His
    450                 455

<210> SEQ ID NO 83
<211> LENGTH: 1448
<212> TYPE: DNA
<213> ORGANISM: artificial
<220> FEATURE:
<223> OTHER INFORMATION: DNA sequence encoding ssBiP - SNAPlike-Shamonda
      N protein-proTEV cleavage site-Histag for expression in S2 cells

<400> SEQUENCE: 83

| | | | | |
|---|---|---|---|---|
| atgaagttat | gcatattact | ggccgtcgtg | gtggcctttg | ttggcctctc gctcgggaga | 60 |
| tctagatctg | acaaagactg | cgaaatgaaa | agaactacat | tggattcacc acttgggaag | 120 |
| ttggaactga | gtggatgcga | gcaaggattg | catgaaatta | agctactggg aaaaggaact | 180 |
| tctgctgctg | atgcagttga | agttccagca | ccagcagctg | ttcttggagg tcctgagccc | 240 |
| ctcatgcaag | ccacagcctg | gcttaacgca | tatttccacc | agcctgaggc cattgaggaa | 300 |
| tttccagtcc | ccgcccttca | ccatcctgtg | tttcagcagg | agagcttcac ccgccaggtc | 360 |
| ctgtggaaat | tgctgaaggt | ggtcaagttt | ggtgaagtga | tttcatatca gcaacttgct | 420 |
| gcattggccg | taaccccgc | agctacagct | gccgtgaaaa | ctgctctcag cggaaatcct | 480 |
| gtgcccatcc | tgatcccttg | tcacagagtc | gtttcatctt | ccggagctgt aggtggctat | 540 |
| gaaggaggac | tggcagttaa | ggagtggctg | ctggctcatg | aaggtcatag acttggaaag | 600 |
| cctgggctgg | gtcctgctgg | tataggcgcg | ccagggtccc | taggtggcgg atccgaaaac | 660 |
| ctgtacttcc | agagcgatat | ctcaagccaa | ttcattttg | aagatgtacc acaacggaat | 720 |
| gcagctacat | ttaacccgga | aggtgggtat | gtggcattta | ttggtaagta tgggcaacaa | 780 |
| ctcaatttcg | gggttgctaa | agtcttcttc | ctcaaccaga | agaaggccaa aatggtccta | 840 |
| cataagacgg | gacaaccaag | tgtcgatctt | acttttggtg | gggtcaaatt cacagtggtt | 900 |
| aataaccatt | tcccccaata | tgtctcaaat | cctgtgccag | acaatgccat tacacttcac | 960 |
| aggatgtcag | gttatctagc | acgctggatt | gctgatacat | gcaaggctag tgtcctcaaa | 1020 |
| ctagctgaag | ctagtgctca | aattgtcatg | ccccttgctg | aggttaaggg atgtacctgg | 1080 |
| gctgatggtt | atacaatgta | tcttggattt | gcacctgggg | ccgaaatgtt ccttgatgct | 1140 |
| tttgattttt | atccgctagt | tatcgaaatg | catagggtcc | ttaaggacaa tatggatgta | 1200 |
| aattttatga | aaaagtcct | ccgccaacgc | tatggaacaa | tgactgctga agaatggatg | 1260 |
| actcagaaaa | taccagaaat | aaaggctgct | ttcaattctg | ttggacaact tgcctgggct | 1320 |
| aaatctggat | tctctcctgc | tgctagaact | ttcttgcagc | aatttggtat caacatcccg | 1380 |
| ggagagaatc | tatattttca | agggcccggc | ggaggtagtc | accatcatca ccatcactaa | 1440 |
| tgaccggt | | | | | 1448 |

<210> SEQ ID NO 84
<211> LENGTH: 458
<212> TYPE: PRT
<213> ORGANISM: artificial
<220> FEATURE:
<223> OTHER INFORMATION: Amino acid sequence of fusion protein
      [SNAPlike-Shamonda N protein-Histag]

<400> SEQUENCE: 84

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile

```
            20                  25                  30
Lys Leu Leu Gly Lys Gly Thr Ser Ala Ala Asp Ala Val Glu Val Pro
             35                  40                  45
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Leu Lys Val Val Lys Phe Gly Glu Val
                100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
            130                 135                 140
Pro Cys His Arg Val Val Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Gly Ser Glu Asn Leu Tyr Phe Gln Ser Asp Ile Ser Ser
            195                 200                 205
Gln Phe Ile Phe Glu Asp Val Pro Gln Arg Asn Ala Ala Thr Phe Asn
            210                 215                 220
Pro Glu Gly Gly Tyr Val Ala Phe Ile Gly Lys Tyr Gly Gln Gln Leu
225                 230                 235                 240
Asn Phe Gly Val Ala Lys Val Phe Phe Leu Asn Gln Lys Lys Ala Lys
                245                 250                 255
Met Val Leu His Lys Thr Gly Gln Pro Ser Val Asp Leu Thr Phe Gly
                260                 265                 270
Gly Val Lys Phe Thr Val Val Asn Asn His Phe Pro Gln Tyr Val Ser
            275                 280                 285
Asn Pro Val Pro Asp Asn Ala Ile Thr Leu His Arg Met Ser Gly Tyr
            290                 295                 300
Leu Ala Arg Trp Ile Ala Asp Thr Cys Lys Ala Ser Val Leu Lys Leu
305                 310                 315                 320
Ala Glu Ala Ser Ala Gln Ile Val Met Pro Leu Ala Glu Val Lys Gly
                325                 330                 335
Cys Thr Trp Ala Asp Gly Tyr Thr Met Tyr Leu Gly Phe Ala Pro Gly
                340                 345                 350
Ala Glu Met Phe Leu Asp Ala Phe Asp Phe Tyr Pro Leu Val Ile Glu
            355                 360                 365
Met His Arg Val Leu Lys Asp Asn Met Asp Val Asn Phe Met Lys Lys
            370                 375                 380
Val Leu Arg Gln Arg Tyr Gly Thr Met Thr Ala Glu Glu Trp Met Thr
385                 390                 395                 400
Gln Lys Ile Pro Glu Ile Lys Ala Ala Phe Asn Ser Val Gly Gln Leu
                405                 410                 415
Ala Trp Ala Lys Ser Gly Phe Ser Pro Ala Arg Thr Phe Leu Gln
            420                 425                 430
Gln Phe Gly Ile Asn Ile Pro Gly Glu Asn Leu Tyr Phe Gln Gly Pro
            435                 440                 445
```

Gly Gly Gly Ser His His His His His
    450             455

<210> SEQ ID NO 85
<211> LENGTH: 1991
<212> TYPE: DNA
<213> ORGANISM: artificial
<220> FEATURE:
<223> OTHER INFORMATION: DNA sequence encoding ssBiP -SNAPlike-proTEV
      cleavage site-N protein from human betacoronavirus strain
      2cEMC/2012- Histag for expression in S2 cells

<400> SEQUENCE: 85

| | | |
|---|---|---|
| atgaagttat gcatattact ggccgtcgtg gtggcctttg ttggcctctc gctcgggaga | 60 |
| tctagatctg acaaagactg cgaaatgaaa agaactacat ggattcacc acttgggaag | 120 |
| ttggaactga gtggatgcga gcaaggattg catgaaatta gctactggg aaaaggaact | 180 |
| tctgctgctg atgcagttga agttccagcc ccagcagctg ttcttggagg tcctgagccc | 240 |
| ctcatgcaag ccacagcctg gcttaacgca tatttccacc agcctgaggc cattgaggaa | 300 |
| tttccagtcc ccgcccttca ccatcctgtg tttcagcagg agagcttcac ccgccaggtc | 360 |
| ctgtggaaat tgctgaaggt ggtcaagttt ggtgaagtga tttcatatca gcaacttgct | 420 |
| gcattggccg taaccccgc agctacagct gccgtgaaaa ctgctctcag cggaaatcct | 480 |
| gtgcccatcc tgatcccttg tcacagagtc gtttcatctt ccggagctgt aggtggctat | 540 |
| gaaggaggac tggcagttaa ggagtggctg ctggctcatg aaggtcatag acttggaaag | 600 |
| cctgggctgg gtcctgctgg tataggcgcg ccagggtccc taggtggcgg atccgaaaac | 660 |
| ctgtacttcc agagcgatat cgcatcccct gctgcacctc gtgctgtttc ctttgccgat | 720 |
| aacaatgata taacaaatac aaacctatct cgaggtagag acgtaatcc aaaaccacga | 780 |
| gctgcaccaa ataacactgt ctcttggtac actgggctta cccaacacgg aaagtccct | 840 |
| cttacctttc cacctgggca gggtgtacct cttaatgcca attctacccc tgcgcaaaat | 900 |
| gctgggtatt ggcggagaca ggacagaaaa attaataccg ggaatggaat taagcaactg | 960 |
| gctcccaggt ggtacttcta ctacactgga actggacccg aagcagcact cccattccgg | 1020 |
| gctgttaagg atggcatcgt ttgggtccat gaagatggcg ccactgatgc tccttcaact | 1080 |
| tttgggacgc ggaaccctaa caatgattca gctattgtta caaattcgc gcccggtact | 1140 |
| aaacttccta aaacttcca cattgagggg actggaggca atagtcaatc atcttcaaga | 1200 |
| gcctctagct taagcagaaa ctcttccagg tctagttcac aaggttcaag atcaggaaac | 1260 |
| tctacccgcg gcacttctcc aggtccatct ggaatcggag cagtaggagg tgatctactt | 1320 |
| taccttgatc ttctgaacag actacaagcc cttgagtctg gcaaagtaaa gcaatcgcag | 1380 |
| ccaaaagtaa tcactaagaa agatgctgct gctgctaaaa ataagatgcg ccacaagcgc | 1440 |
| acttccacca aagtttcaa catggtgcag gcttttggtc ttcgcggacc aggagacctc | 1500 |
| cagggaaact ttggtgatct tcaattgaat aaactcggca ctgaggaccc acgttggccc | 1560 |
| caaattgctg agcttgctcc tacagccagt gcttttatgg gtatgtcgca atttaaactt | 1620 |
| acccatcaga caatgatga tcatggcaac cctgtgtact ccttcggta cagtggagcc | 1680 |
| attaaacttg acccaaagaa tcccaactac aataagtggt tggagcttct tgagcaaaat | 1740 |
| attgatgcct acaaaacctt ccctaagaag gaaagaaac aaaaggcacc aaaagaagaa | 1800 |
| tcaacagacc aaatgtctga acctccaaag gagcagcgtg tgcaaggtag catcactcag | 1860 |
| cgcactcgca cccgtccaag tgttcagcct ggtccaatga ttgatgttaa cactgatggc | 1920 |

```
ccgggagaga atctatattt tcaagggccc ggcggaggta gtcaccatca t

| | | | | | | | | | | | | |
|---|---|---|---|---|---|---|---|---|---|---|---|---|
|Pro|Ser|Thr|Phe|Gly|Thr|Arg|Asn|Pro|Asn|Asn|Asp|Ser|Ala|Ile|Val|
| | | |340| | | |345| | | |350| |

Pro Ser Thr Phe Gly Thr Arg Asn Pro Asn Asn Asp Ser Ala Ile Val
            340                 345                 350

Thr Gln Phe Ala Pro Gly Thr Lys Leu Pro Lys Asn Phe His Ile Glu
        355                 360                 365

Gly Thr Gly Gly Asn Ser Gln Ser Ser Arg Ala Ser Ser Leu Ser
    370                 375                 380

Arg Asn Ser Ser Arg Ser Ser Gln Gly Ser Arg Ser Gly Asn Ser
385                 390                 395                 400

Thr Arg Gly Thr Ser Pro Gly Pro Ser Gly Ile Gly Ala Val Gly Gly
                405                 410                 415

Asp Leu Leu Tyr Leu Asp Leu Leu Asn Arg Leu Gln Ala Leu Glu Ser
            420                 425                 430

Gly Lys Val Lys Gln Ser Gln Pro Lys Val Ile Thr Lys Lys Asp Ala
        435                 440                 445

Ala Ala Ala Lys Asn Lys Met Arg His Lys Arg Thr Ser Thr Lys Ser
    450                 455                 460

Phe Asn Met Val Gln Ala Phe Gly Leu Arg Gly Pro Gly Asp Leu Gln
465                 470                 475                 480

Gly Asn Phe Gly Asp Leu Gln Leu Asn Lys Leu Gly Thr Glu Asp Pro
                485                 490                 495

Arg Trp Pro Gln Ile Ala Glu Leu Ala Pro Thr Ala Ser Ala Phe Met
            500                 505                 510

Gly Met Ser Gln Phe Lys Leu Thr His Gln Asn Asn Asp Asp His Gly
        515                 520                 525

Asn Pro Val Tyr Phe Leu Arg Tyr Ser Gly Ala Ile Lys Leu Asp Pro
    530                 535                 540

Lys Asn Pro Asn Tyr Asn Lys Trp Leu Glu Leu Leu Glu Gln Asn Ile
545                 550                 555                 560

Asp Ala Tyr Lys Thr Phe Pro Lys Lys Glu Lys Lys Gln Lys Ala Pro
                565                 570                 575

Lys Glu Glu Ser Thr Asp Gln Met Ser Glu Pro Lys Glu Gln Arg
            580                 585                 590

Val Gln Gly Ser Ile Thr Gln Arg Thr Arg Thr Arg Pro Ser Val Gln
        595                 600                 605

Pro Gly Pro Met Ile Asp Val Asn Thr Asp Gly Pro Gly Glu Asn Leu
    610                 615                 620

Tyr Phe Gln Gly Pro Gly Gly Ser His His His His His His
625                 630                 635

<210> SEQ ID NO 87
<211> LENGTH: 4465
<212> TYPE: DNA
<213> ORGANISM: artificial
<220> FEATURE:
<223> OTHER INFORMATION: DNA sequence encoding ssBiP- S protein from
      human betacoronavirus strain 2cEMC/2012- SNAPlike - Histag for
      expression in S2 cells

<400> SEQUENCE: 87
atgaagttat gcatattact ggccgtcgtg gtggcctttg ttggcctctc gctcgggaga      60
tctagatctg tagggccaga ttctgttaag tctgcttgta ttgaggttga tatacaacag     120
actttctttg ataaaacttg gcctaggcca attgatgttt ctaaggctga cggtattata     180
taccctcaag gccgtacata ttctaacata actatcactt atcaaggtct ttttccctat    240
cagggagacc atggtgatat gtatgtttac tctgcaggac atgctacagg cacaactcca    300

```
caaaagttgt ttgtagctaa ctattctcag gacgtcaaac agtttgctaa tgggtttgtc      360
gtccgtatag gagcagctgc caattccact ggcactgtta ttattagccc atctaccagc      420
gctactatac gaaaaattta ccctgctttt atgctgggtt cttcagttgg taatttctca      480
gatggtaaaa tgggccgctt cttcaatcat actctagttc ttttgcccga tggatgtggc      540
actttactta gagcttttta ttgtattcta gagcctcgct ctggaaatca ttgtcctgct      600
ggcaattcct atacttcttt tgccacttat cacactcctg caacagattg ttctgatggc      660
aattacaatc gtaatgccag tctgaactct tttaaggagt attttaattt acgtaactgc      720
acctttatgt acacttataa cattaccgaa gatgagattt tagagtggtt tggcattaca      780
caaactgctc aaggtgttca cctcttctca tctcggtatg ttgatttgta cggcggcaat      840
atgtttcaat ttgccacctt gcctgtttat gatactatta agtattattc tatcattcct      900
cacagtattc gttctatcca aagtgataga aaggcttggg ctgccttcta cgtatataaa      960
cttcaaccgt taactttcct gttggatttt tctgttgatg gttatatacg cagagctata     1020
gactgtggtt ttaatgattt gtcacaactc cactgctcat atgaatcctt cgatgttgaa     1080
tctggagttt attcagtttc gtctttcgaa gcaaaacctt ctggctcagt tgtggaacag     1140
gctgaaggtg ttgaatgtga ttttcacct cttctgtctg gcacacctcc tcaggtttat     1200
aatttcaagc gtttggtttt taccaattgc aattataatc ttaccaaatt gctttcactt     1260
ttttctgtga atgattttac ttgtagtcaa atatctccag cagcaattgc aagcaactgt     1320
tattcttcac tgatttttgga ttacttttca tacccactta gtatgaaatc cgatctcagt     1380
gttagttctg ctggtccaat atcccagttt aattataaac agtccttttc taatcccaca     1440
tgtttgattt tagcgactgt tcctcataac cttactacta ttactaagcc tcttaagtac     1500
agctatatta caagtgctc tcgtcttctt tctgatgatc gtactgaagt acctcagtta     1560
gtgaacgcta atcaatactc accctgtgta tccattgtcc catccactgt gtgggaagac     1620
ggtgattatt ataggaaaca actatctcca cttgaaggtg gtggctggct tgttgctagt     1680
ggctcaactg ttgccatgac tgagcaatta cagatgggct ttggtattac agttcaatat     1740
ggtacagaca ccaatagtgt ttgccccaag ctggaatttg ctaatgacac aaaaattgcc     1800
tctcaattag gcaattgcgt ggaatattcc ctctatggtg tttcgggccg tggtgttttt     1860
cagaattgca gagctgtagg tgttcgacag cagcgctttg tttatgatgc gtaccagaat     1920
ttagttggct attattctga tgatggcaac tactactgtt tgcgtgcttg tgttagtgtt     1980
cctgtttctg tcatctatga taaagaaact aaaaacccacg ctactctatt tggtagtgtt     2040
gcatgtgaac acatttcttc taccatgtct caatactccc gttctacgcg atcaatgctt     2100
aaacggcgag attctacata tggcccccctt cagacacctg ttggttgtgt cctaggactt     2160
gttaattcct ctttgttcgt agaggactgc aagttgcctc ttggtcaatc tctctgtgct     2220
cttcctgaca cacctagtac tctcacacct cgcagtgtgc gctctgttcc aggtgaaatg     2280
cgcttggcat ccattgcttt taatcatcct attcaggttg atcaacttaa tagtagttat     2340
tttaaattaa gtatacccac taattttttcc tttggtgtga ctcaggagta cattcagaca     2400
accattcaga aagttactgt tgattgtaaa cagtacgttt gcaatggttt ccagaagtgt     2460
gagcaattac tgcgcgagta tggccagttt tgttccaaaa taaaccaggc tctccatggt     2520
gccaatttac gccaggatga ttctgtacgt aatttgtttg cgagcgtgaa aagctctcaa     2580
tcatctccta tcataccagg ttttggaggt gactttaatt tgacacttct agaacctgtt     2640
tctatatcta ctggcagtcg tagtgcacgt agtgctattg aggatttgct atttgacaaa     2700
```

| | | |
|---|---|---|
| gtcactatag ctgatcctgg ttatatgcaa ggttacgatg attgcatgca gcaaggtcca | 2760 | |
| gcatcagctc gtgatcttat ttgtgctcaa tatgtggctg gttacaaagt attacctcct | 2820 | |
| cttatggatg ttaatatgga agccgcgtat acttcatctt tgcttggcag catagcaggt | 2880 | |
| gttggctgga ctgctggctt atcctccttt gctgctattc catttgcaca gagtatcttt | 2940 | |
| tataggttaa acgtgttgg cattactcaa caggttcttt cagagaacca aaagctcatt | 3000 | |
| gccaataagt ttaatcaggc tctgggagct atgcaaacag gcttcactac aactaatgaa | 3060 | |
| gcctttcaga aggttcagga tgctgtgaac aacaatgcac aggctctatc caaattagcg | 3120 | |
| agcgagctat ctaatacttt tggtgctatt tccgcctcta ttggagacat catacaacgt | 3180 | |
| cttgatgttc tcgaacagga cgcccaaata gacagactta ttaatggccg tttgacaaca | 3240 | |
| ctaaatgctt tgttgcaca gcagcttgtt cgttccgaat cagctgctct ttccgctcaa | 3300 | |
| ttggctaaag ataaagtcaa tgagtgtgtc aaggcacaat ccaagcgttc tggatttgc | 3360 | |
| ggtcaaggca cacatatagt gtcctttgtt gtaaatgccc ctaatggcct ttacttcatg | 3420 | |
| catgttggtt attaccctag caaccacatt gaggttgttt ctgcttatgg tctttgcgat | 3480 | |
| gcagctaacc ctactaattg tatagccct gttaatggct actttattaa aactaataac | 3540 | |
| actaggattg ttgatgagtg gtcatatact ggctcgtcct tctatgcacc tgagcccatt | 3600 | |
| acctccctta atactaagta tgttgcacca caggtgacat accaaaacat ttctactaac | 3660 | |
| ctccctcctc ctcttctcgg caattccacc gggattgact tccaagatga gttggatgag | 3720 | |
| ttttttcaaaa atgttagcac cagtatacct aattttggtt ccctaacaca gattaatact | 3780 | |
| acattactcg atcttaccta cgagatgttg tctcttcaac aagttgttaa agcccttaag | 3840 | |
| cggccgcacg gcggaggtag caaagactgc gaaatgaagc gcaccaccct ggatagccct | 3900 | |
| ctgggcaagc tggaactgtc tgggtgcgaa cagggcctgc acgagatcaa gctgctgggc | 3960 | |
| aaaggaacat ctgccgccga cgccgtggaa gtgcctgccc cagccgccgt gctgggcgga | 4020 | |
| ccagagccac tgatgcaggc caccgcctgg ctcaacgcct actttcacca gcctgaggcc | 4080 | |
| atcgaggagt ccctgtgcc agccctgcac cacccagtgt tccagcagga gagctttacc | 4140 | |
| cgccaggtgc tgtggaaact gctgaaagtg gtgaagttcg agaggtcat cagctaccag | 4200 | |
| cagctggccg ccctggccgg caatcccgcc gccaccgccg ccgtgaaaac cgccctgagc | 4260 | |
| ggaaatcccg tgcccattct gatccctgc caccgggtgg tgtctagctc tggcgccgtg | 4320 | |
| gggggctacg agggcgggct cgccgtgaaa gagtggctgc tggcccacga gggccacaga | 4380 | |
| ctgggcaagc tgggctggg tcctgcaggt ataggcgcgc agggtccct ggagcatcat | 4440 | |
| catcatcatc attgatgacg ggccc | 4465 | |

<210> SEQ ID NO 88
<211> LENGTH: 1463
<212> TYPE: PRT
<213> ORGANISM: artificial
<220> FEATURE:
<223> OTHER INFORMATION: Amino acid sequence of fusion protein [huCOV.S protein -SNAPlike-Histag]

<400> SEQUENCE: 88

```
Arg Ser Val Gly Pro Asp Ser Val Lys Ser Ala Cys Ile Glu Val Asp
1               5                   10                  15

Ile Gln Gln Thr Phe Phe Asp Lys Thr Trp Pro Arg Pro Ile Asp Val
            20                  25                  30

Ser Lys Ala Asp Gly Ile Ile Tyr Pro Gln Gly Arg Thr Tyr Ser Asn
```

-continued

```
                35                  40                  45
Ile Thr Ile Thr Tyr Gln Gly Leu Phe Pro Tyr Gln Gly Asp His Gly
 50                  55                  60
Asp Met Tyr Val Tyr Ser Ala Gly His Ala Thr Gly Thr Thr Pro Gln
 65                  70                  75                  80
Lys Leu Phe Val Ala Asn Tyr Ser Gln Asp Val Lys Gln Phe Ala Asn
                 85                  90                  95
Gly Phe Val Val Arg Ile Gly Ala Ala Ala Asn Ser Thr Gly Thr Val
                100                 105                 110
Ile Ile Ser Pro Ser Thr Ser Ala Thr Ile Arg Lys Ile Tyr Pro Ala
                115                 120                 125
Phe Met Leu Gly Ser Ser Val Gly Asn Phe Ser Asp Gly Lys Met Gly
130                 135                 140
Arg Phe Phe Asn His Thr Leu Val Leu Leu Pro Asp Gly Cys Gly Thr
145                 150                 155                 160
Leu Leu Arg Ala Phe Tyr Cys Ile Leu Glu Pro Arg Ser Gly Asn His
                165                 170                 175
Cys Pro Ala Gly Asn Ser Tyr Thr Ser Phe Ala Thr Tyr His Thr Pro
                180                 185                 190
Ala Thr Asp Cys Ser Asp Gly Asn Tyr Asn Arg Asn Ala Ser Leu Asn
                195                 200                 205
Ser Phe Lys Glu Tyr Phe Asn Leu Arg Asn Cys Thr Phe Met Tyr Thr
210                 215                 220
Tyr Asn Ile Thr Glu Asp Glu Ile Leu Glu Trp Phe Gly Ile Thr Gln
225                 230                 235                 240
Thr Ala Gln Gly Val His Leu Phe Ser Ser Arg Tyr Val Asp Leu Tyr
                245                 250                 255
Gly Gly Asn Met Phe Gln Phe Ala Thr Leu Pro Val Tyr Asp Thr Ile
                260                 265                 270
Lys Tyr Tyr Ser Ile Ile Pro His Ser Ile Arg Ser Ile Gln Ser Asp
                275                 280                 285
Arg Lys Ala Trp Ala Ala Phe Tyr Val Tyr Lys Leu Gln Pro Leu Thr
290                 295                 300
Phe Leu Leu Asp Phe Ser Val Asp Gly Tyr Ile Arg Arg Ala Ile Asp
305                 310                 315                 320
Cys Gly Phe Asn Asp Leu Ser Gln Leu His Cys Ser Tyr Glu Ser Phe
                325                 330                 335
Asp Val Glu Ser Gly Val Tyr Ser Val Ser Ser Phe Glu Ala Lys Pro
                340                 345                 350
Ser Gly Ser Val Val Glu Gln Ala Glu Gly Val Glu Cys Asp Phe Ser
                355                 360                 365
Pro Leu Leu Ser Gly Thr Pro Pro Gln Val Tyr Asn Phe Lys Arg Leu
                370                 375                 380
Val Phe Thr Asn Cys Asn Tyr Asn Leu Thr Lys Leu Leu Ser Leu Phe
385                 390                 395                 400
Ser Val Asn Asp Phe Thr Cys Ser Gln Ile Ser Pro Ala Ala Ile Ala
                405                 410                 415
Ser Asn Cys Tyr Ser Ser Leu Ile Leu Asp Tyr Phe Ser Tyr Pro Leu
                420                 425                 430
Ser Met Lys Ser Asp Leu Ser Val Ser Ser Ala Gly Pro Ile Ser Gln
                435                 440                 445
Phe Asn Tyr Lys Gln Ser Phe Ser Asn Pro Thr Cys Leu Ile Leu Ala
                450                 455                 460
```

```
Thr Val Pro His Asn Leu Thr Ile Thr Lys Pro Leu Lys Tyr Ser
465                 470                 475                 480

Tyr Ile Asn Lys Cys Ser Arg Leu Leu Ser Asp Asp Arg Thr Glu Val
            485                 490                 495

Pro Gln Leu Val Asn Ala Asn Gln Tyr Ser Pro Cys Val Ser Ile Val
        500                 505                 510

Pro Ser Thr Val Trp Glu Asp Gly Asp Tyr Tyr Arg Lys Gln Leu Ser
        515                 520                 525

Pro Leu Glu Gly Gly Gly Trp Leu Val Ala Ser Gly Ser Thr Val Ala
        530                 535                 540

Met Thr Glu Gln Leu Gln Met Gly Phe Gly Ile Thr Val Gln Tyr Gly
545                 550                 555                 560

Thr Asp Thr Asn Ser Val Cys Pro Lys Leu Glu Phe Ala Asn Asp Thr
            565                 570                 575

Lys Ile Ala Ser Gln Leu Gly Asn Cys Val Glu Tyr Ser Leu Tyr Gly
            580                 585                 590

Val Ser Gly Arg Gly Val Phe Gln Asn Cys Thr Ala Val Gly Val Arg
            595                 600                 605

Gln Gln Arg Phe Val Tyr Asp Ala Tyr Gln Asn Leu Val Gly Tyr Tyr
610                 615                 620

Ser Asp Asp Gly Asn Tyr Tyr Cys Leu Arg Ala Cys Val Ser Val Pro
625                 630                 635                 640

Val Ser Val Ile Tyr Asp Lys Glu Thr Lys Thr His Ala Thr Leu Phe
            645                 650                 655

Gly Ser Val Ala Cys Glu His Ile Ser Ser Thr Met Ser Gln Tyr Ser
            660                 665                 670

Arg Ser Thr Arg Ser Met Leu Lys Arg Arg Asp Ser Thr Tyr Gly Pro
            675                 680                 685

Leu Gln Thr Pro Val Gly Cys Val Leu Gly Leu Val Asn Ser Ser Leu
        690                 695                 700

Phe Val Glu Asp Cys Lys Leu Pro Leu Gly Gln Ser Leu Cys Ala Leu
705                 710                 715                 720

Pro Asp Thr Pro Ser Thr Leu Thr Pro Arg Ser Val Arg Ser Val Pro
            725                 730                 735

Gly Glu Met Arg Leu Ala Ser Ile Ala Phe Asn His Pro Ile Gln Val
            740                 745                 750

Asp Gln Leu Asn Ser Ser Tyr Phe Lys Leu Ser Ile Pro Thr Asn Phe
        755                 760                 765

Ser Phe Gly Val Thr Gln Glu Tyr Ile Gln Thr Thr Ile Gln Lys Val
        770                 775                 780

Thr Val Asp Cys Lys Gln Tyr Val Cys Asn Gly Phe Gln Lys Cys Glu
785                 790                 795                 800

Gln Leu Leu Arg Glu Tyr Gly Gln Phe Cys Ser Lys Ile Asn Gln Ala
            805                 810                 815

Leu His Gly Ala Asn Leu Arg Gln Asp Asp Ser Val Arg Asn Leu Phe
            820                 825                 830

Ala Ser Val Lys Ser Ser Gln Ser Ser Pro Ile Ile Pro Gly Phe Gly
            835                 840                 845

Gly Asp Phe Asn Leu Thr Leu Leu Glu Pro Val Ser Ile Ser Thr Gly
        850                 855                 860

Ser Arg Ser Ala Arg Ser Ala Ile Glu Asp Leu Leu Phe Asp Lys Val
865                 870                 875                 880
```

Thr Ile Ala Asp Pro Gly Tyr Met Gln Gly Tyr Asp Asp Cys Met Gln
             885                 890                 895

Gln Gly Pro Ala Ser Ala Arg Asp Leu Ile Cys Ala Gln Tyr Val Ala
         900                 905                 910

Gly Tyr Lys Val Leu Pro Pro Leu Met Asp Val Asn Met Glu Ala Ala
         915                 920                 925

Tyr Thr Ser Ser Leu Leu Gly Ser Ile Ala Gly Val Gly Trp Thr Ala
930                 935                 940

Gly Leu Ser Ser Phe Ala Ala Ile Pro Phe Ala Gln Ser Ile Phe Tyr
945                 950                 955                 960

Arg Leu Asn Gly Val Gly Ile Thr Gln Gln Val Leu Ser Glu Asn Gln
             965                 970                 975

Lys Leu Ile Ala Asn Lys Phe Asn Gln Ala Leu Gly Ala Met Gln Thr
             980                 985                 990

Gly Phe Thr Thr Thr Asn Glu Ala Phe Gln Lys Val Gln Asp Ala Val
             995                 1000                1005

Asn Asn Asn Ala Gln Ala Leu Ser Lys Leu Ala Ser Glu Leu Ser
    1010                1015                1020

Asn Thr Phe Gly Ala Ile Ser Ala Ser Ile Gly Asp Ile Ile Gln
    1025                1030                1035

Arg Leu Asp Val Leu Glu Gln Asp Ala Gln Ile Asp Arg Leu Ile
    1040                1045                1050

Asn Gly Arg Leu Thr Thr Leu Asn Ala Phe Val Ala Gln Gln Leu
    1055                1060                1065

Val Arg Ser Glu Ser Ala Ala Leu Ser Ala Gln Leu Ala Lys Asp
    1070                1075                1080

Lys Val Asn Glu Cys Val Lys Ala Gln Ser Lys Arg Ser Gly Phe
    1085                1090                1095

Cys Gly Gln Gly Thr His Ile Val Ser Phe Val Val Asn Ala Pro
    1100                1105                1110

Asn Gly Leu Tyr Phe Met His Val Gly Tyr Tyr Pro Ser Asn His
    1115                1120                1125

Ile Glu Val Val Ser Ala Tyr Gly Leu Cys Asp Ala Ala Asn Pro
    1130                1135                1140

Thr Asn Cys Ile Ala Pro Val Asn Gly Tyr Phe Ile Lys Thr Asn
    1145                1150                1155

Asn Thr Arg Ile Val Asp Glu Trp Ser Tyr Thr Gly Ser Ser Phe
    1160                1165                1170

Tyr Ala Pro Glu Pro Ile Thr Ser Leu Asn Thr Lys Tyr Val Ala
    1175                1180                1185

Pro Gln Val Thr Tyr Gln Asn Ile Ser Thr Asn Leu Pro Pro Pro
    1190                1195                1200

Leu Leu Gly Asn Ser Thr Gly Ile Asp Phe Gln Asp Glu Leu Asp
    1205                1210                1215

Glu Phe Phe Lys Asn Val Ser Thr Ser Ile Pro Asn Phe Gly Ser
    1220                1225                1230

Leu Thr Gln Ile Asn Thr Thr Leu Leu Asp Leu Thr Tyr Glu Met
    1235                1240                1245

Leu Ser Leu Gln Gln Val Val Lys Ala Leu Lys Arg Pro His Gly
    1250                1255                1260

Gly Gly Ser Lys Asp Cys Glu Met Lys Arg Thr Thr Leu Asp Ser
    1265                1270                1275

Pro Leu Gly Lys Leu Glu Leu Ser Gly Cys Glu Gln Gly Leu His

| | | | | | | | | | |
|---|---|---|---|---|---|---|---|---|---|
| | | 1280 | | | 1285 | | | 1290 | |
| Glu | Ile | Lys | Leu | Leu | Gly | Lys | Gly | Thr | Ser | Ala | Ala | Asp | Ala | Val |
| | | 1295 | | | 1300 | | | 1305 | |

Glu Ile Lys Leu Leu Gly Lys Gly Thr Ser Ala Ala Asp Ala Val
          1295                  1300                1305

Glu Val Pro Ala Pro Ala Ala Val Leu Gly Gly Pro Glu Pro Leu
          1310                  1315                1320

Met Gln Ala Thr Ala Trp Leu Asn Ala Tyr Phe His Gln Pro Glu
          1325                  1330                1335

Ala Ile Glu Glu Phe Pro Val Pro Ala Leu His His Pro Val Phe
          1340                  1345                1350

Gln Gln Glu Ser Phe Thr Arg Gln Val Leu Trp Lys Leu Leu Lys
          1355                  1360                1365

Val Val Lys Phe Gly Glu Val Ile Ser Tyr Gln Gln Leu Ala Ala
          1370                  1375                1380

Leu Ala Gly Asn Pro Ala Ala Thr Ala Ala Val Lys Thr Ala Leu
          1385                  1390                1395

Ser Gly Asn Pro Val Pro Ile Leu Ile Pro Cys His Arg Val Val
          1400                  1405                1410

Ser Ser Ser Gly Ala Val Gly Gly Tyr Glu Gly Gly Leu Ala Val
          1415                  1420                1425

Lys Glu Trp Leu Leu Ala His Glu Gly His Arg Leu Gly Lys Pro
          1430                  1435                1440

Gly Leu Gly Pro Ala Gly Ile Gly Ala Pro Gly Ser Leu Glu His
          1445                  1450                1455

His His His His His
          1460

<210> SEQ ID NO 89
<211> LENGTH: 1325
<212> TYPE: DNA
<213> ORGANISM: artificial
<220> FEATURE:
<223> OTHER INFORMATION: DNA sequence encoding ssBiP - SNAPlike -proTEV-
    C protein from hepatitis C virus strain TCHM-R2/03 of genotype
    1b - -proTEV - Histag for expression in S2 cells

<400> SEQUENCE: 89

| | | |
|---|---|---|
| atgaagttat gcatattact ggccgtcgtg gtggcctttg ttggcctctc gctcgggaga | 60 |
| tctagatctg acaaagactg cgaaatgaaa agaactacat ggattcacc acttgggaag | 120 |
| ttggaactga gtggatgcga gcaaggattg catgaaatta gctactggg aaaaggaact | 180 |
| tctgctgctg atgcagttga agttccagca ccagcagctg ttcttggagg tcctgagccc | 240 |
| ctcatgcaag ccacagcctg gcttaacgca tatttccacc agcctgaggc cattgaggaa | 300 |
| tttccagtcc ccgcccttca ccatcctgtg tttcagcagg agagcttcac ccgccaggtc | 360 |
| ctgtggaaat tgctgaaggt ggtcaagttt ggtgaagtga tttcatatca gcaacttgct | 420 |
| gcattggccg gtaaccccgc agctacagct gccgtgaaaa ctgctctcag cggaaatcct | 480 |
| gtgcccatcc tgatcccttg tcacagagtc gtttcatctt ccggagctgt aggtggctat | 540 |
| gaaggaggac tggcagttaa ggagtggctg ctggctcatg aaggtcatag acttggaaag | 600 |
| cctgggctgg gtcctgctgg tataggcgcg ccagggtccc taggtggcgg atccgaaaac | 660 |
| ctgtacttcc agagcgatat cagtacaaat cctaaacctc aaagaaaaac taaacgaaat | 720 |
| actaatcgtc gtccacaaga tgttaagttt ccgggaggag acaaattgt tggtggagtt | 780 |
| tacctattgc cgcgaagagg tcctcgttta ggtgttcgag caactagaaa aacttctgaa | 840 |
| cgatcacaac tcgtggaag acgacaacct attcctaagg ctcgtcagcc tgaaggtaga | 900 |

```
gcttgggctc agcctggtta tccttggcct ctatatggta atgaaggaat gggttgggca      960
ggatggctac tatcacctcg tggttctcga cctagttggg gtgcaaatga ccctcgacga     1020
agatcacgta atttaggtaa ggtaattgat acacttacat gtggttttgc tgatcttatg     1080
ggatatattc cactagtagg tgctccacta ggtggagctg caagagttct tgcacatggt     1140
gtacgagttc ttgaagatgg agtgaactat gcaacaggta atcttcctgg atgttcattt     1200
tctatttttc tattagcttt gctatcatgt ctgactattc cagcttcagc tggcccggga     1260
gagaatctat attttcaagg gcccggcgga ggtagtcacc atcatcacca tcactaatga     1320
ccggt                                                                 1325
```

<210> SEQ ID NO 90
<211> LENGTH: 417
<212> TYPE: PRT
<213> ORGANISM: artificial
<220> FEATURE:
<223> OTHER INFORMATION: Amino acid sequence of fusion protein
      [SNAPlike-proTEV-C protein of HCV-proTEV-Histag]

<400> SEQUENCE: 90

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Thr
        195                 200                 205

Asn Pro Lys Pro Gln Arg Lys Thr Lys Arg Asn Thr Asn Arg Arg Pro
    210                 215                 220

Gln Asp Val Lys Phe Pro Gly Gly Gly Gln Ile Val Gly Gly Val Tyr
225                 230                 235                 240

Leu Leu Pro Arg Arg Gly Pro Arg Leu Gly Val Arg Ala Thr Arg Lys
                245                 250                 255

Thr Ser Glu Arg Ser Gln Pro Arg Gly Arg Arg Gln Pro Ile Pro Lys
            260                 265                 270
```

Ala Arg Gln Pro Glu Gly Arg Ala Trp Ala Gln Pro Tyr Pro Trp
                275                 280                 285

Pro Leu Tyr Gly Asn Glu Gly Met Gly Trp Ala Gly Trp Leu Leu Ser
            290                 295                 300

Pro Arg Gly Ser Arg Pro Ser Trp Gly Ala Asn Asp Pro Arg Arg Arg
305                 310                 315                 320

Ser Arg Asn Leu Gly Lys Val Ile Asp Thr Leu Thr Cys Gly Phe Ala
                325                 330                 335

Asp Leu Met Gly Tyr Ile Pro Leu Val Gly Ala Pro Leu Gly Gly Ala
            340                 345                 350

Ala Arg Val Leu Ala His Gly Val Arg Val Leu Glu Asp Gly Val Asn
                355                 360                 365

Tyr Ala Thr Gly Asn Leu Pro Gly Cys Ser Phe Ser Ile Phe Leu Leu
            370                 375                 380

Ala Leu Leu Ser Cys Leu Thr Ile Pro Ala Ser Ala Gly Pro Gly Glu
385                 390                 395                 400

Asn Leu Tyr Phe Gln Gly Pro Gly Gly Gly Ser His His His His His
                405                 410                 415

His

<210> SEQ ID NO 91
<211> LENGTH: 1376
<212> TYPE: DNA
<213> ORGANISM: artificial
<220> FEATURE:
<223> OTHER INFORMATION: DNA sequence encoding ssBiP- SNAPlike -
      MSP1(19) antigen from Plasmodium falciparum - proTEV - AMA-1(III)
      antigen from Plasmodium falciparum - Histag for expression in S2
      cells

<400> SEQUENCE: 91
atgaagttat gcatattact ggccgtcgtg gtggcctttg ttggcctctc gctcgggaga        60
tctagatctg acaaagactg cgaaatgaaa agaactacat tggattcacc acttgggaag      120
ttggaactga gtggatgcga gcaaggattg catgaaatta agctactggg aaaaggaact      180
tctgctgctg atgcagttga agttccagca ccagcagctc ttcttggagg tcctgagccc      240
ctcatgcaag ccacagcctg gcttaacgca tatttccacc agcctgaggc cattgaggaa      300
tttccagtcc ccgcccttca ccatcctgtg tttcagcagg agagcttcac cgccaggtc       360 ctgtggaaat tgctgaaggt ggtcaagttt ggtgaagtga tttcatatca gcaacttgct      420
gcattggccg taaccccgc agctacagct gccgtgaaaa ctgctctcag cggaaatcct       480
gtgcccatcc tgatcccttg tcacagagtc gtttcatctt ccggagctgt aggtggctat      540
gaaggaggac tggcagttaa ggagtggctg ctggctcatg aaggtcatag acttggaaag      600
cctgggctgg tcctgctgg tataggcgcg ccagggtccc taggtggcgg atccgaaaac      660
ctgtacttcc agagcgatat caaacaatgt ccacaaaatt ctggatgttt cagacattta      720
gatgaaagag aagaatgtaa atgtttatta aattacaaac aagaaggtga taatgtgtt      780 gaaaatccaa atcttacttg taacgaaaat aatggtggat gtgatgcaga tgccaaatgt      840
accgaagaag attcaggcag caacggaaag aaaatcacat gtgaatgtac taaacctgat      900
tcttatccac tttttcgatgg tatttttcgga ggtggctctg agaatctata ttttcaaggg      960
cccggtggag cgaagttga aacaatttc ccatgttcat tatataaaga tgaaataatg     1020
aaagaaatcg aaagaataatc aaaacgaatt aaattaaatg ataatgatga tgaagggaat     1080
aaaaaaatta tagctccaag aatttttatt tcagatgata agacagtttt aaaatgccca     1140

```
tgtgaccctg aaatggtaag taatagtaca tgtcgtttct ttgtatgtaa atgtgtagaa    1200
agaagggcag aagtaacatc aaataatgaa gttgtagtta aagaagaata taaagatgaa    1260
tatgcagata ttcctgaaca taaaccaact tatgataaaa tgctcccggg agagaatcta    1320
tattttcaag ggcccggcgg aggtagtcac catcatcacc atcactaatg accggt        1376
```

<210> SEQ ID NO 92
<211> LENGTH: 434
<212> TYPE: PRT
<213> ORGANISM: artificial
<220> FEATURE:
<223> OTHER INFORMATION: Amino acid sequence of fusion protein [SNAPlike-MSP1-proTEV-AMA1-Histag]

<400> SEQUENCE: 92

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Lys Gln
        195                 200                 205

Cys Pro Gln Asn Ser Gly Cys Phe Arg His Leu Asp Glu Arg Glu Glu
    210                 215                 220

Cys Lys Cys Leu Leu Asn Tyr Lys Gln Glu Gly Asp Lys Cys Val Glu
225                 230                 235                 240

Asn Pro Asn Leu Thr Cys Asn Glu Asn Asn Gly Gly Cys Asp Ala Asp
                245                 250                 255

Ala Lys Cys Thr Glu Glu Asp Ser Gly Ser Asn Gly Lys Lys Ile Thr
            260                 265                 270

Cys Glu Cys Thr Lys Pro Asp Ser Tyr Pro Leu Phe Asp Gly Ile Phe
        275                 280                 285

Gly Gly Gly Ser Glu Asn Leu Tyr Phe Gln Gly Pro Gly Gly Gly Glu
    290                 295                 300

Val Glu Asn Asn Phe Pro Cys Ser Leu Tyr Lys Asp Glu Ile Met Lys
305                 310                 315                 320
```

```
Glu Ile Glu Arg Glu Ser Lys Arg Ile Lys Leu Asn Asp Asn Asp Asp
            325                 330                 335

Glu Gly Asn Lys Lys Ile Ile Ala Pro Arg Ile Phe Ile Ser Asp Asp
            340                 345                 350

Lys Asp Ser Leu Lys Cys Pro Cys Asp Pro Glu Met Val Ser Asn Ser
            355                 360                 365

Thr Cys Arg Phe Phe Val Cys Lys Cys Val Glu Arg Arg Ala Glu Val
    370                 375                 380

Thr Ser Asn Asn Glu Val Val Val Lys Glu Glu Tyr Lys Asp Glu Tyr
385                 390                 395                 400

Ala Asp Ile Pro Glu His Lys Pro Thr Tyr Asp Lys Met Leu Pro Gly
            405                 410                 415

Glu Asn Leu Tyr Phe Gln Gly Pro Gly Gly Gly Ser His His His His
            420                 425                 430

His His
```

<210> SEQ ID NO 93
<211> LENGTH: 2195
<212> TYPE: DNA
<213> ORGANISM: artificial
<220> FEATURE:
<223> OTHER INFORMATION: DNA sequence encoding ssBiP- SNAPlike -proTEV-
      modified short form of HbpA from Leptospira interrogans serovar
      Lai str.56601 - proTEV- Histag for expression in S2 cells

<400> SEQUENCE: 93

```
atgaagttat gcatattact ggccgtcgtg gtggcctttg ttggcctctc gctcgggaga        60
tctagatctg acaaagactg cgaaatgaaa agaactacat ggattcacc acttgggaag       120 ttggaactga gtggatgcga gcaaggattg catgaaatta gctactggg aaaaggaact       180 tctgctgctg atgcagttga agttccagca ccagcagctg ttcttggagg tcctgagccc      240
ctcatgcaag ccacagcctg gcttaacgca tatttccacc agcctgaggc cattgaggaa      300
tttccagtcc ccgcccttca ccatcctgtg tttcagcagg agagcttcac ccgccaggtc      360
ctgtggaaat gctgaaggt ggtcaagttt ggtgaagtga tttcatatca gcaacttgct      420
gcattggccg gtaaccccgc agctacagct gccgtgaaaa ctgctctcag cggaaatcct     480
gtgcccatcc tgatcccttg tcacagagtc gtttcatctt ccggagctgt aggtggctat     540
gaaggaggac tggcagttaa ggagtggctg ctggctcatg aaggtcatag acttggaaag     600
cctgggctgg gtcctgctgg tataggcgcg ccagggtccc taggtggcgg atccgaaaac     660
ctgtacttcc agagcgatat cttcaacacc acggccaaca tgggcttcag gaacgagtac     720
gtgagcggcg cggtgtccgc aggttacaat aagaaccccg gctacaggtt ggtcccaaac     780
tctcaggcga ctactgggaa cgcctatcag gacttgaaca cggcatcaa cctgaccttc     840 aacccggacg gcaagttcaa ggggaagacg aggattctct accagcacag ggaccagaac     900
ggggtggacg tgacccagtc caaggccgtc ttcgaccgga caacaagac gcacgacttc     960 ttggcgacgg ggtcgttgga gtacgggtta gggaagagga acttgatctc cttcagggg    1020 aacatctcca gtgggagaa caagtactac aacaaccaga ggggtcgga cgagttggac     1080 gtgaagcagt tgaactcgga gttgacgtcg caggggaccg tgcagttgga catggaggcc    1140
tctgagaagc acttcatcac tgtaggtgcg gagtccttcg cgaacgagtt ggagtcggac    1200
cgcttgcaga gcaggtacgt gtacaggacg aggaaggcgg tgttcttcca ggacgagtgg    1260
accgtgtccc ggtcgccgag gattcgggtg gtgccaggag tgaggtacga cgacgactcg    1320
```

-continued

```
cagttcggga accagacgac gccgaagctg gcggcccggt acgacatatt gcagaacttg   1380
gtgtggaggg cgagctacgg gaggggatta cggccgccga gcttgcagga gttgtacctg   1440
cggttcgaga acccggccgt gggttacgtg gtggagggta acccgaactt gaagccggag   1500
cggtcgatca cgatcaactc ggacttggag tacagcccgt tcagcttctt gacgttctcc   1560
ttgagcgtgt accggaacga catcatcaac ctgatccagt acaagttcga ctcgaacaag   1620
gggagggagt tcgcggagtt ccagctgcag aacatcgcga aggcgtacac gagaggagga   1680
gagttcggcg tgcagtacag gttcttgaag tacttcacgc tggagttggg gtacaaccac   1740
acggacacga gggacctgag ctcggacagg ccgttggagg gcagggcgct gcaccaggcg   1800
tcggcgaact tcatctacaa ctcgcccgga ggattccaat tcaacctgag gggcaagcac   1860
ttggacaaga ggccgttcta cagctcgacc aacaacctgt cggcggccgg acaggactac   1920
atccccagcg aggtgaagtt gaacgagaac ccgcccgtga tctacgggaa gccgttcacg   1980
atcttgaacg tgaggatcga gcagaagttc ttcaacaagc acttcgcgct gttcttgggc   2040
gtggacaact tgctcaacca gtacgagctg gcgtacaacc ccacgcggcc gaggttctac   2100
tacggcggct tctcggccca gttccccggga gagaatctat attttcaagg gcccggcgga   2160
ggtagtcacc atcatcacca tcactaatga ccggt                             2195
```

<210> SEQ ID NO 94
<211> LENGTH: 707
<212> TYPE: PRT
<213> ORGANISM: artificial
<220> FEATURE:
<223> OTHER INFORMATION: Amino acid sequence of fusion protein [SNAPlike-proTEV-HbPA1-proTEV-Histag]

<400> SEQUENCE: 94

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Phe Asn
```

```
            195                 200                 205
Thr Thr Ala Asn Met Gly Phe Arg Asn Glu Tyr Val Ser Gly Ala Val
210                 215                 220

Ser Ala Gly Tyr Asn Lys Asn Pro Gly Tyr Arg Leu Val Pro Asn Ser
225                 230                 235                 240

Gln Ala Thr Thr Gly Asn Ala Tyr Gln Asp Leu Asn Thr Gly Ile Asn
                245                 250                 255

Leu Thr Phe Asn Pro Asp Gly Lys Phe Lys Gly Lys Thr Arg Ile Leu
            260                 265                 270

Tyr Gln His Arg Asp Gln Asn Gly Val Asp Val Thr Gln Ser Lys Ala
                275                 280                 285

Val Phe Asp Arg Asn Asn Lys Thr His Asp Phe Leu Ala Thr Gly Ser
        290                 295                 300

Leu Glu Tyr Gly Leu Gly Lys Arg Asn Leu Ile Ser Phe Arg Gly Asn
305                 310                 315                 320

Ile Ser Lys Trp Glu Asn Lys Tyr Tyr Asn Asn Gln Arg Gly Ser Asp
                325                 330                 335

Glu Leu Asp Val Lys Gln Leu Asn Ser Glu Leu Thr Ser Gln Gly Thr
            340                 345                 350

Val Gln Leu Asp Met Glu Ala Ser Glu Lys His Phe Ile Thr Val Gly
        355                 360                 365

Ala Glu Ser Phe Ala Asn Glu Leu Glu Ser Asp Arg Leu Gln Ser Arg
370                 375                 380

Tyr Val Tyr Arg Thr Arg Lys Ala Val Phe Phe Gln Asp Glu Trp Thr
385                 390                 395                 400

Val Ser Arg Ser Pro Arg Ile Arg Val Val Pro Gly Val Arg Tyr Asp
                405                 410                 415

Asp Asp Ser Gln Phe Gly Asn Gln Thr Thr Pro Lys Leu Ala Ala Arg
            420                 425                 430

Tyr Asp Ile Leu Gln Asn Leu Val Trp Arg Ala Ser Tyr Gly Arg Gly
        435                 440                 445

Leu Arg Pro Pro Ser Leu Gln Glu Leu Tyr Leu Arg Phe Glu Asn Pro
450                 455                 460

Ala Val Gly Tyr Val Val Glu Gly Asn Pro Asn Leu Lys Pro Glu Arg
465                 470                 475                 480

Ser Ile Thr Ile Asn Ser Asp Leu Glu Tyr Ser Pro Phe Ser Phe Leu
                485                 490                 495

Thr Phe Ser Leu Ser Val Tyr Arg Asn Asp Ile Ile Asn Leu Ile Gln
            500                 505                 510

Tyr Lys Phe Asp Ser Asn Lys Gly Arg Glu Phe Ala Glu Phe Gln Leu
        515                 520                 525

Gln Asn Ile Ala Lys Ala Tyr Thr Arg Gly Gly Glu Phe Gly Val Gln
530                 535                 540

Tyr Arg Phe Leu Lys Tyr Phe Thr Leu Glu Leu Gly Tyr Asn His Thr
545                 550                 555                 560

Asp Thr Arg Asp Leu Ser Ser Asp Arg Pro Leu Glu Gly Arg Ala Leu
                565                 570                 575

His Gln Ala Ser Ala Asn Phe Ile Tyr Asn Ser Pro Gly Gly Phe Gln
            580                 585                 590

Phe Asn Leu Arg Gly Lys His Leu Asp Lys Arg Pro Phe Tyr Ser Ser
        595                 600                 605

Thr Asn Asn Leu Ser Ala Ala Gly Gln Asp Tyr Ile Pro Ser Glu Val
610                 615                 620
```

```
Lys Leu Asn Glu Asn Pro Pro Val Ile Tyr Gly Lys Pro Phe Thr Ile
625                 630                 635                 640

Leu Asn Val Arg Ile Glu Gln Lys Phe Phe Asn Lys His Phe Ala Leu
            645                 650                 655

Phe Leu Gly Val Asp Asn Leu Leu Asn Gln Tyr Glu Leu Ala Tyr Asn
        660                 665                 670

Pro Thr Arg Pro Arg Phe Tyr Tyr Gly Gly Phe Ser Ala Gln Phe Pro
        675                 680                 685

Gly Glu Asn Leu Tyr Phe Gln Gly Pro Gly Gly Ser His His His
    690                 695                 700

His His His
705

<210> SEQ ID NO 95
<211> LENGTH: 968
<212> TYPE: DNA
<213> ORGANISM: artificial
<220> FEATURE:
<223> OTHER INFORMATION: DNA sequence encoding ssBiP- SNAPlike -proTEV-
      MUB40 - proTEV- Histag for expression in S2 cells

<400> SEQUENCE: 95
atgaagttat gcatattact ggccgtcgtg gtggcctttg ttggcctctc gctcgggaga      60
tcttcgcgag ctagcaccat gaaactatgt attctacttg cagttgttgc gttcgtagga    120
ttgtccttac ctacagctct ggcaagatct gacaaagact gcgaaatgaa aagaactaca    180
ttggattcac cacttgggaa gttggaactg agtggatgcg agcaaggatt gcatgaaatt    240
aagctactgg gaaaaggaac ttctgctgct gatgcagttg aagttccagc accagcagct    300
gttcttggag tcctgagcc cctcatgcaa gccacagcct ggcttaacgc atatttccac    360
cagcctgagg ccattgagga atttccagtc cccgcccttc accatcctgt gtttcagcag    420
gagagcttca cccgccaggt cctgtggaaa ttgctgaagg tggtcaagtt tggtgaagtg    480
atttcatatc agcaacttgc tgcattggcc ggtaaccccg cagctacagc tgccgtgaaa    540
actgctctca gcggaaatcc tgtgcccatc ctgatcccct gtcacagagt cgtttcatct    600
tccggagctg taggtggcta tgaaggagga ctggcagtta aggagtggct gctggctcat    660
gaaggtcata gacttggaaa gcctgggctg ggtcctgctg gtataggcgc gccaggtcc    720 ctaggtggcg gatccgaaaa cctgtacttc cagagcgata tcacggctga aggcatcaag    780
aagtttgaag cgacggtta tgaactgttc aaggacaact tcccagctgg tgagaagttc    840
gataacgatg acaccaacga tcaattctac acggtaatct tcaagcacca tcgtggcccg    900
ggagagaatc tatattttca agggcccggc ggaggtagtc accatcatca ccatcactaa    960
tgaccggt                                                            968

<210> SEQ ID NO 96
<211> LENGTH: 298
<212> TYPE: PRT
<213> ORGANISM: artificial
<220> FEATURE:
<223> OTHER INFORMATION: Amino acid sequence of fusion protein
      [SNAPlike-proTEV-MUB40-proTEV-Histag]

<400> SEQUENCE: 96

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
```

|   |   |   |   | 20  |   |   |   |   | 25  |   |   |   |   | 30  |   |
|---|---|---|---|---|---|---|---|---|---|---|---|---|---|---|---|

Cys Glu Met Lys Arg Thr Thr Leu Asp Ser Pro Leu Gly Lys Leu Glu
                35                        40                        45

Leu Ser Gly Cys Glu Gln Gly Leu His Glu Ile Lys Leu Leu Gly Lys
 50                        55                        60

Gly Thr Ser Ala Ala Asp Ala Val Glu Val Pro Ala Pro Ala Ala Val
 65                        70                        75                        80

Leu Gly Gly Pro Glu Pro Leu Met Gln Ala Thr Ala Trp Leu Asn Ala
                85                        90                        95

Tyr Phe His Gln Pro Glu Ala Ile Glu Glu Phe Pro Val Pro Ala Leu
                         100                       105                       110

His His Pro Val Phe Gln Gln Glu Ser Phe Thr Arg Gln Val Leu Trp
                115                       120                       125

Lys Leu Leu Lys Val Val Lys Phe Gly Glu Val Ile Ser Tyr Gln Gln
130                       135                       140

Leu Ala Ala Leu Ala Gly Asn Pro Ala Ala Thr Ala Ala Val Lys Thr
145                       150                       155                       160

Ala Leu Ser Gly Asn Pro Val Pro Ile Leu Ile Pro Cys His Arg Val
                165                       170                       175

Val Ser Ser Ser Gly Ala Val Gly Gly Tyr Glu Gly Gly Leu Ala Val
                180                       185                       190

Lys Glu Trp Leu Leu Ala His Glu Gly His Arg Leu Gly Lys Pro Gly
                195                       200                       205

Leu Gly Pro Ala Gly Ile Gly Ala Pro Gly Ser Leu Gly Gly Gly Ser
 210                       215                       220

Glu Asn Leu Tyr Phe Gln Ser Asp Ile Thr Ala Glu Gly Ile Lys Lys
225                       230                       235                       240

Phe Glu Gly Asp Gly Tyr Glu Leu Phe Lys Asp Asn Phe Pro Ala Gly
                245                       250                       255

Glu Lys Phe Asp Asn Asp Asp Thr Asn Asp Gln Phe Tyr Thr Val Ile
                260                       265                       270

Phe Lys His His Arg Gly Pro Gly Glu Asn Leu Tyr Phe Gln Gly Pro
                275                       280                       285

Gly Gly Gly Ser His His His His His
     290                       295

<210> SEQ ID NO 97
<211> LENGTH: 1238
<212> TYPE: DNA
<213> ORGANISM: artificial
<220> FEATURE:
<223> OTHER INFORMATION: DNA sequence encoding ssBiP- SNAPlike -proTEV-
      soluble form of mouse C-type like lectin (CLEC5A) - proTEV- Histag
      for expression in S2 cells

<400> SEQUENCE: 97
atgaagttat gcatattact ggccgtcgtg gtggcctttg ttggcctctc gctcgggaga      60
tctagatctg acaaagactg cgaaatgaaa agaactacat ggattcacc acttgggaag     120 ttggaactga gtggatgcga gcaaggattg catgaaatta gctactggg aaaaggaact     180 tctgctgctg atgcagttga agttccagca ccagcagctg ttcttggagg tcctgagccc     240
ctcatgcaag ccacagcctg gcttaacgca tatttccacc agcctgaggc cattgaggaa     300
tttccagtcc ccgcccttca ccatcctgtg tttcagcagg agagcttcac ccgccaggtc     360
ctgtggaaat tgctgaaggt ggtcaagttt ggtgaagtga tttcatatca gcaacttgct     420

```
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat cgttttggc aaaagtaatg atggcttcgt ccccacggag    720
agctacggaa ccactagtgt gcagaatgtc tcacaaatct tgggagaaa tgacgaaagt    780
accatgccta caaggagcta tggaacagtc tgtcccagaa actgggattt tcaccaagga    840
aaatgctttt tcttctcctt ctccgaatca ccttggaaag acagcatgga ttattgtgca    900
acacaagggt ccacactggc aattgtcaac actccagaga aactgaagta tcttcaggac    960
atagctggta ttgagaatta ctttattggt ttggtacgtc agcctggaga gaaaaagtgg   1020
cgctggatca acaactctgt gttcaatggc aatgttacca atcaggacca gaacttcgac   1080
tgtgtcacta taggtctgac gaagacatat gatgctgcat catgtgaagt cagctatcgc   1140
tggatctgcg aaatgaatgc caaaggcccg ggagagaatc tatattttca agggcccggc   1200
ggaggtagtc accatcatca ccatcactaa tgaccggt                            1238
```

<210> SEQ ID NO 98
<211> LENGTH: 388
<212> TYPE: PRT
<213> ORGANISM: artificial
<220> FEATURE:
<223> OTHER INFORMATION: Amino acid sequence of fusion protein [SNAPlike-proTEV-moCLEC5A-proTEV-Histag]

<400> SEQUENCE: 98

Arg Ser Asp Lys Asp Cys Glu Met Lys Arg Thr Thr Leu Asp Ser Pro
1               5                   10                  15
Leu Gly Lys Leu Glu Leu Ser Gly Cys Glu Gln Gly Leu His Glu Ile
            20                  25                  30
Lys Leu Leu Gly Lys Gly Thr Ser Ala Ala Asp Ala Val Glu Val Pro
        35                  40                  45
Ala Pro Ala Ala Val Leu Gly Gly Pro Glu Pro Leu Met Gln Ala Thr
    50                  55                  60
Ala Trp Leu Asn Ala Tyr Phe His Gln Pro Glu Ala Ile Glu Glu Phe
65                  70                  75                  80
Pro Val Pro Ala Leu His His Pro Val Phe Gln Gln Glu Ser Phe Thr
                85                  90                  95
Arg Gln Val Leu Trp Lys Leu Lys Val Val Lys Phe Gly Glu Val
            100                 105                 110
Ile Ser Tyr Gln Gln Leu Ala Ala Leu Ala Gly Asn Pro Ala Ala Thr
        115                 120                 125
Ala Ala Val Lys Thr Ala Leu Ser Gly Asn Pro Val Pro Ile Leu Ile
    130                 135                 140
Pro Cys His Arg Val Val Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Gly Ser Glu Asn Leu Tyr Phe Gln Ser Asp Ile Val Phe
        195                 200                 205
Gly Lys Ser Asn Asp Gly Phe Val Pro Thr Glu Ser Tyr Gly Thr Thr

Ser Val Gln Asn Val Ser Gln Ile Phe Gly Arg Asn Asp Glu Ser Thr
225                 230                 235                 240

Met Pro Thr Arg Ser Tyr Gly Thr Val Cys Pro Arg Asn Trp Asp Phe
            245                 250                 255

His Gln Gly Lys Cys Phe Phe Phe Ser Phe Glu Ser Pro Trp Lys
            260                 265                 270

Asp Ser Met Asp Tyr Cys Ala Thr Gln Gly Ser Thr Leu Ala Ile Val
            275                 280                 285

Asn Thr Pro Glu Lys Leu Lys Tyr Leu Gln Asp Ile Ala Gly Ile Glu
            290                 295                 300

Asn Tyr Phe Ile Gly Leu Val Arg Gln Pro Gly Glu Lys Lys Trp Arg
305                 310                 315                 320

Trp Ile Asn Asn Ser Val Phe Asn Gly Asn Val Thr Asn Gln Asp Gln
                325                 330                 335

Asn Phe Asp Cys Val Thr Ile Gly Leu Thr Lys Thr Tyr Asp Ala Ala
                340                 345                 350

Ser Cys Glu Val Ser Tyr Arg Trp Ile Cys Glu Met Asn Ala Lys Gly
            355                 360                 365

Pro Gly Glu Asn Leu Tyr Phe Gln Gly Pro Gly Gly Ser His His
            370                 375                 380

His His His His
385

<210> SEQ ID NO 99
<211> LENGTH: 1229
<212> TYPE: DNA
<213> ORGANISM: artificial
<220> FEATURE:
<223> OTHER INFORMATION: DNA sequence encoding ssBiP- SNAPlike -proTEV-
      soluble form of human C-type like lectin (CLEC5A) - proTEV- Histag
      for expression in S2 cells

<400> SEQUENCE: 99
atgaagttat gcatattact ggccgtcgtg gtggcctttg ttggcctctc gctcgggaga       60
tctagatctg acaaagactg cgaaatgaaa agaactacat tggattcacc acttgggaag     120
ttggaactga gtggatgcga gcaaggattg catgaaatta agctactggg aaaaggaact     180
tctgctgctg atgcagttga agttccagca ccagcagctc ttcttggagg tcctgagccc     240
ctcatgcaag ccacagcctg gcttaacgca tatttccacc agcctgaggc cattgaggaa     300
tttccagtcc ccgcccttca ccatcctgtg tttcagcagg agagcttcac ccgccaggtc     360
ctgtggaaat tgctgaaggt ggtcaagttt ggtgaagtga tttcatatca gcaacttgct     420
gcattggccg taaccccgc agctacagct gccgtgaaaa ctgctctcag cggaaatcct     480
gtgcccatcc tgatcccttg tcacagagtc gtttcatctt ccggagctgt aggtggctat     540
gaaggaggac tggcagttaa ggagtggctg ctggctcatg aaggtcatag acttggaaag     600
cctgggctgg gtcctgctgg tataggcgcg ccagggtccc taggtggcgg atccgaaaac     660
ctgtacttcc agagcgatat ctttaacaaa agtaacgatg gtttcaccac caccaggagc     720 tatgaacag tctcacagat tttgggagc agttccccaa gtcccaacgg cttcattacc     780
acaaggagct atgaacagt ctgccccaaa gactgggaat tttatcaagc aagatgtttt     840
ttcttatcca cttctgaatc atcttggaat gaaagcaggg acttttgcaa aggaaaaggc     900
tccacattgg caattgtcaa cacgccagag aaactgaagt tcttcagga cataactgat     960

-continued

```
gctgagaagt attttattgg cttaatttac catcgtgaag agaaaaggtg gcgttggatc    1020
aacaactctg tgttcaatgg caatgttacc aatcagaatc agaatttcaa ctgtgcgacc    1080
attggcctaa caaagacatt tgatgctgca tcatgtgaca tcagctaccg caggatctgt    1140
gagaagaatg ccaaaggccc gggagagaat ctatattttc aagggcccgg cggaggtagt    1200
caccatcatc accatcacta atgaccggt                                      1229
```

<210> SEQ ID NO 100
<211> LENGTH: 385
<212> TYPE: PRT
<213> ORGANISM: artificial
<220> FEATURE:
<223> OTHER INFORMATION: Amino acid sequence of fusion protein [SNAPlike-proTEV-huCLEC5A-proTEV-Histag]

<400> SEQUENCE: 100

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Phe Asn
        195                 200                 205

Lys Ser Asn Asp Gly Phe Thr Thr Thr Arg Ser Tyr Gly Thr Val Ser
    210                 215                 220

Gln Ile Phe Gly Ser Ser Ser Pro Ser Pro Asn Gly Phe Ile Thr Thr
225                 230                 235                 240

Arg Ser Tyr Gly Thr Val Cys Pro Lys Asp Trp Glu Phe Tyr Gln Ala
                245                 250                 255

Arg Cys Phe Phe Leu Ser Thr Ser Glu Ser Ser Trp Asn Glu Ser Arg
            260                 265                 270

Asp Phe Cys Lys Gly Lys Gly Ser Thr Leu Ala Ile Val Asn Thr Pro
        275                 280                 285

Glu Lys Leu Lys Phe Leu Gln Asp Ile Thr Asp Ala Glu Lys Tyr Phe
    290                 295                 300

Ile Gly Leu Ile Tyr His Arg Glu Glu Lys Arg Trp Arg Trp Ile Asn

Asn Ser Val Phe Asn Gly Asn Val Thr Asn Gln Asn Gln Asn Phe Asn
305                 310                 315                 320

Cys Ala Thr Ile Gly Leu Thr Lys Thr Phe Asp Ala Ala Ser Cys Asp
            325                 330                 335

Ile Ser Tyr Arg Arg Ile Cys Glu Lys Asn Ala Lys Gly Pro Gly Glu
        340                 345                 350

Asn Leu Tyr Phe Gln Gly Pro Gly Gly Gly Ser His His His His His
    355                 360                 365

His
370                 375                 380

His
385

<210> SEQ ID NO 101
<211> LENGTH: 962
<212> TYPE: DNA
<213> ORGANISM: artificial
<220> FEATURE:
<223> OTHER INFORMATION: DNA sequence encoding BiPlike- SNAPlike- cxVAGO
      protein from Culex quinquefasciatus - Histag for expression in S2
      cells

<400> SEQUENCE: 101

| | | | | | |
|---|---|---|---|---|---|
| atgaaactat | gtattctact | tgcagttgtt | gcgttcgtag | gattgtcctt | aagatctgac | 60 |
| aaagactgcg | aaatgaaaag | aactacattg | gattcaccac | ttgggaagtt | ggaactgagt | 120 |
| ggatgcgagc | aaggattgca | tgaaattaag | ctactgggaa | aaggaacttc | tgctgctgat | 180 |
| gcagttgaag | ttccagcacc | agcagctgtt | cttggaggtc | ctgagcccct | catgcaagcc | 240 |
| acagcctggc | ttaacgcata | tttccaccag | cctgaggcca | ttgaggaatt | tccagtcccc | 300 |
| gcccttcacc | atcctgtgtt | tcagcaggag | agcttcaccc | gccaggtcct | gtggaaattg | 360 |
| ctgaaggtgg | tcaagtttgg | tgaagtgatt | tcatatcagc | aacttgctgc | attggccggt | 420 |
| aaccccgcag | ctacagctgc | cgtgaaaact | gctctcagcg | aaatcctgt | gcccatcctg | 480 |
| atcccttgtc | acagagtcgt | ttcatcttcc | ggagctgtag | gtggctatga | aggaggactg | 540 |
| gcagttaagg | agtggctgct | ggctcatgaa | ggtcatagac | ttggaaagcc | tgggctgggt | 600 |
| cctgctggta | taggcgcgcc | agggtccctg | gagggaggtg | gcgggtctga | agccgttcta | 660 |
| caaaatgccg | agcatccaga | ttaccctgga | aagtgttacg | acgaaggtac | gcagaccgtt | 720 |
| gtagctcccc | tagaaagtgc | gaagctacca | aaatcgtgta | caaaggtatt | ctgctcgact | 780 |
| aacctttcac | tgacctatac | tacgtgtggg | tcagtacttg | tcaatgaccc | gcactgcgag | 840 |
| aagatcgaac | aagacctgac | taaagacttc | ccagagtgct | gtcacaagta | taatgtgaa | 900 |
| ctggagggag | tagtcacgta | ccacggaggt | ggccatcacc | atcaccatca | ctgatgaccg | 960 |
| gt | | | | | | 962 |

<210> SEQ ID NO 102
<211> LENGTH: 300
<212> TYPE: PRT
<213> ORGANISM: artificial
<220> FEATURE:
<223> OTHER INFORMATION: Amino acid sequence of fusion protein
      [SNAPlike-cxVAGO-Histag]

<400> SEQUENCE: 102

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

```
Lys Leu Leu Gly Lys Gly Thr Ser Ala Ala Asp Ala Val Glu Val Pro
         35                  40                  45
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Lys Val Val Lys Phe Gly Glu Val
             100                 105                 110
Ile Ser Tyr Gln Gln Leu Ala Ala Leu Ala Gly Asn Pro Ala Ala Thr
             115                 120                 125
Ala Ala Val Lys Thr Ala Leu Ser Gly Asn Pro Val Pro Ile Leu Ile
130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
             180                 185                 190
Leu Glu Gly Gly Gly Ser Glu Ala Val Leu Gln Asn Ala Glu His
             195                 200                 205
Pro Asp Tyr Pro Gly Lys Cys Tyr Asp Glu Gly Thr Gln Thr Val Val
         210                 215                 220
Ala Pro Leu Glu Ser Ala Lys Leu Pro Lys Ser Cys Thr Lys Val Phe
225                 230                 235                 240
Cys Ser Thr Asn Leu Ser Leu Thr Tyr Thr Thr Cys Gly Ser Val Leu
                245                 250                 255
Val Asn Asp Pro His Cys Glu Lys Ile Glu Gln Asp Leu Thr Lys Asp
             260                 265                 270
Phe Pro Glu Cys Cys His Lys Tyr Lys Cys Glu Leu Glu Gly Val Val
         275                 280                 285
Thr Tyr His Gly Gly Gly His His His His His
         290                 295                 300
```

<210> SEQ ID NO 103
<211> LENGTH: 962
<212> TYPE: DNA
<213> ORGANISM: artificial
<220> FEATURE:
<223> OTHER INFORMATION: DNA sequence encoding BiPlike- SNAPlike- aaVAGO
      protein from Aedes albopictus - Histag for expression in S2 cells

<400> SEQUENCE: 103

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt ccagtcccc    300 gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg gaaatcctgt gcccatcctg     480
```

```
atcccttgtc acagagtcgt ttcatcttcc ggagctgtag gtggctatga aggaggactg    540
gcagttaagg agtggctgct ggctcatgaa ggtcatagac ttggaaagcc tgggctgggt    600
cctgctggta taggcgcgcc agggtccctg gagggaggtg gcgggtctac ggctatcttc    660
ccaaattcgg agaacaaaga tttcccaggc gaatgctatg acacggagac taagattcat    720
ttcaagccag gggaaaatcg tcaacgacct ggcaactgtg aagagatgtc atgcggaact    780
gacttctcga ttcactttt cggatgcgga ctagctatac tagacgatga cccggattgc    840
gagatcccag ttcaggattt cacaaaggac acgcagtgtt gccataagta caagtgtgtg    900
cgtaacggtg aagtcaatta cattggaggt ggccatcacc atcaccatca ctgatgaccg    960
gt                                                                   962
```

<210> SEQ ID NO 104
<211> LENGTH: 300
<212> TYPE: PRT
<213> ORGANISM: artificial
<220> FEATURE:
<223> OTHER INFORMATION: Amino acid sequence of fusion protein
      [SNAPlike-aaVAGO-Histag]

<400> SEQUENCE: 104

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Ser Thr Ala Ile Phe Pro Asn Ser Glu Asn
        195                 200                 205

Lys Asp Phe Pro Gly Glu Cys Tyr Asp Thr Glu Thr Lys Ile His Phe
    210                 215                 220

Lys Pro Gly Glu Asn Arg Gln Arg Pro Gly Asn Cys Glu Glu Met Ser
225                 230                 235                 240

Cys Gly Thr Asp Phe Ser Ile His Phe Phe Gly Cys Gly Leu Ala Ile
                245                 250                 255

Leu Asp Asp Asp Pro Asp Cys Glu Ile Pro Val Gln Asp Phe Thr Lys
            260                 265                 270
```

Asp Thr Gln Cys Cys His Lys Tyr Lys Cys Val Arg Asn Gly Glu Val
        275                 280                 285

Asn Tyr Ile Gly Gly Gly His His His His His
        290                 295             300

<210> SEQ ID NO 105
<211> LENGTH: 4108
<212> TYPE: DNA
<213> ORGANISM: artificial
<220> FEATURE:
<223> OTHER INFORMATION: DNA sequence of OpIE2SP-SNAP cloned into pUC57
      for constitutive expression of secreted chimeric SNAP-target
      protein in invertebrate cells

<400> SEQUENCE: 105

| | | | | |
|---|---|---|---|---|
| tcgcgcgttt | cggtgatgac | ggtgaaaacc | tctgacacat gcagctcccg gagacggtca | 60 |
| cagcttgtct | gtaagcggat | gccgggagca | gacaagcccg tcagggcgcg tcagcgggtg | 120 |
| ttggcgggtg | tcggggctgg | cttaactatg | cggcatcaga gcagattgta ctgagagtgc | 180 |
| accatatgcg | gtgtgaaata | ccgcacagat | gcgtaaggag aaaataccgc atcaggcgcc | 240 |
| attcgccatt | caggctgcgc | aactgttggg | aagggcgatc ggtgcgggcc tcttcgctat | 300 |
| tacgccagct | ggcgaaaggg | ggatgtgctg | caaggcgatt aagttgggta acgccagggt | 360 |
| tttcccagtc | acgacgttgt | aaaacgacgg | ccagtgaat tctcatgatg ataaacaatg | 420 |
| tatggtgcta | atgttgcttc | aacaacaatt | ctgttgaact gtgttttcat gtttgccaac | 480 |
| aagcacctt | atactcggtg | gcctccccac | caccaacttt tttgcactgc aaaaaaacac | 540 |
| gcttttgcac | gcgggcccat | acatagtaca | aactctacgt ttcgtagact attttacata | 600 |
| aatagtctac | accgttgtat | acgctccaaa | tacactacca cacattgaac cttttttgcag | 660 |
| tgcaaaaaag | tacgtgtcgg | cagtcacgta | ggccggcctt atcgggtcgc gtcctgtcac | 720 |
| gtacgaatca | cattatcgga | ccggacgagt | gttgtcttat cgtgacagga cgccagcttc | 780 |
| ctgtgttgct | aaccgcagcc | ggacgcaact | ccttatcgga acaggacgcg cctccatatc | 840 |
| agccgcgcgt | tatctcatgc | gcgtgaccgg | acacgaggcg cccgtcccgc ttatcgcgcc | 900 |
| tataaataca | gcccgcaacg | atctggtaaa | cacagttgaa cagcatctgt tcgaaggatc | 960 |
| cttgatcgag | ctagcatgaa | actatgtatt | ctacttgcag ttgttgcgtt cgtaggattg | 1020 |
| tccttaagat | ctgacaaaga | ctgcgaaatg | aaaagaacta cattggattc accacttggg | 1080 |
| aagttggaac | tgagtggatg | cgagcaagga | ttgcatgaaa ttaagctact gggaaaagga | 1140 |
| acttctgctg | ctgatgcagt | tgaagttcca | gcaccagcag ctgttcttgg aggtcctgag | 1200 |
| cccctcatgc | aagccacagc | ctggcttaac | gcatatttcc accagcctga ggccattgag | 1260 |
| gaatttccag | tccccgccct | tcaccatcct | gtgtttcagc aggagagctt cacccgccag | 1320 |
| gtcctgtgga | aattgctgaa | ggtggtcaag | tttggtgaag tgatttcata tcagcaactt | 1380 |
| gctgcattgg | ccgtaaccc | cgcagctaca | gctgccgtga aaactgctct cagcggaaat | 1440 |
| cctgtgccca | tcctgatccc | ttgtcacaga | gtcgtttcat cttccggagc tgtaggtggc | 1500 |
| tatgaaggag | gactggcagt | taaggagtgg | ctgctggctc atgaaggtca tagacttgga | 1560 |
| aagcctgggc | tgggtcctgc | tggtataggc | gcgccagggt ccctaggtgg cggatccgaa | 1620 |
| aacctgtact | tccagagcga | tatcggaggt | ggaggcccgg gaggtggcgg aagtgactat | 1680 |
| aaagatgacg | acgataagtg | ataagcggcc | gcaaaaccgg ttgagtttat ctgactaaat | 1740 |
| cttagtttgt | attgtcatgt | tttaatacaa | tatgttatgt ttaaatatgt ttttaataaa | 1800 |

-continued

```
ttttataaaa taatttcaac ttttattgta acaacattgt ccatttacac actcctttca    1860
agcgcgtgaa gcttggcgta atcatggtca tagctgtttc ctgtgtgaaa ttgttatccg    1920
ctcacaattc cacacaacat acgagccgga agcataaagt gtaaagcctg gggtgcctaa    1980
tgagtgagct aactcacatt aattgcgttg cgctcactgc ccgctttcca gtcgggaaac    2040
ctgtcgtgcc agctgcatta atgaatcggc caacgcgcgg ggagaggcgg tttgcgtatt    2100
gggcgctctt ccgcttcctc gctcactgac tcgctgcgct cggtcgttcg gctgcggcga    2160
gcggtatcag ctcactcaaa ggcggtaata cggttatcca cagaatcagg ggataacgca    2220
ggaaagaaca tgtgagcaaa aggccagcaa aaggccagga accgtaaaaa ggccgcgttg    2280
ctggcgtttt tccataggct ccgcccccct gacgagcatc acaaaaatcg acgctcaagt    2340
cagaggtggc gaaacccgac aggactataa agataccagg cgtttccccc tggaagctcc    2400
ctcgtgcgct ctcctgttcc gaccctgccg cttaccggat acctgtccgc ctttctccct    2460
tcggaagcg tggcgctttc tcatagctca cgctgtaggt atctcagttc ggtgtaggtc     2520
gttcgctcca agctgggctg tgtgcacgaa ccccccgttc agcccgaccg ctgcgcctta    2580
tccggtaact atcgtcttga gtccaacccg gtaagacacg acttatcgcc actggcagca    2640
gccactggta acaggattag cagagcgagg tatgtaggcg gtgctacaga gttcttgaag    2700
tggtggccta actacggcta cactagaaga acagtatttg gtatctgcgc tctgctgaag    2760
ccagttacct tcggaaaaag agttggtagc tcttgatccg gcaaacaaac caccgctggt    2820
agcggtggtt tttttgtttg caagcagcag attacgcgca gaaaaaaagg atctcaagaa    2880
gatcctttga tcttttctac ggggtctgac gctcagtgga acgaaaactc acgttaaggg    2940
attttggtca tgagattatc aaaaaggatc ttcacctaga tccttttaaa ttaaaaatga    3000
agttttaaat caatctaaag tatatatgag taaacttggt ctgacagtta ccaatgctta    3060
atcagtgagg cacctatctc agcgatctgt ctatttcgtt catccatagt tgcctgactc    3120
cccgtcgtgt agataactac gatacgggag ggcttaccat ctggccccag tgctgcaatg    3180
ataccgcgag acccacgctc accggctcca gatttatcag caataaacca gccagccgga    3240
agggccgagc gcagaagtgg tcctgcaact ttatccgcct ccatccagtc tattaattgt    3300
tgccgggaag ctagagtaag tagttcgcca gttaatagtt tgcgcaacgt tgttgccatt    3360
gctacaggca tcgtggtgtc acgctcgtcg tttggtatgg cttcattcag ctccggttcc    3420
caacgatcaa ggcgagttac atgatccccc atgttgtgca aaaaagcggt tagctccttc    3480
ggtcctccga tcgttgtcag aagtaagttg gccgcagtgt tatcactcat ggttatggca    3540
gcactgcata attctcttac tgtcatgcca tccgtaagat gcttttctgt gactggtgag    3600
tactcaacca agtcattctg agaatagtgt atgcggcgac cgagttgctc ttgcccggcg    3660
tcaatacggg ataataccgc gccacatagc agaactttaa aagtgctcat cattggaaaa    3720
cgttcttcgg ggcgaaaact ctcaaggatc ttaccgctgt tgagatccag ttcgatgtaa    3780
cccactcgtg cacccaactg atcttcagca tcttttactt tcaccagcgt ttctgggtga    3840
gcaaaaacag gaaggcaaaa tgccgcaaaa aagggaataa gggcgacacg gaaatgttga    3900
atactcatac tcttcctttt tcaatattat tgaagcattt atcagggtta ttgtctcatg    3960
agcggataca tatttgaatg tatttagaaa aataaacaaa taggggttcc gcgcacattt    4020
ccccgaaaag tgccacctga cgtctaagaa accattatta tcatgacatt aacctataaa    4080
aataggcgta tcacgaggcc ctttcgtc                                       4108
```

<210> SEQ ID NO 106
<211> LENGTH: 24
<212> TYPE: DNA
<213> ORGANISM: artificial
<220> FEATURE:
<223> OTHER INFORMATION: DNA sequence of C-term peptide tag of OpIE2SP-SNAP

<400> SEQUENCE: 106
gactataaag atgacgacga taag                                          24

<210> SEQ ID NO 107
<211> LENGTH: 8
<212> TYPE: PRT
<213> ORGANISM: artificial
<220> FEATURE:
<223> OTHER INFORMATION: Amino acid sequence of C-term peptide tag of OpIE2SP-SNAP

<400> SEQUENCE: 107

Asp Tyr Lys Asp Asp Asp Asp Lys
 1               5

<210> SEQ ID NO 108
<211> LENGTH: 2200
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Crimean-Congo hemorragic fever virus-proTEV2-Histag for expression in S2 cells

<400> SEQUENCE: 108
atgaagttat gcatattact ggccgtcgtg gcctttgttg gcctctcgct cgggagatct      60
gacaaagact gcgaaatgaa agaactaca  ttggattcac cacttgggaa gttggaactg     120
agtggatgcg agcaaggatt gcatgaaatt aagctactgg aaaaggaac  ttctgctgct     180 gatgcagtta agttccagc  accagcagct gttcttggag tcctgagcc  cctcatgcaa     240 gccacagcct ggcttaacgc atatttccac cagcctgagg ccattgagga atttccagtc     300 cccgccttc  accatcctgt gtttcagcag gagagcttca cccgccaggt cctgtggaaa     360
ttgctgaagg tggtcaagtt tggtgaagtg atttcatatc agcaacttgc tgcattggcc     420
ggtaaccccg cagctacagc tgccgtgaaa actgctctca gcggaaatcc tgtgcccatc     480
ctgatccctt gtcacagagt cgtttcatct tccggagctg taggtggcta tgaaggagga     540
ctggcagtta aggagtggct gctggctcat gaaggtcata gacttggaaa gcctgggctg     600
ggtcctgctg gtataggcgc gccagggtcc ctaggtggcg gatccgaaaa cctgtacttc     660
cagagcgata tcgaaaacaa gatcgaggtg aataacaaag atgagatgaa caggtggttt     720
gaagagttca aaaaggaaa  tggacttgtg gacaccttca caaactccta ttccttttgc     780
gagagtgttc ccaatttgga caggtttgtg tttcagatgg ccagtgccac cgatgatgca     840
cagaaggact ccatctacgc atctgctctg gtggaggcaa caagttttg  tgcacctata     900 tatgagtgcg catgggttag ctccactggc attgtaaaaa agggacttga atggttcgag    960
aaaaatgcag gaaccattaa gtcctgggat gaaagtata  ctgagctaaa ggtcgacgtc   1020
ccgaaaatag agcagcttac gggttaccaa caagctgcct tgaagtggag aaaagacata   1080
ggtttccgtg tcaatgccaa cacagcagct ctgagcaaca agtcctcgc  agaatacaaa   1140 gtccctggtg agattgtgat gtctgtcaaa gagatgctgt cagacatgat taggagaagg   1200
aacctgattc taaacagggg tggtgatgag aacccacgtg gcccagtgag ccatgagcat   1260

-continued

```
gtagactggt gcagggagtt tgtcaaaggc aaatacatca tggccttcaa cccaccatgg   1320
ggggacatca acaagtcagg ccgttcagga atagcacttg ttgcaacagg ccttgctaag   1380
cttgcagaga ctgaaggaaa gggaatattt gatgaagcca aaaagactgt ggaggccctc   1440
aacgggtatc tggacaagca taaggacgaa gttgatagag caagcgccga cagcatgata   1500
acaaaccttc ttaagcatat tgccaaggca caggagctct ataaaaattc atctgcactt   1560
cgtgcacaaa gcgcacagat tgacactgct ttcagctcat actattggct ttacaaggct   1620
ggcgtgactc ctgaaaacctt cccgacggtg tcacagttcc tctttgagct agggaaacag   1680
ccaagaggta ccaagaaaat gaagaaggct cttctgagca ccccaatgaa gtgggggaag   1740
aagctttatg agctctttgc cgatgattct ttccagcaga acaggattta catgcatcct   1800
gccgtgctta cagctggtag aatcagtgaa atggggagtct gctttgggac aatccctgtg   1860
gccaatcctg atgatgctgc ccaaggatct ggacacacta agtctattct caacctccgt   1920
accaacactg agaccaataa tccgtgtgcc aaaaccatcg tcaagctatt tgaagttcaa   1980
aaaacagggt tcaacattca ggacatggac atagtggcct ctgagcactt gctacaccaa   2040
tcccttgttg gcaagcaatc cccattccag aacgcctaca acgtcaaggg caatgccacc   2100
agtgctaaca tcatcccggg agagaatcta tattttcaag ggcccggcgg aggtagtcac   2160
catcatcacc atcactaatg accggtgcgg ccgcaagctt                         2200
```

<210> SEQ ID NO 109
<211> LENGTH: 707
<212> TYPE: PRT
<213> ORGANISM: artificial
<220> FEATURE:
<223> OTHER INFORMATION: Amino acid sequence of fusion protein
      [SNAPlike-proTEV1-CCHF.N-proTEV2-Histag]

<400> SEQUENCE: 109

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190
```

```
Leu Gly Gly Gly Ser Glu Asn Leu Tyr Phe Gln Ser Asp Ile Glu Asn
            195                 200                 205

Lys Ile Glu Val Asn Asn Lys Asp Glu Met Asn Arg Trp Phe Glu Glu
        210                 215                 220

Phe Lys Lys Gly Asn Gly Leu Val Asp Thr Phe Thr Asn Ser Tyr Ser
225                 230                 235                 240

Phe Cys Glu Ser Val Pro Asn Leu Asp Arg Phe Val Phe Gln Met Ala
                245                 250                 255

Ser Ala Thr Asp Asp Ala Gln Lys Asp Ser Ile Tyr Ala Ser Ala Leu
            260                 265                 270

Val Glu Ala Thr Lys Phe Cys Ala Pro Ile Tyr Glu Cys Ala Trp Val
        275                 280                 285

Ser Ser Thr Gly Ile Val Lys Lys Gly Leu Glu Trp Phe Glu Lys Asn
        290                 295                 300

Ala Gly Thr Ile Lys Ser Trp Asp Glu Ser Tyr Thr Glu Leu Lys Val
305                 310                 315                 320

Asp Val Pro Lys Ile Glu Gln Leu Thr Gly Tyr Gln Ala Ala Leu
                325                 330                 335

Lys Trp Arg Lys Asp Ile Gly Phe Arg Val Asn Ala Asn Thr Ala Ala
            340                 345                 350

Leu Ser Asn Lys Val Leu Ala Glu Tyr Lys Val Pro Gly Glu Ile Val
        355                 360                 365

Met Ser Val Lys Glu Met Leu Ser Asp Met Ile Arg Arg Asn Leu
370                 375                 380

Ile Leu Asn Arg Gly Gly Asp Glu Asn Pro Arg Gly Pro Val Ser His
385                 390                 395                 400

Glu His Val Asp Trp Cys Arg Glu Phe Val Lys Gly Lys Tyr Ile Met
                405                 410                 415

Ala Phe Asn Pro Pro Trp Gly Asp Ile Asn Lys Ser Gly Arg Ser Gly
                420                 425                 430

Ile Ala Leu Val Ala Thr Gly Leu Ala Lys Leu Ala Glu Thr Glu Gly
            435                 440                 445

Lys Gly Ile Phe Asp Glu Ala Lys Lys Thr Val Glu Ala Leu Asn Gly
        450                 455                 460

Tyr Leu Asp Lys His Lys Asp Glu Val Asp Arg Ala Ser Ala Asp Ser
465                 470                 475                 480

Met Ile Thr Asn Leu Leu Lys His Ile Ala Lys Ala Gln Glu Leu Tyr
                485                 490                 495

Lys Asn Ser Ser Ala Leu Arg Ala Gln Ser Ala Gln Ile Asp Thr Ala
            500                 505                 510

Phe Ser Ser Tyr Tyr Trp Leu Tyr Lys Ala Gly Val Thr Pro Glu Thr
        515                 520                 525

Phe Pro Thr Val Ser Gln Phe Leu Phe Glu Leu Gly Lys Gln Pro Arg
530                 535                 540

Gly Thr Lys Lys Met Lys Lys Ala Leu Leu Ser Thr Pro Met Lys Trp
545                 550                 555                 560

Gly Lys Lys Leu Tyr Glu Leu Phe Ala Asp Asp Ser Phe Gln Gln Asn
                565                 570                 575

Arg Ile Tyr Met His Pro Ala Val Leu Thr Ala Gly Arg Ile Ser Glu
            580                 585                 590

Met Gly Val Cys Phe Gly Thr Ile Pro Val Ala Asn Pro Asp Asp Ala
        595                 600                 605
```

```
Ala Gln Gly Ser Gly His Thr Lys Ser Ile Leu Asn Leu Arg Thr Asn
    610                 615                 620

Thr Glu Thr Asn Asn Pro Cys Ala Lys Thr Ile Val Lys Leu Phe Glu
625                 630                 635                 640

Val Gln Lys Thr Gly Phe Asn Ile Gln Asp Met Asp Ile Val Ala Ser
                645                 650                 655

Glu His Leu Leu His Gln Ser Leu Val Gly Lys Gln Ser Pro Phe Gln
                660                 665                 670

Asn Ala Tyr Asn Val Lys Gly Asn Ala Thr Ser Ala Asn Ile Ile Pro
            675                 680                 685

Gly Glu Asn Leu Tyr Phe Gln Gly Pro Gly Gly Gly Ser His His His
    690                 695                 700

His His His
705

<210> SEQ ID NO 110
<211> LENGTH: 2974
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Ebola virus-proTEV2-Histag for expression in
      S2 cells

<400> SEQUENCE: 110
atgaagttat gcatattact ggccgtcgtg gcctttgttg gcctctcgct cgggagatct      60
gacaaagact gcgaaatgaa aagaactaca ttggattcac cacttgggaa gttggaactg     120
agtggatgcg agcaaggatt gcatgaaatt aagctactgg aaaaggaac ttctgctgct     180 gatgcagttg aagttccagc accagcagct gttcttggag gtcctgagcc cctcatgcaa     240
gccacagcct ggcttaacgc atatttccac cagcctgagg ccattgagga atttccagtc     300 cccgccttc accatcctgt gtttcagcag gagagcttca cccgccaggt cctgtggaaa     360
ttgctgaagg tggtcaagtt tggtgaagtg atttcatatc agcaacttgc tgcattggcc     420
ggtaaccccg cagctacagc tgccgtgaaa actgctctca gcggaaatcc tgtgcccatc     480 ctgatcccctt gtcacagagt cgtttcatct tccggagctg taggtggcta tgaaggagga     540
ctggcagtta aggagtggct gctggctcat gaaggtcata acttggaaa gcctgggctg     600 ggtcctgctg gtataggcgc gccagggtcc ctaggtggcg atccgaaaa cctgtacttc     660 cagagcgata tcgattctcg tcctcagaaa atctggatgg cgccgagtct cactgaatct     720
gacatggatt accacaaaat cttgacagca ggtctgtccg ttcaacaggg gattgttcgg     780
caaagagtca tcccagtgta tcaagtaaac aatcttgaag aaatttgcca acttatcata     840
caggcctttg aagcaggtgt tgattttcaa gagagtgcgg acagtttcct tctcatgctt     900
tgtcttcatc atgcgtacca gggagattac aaactttctt ggaaagtgg cgcagtcaag     960 tatttggaag gcacgggtt ccgttttgaa gtcaagaagc gtgatggagt gaagcgcctt    1020
gaggaattgc tgccagcagt atctagtgga aaaaacatta gagaacact tgctgccatg    1080 ccggaagagg agacaactga agctaatgcc ggtcagtttc tctcctttgc aagtctattc    1140
cttccgaaat tggtagtagg agaaaaggct tgccttgaga aggttcaaag gcaaattcaa    1200
gtacatgcag agcaaggact gatacaatat ccaacagctt ggcaatcagt aggacacatg    1260
atggtgattt ccgtttgat gcgaacaaat tttctgatca aatttctcct aatacaccaa    1320
gggatgcaca tggttgccgg gcatgatgcc aacgatgctg tgatttcaaa ttcagtggct    1380
```

-continued

```
caagctcgtt tttcaggctt attgattgtc aaaacagtac ttgatcatat cctacaaaag    1440
acagaacgag gagttcgtct ccatcctctt gcaaggaccg ccaaggtaaa aaatgaggtg    1500
aactccttta aggctgcact cagctccctg gccaagcatg gagagtatgc tcctttcgcc    1560
cgacttttga acctttctgg agtaaataat cttgagcatg gtctttcccc tcaactatcg    1620
gcaattgcac tcggagtcgc cacagcacac gggagtaccc tcgcaggagt aaatgttgga    1680
gaacagtatc aacaactcag agaggctgcc actgaggctg agaagcaact ccaacaatat    1740
gcagagtctc gcgaacttga ccatcttgga cttgatgatc aggaaaagaa aattcttatg    1800
aacttccatc agaaaaagaa cgaaatcagc ttccagcaaa caaacgctat ggtaactcta    1860
agaaaagagc gcctggccaa gctgacagaa gctatcactg ctgcgtcact gcccaaaaca    1920
agtggacatt acgatgatga tgacgacatt cctttccag acccatcaa tgatgacgac      1980
aatcctggcc atcaagatga tgatccgact gactcacagg atacgaccat tcccgatgtg    2040
gtggttgatc ccgatgatgg aagctacggc gaataccaga gttactcgga aaacggcatg    2100
aatgcaccag atgacttggt cctattcgat ctggacgagg acgacgagga cactaagcca    2160
gtgcctaata gatcgaccaa gggtggacaa cagaagaaca gtcaaaaggg ccagcatata    2220
gagggcagac agacacaatc caggccaatt caaaatgtcc caggccctca cagaacaatc    2280
caccacgcca gtgcgccact cacggacaat gacagaagaa atgaaccctc cggctcaacc    2340
agccctcgca tgctgacacc aattaacgaa gaggcagacc cactggacga tgccgacgac    2400
gagacgtcta gccttccgcc cttggagtca gatgatgaag agcaggacag ggacggaact    2460
tccaaccgca cacccactgt cgccccaccg gctcccgtat acagagatca ctctgaaaag    2520
aaagaactcc cgcaagacga gcaacaagat caggaccaca ctcaagaggc caggaaccag    2580
gacagtgaca cacccagtc agaacactct tttgaggaga tgtatcgcca cattctaaga    2640
tcacagggc catttgatgc tgttttgtat tatcatatga tgaaggatga gcctgtagtt    2700
ttcagtacca gtgatggcaa agagtacacg tatccagact cccttgaaga ggaatatcca    2760
ccatggctca ctgaaaaaga ggctatgaat gaagagaata gatttgttac attggatggt    2820
caacaatttt attggccggt gatgaatcac aagaataaat tcatggcaat cctgcaacat    2880
catcagggcc cgggagagaa tctatatttt caagggcccg gcggaggtag tcaccatcat    2940
caccatcact aatgaccggt gcggccgcaa gctt                                2974
```

<210> SEQ ID NO 111
<211> LENGTH: 965
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 111

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80
```

```
Pro Val Pro Ala Leu His His Pro Val Phe Gln Gln Glu Ser Phe Thr
                85                  90                  95
Arg Gln Val Leu Trp Lys Leu Leu Lys Val Val Lys Phe Gly Glu Val
            100                 105                 110
Ile Ser Tyr Gln Gln Leu Ala Ala Leu Ala Gly Asn Pro Ala Ala Thr
        115                 120                 125
Ala Ala Val Lys Thr Ala Leu Ser Gly Asn Pro Val Pro Ile Leu Ile
    130                 135                 140
Pro Cys His Arg Val Val Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
            180                 185                 190
Leu Gly Gly Gly Ser Glu Asn Leu Tyr Phe Gln Ser Asp Ile Asp Ser
        195                 200                 205
Arg Pro Gln Lys Ile Trp Met Ala Pro Ser Leu Thr Glu Ser Asp Met
    210                 215                 220
Asp Tyr His Lys Ile Leu Thr Ala Gly Leu Ser Val Gln Gln Gly Ile
225                 230                 235                 240
Val Arg Gln Arg Val Ile Pro Val Tyr Gln Val Asn Asn Leu Glu Glu
                245                 250                 255
Ile Cys Gln Leu Ile Ile Gln Ala Phe Glu Ala Gly Val Asp Phe Gln
            260                 265                 270
Glu Ser Ala Asp Ser Phe Leu Leu Met Leu Cys Leu His His Ala Tyr
        275                 280                 285
Gln Gly Asp Tyr Lys Leu Phe Leu Glu Ser Gly Ala Val Lys Tyr Leu
    290                 295                 300
Glu Gly His Gly Phe Arg Phe Glu Val Lys Lys Arg Asp Gly Val Lys
305                 310                 315                 320
Arg Leu Glu Glu Leu Leu Pro Ala Val Ser Ser Gly Lys Asn Ile Lys
                325                 330                 335
Arg Thr Leu Ala Ala Met Pro Glu Glu Thr Thr Glu Ala Asn Ala
            340                 345                 350
Gly Gln Phe Leu Ser Phe Ala Ser Leu Phe Leu Pro Lys Leu Val Val
        355                 360                 365
Gly Glu Lys Ala Cys Leu Glu Lys Val Gln Arg Gln Ile Gln Val His
    370                 375                 380
Ala Glu Gln Gly Leu Ile Gln Tyr Pro Thr Ala Trp Gln Ser Val Gly
385                 390                 395                 400
His Met Met Val Ile Phe Arg Leu Met Arg Thr Asn Phe Leu Ile Lys
                405                 410                 415
Phe Leu Leu Ile His Gln Gly Met His Met Val Ala Gly His Asp Ala
            420                 425                 430
Asn Asp Ala Val Ile Ser Asn Ser Val Ala Gln Ala Arg Phe Ser Gly
        435                 440                 445
Leu Leu Ile Val Lys Thr Val Leu Asp His Ile Leu Gln Lys Thr Glu
    450                 455                 460
Arg Gly Val Arg Leu His Pro Leu Ala Arg Thr Ala Lys Val Lys Asn
465                 470                 475                 480
Glu Val Asn Ser Phe Lys Ala Ala Leu Ser Ser Leu Ala Lys His Gly
                485                 490                 495
```

```
Glu Tyr Ala Pro Phe Ala Arg Leu Leu Asn Leu Ser Gly Val Asn Asn
                500                 505                 510

Leu Glu His Gly Leu Phe Pro Gln Leu Ser Ala Ile Ala Leu Gly Val
            515                 520                 525

Ala Thr Ala His Gly Ser Thr Leu Ala Gly Val Asn Val Gly Glu Gln
        530                 535                 540

Tyr Gln Gln Leu Arg Glu Ala Ala Thr Glu Ala Glu Lys Gln Leu Gln
545                 550                 555                 560

Gln Tyr Ala Glu Ser Arg Glu Leu Asp His Leu Gly Leu Asp Asp Gln
                565                 570                 575

Glu Lys Lys Ile Leu Met Asn Phe His Gln Lys Lys Asn Glu Ile Ser
            580                 585                 590

Phe Gln Gln Thr Asn Ala Met Val Thr Leu Arg Lys Glu Arg Leu Ala
        595                 600                 605

Lys Leu Thr Glu Ala Ile Thr Ala Ala Ser Leu Pro Lys Thr Ser Gly
610                 615                 620

His Tyr Asp Asp Asp Asp Ile Pro Phe Pro Gly Pro Ile Asn Asp
625                 630                 635                 640

Asp Asp Asn Pro Gly His Gln Asp Asp Pro Thr Asp Ser Gln Asp
                645                 650                 655

Thr Thr Ile Pro Asp Val Val Asp Pro Asp Gly Ser Tyr Gly
            660                 665                 670

Glu Tyr Gln Ser Tyr Ser Glu Asn Gly Met Asn Ala Pro Asp Asp Leu
        675                 680                 685

Val Leu Phe Asp Leu Asp Glu Asp Asp Thr Lys Pro Val Pro
690                 695                 700

Asn Arg Ser Thr Lys Gly Gly Gln Gln Lys Asn Ser Gln Lys Gly Gln
705                 710                 715                 720

His Ile Glu Gly Arg Gln Thr Gln Ser Arg Pro Ile Gln Asn Val Pro
                725                 730                 735

Gly Pro His Arg Thr Ile His His Ala Ser Ala Pro Leu Thr Asp Asn
            740                 745                 750

Asp Arg Arg Asn Glu Pro Ser Gly Ser Thr Ser Pro Arg Met Leu Thr
        755                 760                 765

Pro Ile Asn Glu Glu Ala Asp Pro Leu Asp Asp Ala Asp Glu Thr
770                 775                 780

Ser Ser Leu Pro Pro Leu Glu Ser Asp Asp Glu Gln Asp Arg Asp
785                 790                 795                 800

Gly Thr Ser Asn Arg Thr Pro Thr Val Ala Pro Pro Ala Pro Val Tyr
                805                 810                 815

Arg Asp His Ser Glu Lys Lys Glu Leu Pro Gln Asp Glu Gln Gln Asp
            820                 825                 830

Gln Asp His Thr Gln Glu Ala Arg Asn Gln Asp Ser Asp Asn Thr Gln
        835                 840                 845

Ser Glu His Ser Phe Glu Glu Met Tyr Arg His Ile Leu Arg Ser Gln
850                 855                 860

Gly Pro Phe Asp Ala Val Leu Tyr Tyr His Met Met Lys Asp Glu Pro
865                 870                 875                 880

Val Val Phe Ser Thr Ser Asp Gly Lys Glu Tyr Thr Tyr Pro Asp Ser
                885                 890                 895

Leu Glu Glu Glu Tyr Pro Pro Trp Leu Thr Glu Lys Glu Ala Met Asn
            900                 905                 910

Glu Glu Asn Arg Phe Val Thr Leu Asp Gly Gln Gln Phe Tyr Trp Pro
```

|  | 915 |  | 920 |  | 925 |  |
|---|---|---|---|---|---|---|

Val Met Asn His Lys Asn Lys Phe Met Ala Ile Leu Gln His His Gln
    930                935              940

Gly Pro Gly Glu Asn Leu Tyr Phe Gln Gly Pro Gly Gly Ser His
945              950              955            960

His His His His His
            965

<210> SEQ ID NO 112
<211> LENGTH: 2842
<212> TYPE: DNA
<213> ORGANISM: artificial
<220> FEATURE:
<223> OTHER INFORMATION: DNA sequence encoding ssBiP-SNAPlike-proTEV1-N
     nucleoprotein of the Marburg virus-proTEV2-Histag for expression
     in S2 cells

<400> SEQUENCE: 112

| | |
|---|---|
| atgaagttat gcatattact ggccgtcgtg gcctttgttg cctctcgct cgggagatct | 60 |
| gacaaagact gcgaaatgaa agaactaca ttggattcac cacttgggaa gttggaactg | 120 |
| agtggatgcg agcaaggatt gcatgaaatt aagctactgg aaaaggaac ttctgctgct | 180 |
| gatgcagttg aagttccagc accagcagct gttcttggag gtcctgagcc cctcatgcaa | 240 |
| gccacagcct ggcttaacgc atatttccac cagcctgagg ccattgagga atttccagtc | 300 |
| cccgccctcc accatcctgt gtttcagcag gagagcttca cccgccaggt cctgtggaaa | 360 |
| ttgctgaagg tggtcaagtt tggtgaagtg atttcatatc agcaacttgc tgcattggcc | 420 |
| ggtaaccccg cagctacagc tgccgtgaaa actgctctca gcggaaatcc tgtgcccatc | 480 |
| ctgatcccct tgtcacagag tcgtttcatc tccggagctg taggtggcta tgaaggagga | 540 |
| ctggcagtta aggagtggct gctggctcat gaaggtcata gacttggaaa gcctgggctg | 600 |
| ggtcctgctg gtataggcgc gccagggtcc ctaggtggcg gatccgaaaa cctgtacttc | 660 |
| cagagcgata tcgatttaca cagtttgttg gagttgggta caaaacccac tgcccctcat | 720 |
| gttcgtaata gaaagtgat attatttgac acaaatcatc aggttagtat ctgtaatcag | 780 |
| ataatagatg caataaactc agggattgat cttggtgatc tcctagaagg ggggtttgctg | 840 |
| acgttgtgtg ttgagcatta ctataattct gataaggata aattcaacac aagtcctatc | 900 |
| gcgaagtact acgtgatgc gggctatgaa tttgatgtca tcaagaatgc agatgcaacc | 960 |
| cgctttctgg atgtgattcc taatgaacct cattacagcc ctttaattct agcccttaag | 1020 |
| acattggaaa gtactgaatc tcagagggg agaattgggc tctttttatc attttgcagt | 1080 |
| cttttcctcc caaaacttgt cgtcggagac cgagctagta tcgaaaaggc tttaagacaa | 1140 |
| gtaacagtgc atcaagaaca ggggatcgtc acatacccta atcattggct taccacaggc | 1200 |
| cacatgaaag taattttcgg gattttgagg tccagcttca ttttaaagtt tgtgttgatt | 1260 |
| catcaaggag taaatttggt gacaggtcat gatgcctatg acagtatcat tagtaattca | 1320 |
| gtaggtcaaa ctagattctc aggacttctt atcgtgaaaa cagttctgga gttcatcttg | 1380 |
| caaaaaactg attcaggggt gacactacat cctttggtgc ggacctccaa agtaaaaaat | 1440 |
| gaagttgcta gtttcaagca ggcgttgagc aacctagccc gacatgggga atacgcacca | 1500 |
| tttgcacggg ttctgaattt atcagggatt aacaacctcg aacatggact ctatcctcag | 1560 |
| ctttcagcaa ttgcgctggg tgtggcaaca gcacacggca gtacattggc tggtgtcaat | 1620 |
| gttggcgaac aatatcaaca actacgagag gcggcacatg atgcggaagt aaaactacaa | 1680 |

```
aggcgacatg aacatcagga aattcaagct attgccgagg atgacgagga aaggaagata   1740
ttagaacaat tccaccttca gaaaactgaa atcacacaca gtcagacact agccgtcctc   1800
agccagaaac gagaaaaatt agctcgtctc gctgcagaaa ttgaaaacaa tattgtggaa   1860
gatcagggat ttaagcaatc acagaatcgg gtgtcacagt cgtttttgaa tgaccctaca   1920
cctgtggaag taacggttca agccaggccc atgaatcgac caactgctct gcctccccca   1980
gttgacgaca agattgagca tgaatctaca gaagatagct cttcttcaag tagctttgtt   2040
gacttgaatg atccatttgc actgctgaat gaggacgagg atactcttga tgacagtgtc   2100
atgatccccg gcacaacatc gagagaattt caagggattc ctgaaccgcc aagacaatcc   2160
caagacctca ataacagcca aggaaagcag gaagatgaat ccacaaatcc gattaagaaa   2220
cagtttctga gataccaaga attgcctcct gttcaagagg atgatgaatc ggaatacaca   2280
actgactctc aagaaagcat cgaccaacca ggttccgaca atgaacaagg agttgatctt   2340
ccacctcctc cgttgtacgc tcaggaaaaa agacaggacc caatacagca cccagcagca   2400
aaccctcaag atcccttcgg cagtattggt gatgtaaatg gtgacatctt agaacctata   2460
agatcacctt cttcaccatc tgctcctcag gaagacacaa ggatgaggga agcctatgaa   2520
ttgtcgcctg atttcacaaa tgatgaggat aatcagcaga attggccaca aagagtggtg   2580
acaaagaagg gtagaacttt cctttatcct aatgatcttc tgcaaacaaa tcctccagag   2640
tcacttataa cagccctcgt tgaggaatac caaaatcctg tctcagctaa ggagcttcaa   2700
gcagattggc ccgacatgtc atttgatgaa aggagacatg ttgcgatgaa cttgggcccg   2760
ggagagaatc tatattttca agggcccggc ggaggtagtc accatcatca ccatcactaa   2820
tgaccggtgc ggccgcaagc tt                                            2842
```

<210> SEQ ID NO 113
<211> LENGTH: 921
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 113

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
```

-continued

```
            145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
                180                 185                 190
Leu Gly Gly Gly Ser Glu Asn Leu Tyr Phe Gln Ser Asp Ile Asp Leu
                195                 200                 205
His Ser Leu Leu Glu Leu Gly Thr Lys Pro Thr Ala Pro His Val Arg
    210                  215                 220
Asn Lys Lys Val Ile Leu Phe Asp Thr Asn His Gln Val Ser Ile Cys
225                 230                 235                 240
Asn Gln Ile Ile Asp Ala Ile Asn Ser Gly Ile Asp Leu Gly Asp Leu
                245                 250                 255
Leu Glu Gly Gly Leu Leu Thr Leu Cys Val Glu His Tyr Tyr Asn Ser
                260                 265                 270
Asp Lys Asp Lys Phe Asn Thr Ser Pro Ile Ala Lys Tyr Leu Arg Asp
                275                 280                 285
Ala Gly Tyr Glu Phe Asp Val Ile Lys Asn Ala Asp Ala Thr Arg Phe
                290                 295                 300
Leu Asp Val Ile Pro Asn Glu Pro His Tyr Ser Pro Leu Ile Leu Ala
305                 310                 315                 320
Leu Lys Thr Leu Glu Ser Thr Glu Ser Gln Arg Gly Arg Ile Gly Leu
                325                 330                 335
Phe Leu Ser Phe Cys Ser Leu Phe Leu Pro Lys Leu Val Val Gly Asp
                340                 345                 350
Arg Ala Ser Ile Glu Lys Ala Leu Arg Gln Val Thr Val His Gln Glu
                355                 360                 365
Gln Gly Ile Val Thr Tyr Pro Asn His Trp Leu Thr Thr Gly His Met
                370                 375                 380
Lys Val Ile Phe Gly Ile Leu Arg Ser Ser Phe Ile Leu Lys Phe Val
385                 390                 395                 400
Leu Ile His Gln Gly Val Asn Leu Val Thr Gly His Asp Ala Tyr Asp
                405                 410                 415
Ser Ile Ile Ser Asn Ser Val Gly Gln Thr Arg Phe Ser Gly Leu Leu
                420                 425                 430
Ile Val Lys Thr Val Leu Glu Phe Ile Leu Gln Lys Thr Asp Ser Gly
                435                 440                 445
Val Thr Leu His Pro Leu Val Arg Thr Ser Lys Val Lys Asn Glu Val
                450                 455                 460
Ala Ser Phe Lys Gln Ala Leu Ser Asn Leu Ala Arg His Gly Glu Tyr
465                 470                 475                 480
Ala Pro Phe Ala Arg Val Leu Asn Leu Ser Gly Ile Asn Asn Leu Glu
                485                 490                 495
His Gly Leu Tyr Pro Gln Leu Ser Ala Ile Ala Leu Gly Val Ala Thr
                500                 505                 510
Ala His Gly Ser Thr Leu Ala Gly Val Asn Val Gly Glu Gln Tyr Gln
                515                 520                 525
Gln Leu Arg Glu Ala His Asp Ala Glu Val Lys Leu Gln Arg Arg
                530                 535                 540
His Glu His Gln Glu Ile Gln Ala Ile Ala Glu Asp Glu Glu Arg
545                 550                 555                 560
Lys Ile Leu Glu Gln Phe His Leu Gln Lys Thr Glu Ile Thr His Ser
                565                 570                 575
```

```
Gln Thr Leu Ala Val Leu Ser Gln Lys Arg Glu Lys Leu Ala Arg Leu
            580                 585                 590
Ala Ala Glu Ile Glu Asn Asn Ile Val Glu Asp Gln Gly Phe Lys Gln
        595                 600                 605
Ser Gln Asn Arg Val Ser Gln Ser Phe Leu Asn Asp Pro Thr Pro Val
    610                 615                 620
Glu Val Thr Val Gln Ala Arg Pro Met Asn Arg Pro Thr Ala Leu Pro
625                 630                 635                 640
Pro Pro Val Asp Asp Lys Ile Glu His Glu Ser Thr Glu Asp Ser Ser
                645                 650                 655
Ser Ser Ser Ser Phe Val Asp Leu Asn Asp Pro Phe Ala Leu Leu Asn
            660                 665                 670
Glu Asp Glu Asp Thr Leu Asp Asp Ser Val Met Ile Pro Gly Thr Thr
        675                 680                 685
Ser Arg Glu Phe Gln Gly Ile Pro Glu Pro Arg Gln Ser Gln Asp
    690                 695                 700
Leu Asn Asn Ser Gln Gly Lys Gln Glu Asp Glu Ser Thr Asn Pro Ile
705                 710                 715                 720
Lys Lys Gln Phe Leu Arg Tyr Gln Glu Leu Pro Pro Val Gln Glu Asp
                725                 730                 735
Asp Glu Ser Glu Tyr Thr Thr Asp Ser Gln Glu Ser Ile Asp Gln Pro
            740                 745                 750
Gly Ser Asp Asn Glu Gln Gly Val Asp Leu Pro Pro Pro Leu Tyr
        755                 760                 765
Ala Gln Glu Lys Arg Gln Asp Pro Ile Gln His Pro Ala Ala Asn Pro
    770                 775                 780
Gln Asp Pro Phe Gly Ser Ile Gly Asp Val Asn Gly Asp Ile Leu Glu
785                 790                 795                 800
Pro Ile Arg Ser Pro Ser Ser Pro Ser Ala Pro Gln Glu Asp Thr Arg
                805                 810                 815
Met Arg Glu Ala Tyr Glu Leu Ser Pro Asp Phe Thr Asn Asp Glu Asp
            820                 825                 830
Asn Gln Gln Asn Trp Pro Gln Arg Val Val Thr Lys Lys Gly Arg Thr
        835                 840                 845
Phe Leu Tyr Pro Asn Asp Leu Leu Gln Thr Asn Pro Pro Glu Ser Leu
    850                 855                 860
Ile Thr Ala Leu Val Glu Glu Tyr Gln Asn Pro Val Ser Ala Lys Glu
865                 870                 875                 880
Leu Gln Ala Asp Trp Pro Asp Met Ser Phe Asp Glu Arg Arg His Val
                885                 890                 895
Ala Met Asn Leu Gly Pro Gly Glu Asn Leu Tyr Phe Gln Gly Pro Gly
            900                 905                 910
Gly Gly Ser His His His His His
        915                 920

<210> SEQ ID NO 114
<211> LENGTH: 2461
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Lassa virus-proTEV2-Histag for expression in
      S2 cells

<400> SEQUENCE: 114
```

```
atgaagttat gcatattact ggccgtcgtg gcctttgttg gcctctcgct cgggagatct    60
gacaaagact gcgaaatgaa aagaactaca ttggattcac cacttgggaa gttggaactg   120
agtggatgcg agcaaggatt gcatgaaatt aagctactgg aaaaggaac ttctgctgct   180 gatgcagttg aagttccagc accagcagct gttcttggag gtcctgagcc cctcatgcaa   240
gccacagcct ggcttaacgc atatttccac cagcctgagg ccattgagga atttccagtc   300
cccgcccttc accatcctgt gtttcagcag gagagcttca cccgccaggt cctgtggaaa   360
ttgctgaagg tggtcaagtt tggtgaagtg atttcatatc agcaacttgc tgcattggcc   420
ggtaaccccg cagctacagc tgccgtgaaa actgctctca gcggaaatcc tgtgcccatc   480
ctgatccctt gtcacagagt cgtttcatct tccggagctg taggtggcta tgaaggagga   540
ctggcagtta aggagtggct gctggctcat gaaggtcata gacttggaaa gcctgggctg   600
ggtcctgctg gtataggcgc gccagggtcc ctaggtggcg gatccgaaaa cctgtacttc   660
cagagcgata tcagtgcctc aaaggaaata aaatcctttt tgtggacaca atctttgagg   720
agggaattat ctggttactg ctccaacatc aaactcagg tggtgaaaga tgcccaggct   780
cttttacatg gacttgactt ctccgaagtc agtaatgttc aacggttgat gcgcaaggag   840
agaagggatg acaatgattt gaaacggttg agggacctaa atcaagcggt caacaatctt   900
gttgaattaa aatcaactca acaaagagt atactgagag ttgggactct aacctcagat   960
gacttattaa tcttagccgc tgacctagag aagttaaagt caaaggtgat cagaacagaa  1020
aggccattaa gtgcaggtgt ctatatgggc aacctaagct cacagcaact tgaccaaaga  1080
agagctctcc tgaatatgat aggaatgagt ggtggtaatc aaggggctcg ggctgggaga  1140
gatggagtgg tgagagtttg ggatgtgaaa aatgcagagt tgctcaataa tcagttcggg  1200
accatgccaa gtctgacact ggcatgtctg acaaaacagg ggcaggttga cttgaatgat  1260
gcagtacaag cattgacaga tttgggttg atctacacag caaagtatcc caacacttca  1320
gacttagaca ggctgactca aagtcatccc atcctaaata tgattgacac caagaaaagc  1380
tctttgaata tctcaggtta taattttagc ttgggtgcag ctgtgaaggc aggagcttgc  1440
atgctggatg tgcaatat gttggagaca atcaaggtgt cacctcagac aatggatggt  1500
atcctcaaat ccattttaaa ggtcaagaag gctcttggaa tgttcatttc agacaccct  1560 ggtgaaagga atccttatga aaacatactc tacaagattt gtttgtcagg agatggatgg  1620
ccatatattg catcaagaac ctcaataaca ggaagggcct gggaaaacac tgtcgttgat  1680
ctggaatcag atgggaagcc acagaaagct gacagcaaca attccagtaa atccctgcag  1740
tcggcagggt ttaccgctgg gcttacctat tctcagctga tgaccctcaa ggatgcaatg  1800
ctgcaacttg acccaaatgc taagacctgg atggacattg aaggaagacc tgaagatcca  1860
gtggaaattg ccctctatca accaagttca ggctgctaca tacacttctt ccgtgaacct  1920
actgatttaa agcagttcaa gcaggatgct aagtactcac atgggattga tgtcacagac  1980
ctcttcgcta cacaaccggg cttgaccagt gctgtcattg atgcactccc ccggaatatg  2040
gtcattacct gtcaggggtc cgatgacata aggaaactcc ttgaatcaca aggaagaaaa  2100
gacattaaac taattgatat tgccctcagc aaaactgatt ccaggaagta tgaaaatgca  2160
gtctgggacc agtataaaga cttatgccac atgcacacag gtgtcgttgt tgaaaagaag  2220
aaaagaggcg gtaaagagga aataaccccct cactgtgcac taatggactg catcatgttt  2280
gatgcagcag tgtcaggagg actgaacaca tcggttttga gagcagtgct gcccagagat  2340
atggtgttca gaacatcgac acctagagtc gttctcccgg gagagaatct atattttcaa  2400
```

```
gggcccggcg gaggtagtca ccatcatcac catcactaat gaccggtgcg gccgcaagct    2460
t                                                                    2461
```

<210> SEQ ID NO 115
<211> LENGTH: 794
<212> TYPE: PRT
<213> ORGANISM: artificial
<220> FEATURE:
<223> OTHER INFORMATION: Amino acid sequence of fusion protein
      [SNAPlike-proTEV1-LAS.N-proTEV2-Histag]

<400> SEQUENCE: 115

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ala
        195                 200                 205

Ser Lys Glu Ile Lys Ser Phe Leu Trp Thr Gln Ser Leu Arg Arg Glu
    210                 215                 220

Leu Ser Gly Tyr Cys Ser Asn Ile Lys Leu Gln Val Val Lys Asp Ala
225                 230                 235                 240

Gln Ala Leu Leu His Gly Leu Asp Phe Ser Glu Val Ser Asn Val Gln
                245                 250                 255

Arg Leu Met Arg Lys Glu Arg Arg Asp Asp Asn Asp Leu Lys Arg Leu
            260                 265                 270

Arg Asp Leu Asn Gln Ala Val Asn Asn Leu Val Glu Leu Lys Ser Thr
        275                 280                 285

Gln Gln Lys Ser Ile Leu Arg Val Gly Thr Leu Thr Ser Asp Asp Leu
    290                 295                 300

Leu Ile Leu Ala Ala Asp Leu Glu Lys Leu Lys Ser Lys Val Ile Arg
305                 310                 315                 320

Thr Glu Arg Pro Leu Ser Ala Gly Val Tyr Met Gly Asn Leu Ser Ser
                325                 330                 335
```

```
Gln Gln Leu Asp Gln Arg Arg Ala Leu Leu Asn Met Ile Gly Met Ser
            340                 345                 350

Gly Gly Asn Gln Gly Ala Arg Ala Gly Arg Asp Gly Val Val Arg Val
            355                 360                 365

Trp Asp Val Lys Asn Ala Glu Leu Leu Asn Asn Gln Phe Gly Thr Met
            370                 375                 380

Pro Ser Leu Thr Leu Ala Cys Leu Thr Lys Gln Gly Gln Val Asp Leu
385                 390                 395                 400

Asn Asp Ala Val Gln Ala Leu Thr Asp Leu Gly Leu Ile Tyr Thr Ala
                    405                 410                 415

Lys Tyr Pro Asn Thr Ser Asp Leu Asp Arg Leu Thr Gln Ser His Pro
            420                 425                 430

Ile Leu Asn Met Ile Asp Thr Lys Lys Ser Ser Leu Asn Ile Ser Gly
            435                 440                 445

Tyr Asn Phe Ser Leu Gly Ala Ala Val Lys Ala Gly Ala Cys Met Leu
            450                 455                 460

Asp Gly Gly Asn Met Leu Glu Thr Ile Lys Val Ser Pro Gln Thr Met
465                 470                 475                 480

Asp Gly Ile Leu Lys Ser Ile Leu Lys Val Lys Lys Ala Leu Gly Met
                    485                 490                 495

Phe Ile Ser Asp Thr Pro Gly Glu Arg Asn Pro Tyr Glu Asn Ile Leu
            500                 505                 510

Tyr Lys Ile Cys Leu Ser Gly Asp Gly Trp Pro Tyr Ile Ala Ser Arg
            515                 520                 525

Thr Ser Ile Thr Gly Arg Ala Trp Glu Asn Thr Val Val Asp Leu Glu
530                 535                 540

Ser Asp Gly Lys Pro Gln Lys Ala Asp Ser Asn Asn Ser Ser Lys Ser
545                 550                 555                 560

Leu Gln Ser Ala Gly Phe Thr Ala Gly Leu Thr Tyr Ser Gln Leu Met
                    565                 570                 575

Thr Leu Lys Asp Ala Met Leu Gln Leu Asp Pro Asn Ala Lys Thr Trp
            580                 585                 590

Met Asp Ile Glu Gly Arg Pro Glu Asp Pro Val Glu Ile Ala Leu Tyr
            595                 600                 605

Gln Pro Ser Ser Gly Cys Tyr Ile His Phe Phe Arg Glu Pro Thr Asp
            610                 615                 620

Leu Lys Gln Phe Lys Gln Asp Ala Lys Tyr Ser His Gly Ile Asp Val
625                 630                 635                 640

Thr Asp Leu Phe Ala Thr Gln Pro Gly Leu Thr Ser Ala Val Ile Asp
                    645                 650                 655

Ala Leu Pro Arg Asn Met Val Ile Thr Cys Gln Gly Ser Asp Asp Ile
            660                 665                 670

Arg Lys Leu Leu Glu Ser Gln Gly Arg Lys Asp Ile Lys Leu Ile Asp
            675                 680                 685

Ile Ala Leu Ser Lys Thr Asp Ser Arg Lys Tyr Glu Asn Ala Val Trp
            690                 695                 700

Asp Gln Tyr Lys Asp Leu Cys His Met His Thr Gly Val Val Val Glu
705                 710                 715                 720

Lys Lys Lys Arg Gly Gly Lys Glu Glu Ile Thr Pro His Cys Ala Leu
                    725                 730                 735

Met Asp Cys Ile Met Phe Asp Ala Ala Val Ser Gly Gly Leu Asn Thr
            740                 745                 750

Ser Val Leu Arg Ala Val Leu Pro Arg Asp Met Val Phe Arg Thr Ser
```

Thr Pro Arg Val Val Leu Pro Gly Glu Asn Leu Tyr Phe Gln Gly Pro
 770             775                 780

Gly Gly Gly Ser His His His His His His
785             790

<210> SEQ ID NO 116
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Junin virus-proTEV2-Histag for expression in
      S2 cells

<400> SEQUENCE: 116

| | | | | | |
|---|---|---|---|---|---|
| atgaagttat | gcatattact | ggccgtcgtg | gcctttgttg | gcctctcgct | cgggagatct | 60 |
| gacaaagact | gcgaaatgaa | aagaactaca | ttggattcac | cacttgggaa | gttggaactg | 120 |
| agtggatgcg | agcaaggatt | gcatgaaatt | aagctactgg | gaaaaggaac | ttctgctgct | 180 |
| gatgcagttg | aagttccagc | accagcagct | gttcttggag | gtcctgagcc | cctcatgcaa | 240 |
| gccacagcct | ggcttaacgc | atatttccac | cagcctgagg | ccattgagga | atttccagtc | 300 |
| cccgccttc | accatcctgt | gtttcagcag | gagagcttca | cccgccaggt | cctgtggaaa | 360 |
| ttgctgaagg | tggtcaagtt | tggtgaagtg | atttcatatc | agcaacttgc | tgcattggcc | 420 |
| ggtaaccccg | cagctacagc | tgccgtgaaa | actgctctca | gcggaaatcc | tgtgcccatc | 480 |
| ctgatccctt | gtcacagagt | cgtttcatct | tccggagctg | taggtggcta | tgaaggagga | 540 |
| ctggcagtta | aggagtggct | gctggctcat | gaaggtcata | gacttggaaa | gcctgggctg | 600 |
| ggtcctgctg | gtataggcgc | gccagggtcc | taggtggcg | gatccgaaaa | cctgtacttc | 660 |
| cagagcgata | tcgcacactc | caaggaggtt | cctagcttta | gatggactca | gtccttaagg | 720 |
| agaggtttga | gccaattcac | tcagactgtc | aagtcagatg | ttttgaagga | cgccaagcta | 780 |
| attgctgaca | gcatcgactt | caaccaagtg | gcacaggtgc | agcgggcact | cagaaagact | 840 |
| aaaaaggggg | aagaagacct | caataagttg | agggacctga | ataaagaggt | tgacagactc | 900 |
| atgtccatga | ggagtgttca | cgaaacaca | gttttcaagg | tgggtgatct | ggggagggat | 960 |
| gaactgatgg | agttggcgtc | tgaccttgag | aaattaaaaa | acaagataag | aagagcagag | 1020 |
| acaggctctc | aggggggttta | catgggtaac | ttgtcccagt | cacaacttgc | taaaagatca | 1080 |
| gagatattga | aacactggg | atttcaacag | caagggactg | ggggaaatgg | tgtggtgagg | 1140 |
| atatgggatg | ttaaagaccc | ttcaaagcta | aacaatcagt | ttggctctgt | tcctgcattg | 1200 |
| acaattgcat | gcatgactgt | tcaaggaggt | gagacaatga | acagtgtcat | acaggcttta | 1260 |
| acctcacttg | ggcttctata | cactgtgaag | tatccaaact | taagtgacct | tgacagactg | 1320 |
| actcaggaac | atgactgcct | tcagattgtg | actaaagatg | aaagctccat | caatatttct | 1380 |
| ggttacaact | tcagtctttc | agctgcagta | aaggctggag | catctattct | tgatggtgga | 1440 |
| aacatgttgg | aaacaatcag | agtcaccca | gaaaacttct | cttccctcat | aaaatcaacc | 1500 |
| attcaggtta | acgaagagag | aggcatgttt | attgatgaga | accaggcaa | tagaaatcct | 1560 |
| tatgaaaacc | ttttgtacaa | actttgtctt | tctggcgatg | gttggccta | tattggttca | 1620 |
| agatcacaaa | tcacaggcag | gtcatgggac | aacacaagta | ttgatctgac | aaggaaacca | 1680 |
| gttgctggtc | ctagacagcc | ggaaaaaaac | ggtcagaatt | tgagattggc | taacttgaca | 1740 |
| gagatacaag | aagctgtcat | cagagaggca | gtggggaaac | tcgaccccac | caacacccct | 1800 |

-continued

```
tggctcgaca ttgaaggacc agccactgac cctgttgaga tggcattatt ccaacctgca   1860
ggtaagcagt acattcactg cttcagaaaa ccacatgatg agaaagggtt taaaaatggt   1920
agcagacact ctcacggcat cttaatgaag gacatagaag atgcaatgcc aggagttctt   1980
agttacgtga tcggcttgct gcctccagac atggttgtga ctactcaagg ttccgatgac   2040
atcaggaagt tgtttgacct ccatggaaga agggatctta aactggttga tgttaagctc   2100
acatctgaac aagccaggca gtttgatcaa caggtctggg agaaatatgg tcacttatgc   2160
aaatatcaca tggagtggt tgtcaataag aaaagaggg aaaggatac tcccttcaag     2220
ttggcctcca gtgaaccaca ctgtgctctg ctagactgca taatgtttca gtcagtgcta   2280
gatgggaagc tctatgagga ggaacctaca cctctattac caccgagctt gctgttcctc   2340
ccgaaggcag cctatgcact cccgggagag aatctatatt ttcaagggcc cggcggaggt   2400
agtcaccatc atcaccatca ctaatgaccg gtgcggccgc aagctt                 2446
```

<210> SEQ ID NO 117
<211> LENGTH: 789
<212> TYPE: PRT
<213> ORGANISM: artificial
<220> FEATURE:
<223> OTHER INFORMATION: Aa sequence of fusion protein
      [SNAPlike-proTEV1-JUN.N-proTEV2-Histag]

<400> SEQUENCE: 117

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Val Pro Ser Phe Arg Trp Thr Gln Ser Leu Arg Arg Gly
    210                 215                 220

Leu Ser Gln Phe Thr Gln Thr Val Lys Ser Asp Val Leu Lys Asp Ala
225                 230                 235                 240
```

-continued

```
Lys Leu Ile Ala Asp Ser Ile Asp Phe Asn Gln Val Ala Gln Val Gln
                245                 250                 255

Arg Ala Leu Arg Lys Thr Lys Lys Gly Glu Glu Asp Leu Asn Lys Leu
            260                 265                 270

Arg Asp Leu Asn Lys Glu Val Asp Arg Leu Met Ser Met Arg Ser Val
        275                 280                 285

Gln Arg Asn Thr Val Phe Lys Val Gly Asp Leu Gly Arg Asp Glu Leu
    290                 295                 300

Met Glu Leu Ala Ser Asp Leu Glu Lys Leu Lys Asn Lys Ile Arg Arg
305                 310                 315                 320

Ala Glu Thr Gly Ser Gln Gly Val Tyr Met Gly Asn Leu Ser Gln Ser
                325                 330                 335

Gln Leu Ala Lys Arg Ser Glu Ile Leu Arg Thr Leu Gly Phe Gln Gln
            340                 345                 350

Gln Gly Thr Gly Gly Asn Gly Val Val Arg Ile Trp Asp Val Lys Asp
        355                 360                 365

Pro Ser Lys Leu Asn Asn Gln Phe Gly Ser Val Pro Ala Leu Thr Ile
    370                 375                 380

Ala Cys Met Thr Val Gln Gly Gly Glu Thr Met Asn Ser Val Ile Gln
385                 390                 395                 400

Ala Leu Thr Ser Leu Gly Leu Leu Tyr Thr Val Lys Tyr Pro Asn Leu
                405                 410                 415

Ser Asp Leu Asp Arg Leu Thr Gln Glu His Asp Cys Leu Gln Ile Val
            420                 425                 430

Thr Lys Asp Glu Ser Ser Ile Asn Ile Ser Gly Tyr Asn Phe Ser Leu
        435                 440                 445

Ser Ala Ala Val Lys Ala Gly Ala Ser Ile Leu Asp Gly Gly Asn Met
    450                 455                 460

Leu Glu Thr Ile Arg Val Thr Pro Glu Asn Phe Ser Ser Leu Ile Lys
465                 470                 475                 480

Ser Thr Ile Gln Val Lys Arg Arg Glu Gly Met Phe Ile Asp Glu Lys
                485                 490                 495

Pro Gly Asn Arg Asn Pro Tyr Glu Asn Leu Leu Tyr Lys Leu Cys Leu
            500                 505                 510

Ser Gly Asp Gly Trp Pro Tyr Ile Gly Ser Arg Ser Gln Ile Thr Gly
        515                 520                 525

Arg Ser Trp Asp Asn Thr Ser Ile Asp Leu Thr Arg Lys Pro Val Ala
    530                 535                 540

Gly Pro Arg Gln Pro Glu Lys Asn Gly Gln Asn Leu Arg Leu Ala Asn
545                 550                 555                 560

Leu Thr Glu Ile Gln Glu Ala Val Ile Arg Glu Ala Val Gly Lys Leu
                565                 570                 575

Asp Pro Thr Asn Thr Leu Trp Leu Asp Ile Glu Gly Pro Ala Thr Asp
            580                 585                 590

Pro Val Glu Met Ala Leu Phe Gln Pro Ala Gly Lys Gln Tyr Ile His
        595                 600                 605

Cys Phe Arg Lys Pro His Asp Glu Lys Gly Phe Lys Asn Gly Ser Arg
    610                 615                 620

His Ser His Gly Ile Leu Met Lys Asp Ile Glu Asp Ala Met Pro Gly
625                 630                 635                 640

Val Leu Ser Tyr Val Ile Gly Leu Leu Pro Pro Asp Met Val Val Thr
                645                 650                 655

Thr Gln Gly Ser Asp Asp Ile Arg Lys Leu Phe Asp Leu His Gly Arg
```

```
                    660             665             670
Arg Asp Leu Lys Leu Val Asp Val Lys Leu Thr Ser Glu Gln Ala Arg
                675             680             685

Gln Phe Asp Gln Gln Val Trp Glu Lys Tyr Gly His Leu Cys Lys Tyr
            690             695             700

His Asn Gly Val Val Val Asn Lys Lys Lys Arg Glu Lys Asp Thr Pro
705             710             715             720

Phe Lys Leu Ala Ser Ser Glu Pro His Cys Ala Leu Leu Asp Cys Ile
                725             730             735

Met Phe Gln Ser Val Leu Asp Gly Lys Leu Tyr Glu Glu Pro Thr
            740             745             750

Pro Leu Leu Pro Pro Ser Leu Leu Phe Leu Pro Lys Ala Ala Tyr Ala
            755             760             765

Leu Pro Gly Glu Asn Leu Tyr Phe Gln Gly Pro Gly Gly Gly Ser His
        770             775             780

His His His His His
785

<210> SEQ ID NO 118
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Machupo virus-proTEV2-Histag for expression
      in S2 cells

<400> SEQUENCE: 118
atgaagttat gcatattact ggccgtcgtg gcctttgttg gcctctcgct cgggagatct       60
gacaaagact gcgaaatgaa agaactaca ttggattcac cacttgggaa gttggaactg      120
agtggatgcg agcaaggatt gcatgaaatt aagctactgg aaaaggaac ttctgctgct      180 gatgcagttg aagttccagc accagcagct gttcttggag tcctgagcc cctcatgcaa      240 gccacagcct ggcttaacgc atatttccac cagcctgagg ccattgagga atttccagtc      300 cccgccttc accatcctgt gtttcagcag gagagcttca cccgccaggt cctgtggaaa      360
ttgctgaagg tggtcaagtt tggtgaagtg atttcatatc agcaacttgc tgcattggcc      420
ggtaaccccg cagctacagc tgccgtgaaa actgctctca gcggaaatcc tgtgcccatc      480
ctgatccctt gtcacagagt cgtttcatct tccggagctg taggtggcta tgaaggagga      540
ctggcagtta aggagtggct gctggctcat gaaggtcata gacttggaaa gcctgggctg      600
ggtcctgctg gtataggcgc gccagggtcc ctaggtggcg atccgaaaa cctgtacttc      660 cagagcgata tcgctcactc caaggaaatt cccagctttc ggtggactca gtcactgaga      720
agaggcctga gtcagttcac ccacactgtg aaaacagatg tgttgaaaga tgccaagctc      780
atagctgaca gcatcgactt caaccaggtt tcacaagtgc agagggctct cagaagaac      840 aaaagggggtg aagaggatct gaacaagctg agggatttaa acaagaagt ggataggctc      900 atgtctatga aagcatcca gaaaacacc atattcaaga ttggtgatct ggggagagat      960
gaattgatgg agcttgcatc agacttggaa aactgaaga caagataaa gaggactgag     1020 tcaggtcccc aagggctgta catgggtaat ttgtcacagc tgcaactgac aaagaggtca     1080
gaaatcttga gaccctggg attccaacag cagagaggtg ctggaaatgg tgtggttaga     1140
atctgggatg tctcagatcc atcaaaactg aataatcagt tggttccat gccagctctc     1200 acaatcgctt gtatgactgt ccagggtgga gaaacgatga atagtgtggt ccaagcgttg     1260
```

-continued

```
acatctctgg gcctgttata cactgttaaa tatccgaatt taaatgacct tgacaagcta      1320
acactagagc acgaatgctt gcagatcgta actaaggacg agagctccat caacatctct      1380
ggctataact tcagtctgtc agctgctgtg aaagctggcg cctcaatact tgacggtggg      1440
aacatgctgg aaacaattag ggtcactcct gataatttct ccagcttgat taaatcaact      1500
ctgcaagtca agcgaaaaga ggggatgttt atagacgaga aacctgggaa tcgaaatcct      1560
tatgagaacc ttctgtataa attgtgtctc tcaggtgacg ggtggcctta cattggttcc      1620
agatcacaaa ttcttgggag gtcttgggac aacacaagtg ttgatctaac aaagaaacct      1680
caagttggac cgagacaacc cgagaaaaac ggtcagaatc taagactagc aaacctgact      1740
gaaatgcaag aagcagtgat taaagaggct gtaaagaagt tagaccccac taatacactg      1800
tggcttgaca ttgaagggcc tccaacagac cctgtggaat tggcactata tcagccagcc      1860
aacaagcatt atattcattg ttttagaaag ccacatgatg agaagggctt caaaaatggc      1920
agcagacatt cacatggcat cttgatgcaa gacatcgagg atgcaatgcc aggagtatta      1980
agttatgtaa taggtttact accacaagat atggtgatta caactcaagg ttctgacgac      2040
ataaggaaac ttttagacat tcatggacgg aaggatttaa agctggtaga tgtgaaactc      2100
acatctgatc aagcaagact ctatgatcag caaatttggg agaagtttgg acatctttgc      2160
aaacatcata atggagttgt tgtcaacaag aaaaagagag aaaagactc tccattcaaa      2220 ttgagttctg gtgaacctca ctgtgctctg ttggattgta tcatgtatca atcagtgatg      2280
gatggcaaaa tggtagatga agaaccagtg gcacttttac ctctcagcct tctatttcta      2340
cccaaggcag cctttgcact cccgggagag aatctatatt ttcaagggcc cggcggaggt      2400
agtcaccatc atcaccatca ctaatgaccg gtgcggccgc aagctt                    2446
```

<210> SEQ ID NO 119  
<211> LENGTH: 789  
<212> TYPE: PRT  
<213> ORGANISM: artificial  
<220> FEATURE:  
<223> OTHER INFORMATION: Amino acid sequence of fusion protein [SNAPlike-proTEV1-MAC.N-proTEV2-Histag]

<400> SEQUENCE: 119

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140
```

```
Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Ile Pro Ser Phe Arg Trp Thr Gln Ser Leu Arg Arg Gly
210                 215                 220

Leu Ser Gln Phe Thr His Thr Val Lys Thr Asp Val Leu Lys Asp Ala
225                 230                 235                 240

Lys Leu Ile Ala Asp Ser Ile Asp Phe Asn Gln Val Ser Gln Val Gln
                245                 250                 255

Arg Ala Leu Arg Lys Asn Lys Arg Gly Glu Glu Asp Leu Asn Lys Leu
            260                 265                 270

Arg Asp Leu Asn Lys Glu Val Asp Arg Leu Met Ser Met Lys Ser Ile
        275                 280                 285

Gln Lys Asn Thr Ile Phe Lys Ile Gly Asp Leu Gly Arg Asp Glu Leu
290                 295                 300

Met Glu Leu Ala Ser Asp Leu Glu Lys Leu Lys Asn Lys Ile Lys Arg
305                 310                 315                 320

Thr Glu Ser Gly Pro Gln Gly Leu Tyr Met Gly Asn Leu Ser Gln Leu
                325                 330                 335

Gln Leu Thr Lys Arg Ser Glu Ile Leu Lys Thr Leu Gly Phe Gln Gln
            340                 345                 350

Gln Arg Gly Ala Gly Asn Gly Val Val Arg Ile Trp Asp Val Ser Asp
        355                 360                 365

Pro Ser Lys Leu Asn Asn Gln Phe Gly Ser Met Pro Ala Leu Thr Ile
370                 375                 380

Ala Cys Met Thr Val Gln Gly Gly Glu Thr Met Asn Ser Val Val Gln
385                 390                 395                 400

Ala Leu Thr Ser Leu Gly Leu Leu Tyr Thr Val Lys Tyr Pro Asn Leu
                405                 410                 415

Asn Asp Leu Asp Lys Leu Thr Leu Glu His Glu Cys Leu Gln Ile Val
            420                 425                 430

Thr Lys Asp Glu Ser Ser Ile Asn Ile Ser Gly Tyr Asn Phe Ser Leu
        435                 440                 445

Ser Ala Ala Val Lys Ala Gly Ala Ser Ile Leu Asp Gly Gly Asn Met
450                 455                 460

Leu Glu Thr Ile Arg Val Thr Pro Asp Asn Phe Ser Ser Leu Ile Lys
465                 470                 475                 480

Ser Thr Leu Gln Val Lys Arg Lys Glu Gly Met Phe Ile Asp Glu Lys
                485                 490                 495

Pro Gly Asn Arg Asn Pro Tyr Glu Asn Leu Leu Tyr Lys Leu Cys Leu
            500                 505                 510

Ser Gly Asp Gly Trp Pro Tyr Ile Gly Ser Arg Ser Gln Ile Leu Gly
        515                 520                 525

Arg Ser Trp Asp Asn Thr Ser Val Asp Leu Thr Lys Lys Pro Gln Val
530                 535                 540

Gly Pro Arg Gln Pro Glu Lys Asn Gly Gln Asn Leu Arg Leu Ala Asn
545                 550                 555                 560

Leu Thr Glu Met Gln Glu Ala Val Ile Lys Glu Ala Val Lys Lys Leu
```

```
                   565                 570                 575
Asp Pro Thr Asn Thr Leu Trp Leu Asp Ile Glu Gly Pro Pro Thr Asp
                580                 585                 590

Pro Val Glu Leu Ala Leu Tyr Gln Pro Ala Asn Lys His Tyr Ile His
            595                 600                 605

Cys Phe Arg Lys Pro His Asp Glu Lys Gly Phe Lys Asn Gly Ser Arg
        610                 615                 620

His Ser His Gly Ile Leu Met Gln Asp Ile Glu Asp Ala Met Pro Gly
625                 630                 635                 640

Val Leu Ser Tyr Val Ile Gly Leu Leu Pro Gln Asp Met Val Ile Thr
                645                 650                 655

Thr Gln Gly Ser Asp Asp Ile Arg Lys Leu Leu Asp Ile His Gly Arg
                660                 665                 670

Lys Asp Leu Lys Leu Val Asp Val Lys Leu Thr Ser Asp Gln Ala Arg
            675                 680                 685

Leu Tyr Asp Gln Gln Ile Trp Glu Lys Phe Gly His Leu Cys Lys His
        690                 695                 700

His Asn Gly Val Val Val Asn Lys Lys Arg Glu Lys Asp Ser Pro
705                 710                 715                 720

Phe Lys Leu Ser Ser Gly Glu Pro His Cys Ala Leu Leu Asp Cys Ile
                725                 730                 735

Met Tyr Gln Ser Val Met Asp Gly Lys Met Val Asp Glu Glu Pro Val
                740                 745                 750

Ala Leu Leu Pro Leu Ser Leu Leu Phe Leu Pro Lys Ala Ala Phe Ala
            755                 760                 765

Leu Pro Gly Glu Asn Leu Tyr Phe Gln Gly Pro Gly Gly Ser His
        770                 775                 780

His His His His
785

<210> SEQ ID NO 120
<211> LENGTH: 2434
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Guanarito virus-proTEV2-Histag for expression
      in S2 cells

<400> SEQUENCE: 120
atgaagttat gcatattact ggccgtcgtg gcctttgttg gcctctcgct cgggagatct      60
gacaaagact gcgaaatgaa agaactaca ttggattcac cacttgggaa gttggaactg     120
agtggatgcg agcaaggatt gcatgaaatt aagctactgg aaaaggaac ttctgctgct     180 gatgcagttg aagttccagc accagcagct gttcttggag gtcctgagcc cctcatgcaa     240
gccacagcct ggcttaacgc atatttccac cagcctgagg ccattgagga atttccagtc     300
cccgcccttc accatcctgt gtttcagcag gagagcttca cccgccaggt cctgtggaaa     360
ttgctgaagg tggtcaagtt tggtgaagtg atttcatatc agcaacttgc tgcattggcc     420
ggtaaccccg cagctacagc tgccgtgaaa actgctctca gcggaaatcc tgtgcccatc     480
ctgatccctt gtcacagagt cgtttcatct tccggagctg taggtggcta tgaaggagga     540
ctggcagtta aggagtggct gctggctcat gaaggtcata gacttggaaa gcctgggctg     600
ggtcctgctg gtataggcgc gccagggtcc ctaggtggcg gatccgaaaa cctgtacttc     660
cagagcgata tcgctcactc caaagaaatc cccagcttcc gctggactca atctctaagg     720
```

```
agagaactag ggatgttcac agaaccaacc aaatcaagtg ttcttaatga tgcaaagctc      780
attgcagact cccttgattt cacacaagtt tctcaagttc aaagactcct acgtaagtcc      840
aaacgaggag acactgatct tgataaactt agggacttaa ataaagaagt tgatagactg      900
atgagcatga aaagtgttca gaacaacaca gttctgaaag ttggtgattt gggcaaagat      960
gaattaatgg acttggcctc tgacctagaa aaactaaaga agaagattgg agatagggaa     1020
agcaatagtc caaggatgta catgggaaac ttgacgcagt cacaattgga aaaagagca      1080
gggattctta gaaccctggg attccaacaa caaggggggg ctgcaggtgg ggttgtcagg     1140
ttgtgggatg tatctgatcc ctccaaactg aataaccaat ttggttcaat gccagctctt     1200
accattgcct gcatgacagt tcagggagga gaaacaatga acaatgttgt gcaggcacta     1260
acatcacttg gtcttctcta cactgtcaaa tatcccaatc ttgatgacct ggaaaaacta     1320
actttagaac acgactgcct acagattata acaaaggatg agagtgcact caacatatct     1380
ggttataact tcagtctttc agctgctgta aaagctggtg catcacttat agatggtggc     1440
aacatgctgg agacaataaa agtcacaccc aacaacttct cttctattgt caaggccgca     1500
ttgaacgtca aaagaagaga aggcatgttc atagatgaga gaccgggcaa tagaaaccct     1560
tatgagaacc ttctctacaa gctgtgtttg tctggggagg gttggccata tattggatca     1620
aggtcacaaa tactcgggag gtcttgggac aacacaagtg tcgatttaaa tgcaagacct     1680
gtaacaggtc cccgagctcc tgaaaagaat ggacaaaata tcagactatc aaatctttct     1740
gaaatgcaag aagcgatcgt aaaggaagca atgaggaaat tagattcatc agacacaatc     1800
tggatggaca ttgaaggccc gccaactgat cctgtggagt tggcagtttt ccaaccttct     1860
tcaggaaact atgtacactg tttcagaaaa cctcatgatg agaaaggttt taaaaatgga     1920
agtaggcact cacacggcat actattaaag gaccttgaag atgctcaacc tggtctattg     1980
agttacgtca ttggcttatt gccacagggt tcagttatca ctgttcaagg ggcagatgac     2040
atcaaaaagc tattcgacat acatggaagg aaagatttaa aacttgttga tgtcagactg     2100
actggggaac agtccagaat ttttgaacag gaagtttggg aaaaatttgg ccacctctgc     2160
agagcacaca atggtgtcat tgttcctaag aagaaaaaca aggaggctaa ctccacgaag     2220
gagccacact gtgctcttct cgattgcatc atgtttcagt ctgttcttga tggtcatctt     2280
cccgacacca ttcccattca actgctacca aacacattag tgttccaagc caagagcgca     2340
tttgtgatcc cgggagagaa tctatatttt caagggcccg gcggaggtag tcaccatcat     2400
caccatcact aatgaccggt gcggccgcaa gctt                                  2434
```

<210> SEQ ID NO 121
<211> LENGTH: 785
<212> TYPE: PRT
<213> ORGANISM: artificial
<220> FEATURE:
<223> OTHER INFORMATION: Amino acid sequence of fusion protein
      [SNAPlike-proTEV1-GUA.N-proTEV2-Histag]

<400> SEQUENCE: 121

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

-continued

```
Ala Pro Ala Ala Val Leu Gly Gly Pro Glu Pro Leu Met Gln Ala Thr
 50                  55                  60
Ala Trp Leu Asn Ala Tyr Phe His Gln Pro Glu Ala Ile Glu Glu Phe
 65                  70                  75                  80
Pro Val Pro Ala Leu His His Pro Val Phe Gln Gln Glu Ser Phe Thr
                 85                  90                  95
Arg Gln Val Leu Trp Lys Leu Leu Lys Val Val Lys Phe Gly Glu Val
                100                 105                 110
Ile Ser Tyr Gln Gln Leu Ala Ala Leu Ala Gly Asn Pro Ala Ala Thr
            115                 120                 125
Ala Ala Val Lys Thr Ala Leu Ser Gly Asn Pro Val Pro Ile Leu Ile
130                 135                 140
Pro Cys His Arg Val Val Ser Ser Ser Gly Ala Val Gly Gly Tyr Glu
145                 150                 155                 160
Gly Gly Leu Ala Val Lys Glu Trp Leu Leu Ala His Glu Gly His Arg
                165                 170                 175
Leu Gly Lys Pro Gly Leu Gly Pro Ala Gly Ile Gly Ala Pro Gly Ser
                180                 185                 190
Leu Gly Gly Gly Ser Glu Asn Leu Tyr Phe Gln Ser Asp Ile Ala His
            195                 200                 205
Ser Lys Glu Ile Pro Ser Phe Arg Trp Thr Gln Ser Leu Arg Arg Glu
210                 215                 220
Leu Gly Met Phe Thr Glu Pro Thr Lys Ser Ser Val Leu Asn Asp Ala
225                 230                 235                 240
Lys Leu Ile Ala Asp Ser Leu Asp Phe Thr Gln Val Ser Gln Val Gln
                245                 250                 255
Arg Leu Leu Arg Lys Ser Lys Arg Gly Asp Thr Asp Leu Asp Lys Leu
                260                 265                 270
Arg Asp Leu Asn Lys Glu Val Asp Arg Leu Met Ser Met Lys Ser Val
            275                 280                 285
Gln Asn Asn Thr Val Leu Lys Val Gly Asp Leu Gly Lys Asp Glu Leu
290                 295                 300
Met Asp Leu Ala Ser Asp Leu Glu Lys Leu Lys Lys Ile Gly Asp
305                 310                 315                 320
Arg Glu Ser Asn Ser Pro Arg Met Tyr Met Gly Asn Leu Thr Gln Ser
                325                 330                 335
Gln Leu Glu Lys Arg Ala Gly Ile Leu Arg Thr Leu Gly Phe Gln Gln
                340                 345                 350
Gln Arg Gly Ala Ala Gly Gly Val Val Arg Leu Trp Asp Val Ser Asp
            355                 360                 365
Pro Ser Lys Leu Asn Asn Gln Phe Gly Ser Met Pro Ala Leu Thr Ile
370                 375                 380
Ala Cys Met Thr Val Gln Gly Gly Glu Thr Met Asn Asn Val Val Gln
385                 390                 395                 400
Ala Leu Thr Ser Leu Gly Leu Leu Tyr Thr Val Lys Tyr Pro Asn Leu
                405                 410                 415
Asp Asp Leu Glu Lys Leu Thr Leu Glu His Asp Cys Leu Gln Ile Ile
                420                 425                 430
Thr Lys Asp Glu Ser Ala Leu Asn Ile Ser Gly Tyr Asn Phe Ser Leu
            435                 440                 445
Ser Ala Ala Val Lys Ala Gly Ala Ser Leu Ile Asp Gly Gly Asn Met
450                 455                 460
Leu Glu Thr Ile Lys Val Thr Pro Asn Asn Phe Ser Ser Ile Val Lys
```

-continued

```
           465                 470                 475                 480
       Ala Ala Leu Asn Val Lys Arg Arg Glu Gly Met Phe Ile Asp Glu Arg
                           485                 490                 495
       Pro Gly Asn Arg Asn Pro Tyr Glu Asn Leu Leu Tyr Lys Leu Cys Leu
                       500                 505                 510
       Ser Gly Glu Gly Trp Pro Tyr Ile Gly Ser Arg Ser Gln Ile Leu Gly
                       515                 520                 525
       Arg Ser Trp Asp Asn Thr Ser Val Asp Leu Asn Ala Arg Pro Val Thr
                   530                 535                 540
       Gly Pro Arg Ala Pro Glu Lys Asn Gly Gln Asn Ile Arg Leu Ser Asn
       545                 550                 555                 560
       Leu Ser Glu Met Gln Glu Ala Ile Val Lys Glu Ala Met Arg Lys Leu
                           565                 570                 575
       Asp Ser Ser Asp Thr Ile Trp Met Asp Ile Glu Gly Pro Pro Thr Asp
                       580                 585                 590
       Pro Val Glu Leu Ala Val Phe Gln Pro Ser Ser Gly Asn Tyr Val His
                       595                 600                 605
       Cys Phe Arg Lys Pro His Asp Glu Lys Gly Phe Lys Asn Gly Ser Arg
                   610                 615                 620
       His Ser His Gly Ile Leu Leu Lys Asp Leu Glu Asp Ala Gln Pro Gly
       625                 630                 635                 640
       Leu Leu Ser Tyr Val Ile Gly Leu Leu Pro Gln Gly Ser Val Ile Thr
                           645                 650                 655
       Val Gln Gly Ala Asp Asp Ile Lys Lys Leu Phe Asp Ile His Gly Arg
                       660                 665                 670
       Lys Asp Leu Lys Leu Val Asp Val Arg Leu Thr Gly Glu Gln Ser Arg
                       675                 680                 685
       Ile Phe Glu Gln Glu Val Trp Glu Lys Phe Gly His Leu Cys Arg Ala
                   690                 695                 700
       His Asn Gly Val Ile Val Pro Lys Lys Asn Lys Glu Ala Asn Ser
       705                 710                 715                 720
       Thr Lys Glu Pro His Cys Ala Leu Leu Asp Cys Ile Met Phe Gln Ser
                           725                 730                 735
       Val Leu Asp Gly His Leu Pro Asp Thr Ile Pro Ile Gln Leu Leu Pro
                       740                 745                 750
       Asn Thr Leu Val Phe Gln Ala Lys Ser Ala Phe Val Ile Pro Gly Glu
                       755                 760                 765
       Asn Leu Tyr Phe Gln Gly Pro Gly Gly Ser His His His His
                   770                 775                 780
       His
       785

<210> SEQ ID NO 122
<211> LENGTH: 2440
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Sabia virus-proTEV2-Histag for expression in
      S2 cells

<400> SEQUENCE: 122
atgaagttat gcatattact ggccgtcgtg gcctttgttg gcctctcgct cgggagatct      60
gacaaagact gcgaaatgaa aagaactaca ttggattcac cacttgggaa gttgaactg     120 agtggatgcg agcaaggatt gcatgaaatt aagctactgg gaaaaggaac ttctgctgct    180
```

```
gatgcagttg aagttccagc accagcagct gttcttggag gtcctgagcc cctcatgcaa      240
gccacagcct ggcttaacgc atatttccac cagcctgagg ccattgagga atttccagtc      300
cccgcccttc accatcctgt gtttcagcag gagagcttca cccgccaggt cctgtggaaa      360
ttgctgaagg tggtcaagtt tggtgaagtg atttcatatc agcaacttgc tgcattggcc      420
ggtaaccccg cagctacagc tgccgtgaaa actgctctca gcggaaatcc tgtgcccatc      480
ctgatccctt gtcacagagt cgtttcatct tccggagctg taggtggcta tgaaggagga      540
ctggcagtta aggagtggct gctggctcat gaaggtcata gacttggaaa gcctgggctg      600
ggtcctgctg gtataggcgc gccagggtcc taggtggcg gatccgaaaa cctgtacttc      660
cagagcgata tcagcaactc aaaggaaatc cccagcttca gatggactca atccctgaga      720
agagggctca gtgagttcac aacacccgtg aagaccgatg ttctgaggga tgccaaaatg      780
atacttgatg gtcttgattt caatcaagtc tctcttgttc aaagaatcct tagaaagtct      840
aaaaggaatg atggtgatct tgataaactg agagacctaa ataaagaagt ggacaacctg      900
atgagcatga agagttccca agagacacaa tcttaaaaac ttggtgatct caacaaatct      960
gaactgatga tccttgcatc agacctggag aaactgaaaa gaaagttgg acaaacagaa     1020 agatcagcct caggaggtgt gtacctggga aacctttccc aatcacagct caccaaaagg     1080
tctgatcttt taaggaaact tggttttcaa cagcagcaag tgaggtctcc aggggttgta     1140
aggatttggg acgtagctga tccgaacagg ctgaataatc aatttggatc tgtccctgca     1200
ctgcaaatcg cttgtatgac taaacaaagt gacaatacca tggggatgt tgttcaggca     1260 ctaacatctt tgggacttct ttatacagtt aagttcccca acctgattga cctagaaaaa     1320
cttacagcag aacatgactg tcttcaaata gtgactaaag atgagagcgg cttgaacatc     1380
tcaggatata actatagtct ttctgcagct gttaaagctg gtgcaacgct tctggatggt     1440
ggtaacatgc tggaaaccat aaggatcact cctgacaact tttctcagat cataaagaca     1500
accctatcca taagaaaaa ggaaggcatg tttgtagatg agaaacctgg aaatagaaac     1560
ccttatgaaa accttctgta caaaatctgc ctttcaggag aaggttggcc ttacattggc     1620
tccagatccc agatcaaggg taggtcatgg gaaaacacca ctgttgattt aagcacaaag     1680
ccccaacaag ggccgagaac accagaaaag gcaggtcaga acattagact ctcccacttg     1740
actgagttgc aagagtcagt tgtgagagag gcaatgggta agattgaccc aactctgaca     1800
acatggattg acattgaggg taccagtaat gatccggttg aattagcatt gtaccaacca     1860
gacacaggta attatatcct ctgttatagg aaaccacatg atgagaaggg gttcaaaaat     1920
ggtagcaggc attcacatgg gatgttgcta aaggacctag aatctgcaca gccaggcttg     1980
ctcagctatg ttatagggct ccttcctcaa aacatggtcc tcaccaccca aggttcgat      2040 gatataaggc gcttagtaga tacacacggt cgcaaagact aaagattgt cgacattaaa      2100 ttggcatctg aacaggcgag aaagtttgag gagccaatct ggtcagattt ggtcacctc      2160 tgtaagaaac acaatggagt tatttgtgcca agaaaaaga aagacaaaga catcccacag     2220
tcctcagagc cacactgtgc cctacttgat tgtctaatgt ttcagtcagc catagcaggc     2280
caaccacctc aaaccaaact ggaaggttta ttgcctgatg cattgctctt cacactggag     2340
gcagcattca ccatcccggg agagaatcta tattttcaag ggcccggcgg aggtagtcac     2400
catcatcacc atcactaatg accggtgcgg ccgcaagctt                            2440
```

<210> SEQ ID NO 123

<211> LENGTH: 787
<212> TYPE: PRT
<213> ORGANISM: artificial
<220> FEATURE:
<223> OTHER INFORMATION: Amino acid sequence of fusion protein
      [SNAPlike-proTEV1-SAB.N-proTEV2-Histag]

<400> SEQUENCE: 123

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Asn
        195                 200                 205

Ser Lys Glu Ile Pro Ser Phe Arg Trp Thr Gln Ser Leu Arg Arg Gly
210                 215                 220

Leu Ser Glu Phe Thr Thr Pro Val Lys Thr Asp Val Leu Arg Asp Ala
225                 230                 235                 240

Lys Met Ile Leu Asp Gly Leu Asp Phe Asn Gln Val Ser Leu Val Gln
                245                 250                 255

Arg Ile Leu Arg Lys Ser Lys Arg Asn Asp Gly Asp Leu Asp Lys Leu
            260                 265                 270

Arg Asp Leu Asn Lys Glu Val Asp Asn Leu Met Ser Met Lys Ser Ser
        275                 280                 285

Gln Arg Asp Thr Ile Leu Lys Leu Gly Asp Leu Asn Lys Ser Glu Leu
290                 295                 300

Met Asp Leu Ala Ser Asp Leu Glu Lys Leu Lys Arg Lys Val Gly Gln
305                 310                 315                 320

Thr Glu Arg Ser Ala Ser Gly Val Tyr Leu Gly Asn Leu Ser Gln
                325                 330                 335

Ser Gln Leu Thr Lys Arg Ser Asp Leu Leu Arg Lys Leu Gly Phe Gln
            340                 345                 350

Gln Gln Gln Val Arg Ser Pro Gly Val Val Arg Ile Trp Asp Val Ala
        355                 360                 365

Asp Pro Asn Arg Leu Asn Asn Gln Phe Gly Ser Val Pro Ala Leu Thr
```

-continued

```
            370                 375                 380
Ile Ala Cys Met Thr Lys Gln Ser Asp Asn Thr Met Gly Asp Val Val
385                 390                 395                 400

Gln Ala Leu Thr Ser Leu Gly Leu Leu Tyr Thr Val Lys Phe Pro Asn
                405                 410                 415

Leu Ile Asp Leu Glu Lys Leu Thr Ala Glu His Asp Cys Leu Gln Ile
                420                 425                 430

Val Thr Lys Asp Glu Ser Gly Leu Asn Ile Ser Gly Tyr Asn Tyr Ser
                435                 440                 445

Leu Ser Ala Ala Val Lys Ala Gly Ala Thr Leu Leu Asp Gly Gly Asn
450                 455                 460

Met Leu Glu Thr Ile Arg Ile Thr Pro Asp Asn Phe Ser Gln Ile Ile
465                 470                 475                 480

Lys Thr Thr Leu Ser Ile Lys Lys Lys Glu Gly Met Phe Val Asp Glu
                485                 490                 495

Lys Pro Gly Asn Arg Asn Pro Tyr Glu Asn Leu Leu Tyr Lys Ile Cys
                500                 505                 510

Leu Ser Gly Glu Gly Trp Pro Tyr Ile Gly Ser Arg Ser Gln Ile Lys
                515                 520                 525

Gly Arg Ser Trp Glu Asn Thr Thr Val Asp Leu Ser Thr Lys Pro Gln
530                 535                 540

Gln Gly Pro Arg Thr Pro Glu Lys Ala Gly Gln Asn Ile Arg Leu Ser
545                 550                 555                 560

His Leu Thr Glu Leu Gln Glu Ser Val Val Arg Glu Ala Met Gly Lys
                565                 570                 575

Ile Asp Pro Thr Leu Thr Thr Trp Ile Asp Ile Glu Gly Thr Ser Asn
                580                 585                 590

Asp Pro Val Glu Leu Ala Leu Tyr Gln Pro Asp Thr Gly Asn Tyr Ile
                595                 600                 605

Leu Cys Tyr Arg Lys Pro His Asp Glu Lys Gly Phe Lys Asn Gly Ser
                610                 615                 620

Arg His Ser His Gly Met Leu Leu Lys Asp Leu Glu Ser Ala Gln Pro
625                 630                 635                 640

Gly Leu Leu Ser Tyr Val Ile Gly Leu Leu Pro Gln Asn Met Val Leu
                645                 650                 655

Thr Thr Gln Gly Ser Asp Asp Ile Arg Arg Leu Val Asp Thr His Gly
                660                 665                 670

Arg Lys Asp Leu Lys Ile Val Asp Ile Lys Leu Ala Ser Glu Gln Ala
                675                 680                 685

Arg Lys Phe Glu Glu Pro Ile Trp Ser Asp Phe Gly His Leu Cys Lys
                690                 695                 700

Lys His Asn Gly Val Ile Val Pro Lys Lys Lys Asp Lys Asp Ile
705                 710                 715                 720

Pro Gln Ser Ser Glu Pro His Cys Ala Leu Leu Asp Cys Leu Met Phe
                725                 730                 735

Gln Ser Ala Ile Ala Gly Gln Pro Pro Gln Thr Lys Leu Glu Gly Leu
                740                 745                 750

Leu Pro Asp Ala Leu Leu Phe Thr Leu Glu Ala Ala Phe Thr Ile Pro
                755                 760                 765

Gly Glu Asn Leu Tyr Phe Gln Gly Pro Gly Gly Gly Ser His His His
                770                 775                 780

His His His
785
```

<210> SEQ ID NO 124
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
protein of the Omsk virus-Histag for expression in S2 cells

<400> SEQUENCE: 124

| | |
|---|---|
| atgaaactat gtattctact tgcagttgtt gcgttcgtag gattgtcctt aagatctgac | 60 |
| aaagactgcg aaatgaaaag aactacattg gattcaccac ttgggaagtt ggaactgagt | 120 |
| ggatgcgagc aaggattgca tgaaattaag ctactgggaa aaggaacttc tgctgctgat | 180 |
| gcagttgaag ttccagcacc agcagctgtt cttggaggtc ctgagcccct catgcaagcc | 240 |
| acagcctggc ttaacgcata tttccaccag cctgaggcca ttgaggaatt tccagtcccc | 300 |
| gcccttcacc atcctgtgtt tcagcaggag agcttcaccc gccaggtcct gtggaaattg | 360 |
| ctgaaggtgg tcaagtttgg tgaagtgatt tcatatcagc aacttgctgc attggccggt | 420 |
| aaccccgcag ctacagctgc cgtgaaaact gctctcagcg gaaatcctgt gcccatcctg | 480 |
| atcccttgtc acagagtcgt ttcatcttcc ggagctgtag gtggctatga aggaggactg | 540 |
| gcagttaagg agtggctgct ggctcatgaa ggtcatagac ttggaaagcc tgggctgggt | 600 |
| cctgctggta taggcgcgcc aggaggtggc gggctgaaaa aactcaagat gaagggtctt | 660 |
| acctatacaa tgtgcgacaa ggcaaagttc acgtggaaaa gagctcccac agacagtggg | 720 |
| cacgacacag ttgtcatgga agtcgctttc tctggaacaa agccttgcag aataccgtc | 780 |
| agggctgtgg cacatggttc cccagatgtg gatgtggcca tgctcataac gccaaatcca | 840 |
| acaatcgaaa acaatggagg tggctttata gagatgcagc tcccccccagg agacaacatc | 900 |
| atctatgttg gggaactaaa acaccagtgg ttccagaagg ggagtagcat tggcggaggt | 960 |
| ggccatcacc atcaccatca ctgatgaccg gt | 992 |

<210> SEQ ID NO 125
<211> LENGTH: 310
<212> TYPE: PRT
<213> ORGANISM: artificial
<220> FEATURE:
<223> OTHER INFORMATION: Amino acid sequence of fusion protein
[SNAPlike-OMSK.EDIII-Histag]

<400> SEQUENCE: 125

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr

```
              115                 120                 125
Ala Ala Val Lys Thr Ala Leu Ser Gly Asn Pro Val Pro Ile Leu Ile
        130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Leu Glu Lys Leu Lys Met Lys Gly Leu Thr Tyr Thr Met Cys
        195                 200                 205

Asp Lys Ala Lys Phe Thr Trp Lys Arg Ala Pro Thr Asp Ser Gly His
    210                 215                 220

Asp Thr Val Val Met Glu Val Ala Phe Ser Gly Thr Lys Pro Cys Arg
225                 230                 235                 240

Ile Pro Val Arg Ala Val Ala His Gly Ser Pro Asp Val Asp Val Ala
                245                 250                 255

Met Leu Ile Thr Pro Asn Pro Thr Ile Glu Asn Asn Gly Gly Gly Phe
            260                 265                 270

Ile Glu Met Gln Leu Pro Pro Gly Asp Asn Ile Ile Tyr Val Gly Glu
        275                 280                 285

Leu Lys His Gln Trp Phe Gln Lys Gly Ser Ser Ile Gly Gly Gly Gly
    290                 295                 300

His His His His His His
305                 310

<210> SEQ ID NO 126
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Kyasanur Forest Disease virus-Histag for expression
      in S2 cells

<400> SEQUENCE: 126
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt ccagtcccc      300 gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg aaatcctgt gcccatcctg      480 atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc aggaggtggc gggcttgaaa aacttaagat gaaagggatg     660
acatacacgg tttgtgaggg atcaaaattt gcttggaaaa ggccgccaac cgacagtgga     720
catgataccg tagtcatgga ggtgacttac accgggagca agccatgcag aataccagtg     780
agagccgtgg cccatggaga acccaatgtt aacgtgcaa gtctaataac cccaaaccca      840
tccatggaaa caactggagg agggttcgtt gagctacagc taccaccagg agacaacatc     900
```

```
atctatgttg gtgagctgag ccaccagtgg tttcagaagg gcagcacaat tggcggaggt    960
ggccatcacc atcaccatca ctgatgaccg gt                                  992
```

<210> SEQ ID NO 127
<211> LENGTH: 310
<212> TYPE: PRT
<213> ORGANISM: artificial
<220> FEATURE:
<223> OTHER INFORMATION: Amino acid sequence of fusion protein
      [SNAPlike-KYA.EDIII-Histag]

<400> SEQUENCE: 127

```
Arg Ser Asp Lys Asp Cys Glu Met Lys Arg Thr Thr Leu Asp Ser Pro
1               5                  10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Leu Glu Lys Leu Lys Met Lys Gly Met Thr Tyr Thr Val Cys
        195                 200                 205

Glu Gly Ser Lys Phe Ala Trp Lys Arg Pro Pro Thr Asp Ser Gly His
    210                 215                 220

Asp Thr Val Val Met Glu Val Thr Tyr Thr Gly Ser Lys Pro Cys Arg
225                 230                 235                 240

Ile Pro Val Arg Ala Val Ala His Gly Glu Pro Asn Val Asn Val Ala
                245                 250                 255

Ser Leu Ile Thr Pro Asn Pro Ser Met Glu Thr Thr Gly Gly Gly Phe
            260                 265                 270

Val Glu Leu Gln Leu Pro Pro Gly Asp Asn Ile Ile Tyr Val Gly Glu
        275                 280                 285

Leu Ser His Gln Trp Phe Gln Lys Gly Ser Thr Ile Gly Gly Gly Gly
    290                 295                 300

His His His His His His
305                 310
```

<210> SEQ ID NO 128
<211> LENGTH: 992

<212> TYPE: DNA
<213> ORGANISM: artificial
<220> FEATURE:
<223> OTHER INFORMATION: DNA sequence encoding BiPlike-SNAPlike- EDIII
      protein of the Alkhumra virus-Histag for expression in S2 cells

<400> SEQUENCE: 128

```
atgaaactat gtattctact tgcagttgtt gcgttcgtag gattgtcctt aagatctgac      60
aaagactgcg aaatgaaaag aactacattg gattcaccac ttgggaagtt ggaactgagt     120
ggatgcgagc aaggattgca tgaaattaag ctactgggaa aaggaacttc tgctgctgat     180
gcagttgaag ttccagcacc agcagctgtt cttggaggtc ctgagcccct catgcaagcc     240
acagcctggc ttaacgcata tttccaccag cctgaggcca ttgaggaatt tccagtcccc     300
gcccttcacc atcctgtgtt tcagcaggag agcttcaccc gccaggtcct gtggaaattg     360
ctgaaggtgg tcaagtttgg tgaagtgatt tcatatcagc aacttgctgc attggccggt     420
aaccccgcag ctacagctgc cgtgaaaact gctctcagcg gaaatcctgt gcccatcctg     480
atcccttgtc acagagtcgt ttcatcttcc ggagctgtag gtggctatga aggaggactg     540
gcagttaagg agtggctgct ggctcatgaa ggtcatagac ttggaaagcc tgggctgggt     600
cctgctggta taggcgcgcc aggaggtggc gggcttgaaa aactcaagat gaaggaatg     660
acatacacgg tctgtgaggg atcaaagttt gcttggaaga ggccgccaac cgacagtggg     720
catgacactg tggtcatgga agtgacttac actgggagca agccatgcag aataccagtg     780
agagccgtgg cccatggaga acctaatgtc aatgtagcta gcctgataac tccaaatcca     840
tccatggaga caactggagg aggtttcgtt gaactgcagc tgccaccagg agacaacatc     900
atctatgttg gtgagctgag tcaccagtgg tttcagaagg gtagtacaat aggcggaggt     960
ggccatcacc atcaccatca ctgatgaccg gt                                  992
```

<210> SEQ ID NO 129
<211> LENGTH: 310
<212> TYPE: PRT
<213> ORGANISM: artificial
<220> FEATURE:
<223> OTHER INFORMATION: Amino acid sequence of fusion protein
      [SNAPlike-ALK.EDIII-Histag]

<400> SEQUENCE: 129

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140
```

Pro Cys His Arg Val Val Ser Ser Gly Ala Val Gly Gly Tyr Glu
145                 150                 155                 160

Gly Gly Leu Ala Val Lys Glu Trp Leu Leu Ala His Glu Gly His Arg
            165                 170                 175

Leu Gly Lys Pro Gly Leu Gly Pro Ala Gly Ile Gly Ala Pro Gly Gly
        180                 185                 190

Gly Gly Leu Glu Lys Leu Lys Met Lys Gly Met Thr Tyr Thr Val Cys
    195                 200                 205

Glu Gly Ser Lys Phe Ala Trp Lys Arg Pro Thr Asp Ser Gly His
210                 215                 220

Asp Thr Val Val Met Glu Val Thr Tyr Thr Gly Ser Lys Pro Cys Arg
225                 230                 235                 240

Ile Pro Val Arg Ala Val Ala His Gly Glu Pro Asn Val Asn Val Ala
                245                 250                 255

Ser Leu Ile Thr Pro Asn Pro Ser Met Glu Thr Thr Gly Gly Gly Phe
            260                 265                 270

Val Glu Leu Gln Leu Pro Pro Gly Asp Asn Ile Ile Tyr Val Gly Glu
        275                 280                 285

Leu Ser His Gln Trp Phe Gln Lys Gly Ser Thr Ile Gly Gly Gly Gly
    290                 295                 300

His His His His His His
305                 310

<210> SEQ ID NO 130
<211> LENGTH: 1288
<212> TYPE: DNA
<213> ORGANISM: artificial
<220> FEATURE:
<223> OTHER INFORMATION: DNA sequence encoding ssBiP- Glycoprotein GP1
      from Lassa virus- SNAPlike-Histag for expression in S2 cells

<400> SEQUENCE: 130
atgaagttat gcatattact ggccgtcgtg gcctttgttg cctctcgct cgggagatct      60 accagtctgt acaaggggt gtacgagctt cagactctgg aactgaacat ggagacactc     120
aacatgacca tgcctctctc ctgcacaaag aacaacagtc atcattacat aatggtgggc     180
aatgagacag gactggaact gaccttgacc aacacgagca tcatcaatca caagttctgc     240
aacctgtctg atgcccacaa gaagaacctc tacgaccacg ctctgatgag cataatctca     300
actttccact tgtccatccc caacttcaac cagtacgagg caatgagctg cgatttcaat     360
gggggcaaga tcagtgtgca gtacaacctg agtcacagct acgctgggga tgcagccaac     420
cattgtggca ctgtggcaaa cggtgtgttg cagactttca tgaggatggc ttggggcggg     480
agctacatcg ctcttgactc aggccgtggc aactggact gtatcatgac tagttaccaa     540
tacctgataa tccagaacac aacctgggaa gatcactgcc aattctccag accatctccc     600
atcggctacc tcgggctcct ctcacaaagg actagagata tttacatcag tagaagattg     660
ctgcggccgc acggcggagg tagcaaagac tgcgaaatga gcgcaccac cctggatagc     720 cctctgggca gctggaact gtctgggtgc gaacagggcc tgcacgagat caagctgctg     780
ggcaaaggaa catctgccgc cgacgccgtg gaagtgcctg ccccagccgc cgtgctgggc     840
ggaccagagc cactgatgca ggccaccgcc tggctcaacg cctactttca ccagcctgag     900
gccatcgagg agttccctgt gccagccctg caccacccag tgttccagca ggagagcttt     960
acccgccagg tgctgtggaa actgctgaaa gtggtgaagt tcggagaggt catcagctac    1020

```
cagcagctgg ccgccctggc cggcaatccc gccgccaccg ccgccgtgaa aaccgccctg    1080
agcggaaatc ccgtgcccat tctgatcccc tgccaccggg tggtgtctag ctctggcgcc    1140 gtgggggggct acgagggcgg gctcgccgtg aaagagtggc tgctggccca cgagggccac    1200
agactgggca agcctgggct gggtcctgca ggtataggcg cgccagggtc cctggagcat    1260
catcatcatc atcattgatg acgggccc                                      1288
```

<210> SEQ ID NO 131
<211> LENGTH: 407
<212> TYPE: PRT
<213> ORGANISM: artificial
<220> FEATURE:
<223> OTHER INFORMATION: Amino acid sequence of fusion protein [LAS.ectoGP1-SNAPlike-Histag]

<400> SEQUENCE: 131

```
Arg Ser Thr Ser Leu Tyr Lys Gly Val T

```
305                 310                 315                 320
Ser Tyr Gln Gln Leu Ala Ala Leu Ala Gly Asn Pro Ala Ala Thr Ala
                325                 330                 335

Ala Val Lys Thr Ala Leu Ser Gly Asn Pro Val Pro Ile Leu Ile Pro
            340                 345                 350

Cys His Arg Val Val Ser Ser Gly Ala Val Gly Gly Tyr Glu Gly
        355                 360                 365

Gly Leu Ala Val Lys Glu Trp Leu Leu Ala His Glu Gly His Arg Leu
    370                 375                 380

Gly Lys Pro Gly Leu Gly Pro Ala Gly Ile Gly Ala Pro Gly Ser Leu
385                 390                 395                 400

Glu His His His His His His
                405

<210> SEQ ID NO 132
<211> LENGTH: 1264
<212> TYPE: DNA
<213> ORGANISM: artificial
<220> FEATURE:
<223> OTHER INFORMATION: DNA sequence encoding ssBiP- Glycoprotein GP1
      from Junin virus- SNAPlike-Histag for expression in S2 cells

<400> SEQUENCE: 132
atgaagttat gcatattact ggccgtcgtg gcctttgttg gcctctcgct cgggagatct        60
gaggaggctt tcaagatcgg cctgcacacc gagttccaga cggtgtcctt ctcgatggtg       120
ggcctcttct ccaacaaccc acacgacctg cctttgttgt gtaccttgaa caagagccat       180
ctgtacatta agggggggcaa cgcttcattc cagatcagct cgacgacat cgcggtgttg       240 ttgccacagt acgacgttat catccagcac ccagcagaca tgagctggtg ctccaagagt       300
gatgatcaga tttggttgtc tcagtggttc atgaatgctg tgggacatga ttggcaccta       360
gacccaccat tcctgtgtag gaaccgtaca aagacagaag gcttcatctt ccaagtcaac       420
acctccaaga ctggtgttaa tgaaaattat gctaagaagt tcaagactgg catgcaccac       480
ttgtatagag agtaccctga ctcttgcccg aacggcaagc tgtgcttaat gaaggcacaa       540
cctaccagtt ggcctctcca atgtccactc gaccacgtca acacattaca cttccttaca       600
agaggcaaga acattcagct tccaaggagg tccttgaagc ggccgcacgg cggaggtagc       660
aaagactgcg aaatgaagcg caccaccctg atagccctc tgggcaagct ggaactgtct       720
gggtgcgaac agggcctgca cgagatcaag ctgctgggca aggaacatc tgccgccgac       780 gccgtggaag tgcctgcccc agccgccgtg ctgggcggac agagccact gatgcaggcc       840 accgcctggc tcaacgccta cttccaccag cctgaggcca tcgaggagtt ccctgtgcca       900
gccctgcacc acccagtgtt ccagcaggag agctttaccc gccaggtgct gtggaaactg       960
ctgaaagtgg tgaagttcgg agaggtcatc agctaccagc agctggccgc cctggccggc      1020
aatcccgccg ccaccgccgc cgtgaaaacc gccctgagcg gaaatcccgt gcccattctg      1080 atccctgcc accgggtggt gtctagctct ggcgccgtgg ggggctacga gggcgggctc      1140
gccgtgaaag agtggctgct ggcccacgag ggccacagac tgggcaagcc tgggctgggt      1200
cctgcaggta taggcgcgcc agggtccctg gagcatcatc atcatcatca ttgatgacgg      1260
gccc                                                                  1264

<210> SEQ ID NO 133
<211> LENGTH: 399
<212> TYPE: PRT
```

<213> ORGANISM: artificial
<220> FEATURE:
<223> OTHER INFORMATION: Amino acid sequence of fusion protein
[JUN.ectoGP1- SNAPlike-Histag]

<400> SEQUENCE: 133

```
Arg Ser Glu Glu Ala Phe Lys Ile Gly Leu His Thr Glu Phe Gln Thr
1               5                   10                  15
Val Ser Phe Ser Met Val Gly Leu Phe Ser Asn Asn Pro His Asp Leu
            20                  25                  30
Pro Leu Leu Cys Thr Leu Asn Lys Ser His Leu Tyr Ile Lys Gly Gly
        35                  40                  45

Asn Ala Ser Phe Gln Ile Ser Phe Asp Asp Ile Ala Val Leu Leu Pro
    50                  55                  60

Gln Tyr Asp Val Ile Ile Gln His Pro Ala Asp Met Ser Trp Cys Ser
65                  70                  75                  80

Lys Ser Asp Asp Gln Ile Trp Leu Ser Gln Trp Phe Met Asn Ala Val
                85                  90                  95

Gly His Asp Trp His Leu Asp Pro Pro Phe Leu Cys Arg Asn Arg Thr
            100                 105                 110

Lys Thr Glu Gly Phe Ile Phe Gln Val Asn Thr Ser Lys Thr Gly Val
        115                 120                 125

Asn Glu Asn Tyr Ala Lys Lys Phe Lys Thr Gly Met His His Leu Tyr
    130                 135                 140

Arg Glu Tyr Pro Asp Ser Cys Pro Asn Gly Lys Leu Cys Leu Met Lys
145                 150                 155                 160

Ala Gln Pro Thr Ser Trp Pro Leu Gln Cys Pro Leu Asp His Val Asn
                165                 170                 175

Thr Leu His Phe Leu Thr Arg Gly Lys Asn Ile Gln Leu Pro Arg Arg
            180                 185                 190

Ser Leu Lys Arg Pro His Gly Gly Gly Ser Lys Asp Cys Glu Met Lys
        195                 200                 205

Arg Thr Thr Leu Asp Ser Pro Leu Gly Lys Leu Glu Leu Ser Gly Cys
    210                 215                 220

Glu Gln Gly Leu His Glu Ile Lys Leu Leu Gly Lys Gly Thr Ser Ala
225                 230                 235                 240

Ala Asp Ala Val Glu Val Pro Ala Pro Ala Ala Val Leu Gly Gly Pro
                245                 250                 255

Glu Pro Leu Met Gln Ala Thr Ala Trp Leu Asn Ala Tyr Phe His Gln
            260                 265                 270

Pro Glu Ala Ile Glu Glu Phe Pro Val Pro Ala Leu His His Pro Val
        275                 280                 285

Phe Gln Gln Glu Ser Phe Thr Arg Gln Val Leu Trp Lys Leu Leu Lys
    290                 295                 300

Val Val Lys Phe Gly Glu Val Ile Ser Tyr Gln Gln Leu Ala Ala Leu
305                 310                 315                 320

Ala Gly Asn Pro Ala Ala Thr Ala Ala Val Lys Thr Ala Leu Ser Gly
                325                 330                 335

Asn Pro Val Pro Ile Leu Ile Pro Cys His Arg Val Val Ser Ser Ser
            340                 345                 350

Gly Ala Val Gly Gly Tyr Glu Gly Gly Leu Ala Val Lys Glu Trp Leu
        355                 360                 365

Leu Ala His Glu Gly His Arg Leu Gly Lys Pro Gly Leu Gly Pro Ala
    370                 375                 380
```

Gly Ile Gly Ala Pro Gly Ser Leu Glu His His His His His His
385                 390                 395

<210> SEQ ID NO 134
<211> LENGTH: 1297
<212> TYPE: DNA
<213> ORGANISM: artificial
<220> FEATURE:
<223> OTHER INFORMATION: DNA sequence encoding ssBiP- Glycoprotein GP1
      from Machupo virus- SNAPlike-Histag for expression in S2 cells

<400> SEQUENCE: 134
atgaagttat gcatattact ggccgtcgtg gcctttgttg gcctctcgct cgggagatct      60
gacggcacat tcaagatcgg cctgcacacg gagttccagt cagtcaccct caccatgcag     120
agacttttgg ctaaccattc aaacgagctc ccgtctctct gcatgctgaa caacagtttc     180
tattatatga ggggaggtgt gaacaccttc ctgatccgtg tttctgatat ttcagtcctc     240
atgaaggagt acgatgtatc aatctacgag ccagaggacc tcggaaactg tctgaacaag     300
tctgactcaa gctgggctat ccattggttc tcaaacgctt tggacatgat ctggctgatg     360
gaccctccaa tgctctgtag aaacaagaca aagaaggagg atctaacat ccaattcaac      420 atcagcaagg ctgatgatgc cagagtgtat ggaaagaaga tcagaaacgg tatgaggcat     480
ctcttcaggg gcttccatga cccgtgtgag aagggaagg tgtgctacct gaccatcaac      540
cagtgtggtg accccagttc cttcgactac tgtggcgtga accatctgtc caagtgtcag     600
ttcgaccatg tgaacaccct gcatttcctg gtgagaagta agacacatct caacttcgag     660
aggtctttga gcggccgca cggcggaggt agcaaagact gcgaaatgaa gcgcaccacc     720
ctggatagcc ctctgggcaa gctggaactg tctgggtgcg aacagggcct gcacgagatc     780
aagctgctgg gcaaaggaac atctgccgcc gacgccgtgg aagtgcctgc cccagccgcc     840
gtgctgggcg accagagcc actgatgcag gccaccgcct ggctcaacgc ctactttcac     900
cagcctgagg ccatcgagga gttccctgtg ccagccctgc accaccagt gttccagcag     960 gagagcttta cccgccaggt gctgtggaaa ctgctgaaag tggtgaagtt cggagaggtc     1020
atcagctacc agcagctggc cgccctggcc ggcaatcccg ccgccaccgc cgccgtgaaa     1080
accgccctga gcggaaatcc cgtgcccatt ctgatcccct gccaccgggt ggtgtctagc     1140
tctggcgccg tgggggcta cgagggcggg ctcgccgtga agagtggct gctgccccac     1200 gagggccaca gactgggcaa gcctgggctg gtcctgcag gtataggcgc gccagggtcc     1260
ctggagcatc atcatcatca tcattgatga cgggccc                              1297

<210> SEQ ID NO 135
<211> LENGTH: 410
<212> TYPE: PRT
<213> ORGANISM: artificial
<220> FEATURE:
<223> OTHER INFORMATION: Amino acid sequence of fusion protein
      [MAC.ectoGP1- SNAPlike-Histag]

<400> SEQUENCE: 135

Arg Ser Asp Gly Thr Phe Lys Ile Gly Leu His Thr Glu Phe Gln Ser
1               5                   10                  15

Val Thr Leu Thr Met Gln Arg Leu Leu Ala Asn His Ser Asn Glu Leu
            20                  25                  30

Pro Ser Leu Cys Met Leu Asn Asn Ser Phe Tyr Tyr Met Arg Gly Gly
        35                  40                  45

Val Asn Thr Phe Leu Ile Arg Val Ser Asp Ile Ser Val Leu Met Lys

```
                    50                  55                  60
Glu Tyr Asp Val Ser Ile Tyr Glu Pro Glu Asp Leu Gly Asn Cys Leu
 65                  70                  75                  80

Asn Lys Ser Asp Ser Ser Trp Ala Ile His Trp Phe Ser Asn Ala Leu
                     85                  90                  95

Gly His Asp Trp Leu Met Asp Pro Met Leu Cys Arg Asn Lys Thr
                100                 105                 110

Lys Lys Glu Gly Ser Asn Ile Gln Phe Asn Ile Ser Lys Ala Asp Asp
                115                 120                 125

Ala Arg Val Tyr Gly Lys Lys Ile Arg Asn Gly Met Arg His Leu Phe
            130                 135                 140

Arg Gly Phe His Asp Pro Cys Glu Glu Gly Lys Val Cys Tyr Leu Thr
145                 150                 155                 160

Ile Asn Gln Cys Gly Asp Pro Ser Ser Phe Asp Tyr Cys Gly Val Asn
                165                 170                 175

His Leu Ser Lys Cys Gln Phe Asp His Val Asn Thr Leu His Phe Leu
                180                 185                 190

Val Arg Ser Lys Thr His Leu Asn Phe Glu Arg Ser Leu Lys Arg Pro
            195                 200                 205

His Gly Gly Gly Ser Lys Asp Cys Glu Met Lys Arg Thr Thr Leu Asp
210                 215                 220

Ser Pro Leu Gly Lys Leu Glu Leu Ser Gly Cys Glu Gln Gly Leu His
225                 230                 235                 240

Glu Ile Lys Leu Leu Gly Lys Gly Thr Ser Ala Ala Asp Ala Val Glu
                245                 250                 255

Val Pro Ala Pro Ala Ala Val Leu Gly Gly Pro Glu Pro Leu Met Gln
            260                 265                 270

Ala Thr Ala Trp Leu Asn Ala Tyr Phe His Gln Pro Glu Ala Ile Glu
                275                 280                 285

Glu Phe Pro Val Pro Ala Leu His His Pro Val Phe Gln Gln Glu Ser
            290                 295                 300

Phe Thr Arg Gln Val Leu Trp Lys Leu Leu Lys Val Val Lys Phe Gly
305                 310                 315                 320

Glu Val Ile Ser Tyr Gln Gln Leu Ala Ala Leu Ala Gly Asn Pro Ala
                325                 330                 335

Ala Thr Ala Ala Val Lys Thr Ala Leu Ser Gly Asn Pro Val Pro Ile
            340                 345                 350

Leu Ile Pro Cys His Arg Val Val Ser Ser Ser Gly Ala Val Gly Gly
                355                 360                 365

Tyr Glu Gly Gly Leu Ala Val Lys Glu Trp Leu Leu Ala His Glu Gly
            370                 375                 380

His Arg Leu Gly Lys Pro Gly Leu Gly Pro Ala Gly Ile Gly Ala Pro
385                 390                 395                 400

Gly Ser Leu Glu His His His His His His
                405                 410

<210> SEQ ID NO 136
<211> LENGTH: 1246
<212> TYPE: DNA
<213> ORGANISM: artificial
<220> FEATURE:
<223> OTHER INFORMATION: DNA sequence encoding ssBiP- Glycoprotein GP1
      from Guanarito virus- SNAPlike-Histag for expression in S2 cells

<400> SEQUENCE: 136
```

```
atgaagttat gcatattact ggccgtcgtg gcctttgttg gcctctcgct cgggagatct      60
ttcaaggttg gtcatcatac gaacttcgag tcgttcacgg ttaagctggg aggtgtcttc     120
catgaattgc cttcgctgtg tagggtcaac aactcctaca gtctgatcag gctctcccat     180
aacagtaacc aggcattgtc ggttgagtac gtggatgtgc accctgtcct ctgttcgtcc     240
agtccaacca tcctcgacaa ctacacgcaa tgtatcaagg gctcgccaga gttcgattgg     300
attctcgggt ggacgatcaa gggattggga catgacttct tgagagatcc aagaatctgc     360
tgtgagccta agaagacgac taacgctgag ttcacgttcc aattgaactt gacggatagt     420
cctgagaccc atcactacag gagcaagatt gaggtaggca tccgacactt gttcgggaac     480
tacatcacca acgatagcta ctcgaagatg tccgtggtta tgaggaacac cacctgggaa     540
ggtcaatgct cgaacagtca tgtgaacacg ctgagattcc tcgttaagaa cgcaggttac     600
ctcgttggaa ggaagccact gcggccgcac ggcggaggta gcaaagactg cgaaatgaag     660
cgcaccaccc tggatagccc tctgggcaag ctggaactgt ctgggtgcga acagggcctg     720
cacgagatca agctgctggg caaaggaaca tctgccgccg acgccgtgga agtgcctgcc     780
ccagccgccg tgctgggcgg accagagcca ctgatgcagg ccaccgcctg gctcaacgcc     840
tactttcacc agcctgaggc catcgaggag ttccctgtgc agccctgca ccacccagtg     900
ttccagcagg agagctttac ccgccaggtg ctgtggaaac tgctgaaagt ggtgaagttc     960
ggagaggtca tcagctacca gcagctggcc gccctggccg caatcccgc cgccaccgcc    1020
gccgtgaaaa ccgccctgag cggaaatccc gtgcccattc tgatcccctg ccaccgggtg    1080
gtgtctagct ctggcgccgt gggggggctac gagggcgggc tcgccgtgaa agagtggctg    1140
ctggcccacg agggccacag actgggcaag cctgggctgg gtcctgcagg tataggcgcg    1200
ccagggtccc tggagcatca tcatcatcat cattgatgac gggccc                   1246
```

<210> SEQ ID NO 137
<211> LENGTH: 393
<212> TYPE: PRT
<213> ORGANISM: artificial
<220> FEATURE:
<223> OTHER INFORMATION: Amino acid sequence of fusion protein
      [GUA.ectoGP1- SNAPlike-Histag]

<400> SEQUENCE: 137

```
Arg Ser Phe Lys Val Gly His His Thr Asn Phe Glu Ser Phe Thr Val
1               5                   10                  15

Lys Leu Gly Gly Val Phe His Glu Leu Pro Ser Leu Cys Arg Val Asn
            20                  25                  30

Asn Ser Tyr Ser Leu Ile Arg Leu Ser His Asn Ser Asn Gln Ala Leu
        35                  40                  45

Ser Val Glu Tyr Val Asp Val His Pro Val Leu Cys Ser Ser Ser Pro
    50                  55                  60

Thr Ile Leu Asp Asn Tyr Thr Gln Cys Ile Lys Gly Ser Pro Glu Phe
65                  70                  75                  80

Asp Trp Ile Leu Gly Trp Thr Ile Lys Gly Leu Gly His Asp Phe Leu
                85                  90                  95

Arg Asp Pro Arg Ile Cys Cys Glu Pro Lys Lys Thr Thr Asn Ala Glu
            100                 105                 110

Phe Thr Phe Gln Leu Asn Leu Thr Asp Ser Pro Glu Thr His His Tyr
        115                 120                 125

Arg Ser Lys Ile Glu Val Gly Ile Arg His Leu Phe Gly Asn Tyr Ile
    130                 135                 140
```

Thr Asn Asp Ser Tyr Ser Lys Met Ser Val Met Arg Asn Thr Thr
145                 150                 155                 160

Trp Glu Gly Gln Cys Ser Asn Ser His Val Asn Thr Leu Arg Phe Leu
            165                 170                 175

Val Lys Asn Ala Gly Tyr Leu Val Gly Arg Lys Pro Leu Arg Pro His
        180                 185                 190

Gly Gly Gly Ser Lys Asp Cys Glu Met Lys Arg Thr Thr Leu Asp Ser
    195                 200                 205

Pro Leu Gly Lys Leu Glu Leu Ser Gly Cys Glu Gln Gly Leu His Glu
210                 215                 220

Ile Lys Leu Leu Gly Lys Gly Thr Ser Ala Ala Asp Ala Val Glu Val
225                 230                 235                 240

Pro Ala Pro Ala Ala Val Leu Gly Gly Pro Glu Pro Leu Met Gln Ala
                245                 250                 255

Thr Ala Trp Leu Asn Ala Tyr Phe His Gln Pro Glu Ala Ile Glu Glu
            260                 265                 270

Phe Pro Val Pro Ala Leu His His Pro Val Phe Gln Gln Glu Ser Phe
        275                 280                 285

Thr Arg Gln Val Leu Trp Lys Leu Leu Lys Val Val Lys Phe Gly Glu
    290                 295                 300

Val Ile Ser Tyr Gln Gln Leu Ala Ala Leu Ala Gly Asn Pro Ala Ala
305                 310                 315                 320

Thr Ala Ala Val Lys Thr Ala Leu Ser Gly Asn Pro Val Pro Ile Leu
                325                 330                 335

Ile Pro Cys His Arg Val Val Ser Ser Gly Ala Val Gly Gly Tyr
            340                 345                 350

Glu Gly Gly Leu Ala Val Lys Glu Trp Leu Leu Ala His Glu Gly His
        355                 360                 365

Arg Leu Gly Lys Pro Gly Leu Gly Pro Ala Gly Ile Gly Ala Pro Gly
    370                 375                 380

Ser Leu Glu His His His His His His
385                 390

<210> SEQ ID NO 138
<211> LENGTH: 1273
<212> TYPE: DNA
<213> ORGANISM: artificial
<220> FEATURE:
<223> OTHER INFORMATION: DNA sequence encoding ssBiP- Glycoprotein GP1
      from Sabia virus- SNAPlike-Histag for expression in S2 cells

<400> SEQUENCE: 138
atgaagttat gcatattact ggccgtcgtg gcctttgttg gcctctcgct cgggagatct      60
ttcagaatcg gaaggagcac agaattgcag aacatcacgt tcgatatgtt gaaggtgttc     120
gaggaccacc ccacatcctg catggtgaac cattccacct actacgtcca tgagaacaag     180
aacgccactt ggtgtctgga ggtgtccgtg actgatgtta ccctgctcat ggctgaacat     240
gatcgtcaag tcctcaacaa cctgtcgaac tgtgtgcacc ctgcagtcga gcacagaagc     300
aggatggttg gcttgctgga gtggatcttc agagccctga gtacgacttc aaccatgat     360 ccaacaccgt tgtgtcagaa gcagacttcg acagtgaacg agacacgtgt gcagatcaac     420
atcactgagg ggtcgggtc ccacgggttc gaagatacca tcctccagag actcggggtt     480
ctgttcggtt cgagaattgc attctcgaac atccaggact gggtaagaa gaggttcttg     540 ttgatcagga actcgacttg gaagaaccaa tgcgagatga accatgtgaa ctccatgcac     600

```
ttgatgttgg cgaacgctgg tcgctcgtcc ggttcgagaa gaccactgcg gccgcacggc    660
ggaggtagca aagactgcga aatgaagcgc accaccctgg atagccctct gggcaagctg    720
gaactgtctg ggtgcgaaca gggcctgcac gagatcaagc tgctgggcaa aggaacatct    780
gccgccgacg ccgtggaagt gcctgcccca gccgccgtgc tgggcggacc agagccactg    840
atgcaggcca ccgcctggct caacgcctac tttcaccagc ctgaggccat cgaggagttc    900
cctgtgccag ccctgcacca cccagtgttc cagcaggaga gctttacccg ccaggtgctg    960
tggaaactgc tgaaagtggt gaagttcgga gaggtcatca gctaccagca gctggccgcc   1020
ctggccggca atcccgccgc caccgccgcc gtgaaaaccg ccctgagcgg aaatcccgtg   1080
cccattctga tcccctgcca ccgggtggtg tctagctctg gcgccgtggg gggctacgag   1140
ggcgggctcg ccgtgaaaga gtggctgctg gcccacgagg gccacagact gggcaagcct   1200
gggctgggtc ctgcaggtat aggcgcgcca gggtccctgg agcatcatca tcatcatcat   1260
tgatgacggg ccc                                                      1273
```

```
<210> SEQ ID NO 139
<211> LENGTH: 396
<212> TYPE: PRT
<213> ORGANISM: artificial
<220> FEATURE:
<223> OTHER INFORMATION: Amino acid sequence of fusion protein
      [SAB.ectoGP1- SNAPlike-Histag]

<400> SEQUENCE: 139

Arg Ser Thr Glu Leu Gln Asn Ile Thr Phe Asp Met Leu Lys Val Phe
1               5                   10                  15

Glu Asp His Pro Thr Ser Cys Met Val Asn His Ser Thr Tyr Tyr Val
            20                  25                  30

His Glu Asn Lys Asn Ala Thr Trp Cys Leu Glu Val Ser Val Thr Asp
        35                  40                  45

Val Thr Leu Leu Met Ala Glu His Asp Arg Gln Val Leu Asn Asn Leu
    50                  55                  60

Ser Asn Cys Val His Pro Ala Val Glu His Arg Ser Arg Met Val Gly
65                  70                  75                  80

Leu Leu Glu Trp Ile Phe Arg Ala Leu Lys Tyr Asp Phe Asn His Asp
                85                  90                  95

Pro Thr Pro Leu Cys Gln Lys Gln Thr Ser Thr Val Asn Glu Thr Arg
            100                 105                 110

Val Gln Ile Asn Ile Thr Glu Gly Phe Gly Ser His Gly Phe Glu Asp
        115                 120                 125

Thr Ile Leu Gln Arg Leu Gly Val Leu Phe Gly Ser Arg Ile Ala Phe
    130                 135                 140

Ser Asn Ile Gln Asp Leu Gly Lys Lys Arg Phe Leu Leu Ile Arg Asn
145                 150                 155                 160

Ser Thr Trp Lys Asn Gln Cys Glu Met Asn His Val Asn Ser Met His
                165                 170                 175

Leu Met Leu Ala Asn Ala Gly Arg Ser Ser Gly Ser Arg Arg Pro Leu
            180                 185                 190

Arg Pro His Gly Gly Gly Ser Lys Asp Cys Glu Met Lys Arg Thr Thr
        195                 200                 205

Leu Asp Ser Pro Leu Gly Lys Leu Glu Leu Ser Gly Cys Glu Gln Gly
    210                 215                 220

Leu His Glu Ile Lys Leu Leu Gly Lys Gly Thr Ser Ala Ala Asp Ala
```

| | | | | | 225 | | | | | 230 | | | | | 235 | | | | | 240 |

Val Glu Val Pro Ala Pro Ala Ala Val Leu Gly Gly Pro Glu Pro Leu
                    245                 250                 255

Met Gln Ala Thr Ala Trp Leu Asn Ala Tyr Phe His Gln Pro Glu Ala
                260                 265                 270

Ile Glu Glu Phe Pro Val Pro Ala Leu His His Pro Val Phe Gln Gln
            275                 280                 285

Glu Ser Phe Thr Arg Gln Val Leu Trp Lys Leu Leu Lys Val Val Lys
        290                 295                 300

Phe Gly Glu Val Ile Ser Tyr Gln Gln Leu Ala Ala Leu Ala Gly Asn
305                 310                 315                 320

Pro Ala Ala Thr Ala Ala Val Lys Thr Ala Leu Ser Gly Asn Pro Val
                    325                 330                 335

Pro Ile Leu Ile Pro Cys His Arg Val Val Ser Ser Gly Ala Val
                340                 345                 350

Gly Gly Tyr Glu Gly Gly Leu Ala Val Lys Glu Trp Leu Leu Ala His
            355                 360                 365

Glu Gly His Arg Leu Gly Lys Pro Gly Leu Gly Pro Ala Gly Ile Gly
        370                 375                 380

Ala Pro Gly Ser Leu Glu His His His His His
385                 390                 395

<210> SEQ ID NO 140
<211> LENGTH: 1189
<212> TYPE: DNA
<213> ORGANISM: artificial
<220> FEATURE:
<223> OTHER INFORMATION: DNA sequence encoding ssBiP- Glycoprotein GP2
      from Lassa virus- SNAPlike-Histag for expression in S2 cells

<400> SEQUENCE: 140
atgaagttat gcatattact ggccgtcgtg gcctttgttg gcctctcgct cgggagatct      60
ggcacattca catggacact gtcggattct gaaggtaagg acacaccagg gggatactgt    120
ctgaccaggt ggatgctgat cgaggctgaa ctgaagtgct cgggaacac agctgtggcg     180 aagtgtaacg agaagcatga tgaggagttc tgtgacatgc tgaggctgtt cgacttcaac    240
aagcaagcca tccagaggtt gaaggctgaa gcacagatga gcatccagtt gatcaacaag    300
gcagtgaatg ccttgatcaa cgaccaactg atcatgaaga accatctgcg ggacatcatg    360
ggtatcccat actgtaacta cagcaagtac tggtacctca accacacaac tactgggaga    420
acatcgctgc ccaagtgttg gctggtgtcg aacggttcgt acttgaacga ccccacttc    480 tccgatgaca tcgaacaaca agctgacaac atgatcactg agatgttgca gaaggagtac    540
atggagaggc aggggaagac accgcggccg cacggcggag gtagcaaaga ctgcgaaatg    600
aagcgcacca ccctggatag ccctctgggc aagctggaac tgtctgggtg gaacagggc    660 ctgcacgaga tcaagctgct gggcaaagga catctgccg ccgacgccgt ggaagtgcct    720
gccccagccg ccgtgctggg cggaccagag ccactgatgc aggccaccgc ctggctcaac    780
gcctactttc accagcctga ggccatcgag gagttccctg tgccagccct gcaccaccca    840
gtgttccagc aggagagctt tacccgccag gtgctgtgga aactgctgaa agtggtgaag    900
ttcggagagg tcatcagcta ccagcagctg gccgccctgg ccggcaatcc cgccgccacc    960
gccgccgtga aaaccgccct gagcggaaat cccgtgccca ttctgatccc ctgccaccga   1020
gtggtgtcta gctctggcgc cgtgggggc tacgagggcg gctcgccgt gaaagagtgg    1080

```
ctgctggccc acgagggcca cagactgggc aagcctgggc tgggtcctgc aggtataggc    1140
gcgccagggt ccctggagca tcatcatcat catcattgat gacgggccc               1189
```

<210> SEQ ID NO 141
<211> LENGTH: 374
<212> TYPE: PRT
<213> ORGANISM: artificial
<220> FEATURE:
<223> OTHER INFORMATION: Amino acid sequence of fusion protein [LAS.ectoGP2- SNAPlike-Histag]

<400> SEQUENCE: 141

```
Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45

Asp Glu Glu Phe Cys Asp Met Leu Arg Leu Phe Asp Phe Asn Lys Gln
    50                  55                  60

Ala Ile Gln Arg Leu Lys Ala Glu Ala Gln

```
            340                 345                 350
Lys Pro Gly Leu Gly Pro Ala Gly Ile Gly Ala Pro Gly Ser Leu Glu
        355                 360                 365

His His His His His His
    370

<210> SEQ ID NO 142
<211> LENGTH: 1189
<212> TYPE: DNA
<213> ORGANISM: artificial
<220> FEATURE:
<223> OTHER INFORMATION: DNA sequence encoding ssBiP- Glycoprotein GP2
      from Junin virus- SNAPlike-Histag for expression in S2 cells

<400> SEQUENCE: 142
atgaagttat gcatattact ggccgtcgtg gcctttgttg cctctcgct cgggagatct    60 gcattcttct cctggtcgtt gacagactca tccggcaagg ataccctgg aggctactgc    120 ctggaagagt ggatgctcgt ggcagccaag atgaagtgct cggcaacac tgctgtggcc    180 aagtgcaact tgaaccatga ctcggagttc tgtgacatgt tgaggctgtt cgattacaac    240
aagaacgcta tcaagaccct gaacgatgag actaagaagc aagtgaacct gatggggcag    300
acaatcaacg ccctgatctc ggacaacttg ttgatgaaga caagatcag ggaactgatg    360 agtgtcccctt actgcaacta cacgaagttc tggtacgtca accacacact ctccggacaa    420
cactcgttgc caaggtgctg gttgatcaag aacaacagct acttgaacat ctccgacttc    480
cgtaacgact ggatcttgga gagtgacttc ttgatctccg agatgctgag caaggagtac    540
tcggacaggc agggtaagac tccgcggccg cacggcggag gtagcaaaga ctgcgaaatg    600
aagcgcacca ccctggatag ccctctgggc aagctggaac tgtctgggtg cgaacagggc    660
ctgcacgaga tcaagctgct gggcaaagga acatctgccg ccgacgccgt ggaagtgcct    720
gccccagccg ccgtgctggg cggaccagag ccactgatgc aggccaccgc ctggctcaac    780
gcctactttc accagcctga ggccatcgag gagttccctg tgccagccct gcaccaccca    840
gtgttccagc aggagagctt tacccgccag gtgctgtgga aactgctgaa agtggtgaag    900
ttcggagagg tcatcagcta ccagcagctg gccgccctgg ccggcaatcc cgccgccacc    960
gccgccgtga aaaccgccct gagcggaaat cccgtgccca ttctgatccc ctgccaccgg    1020
gtggtgtcta gctctggcgc cgtgggggggc tacgagggcg gctcgccgt gaaagagtgg    1080 ctgctggccc acgagggcca cagactgggc aagcctgggc tgggtcctgc aggtataggc    1140
gcgccagggt ccctggagca tcatcatcat catcattgat gacgggccc                1189

<210> SEQ ID NO 143
<211> LENGTH: 374
<212> TYPE: PRT
<213> ORGANISM: artificial
<220> FEATURE:
<223> OTHER INFORMATION: Amino acid sequence of fusion protein
      [JUN.ectoGP2- SNAPlike-Histag]

<400> SEQUENCE: 143

Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45
```

```
Asp Glu Glu Phe Cys Asp Met Leu Arg Leu Phe Asp Phe Asn Lys Gln
    50                  55                  60

Ala Ile Gln Arg Leu Lys Ala Glu Ala Gln Met Ser Ile Gln Leu Ile
65                  70                  75                  80

Asn Lys Ala Val Asn Ala Leu Ile Asn Asp Gln Leu Ile Met Lys Asn

```
aagtgtaacc agaaccatga ctcagagttc tgtgatatgc tgaggctatt cgactacaac      240
aagaacgcaa tcaagaccct caacgatgaa tcgaagaagg agatcaacct gctaagccag      300
accgtgaacg ccttgatctc ggataacttg ttaatgaaga caagatcaa ggagctaatg      360 agcatccctt actgtaatta cacgaagttc tggtacgtca accatacccct gacagggcag     420 cacacgctgc caaggtgttg gttgatcagg aacggaagtt acctcaacac ctcggagttc      480
aggaacgact ggatcttgga gagtgatcac ctcatctcgg agatgttgag taaggaatac      540
gctgagaggc aaggcaagac cccgcggccg cacggcggag gtagcaaaga ctgcgaaatg      600
aagcgcacca cccctggatag ccctctgggc aagctggaac tgtctgggtg cgaacagggc      660
ctgcacgaga tcaagctgct gggcaaagga acatctgccg ccgacgccgt ggaagtgcct      720
gccccagccg ccgtgctggg cggaccagag ccactgatgc aggccaccgc ctggctcaac      780
gcctactttc accagcctga ggccatcgag gagttccctg tgccagccct gcaccaccca      840
gtgttccagc aggagagctt tacccgccag gtgctgtgga aactgctgaa agtggtgaag      900
ttcggagagg tcatcagcta ccagcagctg ccgcccctgg ccggcaatcc cgccgccacc      960
gccgccgtga aaaccgccct gagcggaaat cccgtgccca ttctgatccc ctgccaccgg     1020
gtggtgtcta gctctggcgc cgtgggggc tacgagggcg ggctcgccgt gaaagagtgg     1080
ctgctggccc acgagggcca cagactgggc aagcctgggc tgggtcctgc aggtataggc     1140
gcgccagggt ccctggagca tcatcatcat catcattgat gacgggccc                 1189

<210> SEQ ID NO 145
<211> LENGTH: 374
<212> TYPE: PRT
<213> ORGANISM: artificial
<220> FEATURE:
<223> OTHER INFORMATION: Amino acid sequence of fusion protein
      [MAC.ectoGP2- SNAPlike-Histag]

<400> SEQUENCE: 145

Arg Ser Ala Phe Phe Ser Trp Ser Leu Thr Asp Ser Ser Gly Lys Asp
1               5                   10                  15

Met Pro Gly Gly Tyr Cys Leu Glu Glu Trp Met Leu Ile Ala Ala Lys
            20                  25                  30

Met Lys Cys Phe Gly Asn Thr Ala Val Ala Lys Cys Asn Gln Asn His
        35                  40                  45

Asp Ser Glu Phe Cys Asp Met Leu Arg Leu Phe Asp Tyr Asn Lys Asn
    50                  55                  60

Ala Ile Lys Thr Leu Asn Asp Glu Ser Lys Lys Glu Ile Asn Leu Leu
65                  70                  75                  80

Ser Gln Thr Val Asn Ala Leu Ile Ser Asp Asn Leu Leu Met Lys Asn
                85                  90                  95

Lys Ile Lys Glu Leu Met Ser Ile Pro Tyr Cys Asn Tyr Thr Lys Phe
            100                 105                 110

Trp Tyr Val Asn His Thr Leu Thr Gly Gln His Thr Leu Pro Arg Cys
        115                 120                 125

Trp Leu Ile Arg Asn Gly Ser Tyr Leu Asn Thr Ser Glu Phe Arg Asn
    130                 135                 140

Asp Trp Ile Leu Glu Ser Asp His Leu Ile Ser Glu Met Leu Ser Lys
145                 150                 155                 160

Glu Tyr Ala Glu Arg Gln Gly Lys Thr Pro Arg Pro His Gly Gly Gly
                165                 170                 175
```

```
Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala P

```
ttcggagagg tcatcagcta ccagcagctg gccgccctgg ccggcaatcc cgccgccacc      960
gccgccgtga aaaccgccct gagcggaaat cccgtgccca ttctgatccc ctgccaccgg     1020
gtggtgtcta gctctggcgc cgtgggggc tacgagggcg ggctcgccgt gaaagagtgg     1080
ctgctggccc acgagggcca cagactgggc aagcctgggc tgggtcctgc aggtataggc     1140
gcgccagggt ccctggagca tcatcatcat catcattgat gacgggccc                 1189
```

<210> SEQ ID NO 147
<211> LENGTH: 374
<212> TYPE: PRT
<213> ORGANISM: artificial
<220> FEATURE:
<223> OTHER INFORMATION: Amino acid sequence of fusion protein [GUA.ectoGP2- SNAPlike-Histag]

<400> SEQUENCE: 147

```
Arg Ser Ala Phe Phe Ser Trp Ser Leu Ser Asp Pro Lys Gly Asn Asp
1               5                   10                  15

Met Pro Gly Gly Tyr Cys Leu Glu Arg Trp Met Leu Val Ala Gly Asp
                20                  25                  30

Leu Lys Cys Phe Gly Asn Thr Ala Val Ala Lys Cys Asn Leu Asn His
            35                  40                  45

Asp Ser Glu Phe Cys Asp Met Leu Arg Leu Phe Asp Phe Asn Lys Asn
        50                  55                  60

Ala Ile Glu Lys Leu Asn Asn Gln Thr Lys Thr Ala Val Asn Met Leu
65                  70                  75                  80

Thr His Ser Ile Asn Ser Leu Ile Ser Asp Asn Leu Leu Met Arg Asn
                85                  90                  95

Lys Leu Lys Glu Ile Leu Lys Val Pro Tyr Cys Asn Tyr Thr Arg Phe
                100                 105                 110

Trp Tyr Ile Asn His Thr Lys Ser Gly Glu His Ser Leu Pro Arg Cys
            115                 120                 125

Trp Leu Val Ser Asn Gly Ser Tyr Leu Asn Glu Ser Asp Phe Arg Asn
        130                 135                 140

Glu Trp Ile Leu Glu Ser Asp His Leu Ile Ala Glu Met Leu Ser Lys
145                 150                 155                 160

Glu Tyr Gln Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Thr Ala Ala
    290                 295                 300
```

```
Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370

<210> SEQ ID NO 148
<211> LENGTH: 1189
<212> TYPE: DNA
<213> ORGANISM: artificial
<220> FEATURE:
<223> OTHER INFORMATION: DNA sequence encoding ssBiP-Glycoprotein GP2
      from Sabia virus- SNAPlike-Histag for expression in S2 cells

<400> SEQUENCE: 148
atgaagttat gcatattact ggccgtcgtg gcctttgttg gcctctcgct cgggagatct      60
ggcatcttct cctggacgat cacggatgca gtgggcaacg acatgcctgg tggttactgt     120
ctggagagat ggatgctggt gacgtcggat cttaagtgct tcggcaacac ggcactggcg     180
aagtgtaacc tcgaccacga ttcggagttc tgtgacatgt tgaagttgtt cgagttcaac     240
aagaaggcga tcgagacatt gaacgacaac acgaagaaca aggtgaactt gctgacccac     300
tcgatcaacg cattgatctc cgacaacttg ctgatgaaga accgactcaa ggaattgttg     360
aacacgcctt actgtaacta caccaagttc tggtatgtca accacacggc atccggggag     420
cactcattgc cacggtgctg gctggttagg aacaatagct acttgaacga gagtgagttc     480
aggaatgatt ggatcatcga gagtgatcac ttgttgtccg agatgctcaa caaggaatac     540
atcgatagac agggcaagac gccgcggccg cacggcggag gtagcaaaga ctgcgaaatg     600
aagcgcacca ccctggatag ccctctgggc aagctggaac tgtctgggtg cgaacagggc     660
ctgcacgaga tcaagctgct gggcaaagga acatctgccg ccgacgccgt ggaagtgcct     720
gccccagccg ccgtgctggg cggaccagag ccactgatgc aggccaccgc ctggctcaac     780
gcctactttc accagcctga ggccatcgag gagttccctg tgccagccct gcaccaccca     840
gtgttccagc aggagagctt tacccgccag gtgctgtgga aactgctgaa agtggtgaag     900
ttcggagagg tcatcagcta ccagcagctg gccgccctgg ccggcaatcc cgccgccacc     960
gccgccgtga aaaccgccct gagcggaaat cccgtgccca ttctgatccc ctgccaccgg    1020
gtggtgtcta gctctggcgc cgtgggggc tacgagggcg ggctcgccgt gaaagagtgg    1080
ctgctggccc acgagggcca cagactgggc aagcctgggc tgggtcctgc aggtataggc    1140
gcgccagggt ccctggagca tcatcatcat catcattgat gacgggccc               1189

<210> SEQ ID NO 149
<211> LENGTH: 374
<212> TYPE: PRT
<213> ORGANISM: artificial
<220> FEATURE:
<223> OTHER INFORMATION: Amino acid sequence of fusion protein
      [SAB.ectoGP2- SNAPlike-Histag]

<400> SEQUENCE: 149

Arg Ser Gly Ile Phe Ser Trp Thr Ile Thr Asp Ala Val Gly Asn Asp
1               5                   10                  15
```

```
Met Pro Gly Gly Tyr Cys Leu Glu Arg Trp Met Leu Val Thr Ser Asp
                20                  25                  30

Leu Lys Cys Phe Gly Asn Thr Ala Leu Ala Lys Cys Asn Leu Asp His
         35                  40                  45

Asp Ser Glu Phe Cys Asp Met Leu Lys Leu Phe Glu Phe Asn Lys Lys
 50                  55                  60

Ala Ile Glu Thr Leu Asn Asp Asn Thr Lys Asn Lys Val Asn Leu Leu
 65                  70                  75                  80

Thr His Ser Ile Asn Ala Leu Ile Ser Asp Asn Leu Leu Met Lys Asn
                 85                  90                  95

Arg Leu Lys Glu Leu Leu Asn Thr Pro Tyr Cys Asn Tyr Thr Lys Phe
            100                 105                 110

Trp Tyr Val Asn His Thr Ala Ser Gly Glu His Ser Leu Pro Arg Cys
        115                 120                 125

Trp Leu Val Arg Asn Asn Ser Tyr Leu Asn Glu Ser Glu Phe Arg Asn
130                 135                 140

Asp Trp Ile Ile Glu Ser Asp His Leu Leu Ser Glu Met Leu Asn Lys
145                 150                 155                 160

Glu Tyr Ile Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
290                 295                 300

Val Lys Thr Ala Leu Ser Gly Asn Pro Val Pro Ile Leu Ile Pro Cys
305                 310                 315                 320

His Arg Val Val Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 150
<211> LENGTH: 2774
<212> TYPE: DNA
<213> ORGANISM: artificial
<220> FEATURE:
<223> OTHER INFORMATION: DNA sequence encoding BiPlike-
      SNAPlike-proTEV1-C protein of Hepatitis E virus- proTEV2-Histag
      for expression in S2 cells

<400> SEQUENCE: 150

```
atgaaactat gtattctact tgcagttgtt gcgttcgtag gattgtcctt acctacagct      60
ctggcaagat ctgacaaaga ctgcgaaatg aaaagaacta cattggattc accacttggg     120
aagttggaac tgagtggatg cgagcaagga ttgcatgaaa ttaagctact gggaaaagga     180
acttctgctg ctgatgcagt tgaagttcca gcaccagcag ctgttcttgg aggtcctgag     240
cccctcatgc aagccacagc ctggcttaac gcatatttcc accagcctga ggccattgag     300
gaatttccag tccccgccct tcaccatcct gtgtttcagc aggagagctt cacccgccag     360
gtcctgtgga aattgctgaa ggtggtcaag tttggtgaag tgatttcata tcagcaactt     420
gctgcattgg ccggtaaccc cgcagctaca gctgccgtga aaactgctct cagcggaaat     480
cctgtgccca tcctgatccc ttgtcacaga gtcgtttcat cttccggagc tgtaggtggc     540
tatgaaggag gactggcagt taaggagtgg ctgctggctc atgaaggtca tagacttgga     600
aagcctgggc tgggtcctgc tggtataggc gcgccaggt  ccctaggtgg cggatccgaa     660
aacctgtact ccagagcga tatcaataac atgttctttt gctctgtgca tggagatgcc     720
accatgcgct ctcgggcttt tctgttttttg ttcctcgtgt ttctgcctat gctgcccgcg     780
ccaccggccg gtcagccgtc tggccgccgc cgcgggcggc gcagcggcgg tgccggcggt     840
ggtttctggg gtgaccggat tgattctcag cccttcgccc tccctatat tcatccaacc     900
aaccccttcg cacctgacat tccagccgca gccggggctg gagctcgccc tcggcagcca     960
gcccgcccac tcggctccgc ttggcgtgac caatcccagc gccccgccac ttccgcccgt    1020
cgtcgatctg ccccagctgg ggcttcgccg ctgactgctg tggccccggc cccgatact     1080
gttcctgttc ccgatgtcga ttctcgcggc gctatattac gccgccagta taatttatca    1140
acatccccgc taacatctac tattgccact ggtactaacc ttgttctata tgctgctccg    1200
ctgagcccctt tgcttccgct ccaagatgga actaacactc acattatggc cactgaagca    1260
tcaaattatg cccagtaccg tgttgtccgc gctaccatcc ggtaccgtcc gcttgtgccg    1320
aacgctgtcg gcggatacgc tatatctatc tctttctggc ctcagacaac tactacccg    1380
acatctgtgg acatgaactc tatcacctcc acgatgtcc gaatccttgt ccagcctggt    1440
attgcttcag aacttgtgat ccccagtgag cgcctgcatt atcgtaacca aggctggcgc    1500
tctgttgaga cctctggtgt tgcggaggag gaggcgacct ccggccttgt catgctttgc    1560
atccacggat cacctgtaaa ttcttacacc aatacgcctt atactggtgc ccttggcttg    1620
cttgatttcg cactcgagct cgagttccgc aatttgacac tggtaacac gaacacacgt    1680
gtttcccgct actcgagtag tgcgcgccac aagctacgcc gagggcctga tggcactgct    1740
gagttaacta cgactgctgc tacacgcttt atgaaggacc ttcattttac agggactaat    1800
ggagttggtg aagtcggtcg tggtatagcg ctaactctgt tcaaccttgc tgatacgctt    1860
ctcggcgggc tcccgacaga attgatttcg tcggctggtg gtcagctatt ttattctcgc    1920
cccgtcgtct cagccaatgg cgagccgacg gtgaagctct acacttcagt cgagaacgct    1980
cagcaggata agggtatagc tatcccacat gatattgatc ttggtgagtc ccgtgttgtc    2040
attcaggatt atgataacca acatgagcag gatcgtccca ccccttctcc tgctccctct    2100
cggccttttt ctgtccttcg tgctaatgat gtgctatggc tttcacttac agcagctgag    2160
tatgatcaga ctacctatgg ctcctctact aatcccatgt atgtctctga taccgtgaca    2220
tttgtcaatg ttgctactgg tgcccagggg gtatctcgct ctctggactg gtctaaagtc    2280
```

```
accccttgatg ggcgcccact tatgactatc cagcagtatt ctaagacttt ctttgttctg    2340
cccctccgtg gcaagctctc cttctgggag gccggtacca ctaaggccgg ctacccttat    2400
aattataata ctactgccag tgaccagatt ttaattgaga atgcagctgg tcaccgtgta    2460
tgcatctcaa cctacactac taatcttgga tctggccctg tttctatttc tgctgtcggt    2520
gtcctcgcac ctcactctgc gttggccgct ttagaggaca ctgttgacta tcctgctcgt    2580
gctcacactt ttgatgattt ctgccctgag tgccgtacac tcggccttca gggttgtgct    2640
ttccaatcaa ctgttgctga gctacagcgt cttaaaatga aggtgggtaa aactcgggag    2700
tacccgggag agaatctata ttttcaaggg cccggcggag gtagtcacca tcatcaccat    2760
cactaatgac cggt                                                      2774
```

<210> SEQ ID NO 151
<211> LENGTH: 899
<212> TYPE: PRT
<213> ORGANISM: artificial
<220> FEATURE:
<223> OTHER INFORMATION: Aa sequence of fusion protein
      [SNAPlike-proTEV1-HEV.C-proTEV2-Histag]

<400> SEQUENCE: 151

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Asn Asn
        195                 200                 205

Met Phe Phe Cys Ser Val His Gly Asp Ala Thr Met Arg Ser Arg Ala
    210                 215                 220

Phe Leu Phe Leu Phe Leu Val Phe Leu Pro Met Leu Pro Ala Pro Pro
225                 230                 235                 240

Ala Gly Gln Pro Ser Gly Arg Arg Gly Arg Arg Ser Gly Gly Ala
                245                 250                 255

Gly Gly Gly Phe Trp Gly Asp Arg Ile Asp Ser Gln Pro Phe Ala Leu
            260                 265                 270
```

```
Pro Tyr Ile His Pro Thr Asn Pro Phe Ala Pro Asp Ile Pro Ala Ala
        275                 280                 285

Ala Gly Ala Gly Ala Arg Pro Arg Gln Pro Ala Arg Pro Leu Gly Ser
290                 295                 300

Ala Trp Arg Asp Gln Ser Gln Arg Pro Ala Thr Ser Ala Arg Arg Arg
305                 310                 315                 320

Ser Ala Pro Ala Gly Ala Ser Pro Leu Thr Ala Val Ala Pro Ala Pro
                325                 330                 335

Asp Thr Val Pro Val Pro Asp Val Asp Ser Arg Gly Ala Ile Leu Arg
                340                 345                 350

Arg Gln Tyr Asn Leu Ser Ser Pro Leu Thr Ser Thr Ile Ala Thr
        355                 360                 365

Gly Thr Asn Leu Val Leu Tyr Ala Ala Pro Leu Ser Pro Leu Leu Pro
        370                 375                 380

Leu Gln Asp Gly Thr Asn Thr His Ile Met Ala Thr Glu Ala Ser Asn
385                 390                 395                 400

Tyr Ala Gln Tyr Arg Val Val Arg Ala Thr Ile Arg Tyr Arg Pro Leu
                405                 410                 415

Val Pro Asn Ala Val Gly Gly Tyr Ala Ile Ser Ile Ser Phe Trp Pro
        420                 425                 430

Gln Thr Thr Thr Thr Pro Thr Ser Val Asp Met Asn Ser Ile Thr Ser
        435                 440                 445

Thr Asp Val Arg Ile Leu Val Gln Pro Gly Ile Ala Ser Glu Leu Val
450                 455                 460

Ile Pro Ser Glu Arg Leu His Tyr Arg Asn Gln Gly Trp Arg Ser Val
465                 470                 475                 480

Glu Thr Ser Gly Val Ala Glu Glu Ala Thr Ser Gly Leu Val Met
                485                 490                 495

Leu Cys Ile His Gly Ser Pro Val Asn Ser Tyr Thr Asn Thr Pro Tyr
                500                 505                 510

Thr Gly Ala Leu Gly Leu Leu Asp Phe Ala Leu Glu Leu Glu Phe Arg
        515                 520                 525

Asn Leu Thr Pro Gly Asn Thr Asn Thr Arg Val Ser Arg Tyr Ser Ser
        530                 535                 540

Ser Ala Arg His Lys Leu Arg Arg Gly Pro Asp Gly Thr Ala Glu Leu
545                 550                 555                 560

Thr Thr Thr Ala Ala Thr Arg Phe Met Lys Asp Leu His Phe Thr Gly
                565                 570                 575

Thr Asn Gly Val Gly Glu Val Gly Arg Gly Ile Ala Leu Thr Leu Phe
                580                 585                 590

Asn Leu Ala Asp Thr Leu Leu Gly Gly Leu Pro Thr Glu Leu Ile Ser
        595                 600                 605

Ser Ala Gly Gly Gln Leu Phe Tyr Ser Arg Pro Val Val Ser Ala Asn
610                 615                 620

Gly Glu Pro Thr Val Lys Leu Tyr Thr Ser Val Glu Asn Ala Gln Gln
625                 630                 635                 640

Asp Lys Gly Ile Ala Ile Pro His Asp Ile Asp Leu Gly Glu Ser Arg
                645                 650                 655

Val Val Ile Gln Asp Tyr Asp Asn Gln His Glu Gln Asp Arg Pro Thr
                660                 665                 670

Pro Ser Pro Ala Pro Ser Arg Pro Phe Ser Val Leu Arg Ala Asn Asp
                675                 680                 685
```

```
Val Leu Trp Leu Ser Leu Thr Ala Ala Glu Tyr Asp Gln Thr Thr Tyr
    690             695                 700

Gly Ser Ser Thr Asn Pro Met Tyr Val Ser Asp Thr Val Thr Phe Val
705             710                 715                     720

Asn Val Ala Thr Gly Ala Gln Gly Val Ser Arg Ser Leu Asp Trp Ser
            725                 730                 735

Lys Val Thr Leu Asp Gly Arg Pro Leu Met Thr Ile Gln Gln Tyr Ser
            740                 745                 750

Lys Thr Phe Phe Val Leu Pro Leu Arg Gly Lys Leu Ser Phe Trp Glu
        755                 760                 765

Ala Gly Thr Thr Lys Ala Gly Tyr Pro Tyr Asn Tyr Asn Thr Thr Ala
770                 775                 780

Ser Asp Gln Ile Leu Ile Glu Asn Ala Ala Gly His Arg Val Cys Ile
785                 790                 795                 800

Ser Thr Tyr Thr Thr Asn Leu Gly Ser Gly Pro Val Ser Ile Ser Ala
                805                 810                 815

Val Gly Val Leu Ala Pro His Ser Ala Leu Ala Ala Leu Glu Asp Thr
            820                 825                 830

Val Asp Tyr Pro Ala Arg Ala His Thr Phe Asp Asp Phe Cys Pro Glu
            835                 840                 845

Cys Arg Thr Leu Gly Leu Gln Gly Cys Ala Phe Gln Ser Thr Val Ala
850                 855                 860

Glu Leu Gln Arg Leu Lys Met Lys Val Gly Lys Thr Arg Glu Tyr Pro
865                 870                 875                 880

Gly Glu Asn Leu Tyr Phe Gln Gly Pro Gly Gly Gly Ser His His His
                885                 890                 895

His His His

<210> SEQ ID NO 152
<211> LENGTH: 51
<212> TYPE: DNA
<213> ORGANISM: artificial
<220> FEATURE:
<223> OTHER INFORMATION: DNA encoding biPlike sequence

<400> SEQUENCE: 152
atgaaactat gtattctact tgcagttgtt gcgttcgtag gattgtcctt a            51

<210> SEQ ID NO 153
<211> LENGTH: 17
<212> TYPE: PRT
<213> ORGANISM: artificial
<220> FEATURE:
<223> OTHER INFORMATION: Amino acid of BIPlike sequence

<400> SEQUENCE: 153

Met Lys Leu Cys Ile Leu Leu Ala Val Val Ala Phe Val Gly Leu Ser
1               5                   10                  15

Leu
```